United States Patent
Furet et al.

(10) Patent No.: US 8,822,468 B2
(45) Date of Patent: Sep. 2, 2014

(54) 3-METHYL-IMIDAZO[1,2-B]PYRIDAZINE DERIVATIVES

(75) Inventors: Pascal Furet, Horsham (GB); Clive McCarthy, Horsham (GB); Joseph Schoepfer, Basel (CH); Carsten Spanka, Basel (CH); Melanie Stang, Basel (CH); Frederic Stauffer, Basel (CH)

(73) Assignee: Novartis AG, Basel (CH)

( * ) Notice: Subject to any disclaimer, the term of this patent is extended or adjusted under 35 U.S.C. 154(b) by 1132 days.

(21) Appl. No.: 12/396,137

(22) Filed: Mar. 2, 2009

(65) Prior Publication Data
US 2009/0264406 A1 Oct. 22, 2009

(30) Foreign Application Priority Data
Feb. 28, 2008 (EP) .................................. 08152068

(51) Int. Cl.
C07D 519/00 (2006.01)
C07D 487/04 (2006.01)
A61K 31/5025 (2006.01)
A61P 35/00 (2006.01)

(52) U.S. Cl.
CPC ............ C07D 487/04 (2013.01); C07D 519/00 (2013.01)
USPC .......................................... 514/248; 544/236

(58) Field of Classification Search
CPC ............... C07D 487/04; C07D 519/00; A61K 31/5025; A61K 31/519
USPC .......................................... 544/236; 514/248
See application file for complete search history.

(56) References Cited

U.S. PATENT DOCUMENTS

| | | | |
|---|---|---|---|
| 3,489,755 A | 1/1970 | Lombardino | |
| 4,910,199 A | 3/1990 | Bourguignon et al. | |
| 7,078,405 B2 | 7/2006 | Hibi et al. | |
| 7,348,325 B2 | 3/2008 | Cai et al. | |
| 8,198,448 B2 * | 6/2012 | Albrecht et al. | 546/119 |
| 2006/0148801 A1 | 7/2006 | Hsieh et al. | |
| 2007/0167460 A1 | 7/2007 | McArthur et al. | |
| 2007/0265272 A1 | 11/2007 | Cheng et al. | |
| 2008/0039457 A1 | 2/2008 | Zhou et al. | |
| 2008/0153813 A1 | 6/2008 | Chen et al. | |
| 2009/0124609 A1 | 5/2009 | Albrecht et al. | |

FOREIGN PATENT DOCUMENTS

| | | |
|---|---|---|
| EP | 0 306 408 B1 | 9/1988 |
| EP | 0 490 587 A1 | 12/1991 |
| EP | 1 277 754 B1 | 7/2005 |
| JP | 2009-227599 A | 10/2001 |
| WO | WO 01/83481 A1 | 11/2001 |
| WO | WO 02/062800 A1 | 8/2002 |
| WO | WO 2004/058749 A1 | 7/2004 |
| WO | WO 2005/004807 A1 | 1/2005 |
| WO | WO 2005/004808 A2 | 1/2005 |
| WO | WO 2005/010005 A1 | 2/2005 |
| WO | WO 2005/041971 A1 | 5/2005 |
| WO | WO 2005/051906 A2 | 6/2005 |
| WO | WO 2005/073224 A2 | 8/2005 |
| WO | WO 2005/080355 A1 | 9/2005 |
| WO | WO 2008/064157 A1 | 5/2006 |
| WO | WO 2006/124354 A2 | 11/2006 |
| WO | WO 2007/013673 A1 | 2/2007 |
| WO | WO 2007/038314 A2 | 4/2007 |
| WO | WO 2007/064797 A2 | 6/2007 |
| WO | WO 2007/075567 A1 | 7/2007 |
| WO | WO 2007/138472 A2 | 12/2007 |
| WO | WO 2008/008539 A2 | 1/2008 |
| WO | WO 2008/016192 A2 | 2/2008 |
| WO | WO 2008/030579 A2 | 3/2008 |
| WO | WO 2008/030744 A2 | 3/2008 |
| WO | WO 2008/051805 A2 | 5/2008 |
| WO | WO 2008/155378 A1 | 12/2008 |
| WO | WO 2009/011954 A1 | 2/2009 |
| WO | WO 2009/060197 A1 | 5/2009 |
| WO | WO 2009/088955 A2 | 6/2009 |
| WO | 2009091374 A2 | 7/2009 |

* cited by examiner

Primary Examiner — Susanna Moore
(74) Attorney, Agent, or Firm — Qian Zhang

(57) ABSTRACT

The invention relates to compounds of formula (I) and salts thereof

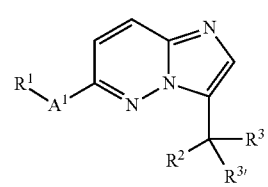

(I)

wherein the substituents are as defined in the specification, the application of a compound of formula (I) in a process for the treatment of the human or animal body, in particular with regard to C-Met tyrosine kinase mediated disease; the use of a compound of formula (I) for manufacturing a medicament for the treatment of such diseases; pharmaceutical compositions comprising a compound of the formula (I), optionally in the presence of a combination partner; processes for the preparation of a compound of formula (I).

3 Claims, No Drawings

3-METHYL-IMIDAZO[1,2-B]PYRIDAZINE DERIVATIVES

This application claims priority to European Patent Application Serial No. 08152068.6 filed 28 Feb 2008, the contents of which are incorporated herein by reference in their entirety.

The invention relates to 3-Methyl-imidazo[1,2-b]pyridazine derivatives of the formula (I) given below, as well as salts thereof; the application of a compound of formula (I) in a process for the treatment of the human or animal body, in particular with regard to a proliferative disease; the use of a compound of formula (I) for manufacturing a medicament for the treatment of such diseases; pharmaceutical compositions comprising a compound of the formula (I), optionally in the presence of a combination partner; processes for the preparation of a compound of formula (I).

The Hepatocyte Growth Factor Receptor, herein referred to as c-Met, is a receptor tyrosine kinase that has been shown to be over-expressed and/or genetically altered in a variety of malignancies, specifically, gene amplification and a number of c-Met mutations are found in various solid tumors, see e.g. WO2007/126799. Further, the receptor tyrosine kinase c-Met is involved in the processes of migration, invasion and morphogenesis that accompany embryogenesis and tissue regeneration. C-met is also involved in the process of metastasis. Several lines of evidence have indicated that c-Met plays a role in tumor pathogenesis. Gain of function germ line mutations in c-Met is associated with development of hereditary papillary renal cell carcinoma (PRCC). Amplification or mutations in c-Met have also been reported in sporadic forms of PRCC, in head and neck squamous cell carcinoma, in gastric carcinoma, in pancreatic carcinoma and in lung cancer. Such alterations have been shown in selected instances to confer dependence of the tumor on c-Met and/or resistance to other targeted therapies. Elevated levels of c-Met, together with its unique ligand HGF/SF, are observed at high frequency in multiple clinically relevant tumors. A correlation between increased expression and disease progression, metastases and patient mortality has been reported in several cancers, including bladder, breast, squamous cell carcinoma and gastric carcinoma as well as leiomyosarcoma and glioblastoma.

WO 2008/008539 discloses certain fused heterocyclic derivatives which are useful in the treatment of HGF mediated diseases. WO 2007/013673 discloses fused heterocyclic derivatives as Lck inhibitors which are useful as immunosuppressive agents. EP0490587 discloses certain pyrazolopyrimidines which are useful as angiotensin II antagonists.

It is thus an aim of the present invention to provide further compounds that modulate (in particular inhibit) c-Met and/or show good metabolic stability.

It has now been found that the compounds of the formula (I) given below have advantageous pharmacological properties and inhibit, for example c-Met. It has further been found that the compounds of formula (I) given below show improved metabolic stability. Hence, the compounds of formula (I) are suitable, for example, to be used in the treatment of diseases dependent on c-Met activity, especially solid tumors or metastasis derived therefrom. Through the inhibition of c-Met, compounds of the invention also have utility as anti-inflammatory agents, for example for the treatment of an inflammatory condition which is due to an infection.

In a first aspect, the invention relates to compounds of the formula (I),

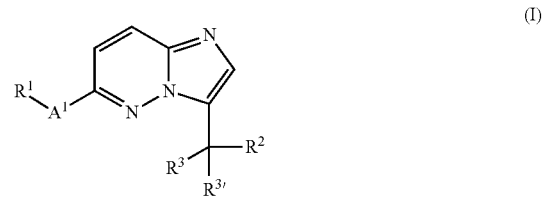

wherein
$R^1$ represents unsubstituted or substituted heterocyclyl, unsubstituted or substituted aryl, unsubstituted or substituted cycloalkyl, unsubstituted or substituted alkyl, unsubstituted or substituted alkoxy, cyano, carboxamide, or halogen;
$R^2$ represents unsubstituted or substituted heterocyclyl, unsubstituted or substituted aryl;
$R^3$ represents H, deuterium, lower alkyl and $R^{3'}$ represents H, deuterium, lower alkyl, halogen, hydroxy or
$R^3$ represents halogen and $R^{3'}$ represents halogen or
$R^3$ and $R^{3'}$ represent, together with the carbon atom to which they are attached, cycloalkyl or vinyl;
$A^1$ represents either a direct bond, an —SO$_2$— group, or a group

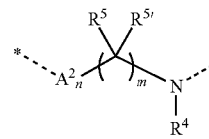

wherein
the bond marked * is attached to $R^1$,
n represents 0 or 1;
m represents 0, 1, 2, 3, 4 or 5;
$R^4$ represents H or unsubstituted alkyl;
$R^5$, $R^{5'}$ represent independent form each other H or unsubstituted alkyl;
$A^2$ represents O or $NR^4$;
or salts thereof.

The invention may be more fully appreciated by reference to the following description, including the following glossary of terms and the concluding examples. For the sake of brevity, the disclosures of the publications cited in this specification are herein incorporated by reference. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula (I), such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. Various isotopically labeled compounds of the present invention, for example those into which radioactive isotopes such as $^{3}H$, $^{13}C$, and $^{14}C$ are incorporated. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

The acid addition salt of compounds of formula (I) are preferably pharmaceutically acceptable salts. Such salts are known in the field.

The following general definitions shall apply in this specification, unless otherwise specified:

Halogen (or halo) denotes fluorine, bromine, chlorine or iodine, in particular fluorine, chlorine. Halogen-substituted groups and moieties, such as alkyl substituted by halogen (halogenalkyl) can be mono-, poly- or per-halogenated.

Hetero atoms are atoms other than C and H, preferably nitrogen (N), oxygen (O), sulfur (S).

Carbon containing groups, moieties or molecules contain 1 to 8, preferably 1 to 6, more preferably 1 to 4, most preferably 1 or 2, carbon atoms. Any non-cyclic carbon containing group or moiety with more than 1 carbon atom is straight-chain or branched.

"Alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tertbutyl, n-pentyl, neo-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to hydroxyl, alkoxy, halogen and amino. An example of a substituted alkyl is trifluoro-methyl. Cycloalkyl may also be a substituent to alkyl. An example of such a case is the moiety (alkyl)cyclopropyl or alkandiyl-cyclopropyl, e.g. —CH$_2$-cyclopropyl. $C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxycarbonylalkyl", "alkylsulfonyl", "alkylsulfinyl", "alkylamino", "halogenalkyl" shall have the same meaning as described in the above-mentioned definition of "alkyl". The prefix "lower" or "$C_1$-$C_7$" denotes a radical having up to and including a maximum of 7, especially up to and including a maximum of 4 carbon atoms, the radicals in question being either linear or branched with single or multiple branching.

"Alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—CH$_2$—), 1,2-ethanediyl (—CH$_2$—CH$_2$—), 1,1-ethanediyl ((—CH(CH$_3$)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

"Alkendiyl" refers to a straight-chain or branched-chain alkendiyl group bound by two different Carbon atoms to the molecule, it preferably represents a straight-chain or branched-chain $C_{2-6}$ alkandiyl; for example, —CH=CH—, —CH=C(CH$_3$)—, —CH=CH—CH$_2$—, —C(CH$_3$)=CH—CH$_2$—, —CH=C(CH$_3$)—CH$_2$—, —CH=CH—C(CH$_3$)H—, —CH=CH—CH=CH—, —C(CH$_3$)=CH—CH=CH—, —CH=C(CH$_3$)—CH=CH—, with particular preference given to —CH=CH—CH$_2$—, —CH=CH—CH=CH—. Alkendiyl may be substituted or unsubstituted.

"Cycloalkyl" refers to a saturated or partially saturated, monocyclic, fused polycyclic, or Spiro polycyclic, carbocycle having from 3 to 12 ring atoms per carbocycle. Illustrative examples of cycloalkyl groups include the following moieties: cyclopropyl, cyclobutyl, cyclpentyl and cylclohexyl. Cycloalkyl may be unsubstituted or substituted; exemplary substituents are provided in the definition for alkyl.

"Aryl" refers to an aromatic homocyclic ring system with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxo-pyrrolidino, $C_1$-$C_7$-alkyl-pyrrolidinyl, 2,5-di-($C_1$-$C_7$alkyl)pyrrolidinyl, such as 2,5-di-($C_1$-$C_7$alkyl)pyrrolidino, tetrahydrofuranyl, thiophenyl, $C_1$-$C_7$-alkylpyrazolidinyl, pyridinyl, $C_1$-$C_7$-alkyl-piperidinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkylpiperazino, morpholino, thiomorpholino, S-oxo-thiomorpholino or S,S-dioxothiomorpholino; $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxy]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$-alkanoylamino, $C_1$-$C_7$-alkanesulfonylamino, carboxy, lower alkoxy carbonyl, e.g.; phenyl- or naphthyl-lower alkoxycarbonyl, such as benzyloxycarbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (loweralkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, sulfo (—$SO_3H$), lower alkanesulfonyl, phenyl- or naphthyl-sulfonyl, phenyl- or naphthyl-lower alkylsulfonyl, alkylphenylsulfonyl, halogen-lower alkylsulfonyl, such as trifluoromethanesulfonyl; sulfonamido, benzosulfonamido, azido, azido-$C_1$-$C_7$-alkyl, especially azidomethyl, $C_1$-$C_7$-alkane-sulfonyl, sulfamoyl, N-mono- or N,N-di-($C_1$-$C_7$-alkyl)-sulfamoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxycarbonyl, carbamoyl, cyano and/or sulfamoyl.

"Heterocyclyl" refers to a heterocyclic radical that is unsaturated (=carrying the highest possible number of conjugated double bonds in the ring(s), in which case heterocyclyl is alternatively stated as heteroaryl), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; wherein one or more, preferably one to four, especially one or two carbon ring atoms are replaced by a heteroatom, the bonding ring preferably having 4 to 12, especially 5 to 7 ring atoms. The heterocyclic radical (heterocyclyl) may be unsubstituted or substituted by one or more, especially 1 to 3, substituents independently selected from the group consisting of the substituents defined above for substituted alkyl or aryl and/or from one or more of the following substituents: oxo (=O), thiocarbonyl (=S), imino(=NH), imino-lower alkyl. Further, heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]dioxol-5-yl and 2,3-dihydro-benzo[1,4]dioxin-6-yl, each of these radicals being unsubstituted or substituted by one or more, preferably up to three, substituents selected from those mentioned above for substituted aryl and/or from one or more of the following substituents: oxo (=O), thiocarbonyl (=S), imino(=NH), imino-lower alkyl.

"Arylalkyl" refers to an aryl group bound to the molecule via an alkyl group, such as a methyl or ethyl group, preferably phenethyl or benzyl, in particular benzyl. Similarly, cycloalkylalkyl and heterocyclyl represents a cycloalkyl group bound to the molecule via an alkyl group or a heterocyclyl group bound to the molecule via an alkyl group. In each instance, aryl, heterocyclyl, cycloalkyl and alkyl may be substituted as defined above.

"Salts" (which, what is meant by "or salts thereof" or "or a salt thereof", can be present alone or in mixture with free compound of the formula (I)) are preferably pharmaceutically acceptable salts. Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

"C-Met tyrosine kinase mediated diseases" are especially such disorders that respond in a beneficial way (e.g. amelioration of one or more symptoms, delay of the onset of a disease, up to temporary or complete cure from a disease) to the inhibition of a protein tyrosine kinase, especially inhibition of a c-Met kinase. These disorders include proliferative diseases such as tumor diseases, in particular solid tumors and metastasis derived thereof, e.g. hereditary papillary renal cell carcinoma (PRCC), sporadic forms of PRCC, head and neck cancer, squamous cell carcinoma, gastric carcinoma, pancreatic carcinoma, lung cancer, bladder cancer, breast cancer, leiomyosarcoma, glioblastoma, melanoma, alveolar soft part sarcoma.

These disorders further include inflammatory conditions, such as inflammatory conditions due to an infection.

"Treatment" includes prophylactic (preventive) and therapeutic treatment as well as the delay of progression of a disease, disorder or condition.

"Combination" refers to either a fixed combination in one dosage unit form, or a kit of parts for the combined administration where a compound of the formula (I) and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula (I), in free base form or in acid addition salt form, wherein the substituents are as defined herein.

In an embodiment, the invention relates to a compound of formula (IA)

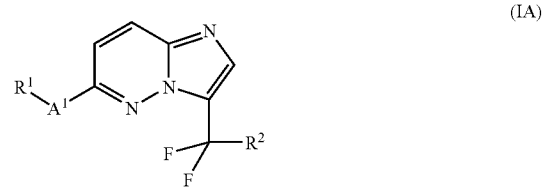

(IA)

wherein the substituents are as defined for a compound of formula (I).

In a further embodiment, the invention relates to a compound of formula (IB)

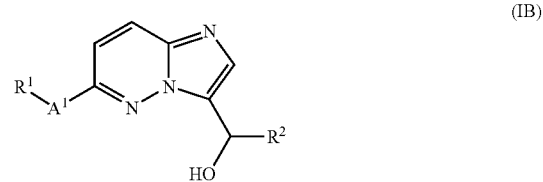

(IB)

wherein the substituents are as defined for a compound of formula (I).

In a further embodiment, the invention relates to a compound of formula (IC)

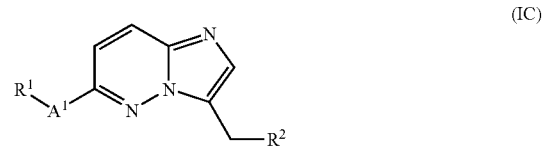

(IC)

wherein the substituents are as defined for a compound of formula (I).

In a further embodiment, the invention relates to a compound of formula (ID)

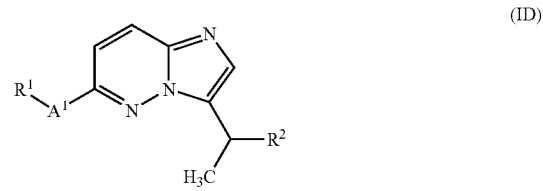

(ID)

wherein the substituents are as defined for a compound of formula (I).

In a further embodiment, the invention relates to a compound of formula (IE)

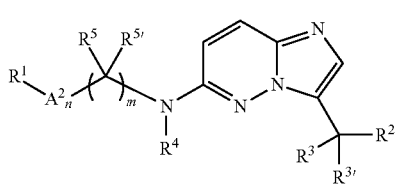
(IE)

wherein R$^1$ represents unsubstituted or substituted cycloalkyl; unsubstituted or substituted alkyl and n, m, A$^2$, R$^2$, R$^3$, R$^{3'}$, R$^4$, R$^5$, R$^{5'}$ are as defined herein.

In a further embodiment, the invention relates to a compound of formula (IF)

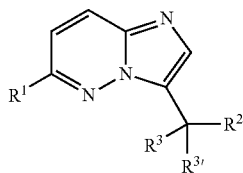
(IF)

wherein R$^1$ represents unsubstituted or substituted heterocyclyl, unsubstituted or substituted aryl and R$^2$, R$^3$, R$^{3'}$ are as defined herein.

In a further embodiment, the invention relates to a compound of formula (IG)

(IG)

In a further embodiment, the invention relates to a compound of formula (IH)

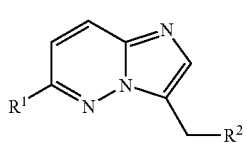
(IH)

wherein the substituents are as defined for a compound of formula (I).

In a further embodiment, the invention relates to a compound of formula (IJ)

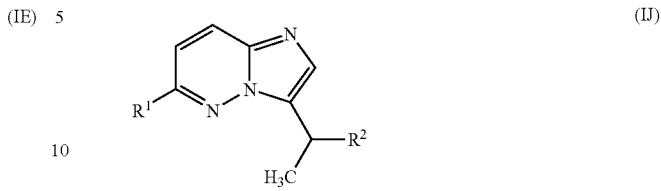
(IJ)

wherein the substituents are as defined for a compound of formula (I).

In a further embodiment, the invention relates to a compound of formula (IK)

(IK)

wherein the substituents are as defined for a compound of formula (I).

Preferred compounds of the present invention are those wherein A$^1$ is a direct bond, i.e. wherein the R$^1$ moiety is directly bonded to the imidazo[1,2-b]pyridazine bicyclic system.

R$^1$ preferably represents unsubstituted or substituted heterocyclyl;
  wherein said heterocyclyl is selected from unsaturated, saturated or partially saturated heterocycles which are monocyclic, bicyclic, tricyclic or spirocyclic and have 4 to 16, ring atoms wherein one to four heteroatoms are present;
  wherein said substituents are independently selected from one or more, preferably one to four of the following moieties: halo, hydroxy, cyano, nitro, carboxy, C$_1$-C$_7$-alkyl, C$_3$-C$_{12}$-cyclo-alkyl, phenyl-C$_1$-C$_7$-alkyl, halo-C$_1$-C$_7$-alkyl, hydroxy-C$_1$-C$_7$-alkyl, amino-C$_1$-C$_7$-alkyl, N—C$_1$-C$_7$-alkanoylamino-C$_1$-C$_7$-alkyl, N—C$_1$-C$_7$-alkanesulfonyl-amino-C$_1$-C$_7$-alkyl, pyrrolidino-C$_1$-C$_7$-alkyl, oxo-pyrrolidino-C$_1$-C$_7$-alkyl, piperidino-C$_1$-C$_7$-alkyl, piperazin-1-yl-C$_1$-C$_7$-alkyl, 4-(C$_1$-C$_7$-alkyl, C$_1$-C$_7$-alkoxy-C$_1$-C$_7$-alkyl, halo-C$_1$-C$_7$-alkyl or C$_3$-C$_{10}$-cycloalkyl)-piperazin-1-yl-C$_1$-C$_7$-alkyl, 4-(amino-C$_1$-C$_7$-alkyl)-piperazin-1-yl-C$_1$-C$_7$-alkyl, 4-[N-mono- or N,N-di-(C$_1$-C$_7$-alkylamino)-C$_1$-C$_7$-alkyl]-piperazin-1-yl-C$_1$-C$_7$-alkyl, morpholino-C$_1$-C$_7$-alkyl, thiomorpholino-C$_1$-C$_7$-alkyl, S-mono- or S,S-di-oxo-thiomorpholino-C$_1$-C$_7$-alkyl, carbamoyl-C$_1$-C$_7$-alkyl, [N-mono- or N,N-di-(C$_1$-C$_7$-alkyl)carbamoyl]-C$_1$-C$_7$-alkyl, C$_1$-C$_7$-alkanesulfinyl-C$_1$-C$_7$-alkyl, C$_1$-C$_7$-alkanesulfonyl-C$_1$-C$_7$-alkyl, C$_1$-C$_7$-alkoxy, halo-C$_1$-C$_7$-alkoxy, amino, N-mono- or N,N-di-(C$_1$-C$_7$-alkyl)-amino, C$_1$-C$_7$-alkanoylamino, N—C$_1$-C$_7$-alkanoyl-N—C$_1$-C$_7$-alkyl-amino, C$_1$-C$_7$-alkyloxycarbonylamino, N—C$_1$-C$_7$-alkyloxycarbonyl-N—C$_1$-C$_7$-alkyl-amino, pyrrolidino, oxo-pyrrolidino, piperidino, piperazin-1-yl, 4-(C$_1$-C$_7$-alkyl, C$_1$-C$_7$-alkoxy-C$_1$-C$_7$-alkyl, halo-C$_1$-C$_7$-alkyl or C$_3$-C$_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothio-morpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, $C_1$-$C_7$-alkylcarbonyl, $C_1$-$C_7$-alkoxycarbonyl, formyl, $C_1$-$C_7$-alkylcarbonyl, amino-carbonyl, amino-$C_1$-$C_7$-alkylcarbonyl, halo-$C_1$-$C_7$-alkylcarbonyl, halo-$C_1$-$C_7$-alkoxycarbonyl, N—$C_1$-$C_7$-alkanoylamino-$C_1$-$C_7$-alkylcarbonyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothio-morpholin-1-carbonyl, sulfo, $C_1$-$C_7$-alkylsulfonyl, $C_1$-$C_7$-alkylsulfinyl, $C_1$-$C_7$-alkylthio, sulfamoyl, N-mono- or N,N-di-($C_1$-$C_7$-alkyl)-sulfamoyl, morpholinosulfonyl, thiomorpholinosulfonyl; oxo (e.g. C=O or $N^{(+)}$—$O^{(-)}$) or $C_{1-6}$ alkandiyl.

$R^1$ particular preferably represents unsubstituted or substituted heterocyclyl;
wherein said heterocyclyl is selected from the group consisting of indanyl, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, chinoline, thionaphtene and wherein said heterocyclyl is substituted by one or more, preferably one to three moieties independently selected from the group consisting of halo, hydroxy, cyano, nitro, carboxy, amino-carbonyl, $C_1$-$C_7$-alkylsulfonylamino, $C_1$-$C_7$-alkyl, (amino, $C_1$-$C_7$-alkylamino, $C_1$-$C_7$-dialkylamino)-$C_1$-$C_7$-alkyl, (amino, $C_1$-$C_7$-alkyl-amino, $C_1$-$C_7$-dialkylamino)-$C_1$-$C_7$-alkyloxy, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkyl-amino)-$C_1$-$C_7$-alkyl]-piperazin-1-yl, morpholino, thiomorpholino, S-oxo- or S,S-dioxo-thio-morpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholino-sulfonyl, thiomorpholinosulfonyl, methandiyl, ethandiyl and oxo.

$R^1$ very particular preferably represents unsubstituted or substituted heterocyclyl;
wherein said heterocyclyl is selected from the group consisting of pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane, dioxolane, thiophene, dihydrothiophene, tetrahydrothiophene, oxazole, oxazoline, oxazolidine, isoxazole, isoxazoline, isoxazolidine, thiazole, thiazoline, thiaziolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, chinoline, thionaphtene and wherein said heterocyclyl is substituted by one or more, preferably one or two moieties independently selected from the group consisting of halo, $C_1$-$C_4$-alkyl, benzyl, $C_1$-$C_4$-alkyloxy, halo-$C_1$-$C_4$-alkyl, pyrrolidino-$C_1$-$C_2$-alkyl, piperidino-$C_1$-$C_2$-alkyl, oxo.

$R^1$ further preferably represents unsubstituted or substituted aryl;
wherein said aryl is selected from aromatic moieties with 6 to 14 ring carbon atoms;
wherein said substituents are independently selected from one or more, preferably one or two of the following moieties: halo, hydroxy, cyano, nitro, carboxy, $C_1$-$C_7$-alkyl, $C_3$-$C_{12}$-cycloalkyl, phenyl-$C_1$-$C_7$-alkyl, halo-$C_1$-$C_7$-alkyl, hydroxy-$C_1$-$C_7$-alkyl amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, $C_1$-$C_7$-alkoxy, halo-$C_1$-$C_7$-alkoxy, amino, N-mono- or N,N-di-($C_1$-$C_7$-alkyl)-amino, $C_1$-$C_7$-alkanoylamino, N—$C_1$-$C_7$-alkanoyl-N—$C_1$-$C_7$-alkyl-amino, $C_1$-$C_7$-alkyloxycarbonyl-amino, N—$C_1$-$C_7$-alkyloxycarbonyl-N—$C_1$-$C_7$-alkyl-amino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1- yl, morpholino, thiomorpholino, S-oxo- or S,S-dioxothio-morpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, $C_1$-$C_7$-alkylcarbonyl, $C_1$-$C_7$-alkoxycarbonyl, formyl, $C_1$-$C_7$-alkylcarbonyl, aminocarbonyl, amino-$C_1$-$C_7$-alkylcarbonyl, halo-$C_1$-$C_7$-alkyl-carbonyl, halo-$C_1$-$C_7$-alkoxy-carbonyl, N—$C_1$-$C_7$-alkanoylamino-$C_1$-$C_7$-alkylcarbonyl, pyrrolidin-1-carbonyl, piperidin-1-carbonyl, piperazin-1-carbonyl, 4-($C_1$-$C_7$-alkyl)-piperazin-1-carbonyl, morpholin-1-carbonyl, thiomorpholin-1-carbonyl, S-oxo- or S,S-dioxothio-morpholin-1-carbonyl, sulfo, $C_1$-$C_7$-alkylsulfonyl, $C_1$-$C_7$-alkylsulfinyl, $C_1$-$C_7$-alkylthio, sulfamoyl, N-mono- or N,N-di-($C_1$-$C_7$-alkyl)-sulfamoyl, morpholinosulfonyl, thiomorpholinosulfonyl.

$R^1$ further particular preferably represents unsubstituted or substituted phenyl or napthyl, the substituents being selected from one or more, preferably one to three moieties independently selected from the group consisting of halo, hydroxy, cyano, nitro, aminocarbonyl, $C_1$-$C_7$-alkylsulfonylamino, $C_1$-$C_7$-alkyl, (amino, $C_1$-$C_7$-alkyl-amino, $C_1$-$C_7$-dialkyl-amino)-$C_1$-$C_7$-alkyl, (amino, $C_1$-$C_7$-alkyl-amino, $C_1$-$C_7$-dialkyl-amino)-$C_1$-$C_7$-alkyloxy, halo-$C_1$-$C_7$-alkyl, N—$C_1$-$C_7$-alkanoylamino-$C_1$-$C_7$-alkyl, N—$C_1$-$C_7$-alkanesulfonylamino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxo-thiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl.

$R^1$ further preferably represents halogen, in particular when the group $A^1$ is a direct bond. In particular, $R^1$ is chloro in this embodiment.

$R^1$ further preferably represents $C_1$-$C_7$-alkoxy, for example ethoxy.

$R^1$ further preferably represents $C_1$-$C_7$-alkyl, $C_1$-$C_7$-haloalkyl or $C_3$-$C_{12}$ cycloalkyl.

$R^1$ further preferably represents $C_1$-$C_7$-alkoxy, cyano, carboxamide, or halogen.

$R^1$ further particular preferably represents $C_1$-$C_4$-alkyl, $C_1$-$C_4$-fluoroalkyl or $C_5$-$C_8$ cycloalkyl.

$R^1$ further very particular preferably represents methyl, ethyl, n- or iso-propyl, n-, iso-, sec- or tert-butyl, n-pentyl, neopentyl, trifluoromethyl, cyclopentyl, cyclohexyl, cyclooctyl.

$R^2$ preferably represents unsubstituted or substituted heterocyclyl or unsubstituted or substituted aryl;
wherein said heterocyclyl is selected from unsaturated, saturated or partially saturated heterocycles which are monocyclic, bicyclic, tricyclic or spirocyclic and have 4 to 16, ring atoms wherein one to four heteroatoms are present;
wherein said aryl is selected from aromatic moieties with 6 to 14 ring carbon atoms;
wherein said substitutents are independently selected from one or more, preferably one to four of the following moieties: halo, hydroxy, cyano, nitro, carboxy, $C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, $C_1$-$C_7$-alkoxy, amino, N-mono- or N,N-di-($C_1$-$C_7$-alkyl)-amino, $C_1$-$C_7$-alkanoyl-amino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothio-morpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl) carbamoyl, $C_1$-$C_7$-alkylcarbonyl, $C_1$-$C_7$-alkoxycarbonyl, amino-carbonyl, amino-$C_1$-$C_7$-alkylcarbonyl, halo-$C_1$-$C_7$-alkylcarbonyl, halo-$C_1$-$C_7$-alkoxycarbonyl, N—$C_1$-$C_7$-alkanoylamino-$C_1$-$C_7$-alkylcarbonyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothio-morpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl and oxo (C=O or $N^{(+)}$—$O^{(-)}$ provided $R^2$ represents heterocyclyl).

$R^2$ particular preferably represents unsubstituted or substituted heterocyclyl or unsubstituted or substituted aryl;
wherein said heterocyclyl or aryl is selected from the group consisting of phenyl, naphthyl, indanyl, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiaziolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline and wherein said heterocyclyl or aryl is substituted by one or more, preferably one to three moieties independently selected from the group consisting of halo, hydroxy, cyano, nitro, carboxy, aminocarbonyl, $C_1$-$C_7$-alkylsulfonylamino, $C_1$-$C_7$-alkyl, (amino, $C_1$-$C_7$-alkyl-amino, $C_1$-$C_7$-dialkyl-amino)-$C_1$-$C_7$-alkyl, (amino, $C_1$-$C_7$-alkyl-amino, $C_1$-$C_7$-dialkylamino)-$C_1$-$C_7$-alkyloxy, halo-$C_1$-$C_7$-alkyl, N—$C_1$-$C_7$-alkanoylamino-$C_1$-$C_7$-alkyl, N—$C_1$-$C_7$-alkyl-sulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkyl-sulfonyl-$C_1$-$C_7$-alkyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl) carbamoyl, pyrrolidin-1-carbonyl, piperidin-1-carbonyl, piperazin-1-carbonyl, 4-($C_1$-$C_7$-alkyl) piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkyl-sulfinyl, sulfamoyl, N-mono- or N,N-di-($C_1$-$C_7$-alkyl)-sulfamoyl, morpholinosulfonyl, thiomorpholinosulfonyl and oxo (provided $R^2$ represents heterocyclyl).

$R^2$ very particular preferably represents phenyl or a heterocyclyl selected from the following list

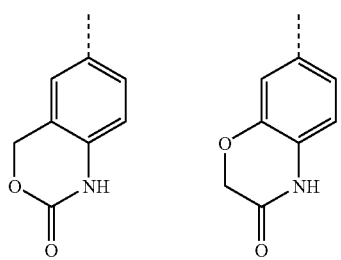

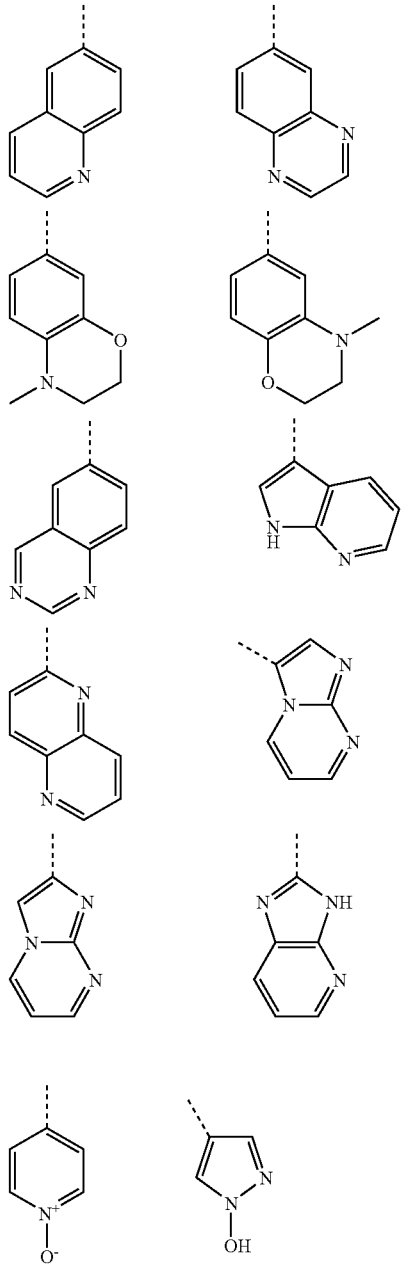

-continued

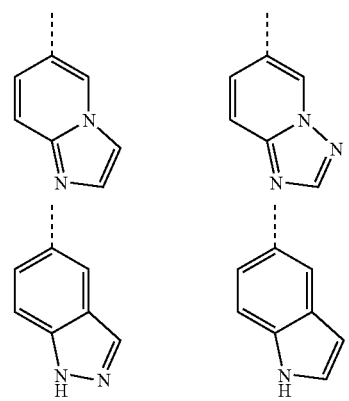

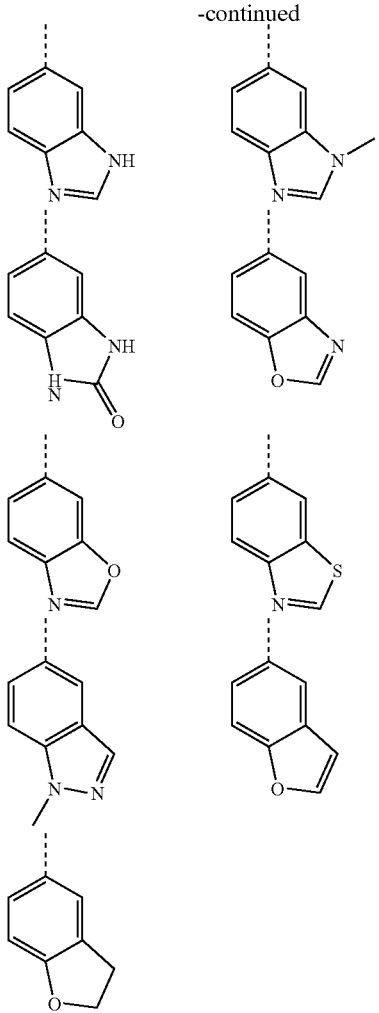

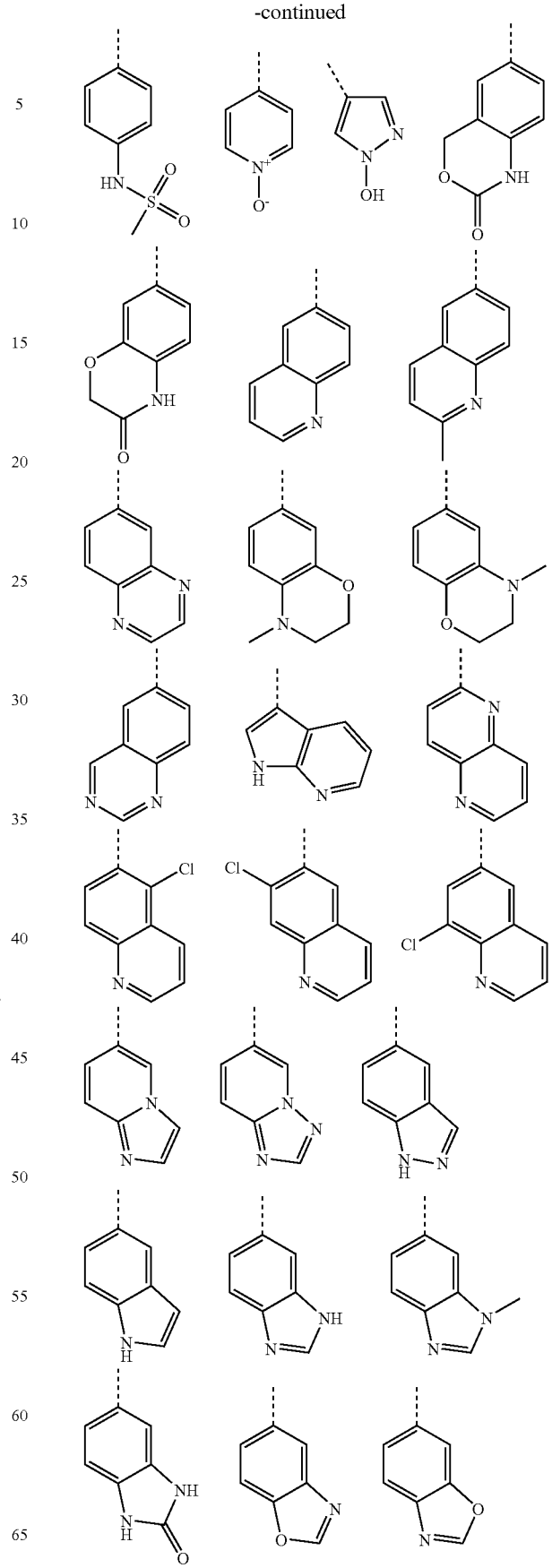

wherein said phenyl or heterocyclyl in each case is unsubstituted or substituted by one or more substituents, said substituent being selected from the group consisting of fluoro, chloro, bromo, 1-methyl-1H-pyrazol (in particular 1-methyl-1H-pyrazol-4-yl), pyridyl (in particular 3-pyridyl), phenyl (in particular substituted phenyl, more particularly 3-benzonitrile), hydroxy, amino, aminocarbonyl, cyano, $C_1$-$C_4$-alkyl (in particular methyl, ethyl), vinyl, $C_1$-$C_4$-alkyloxy (in particular methoxy), formyl, $C_1$-$C_4$-alkylcarbonyl (in particular 1-ethanone), hydroxyl-$C_1$-$C_4$-alkyl (in particular hydroxymethyl, 2-hydroxyethyl, ethane-1,2-diol), halo-$C_1$-$C_4$-alkyl (in particular $CF_3$), $C_1$-$C_4$-alkyloxy-$C_1$-$C_4$-alkyl (in particular methoxymethyl), $C_1$-$C_4$-alkylsulfonylamino (in particular methylsulfonylamino).

$R^2$ in a particular preferred embodiment relates to the moieties of the following list:

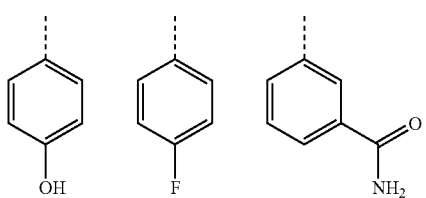

-continued
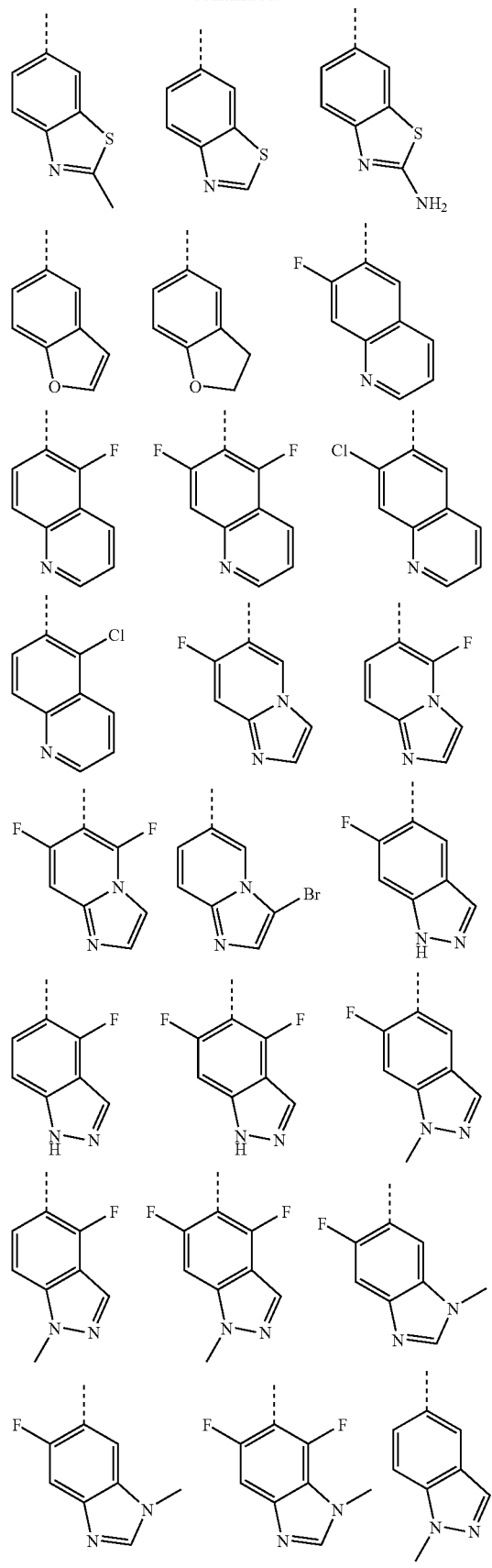
R² in a more preferred embodiment relates to the moieties of the following list:
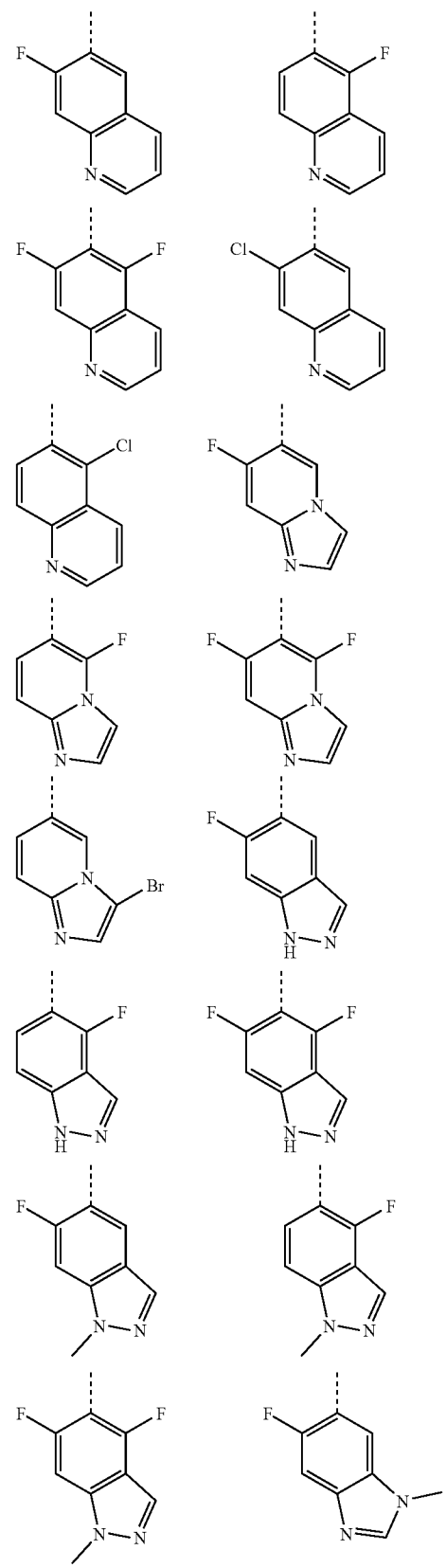

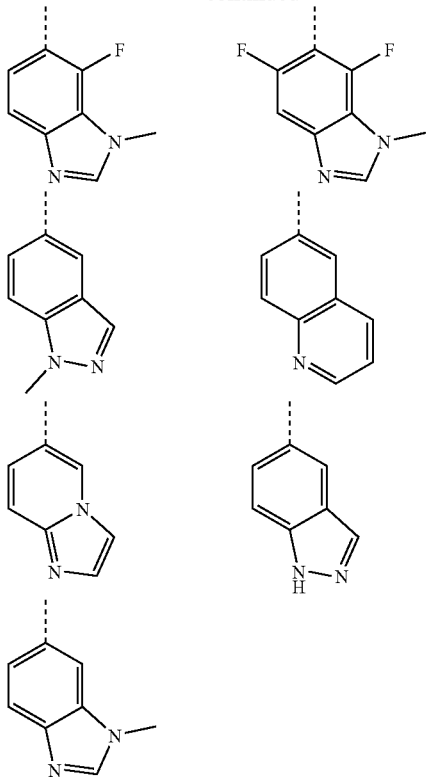

R³ preferably represents H, methyl, ethyl, n- or iso-propyl, halo-$C_1$-$C_7$-alkyl (in particular $CF_3$), and R³' preferably represents H, methyl, ethyl, n- or iso-propyl, fluoro, chloro, hydroxy or R³ and R³' represent either both fluoro or chloro or R³ and R³' represent, together with the carbon atom to which they are attached, cyclopropyl.

R³ and R³' are particular preferably selected according to the following list:

| R³ | R³' |
|---|---|
| H | H |
| D | D |
| H | F |
| H | OH |
| H | $CH_3$ |
| $CH_3$ | $CH_3$ |
| $CH_3$ | OH |
| F | F |
| Cyclopropyl | |

R⁴ preferably represents H, $C_1$-$C_7$-alkyl (in particular H).
R⁵ preferably represents H, $C_1$-$C_7$-alkyl (in particular H).
R⁵' preferably represents H, $C_1$-$C_7$-alkyl (in particular H).
n preferably represents 0 or 1.
n particular preferably represents 0.
m preferably represents 0, 1 or 2.
m particular preferably represents 0.
A² preferably represents Oxygen.

The invention further relates to pharmaceutically acceptable prodrugs of a compound of formula (I). The invention further relates to pharmaceutically acceptable metabolites of a compound of formula (I).

The invention relates especially to the compounds of the formula (I) given in the Examples, as well as the methods of manufacture described therein.

The compounds of formula (I) have valuable pharmacological properties, as described hereinbefore and hereinafter.

In a second aspect, the invention provides a method for treating a c-Met related disorder or condition. The disorder or condition to be treated is preferably a proliferative disease such as a cancer or an inflammatory condition. Compounds of formula (I) are further useful for treating an unwanted cell, in particular, a cell associated with a c-Met-related condition.

A: Proliferative diseases: Compounds of formula (I) are particular useful for the treatment of one or more of the following proliferative diseases:

Compounds of formula (I) are useful in the treatment of cancer wherein the cancer is selected from the group consisting of brain cancer, stomach cancer, genital cancer, urinary cancer, prostate cancer, bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric cancer, gastrointestinal cancer, liver cancer, hepatocellular carcinoma (HCC) including childhood HCC, head and neck cancer (including head and neck squamous-cell carcinoma, nasopharyngeal carcinoma), Hurthle cell carcinoma, epithelial cancer, skin cancer, melanoma (including malignant melanoma), mesothelioma, lymphoma, myeloma (including multiple myeloma), leukemias, lung cancer (including non-small cell lung cancer (including all histological subtypes: adenocarcinoma, squamous cell carcinoma, bronchoalveolar carcinoma, large-cell carcinoma, and adenosquamous mixed type), small-cell lung cancer), ovarian cancer, pancreatic cancer, prostate cancer, kidney cancer (including but not limited to papillary renal cell carcinoma), intestine cancer, renal cell cancer (including hereditary and sporadic papillary renal cell cancer, Type I and Type II, and clear cell renal cell cancer); sarcomas, in particular osteosarcomas, clear cell sarcomas, and soft tissue sarcomas (including alveolar and embryonal rhabdomyosarcomas, alveolar soft part sarcomas); thyroid carcinoma (papillary and other subtypes).

Compounds of formula (I) are useful in the treatment of cancer wherein the cancer is stomach, colon, liver, genital, urinary, melanoma, or prostate. In a particular embodiment, the cancer is liver or esophageal.

Compounds of formula (I) are useful in the treatment of colon cancer, including metastases, e.g. in the liver, and of non-small-cell lung carcinoma.

Compounds of formula (I) may also be used in the treatment of hereditary papillary renal carcinoma (Schmidt, L. et al. Nat. Genet. 16, 68-73, 1997) and other proliferative diseases in which c-MET is overexpressed or constitutively activated by mutations (Jeffers and Vande Woude. Oncogene 18, 5120-5125, 1999; and reference cited therein) or chromosomal rearrangements (e.g. TPR-MET; Cooper et al. Nature 311, 29-33, 1984; Park. et al. Cell 45, 895-904, 1986).

Compounds of formula (I) are further useful in the treatment of additional cancers and conditions as provided herein or known in the art.

B: Inflammatory conditions: Compounds of formula (I) are particular suitable for the treatment of one or more inflammatory conditions.

In a further embodiment, the inflammatory condition is due to an infection. In one embodiment, the method of treatment would be to block pathogen infection. In a particular embodiment, the infection is a bacterial infection, e.g., a Listeria infection. See, e.g., Shen et al. Cell 103: 501-10, (2000) whereby a bacterial surface protein activates c-Met kinase through binding to the extracellular domain of the receptor, thereby mimicking the effect of the cognate ligand HGF/SF.

Compounds of formula (I) are further useful in the treatment of additional inflammatory disorders and conditions as provided herein or known in the art.

C: Combination therapy: In certain embodiments, any of the above methods involve further administering a chemotherapeutic agent.

In a related embodiment, the chemotherapeutic agent is an anti-cancer agent. Specific combinations are provided throughout the application.

In a further related embodiment, any of the above methods involve further administering a pathway specific inhibitor. The pathway specific inhibitor may be a chemotherapeutic agent or may be a biologic agent, e.g., such as antibodies. Pathway specific inhibitors include, but are not limited to, inhibitors of EGFR, Her-2, Her-3, VEGFR, Ron, IGF-IR, PI-3K, mTOR, Raf.

In a further related embodiment to several of the above methods, following administering to the subject or contacting the cell, these methods can further involve observing amelioration or retardation of development or metastasis of the cancer.

Thus, in one embodiment, the invention relates to a method of treating a c-Met related disorder of condition which involves administering to a subject in need thereof an effective amount of any of a compound of formula (I).

In a further embodiment, the invention relates to a compound of formula (I) or a pharmaceutically acceptable salt, as a medicament/for use as a medicament, in particular for the treatment of one or more C-Met tyrosine kinase mediated diseases.

In a further embodiment, the invention relates to the use of a compound of formula (I) or a pharmaceutically acceptable salt, as active ingredient in a medicament, in particular for the treatment of one or more C-Met tyrosine kinase mediated diseases.

In a further embodiment, the invention relates to the use of a compound of formula (I) or a pharmaceutically acceptable salt, as medicament, in particular for the treatment of one or more C-Met tyrosine kinase mediated diseases.

In a further embodiment, the invention relates to the use of a compound of formula (I) or a pharmaceutically acceptable salt, for the manufacture of a medicament for the treatment of one or more C-Met tyrosine kinase mediated diseases.

In a further embodiment, the invention relates to a compound of formula (I) or a pharmaceutically acceptable salt of such a compound, for use in a method for the treatment of a subject in need thereof, especially for the treatment of a C-Met tyrosine kinase mediated disease, most especially in a patient requiring such treatment.

In a further embodiment, the invention relates to a method for the treatment of a disease or disorder which responds to an inhibition of C-Met tyrosine kinase, which comprises administering a compound of formula (I) or a pharmaceutically acceptable salt thereof, wherein the radicals and symbols have the meanings as defined above, especially in a quantity effective against said disease, to a warm-blooded animal requiring such treatment.

In a further embodiment, the invention relates to a pharmaceutical composition comprising a compound of formula (I) as active ingredient in association with at least one pharmaceutical carrier or diluent. Such compositions may be manufactured in conventional manner.

In a further embodiment, the invention relates to a method of treatment of one or more C-Met tyrosine kinase mediated diseases, in a subject in need of such treatment, which comprises administering to such subject a therapeutically effective amount of compound of formula (I).

In a further embodiment, the invention relates to pharmaceutical compositions comprising: (a) an effective amount of compound of formula (I) and pharmaceutically acceptable salts, pharmaceutically acceptable prodrugs, and pharmaceutically active metabolites thereof; and (b) one or more pharmaceutically acceptable excipients and/or diluents.

In a further embodiment, the invention relates to a pharmaceutical composition for treatment of a disease, e.g. of solid or liquid tumours in warm-blooded animals, including humans, comprising a dose effective in the treatment of said disease of a compound of the formula (I) as described above or a pharmaceutically acceptable salt of such a compound together with a pharmaceutically acceptable carrier (=carrier material).

In a third aspect, the invention provides a pharmaceutical preparation (composition), comprising a compound of formula (I) as defined herein, or a pharmaceutically acceptable salt of such a compound, or a hydrate or solvate thereof, and at least one pharmaceutically acceptable carrier and/or diluents and optionally one or more further therapeutic agents.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned diseases (=disorders), of a compound of formula (I) or a pharmaceutically acceptable salt thereof together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approximately 1% to approximately 20%, active ingredient(s).

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of a compound of the formula (I) or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, divided preferably into 1 to 3 single doses which may, for example, be of the same size. Usually, children receive half of the adult dose.

In a fourth aspect, the invention relates to a combination of a compound of formula (I) with one or more other therapeutically active agents. Thus, a compound of formula (I) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents.

A compound of formula (I) can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Thus, a compound of the formula (I) may be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity; anti-angiogenic compounds; compounds which target, decrease or inhibit the activity of a protein or lipid phosphatase; gonadorelin agonists; antiandrogens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; kinesin spindle protein inhibitors; MEK inhibitors; leucovorin; EDG binders; antileukemia compounds; ribonucleotide reductase inhibitors; S-adenosylmethionine decarboxylase inhibitors; angiostatic steroids; corticosteroids; other chemotherapeutic compounds (as defined below); photosensitizing compounds.

Further, alternatively or in addition they may be used in combination with other tumor treatment approaches, including surgery, ionizing radiation, photodynamic therapy, implants, e.g. with corticosteroids, hormones, or they may be used as radiosensitizers.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505. The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof.

Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E -2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA). Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, c-Met tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin kinase family inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d] pyrimidine derivatives which are disclosed in WO 03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

n) compounds targeting, decreasing or inhibiting the activity of the Ron receptor tyrosine kinase.

Further anti-angiogenic compounds include compounds having another mechanism for their activity, e.g. unrelated to protein or lipid kinase inhibition e.g. thalidomide (THALOMID) and TNP-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof.

The term "Compounds which induce cell differentiation processes" includes, but is not limited to e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

The term "Compounds which target, decrease or inhibit the activity of FMS-like tyrosine kinase receptors (Flt-3R)" are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG, 17-DMAG), a geldanamycin derivative; other geldanamycin related compounds; radicicol and HDAC inhibitors; IPI-504, CNF1010, CNF2024, CNF1010 from Conforma Therapeutics; temozolomide (TEMODAL®), AUY922 from Novartis.

The term "antiproliferative antibodies" as used herein includes, but is not limited to, trastuzumab (Herceptin™), Trastuzumab-DM1, erbitux, bevacizumab (Avastin™), rituximab (Rituxan™), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

"Somatostatin receptor antagonists" as used herein refers to compounds which target, treat or inhibit the somatostatin receptor such as octreotide, and SOM230.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "kinesin spindle protein inhibitors" is known in the field and includes SB715992 or SB743921 from GlaxoSmithKline, pentamidine/chlorpromazine from CombinatoRx;

The term "MEK inhibitors" is known in the field and includes ARRY142886 from Array PioPharma, AZD6244 from AstraZeneca, PD181461 from Pfizer, leucovorin.

The term "ribonucleotide reductase inhibitors" includes, but is not limited to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF/VEGFR disclosed in WO 98135958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

"Photodynamic therapy" as used herein refers to therapy which uses certain chemicals known as photosensitizing compounds to treat or prevent cancers. Examples of photodynamic therapy includes treatment with compounds, such as e.g. VISUDYNE and porfimer sodium.

"Angiostatic steroids" as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

"Corticosteroids" as used herein includes, but is not limited to compounds, such as e.g. fluocinolone, dexamethasone; in particular in the form of implants.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

A compound of formula (I) may also be used in combination with one or more further drug substances selected from the group of anti-inflammatory drug substances; antihistamine drug substances; bronchodilatatory drug substances, NSAID; antagonists of chemokine receptors.

The compounds of the invention are also useful as co-therapeutic compounds for use in combination with such further drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with such other drug substance in a fixed pharmaceutical composition or it may be administered separately (i.e. before, simultaneously with or after the other drug substance). Accordingly, the invention includes a combination of a compound of formula (I) with one or more further drug substance selected from the group of anti-inflammatory drug substances; antihistamine drug substances; bronchodilatatory drug substances, NSAID antagonists of chemokine receptors; said compound of the formula (I) and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo®) GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta -Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

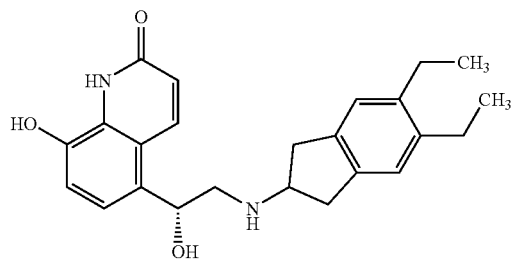 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable chemokine receptors include, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dim ethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, an antibody against the ligand VEGF, or the PDGF receptor tyrosine kinase, e.g. STI571 (Glivec®), PI3K (such as BEZ235 from Novartis) and mToR inhibitors, such as rapamycin, RAD001, a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The above-mentioned compounds, which can be used in combination with a compound of the formula (I), can be prepared and administered as described in the art, such as in the documents cited above.

Thus, the invention relates in a further embodiment to a combination, particularly a pharmaceutical composition) comprising a therapeutically effective amount of a compound of formula (I) in free form or in pharmaceutically acceptable salt form and a second therapeutically active agent, for simultaneous or sequential administration. The additional therapeutic agent is preferably selected from the group consisting of an anti-cancer agent; an anti-inflammatory agent.

The invention further relates to a method for the treatment of a disease or disorder which responds to a C-Met tyrosine kinase, especially a proliferative disorder or disease, in particular a cancer, said method comprises administration of an effective amount of a combination of pharmaceutical agents which comprise: (a) a compound of formula (I); and (b) one or more pharmaceutically active agents, to a subject in need thereof, especially human.

The invention further relates to the use of a combination of pharmaceutical agents which comprise: (a) a compound of formula (I); and (b) one or more pharmaceutically active agents for the treatment of a disease or disorder which responds to a C-Met tyrosine kinase, especially a proliferative disorder or disease, in particular a cancer.

The invention further relates to the use of a combination of pharmaceutical agents which comprise: (a) a compound of formula (I); and (b) one or more pharmaceutically active agents for the manufacture of a medicament for the treatment of a disease or disorder which responds to a C-Met tyrosine kinase, especially a proliferative disorder or disease, in particular a cancer.

The invention further relates to pharmaceutical compositions comprising (a) a compound of formula (I) and (b) a pharmaceutically active agent; and (c) a pharmaceutically acceptable carrier; wherein at least one pharmaceutically active agent is an anti-cancer therapeutic.

The present invention further relates to a commercial package or product comprising: (a) a compound of formula (I); and (b) a pharmaceutical formulation of a pharmaceutically active agent for simultaneous, concurrent, separate or sequential use; wherein at least one pharmaceutically active agent is an anti-cancer therapeutic.

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

The term "Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). A joint therapeutic effect can, inter alia, be determined by following the blood levels, showing that both compounds are present in the blood of the human to be treated at least during certain time intervals.

The term "Pharmaceutically effective" preferably relates to an amount that is therapeutically or in a broader sense also prophylactically effective against the progression of a disease or disorder as disclosed herein.

The term "a commercial package" or "a product", as used herein defines especially a "kit of parts" in the sense that the components (a) and (b) as defined above can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal effect) or the like.

In a further aspect, the invention relates to methods of manufacturing a compound of formula (I) and intermediates thereof. A compound of the formula (I) may be prepared by processes that, though not applied hitherto for the new compounds of the present invention where they thus form new processes, are known per se. The following schemes illustrate methods for such preparations. Scheme 1 provides a general overview of synthetic strategies to obtain a compound of formula (I)

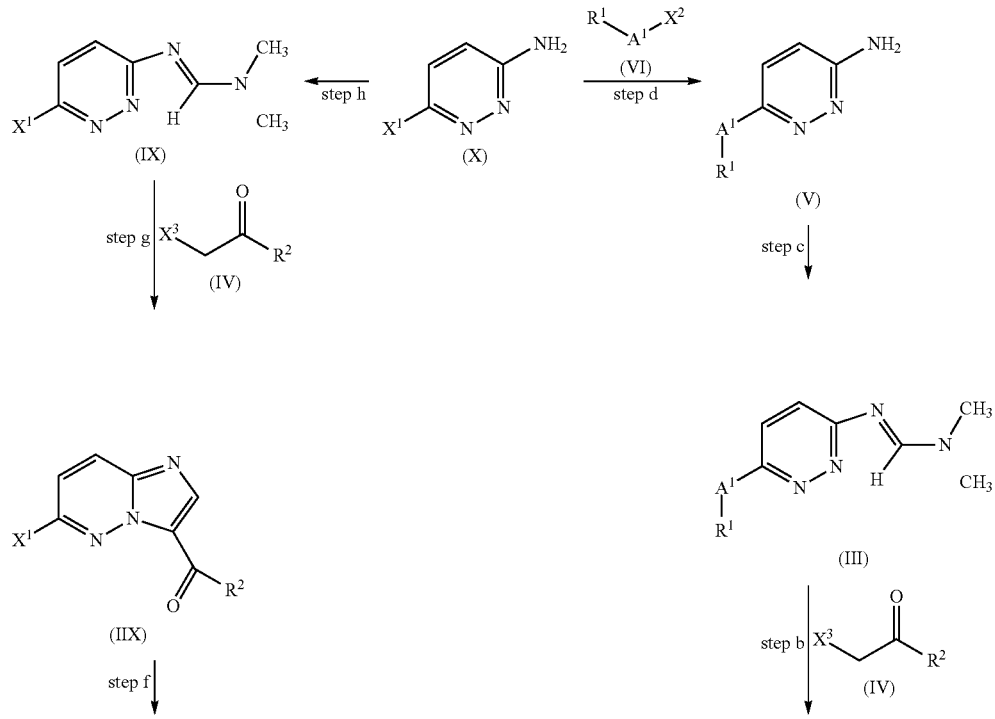
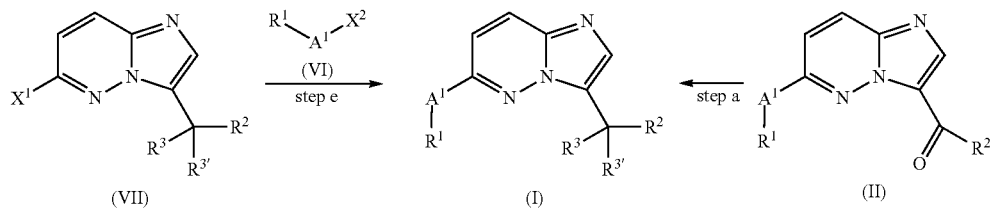
Scheme 2 provides details for step a) outlined above, providing an overview of synthetic strategies to obtain preferred compounds of formula (IA), (IB) and (IC).
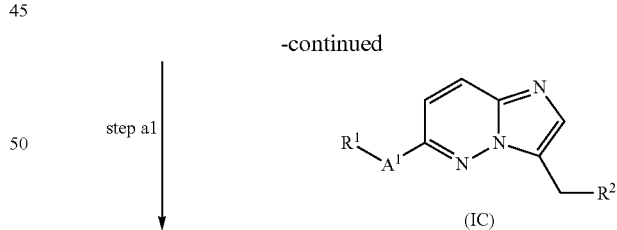
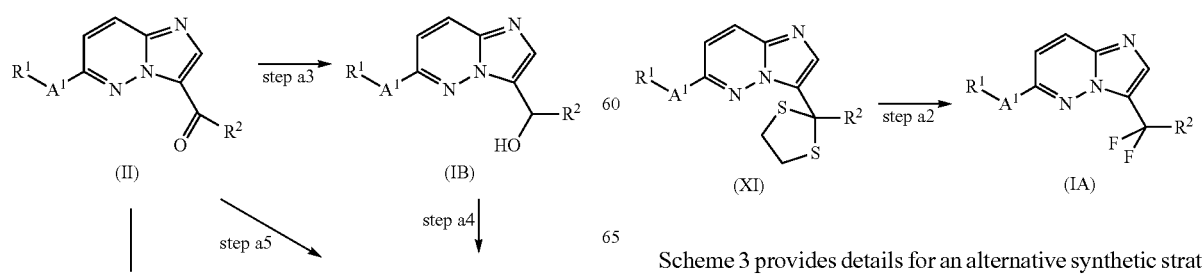
Scheme 3 provides details for an alternative synthetic strategy to obtain preferred compounds of formula (IB).

Scheme 3
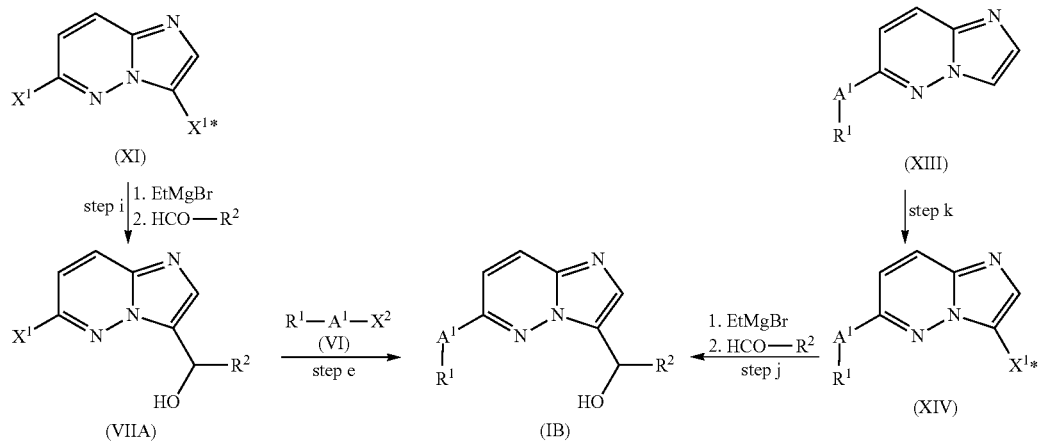
Scheme 4 provides details for an alternative synthetic strategy to obtain the preferred compound of formula (IC).
Scheme 4
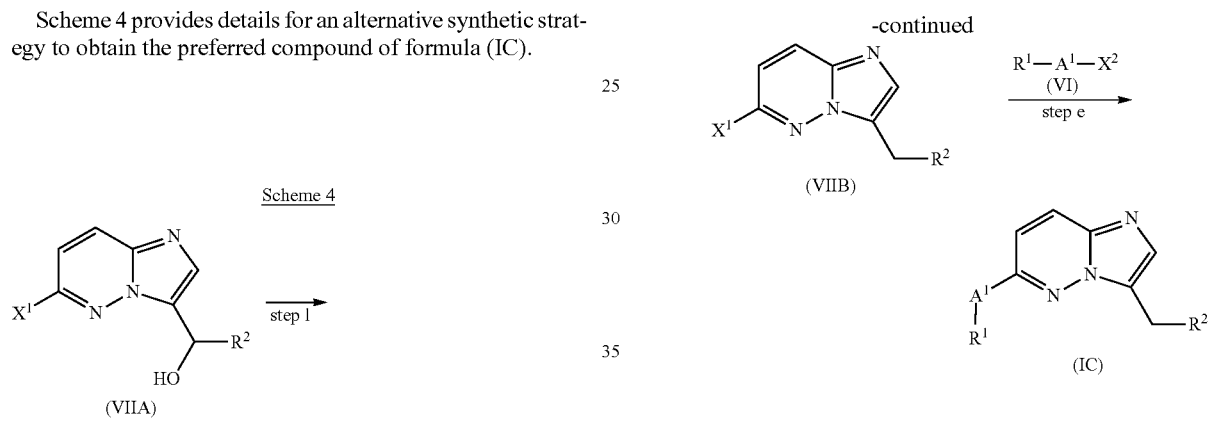
Scheme 5 provides details for a synthetic strategy to obtain the preferred compound of formula (ID) and (IG).
Scheme 5
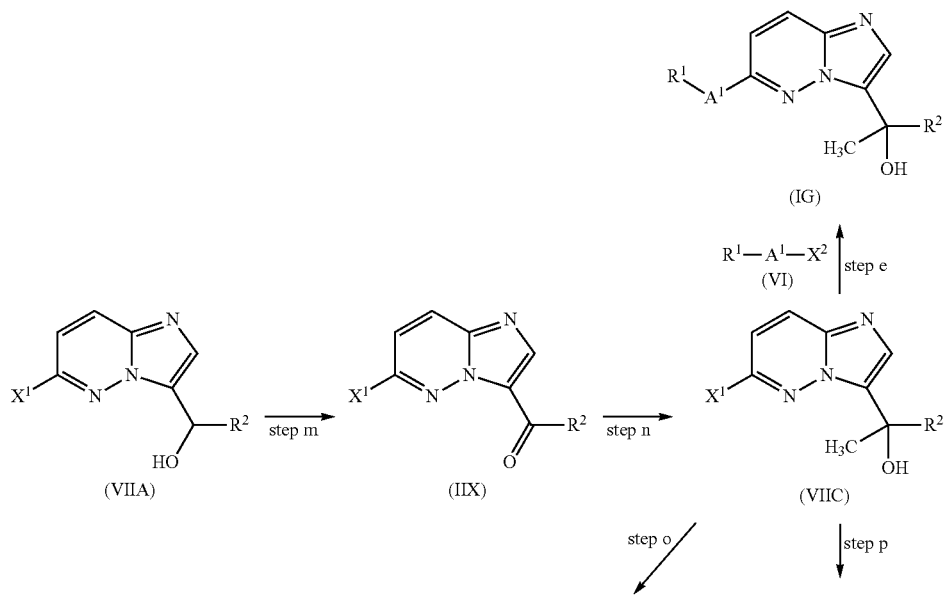

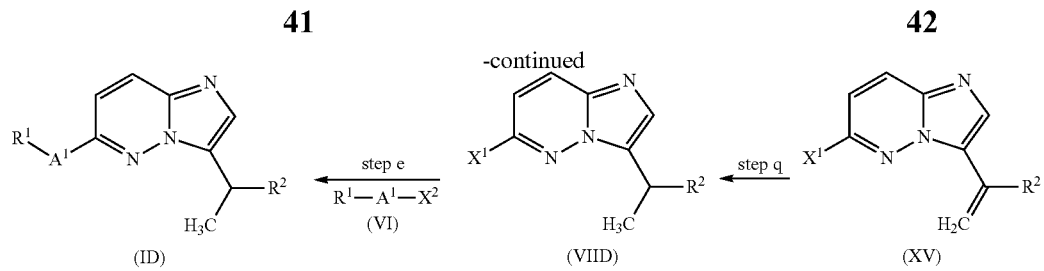

Scheme 6 provides an overview for deprotection of compounds (XVI) and (XVII) by removal of a protecting group P to obtain a compound of formula (I).

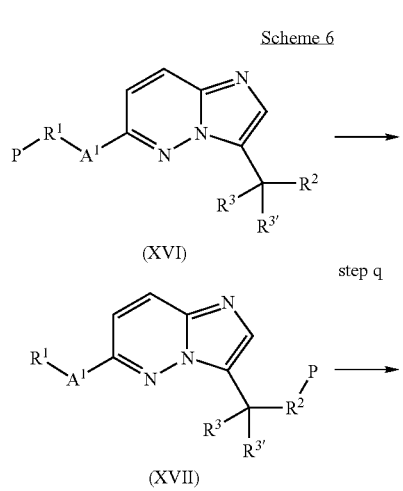

Thus, the invention relates in a further aspect to a manufacturing process (a method for manufacturing) a compound of formula (I) comprising either—method A—converting a compound of formula (II)

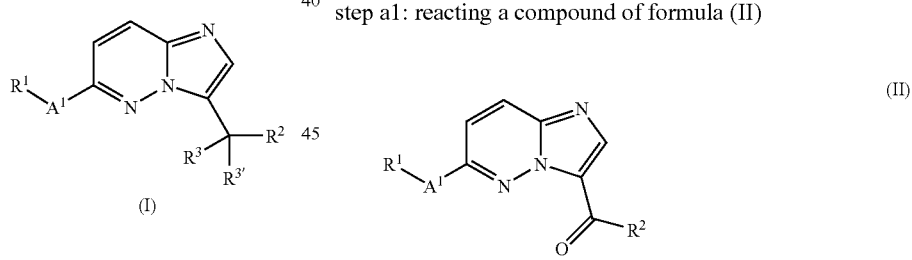

wherein the substituent are as defined herein into a compound of formula (I) or—method B—reacting a compound of formula (VII)

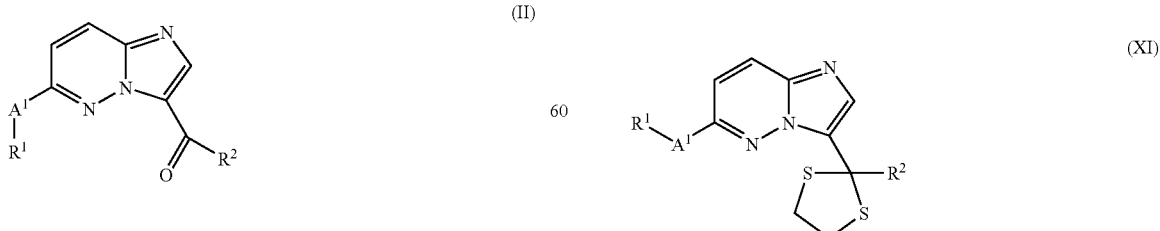

wherein the substituents are as defined herein and $X^1$ represents a leaving group, such as tosylate, mesylate or halo, in particular chloride, with a compound of formula (VI)

$$R^1\text{-}A^1\text{-}X^2 \qquad (VI)$$

wherein $X^2$ represents hydrogen or an alkali metal, $R^1$ and $A^1$ are as defined herein, to obtain a compound of formula (I) and, if desired, converting a compound of the formula (I) obtained according to method A) or method B) into a different compound of the formula (I), and/or converting an obtainable salt of a compound of the formula (I) into a different salt thereof, and/or converting an obtainable free compound of the formula (I) into a salt thereof, and/or separating an obtainable isomer of a compound of the formula (I) from one or more different obtainable isomers of the formula (I).

The invention also relates in a further aspect to a manufacturing process for a compound of formula (IA) comprising step a1: reacting a compound of formula (II)

wherein the substituents are as defined herein, with 1,2-ethanedithiol, optionally in the presence of an reaction aid, such as Boron trifluoride acetic acid complex, to obtain a compound of formula (XI)

wherein the substituents are as defined herein, and step a2: reacting the thus obtained compound of formula (XI) with a fluorinating agent, such as DAST, optionally in the presence of a reaction aid, such as NBS, to obtain a compound of formula (IA)

and, if desired, converting a compound of the formula (IA) obtained into a different compound of the formula (IA), and/or converting an obtainable salt of a compound of the formula (IA) into a different salt thereof, and/or converting an obtainable free compound of the formula (IA) into a salt thereof, and/or separating an obtainable isomer of a compound of the formula (IA) from one or more different obtainable isomers of the formula (IA).

The invention also relates in a further aspect to a manufacturing process for a compound of formula (IB) comprising
step a3: reacting a compound of formula (II)

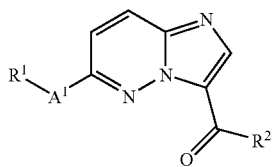

(II)

wherein the substituents are as defined herein with a reducing agent, such as a boron hydride, to obtain a compound of formula (IB)

and, if desired, converting a compound of the formula (IB) obtained into a different compound of the formula (IB), and/or converting an obtainable salt of a compound of the formula (IB) into a different salt thereof, and/or converting an obtainable free compound of the formula (IB) into a salt thereof, and/or separating an obtainable isomer of a compound of the formula (IB) from one or more different obtainable isomers of the formula (IB).

The invention also relates in a further aspect to a manufacturing process for a compound of formula (IC) comprising
step a4: reacting a compound of formula (IB)

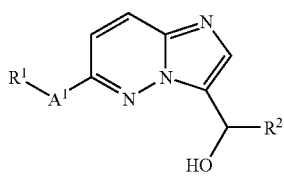

(IB)

wherein the substituents are as defined herein, with a reducing agent, such as a silane or a mixture of hypophosphoric acid and iodine, or step a5: reacting a compound of formula (II)

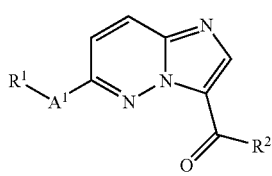

(II)

wherein the substituents are as defined herein, with a reducing agent, such as hydrogen in the presence of a hydrogenating catalyst, to obtain a compound of formula (IC) and, if desired, converting a compound of the formula (IC) obtained into a different compound of the formula (IC), and/or converting an obtainable salt of a compound of the formula (IC) into a different salt thereof, and/or converting an obtainable free compound of the formula (IC) into a salt thereof, and/or separating an obtainable isomer of a compound of the formula (IC) from one or more different obtainable isomers of the formula (IC).

The invention also relates in a further aspect to a manufacturing process for a compound of formula (IB) comprising
step i: reacting a compound of formula (XI)

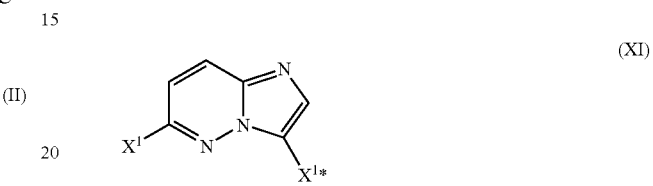

(XI)

wherein $X^1$ represents a halogen, in particular chloro and X1* represents a halogen, in particular bromo, first with a Mg-compound of the Gringnard type, in particular EtMgBr, followed by a reaction with an aldelhyde of formula (XII)

(XII)

wherein $R^2$ is as defined herein, and step e: reacting the obtained compound of formula (VIIA) (which is a compound of formula (VII) wherein $R^3$ represents hydrogen and $R^{3'}$ represents hydroxyl)

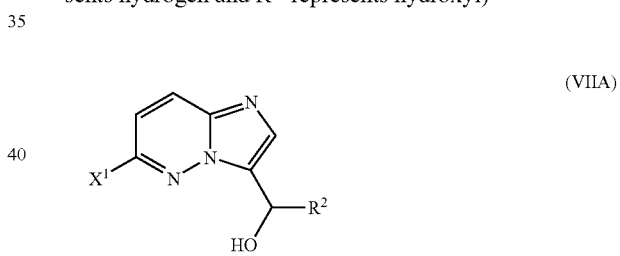

(VIIA)

wherein $R^2$ is as defined herein, with a compound (VI)

(VI)

$R^1$-$A^1$-$X^2$ (VI) being preferably a bororonic acid or ester reacted in presence of a palladium catalyst (Suzuki reaction); or aternatively an aliphatic or aromatic amine, or a further compound containing nucleophilic hetero-atoms, reacted by nucleophilic aromatic substitution, wherein the substituents are as defined herein, to afford a compound of formula (I); or step k: reacting a compound of formula (XIII)

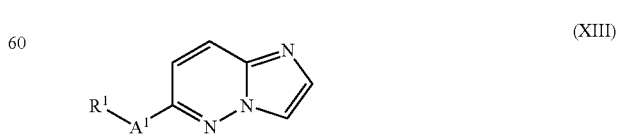

(XIII)

wherein $R^1$ and $A^1$ are as defined herein with a halogenating agent, such as NBS, and step j: reacting the obtained compound of formula (XIV)

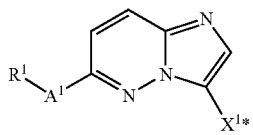
(XIV)

wherein $R^1$ and $A^1$ are as defined herein and $X^{1*}$ represents a halogen, in particular bromo, first with a Mg-compound of the Gringnard type, in particular EtMgBr, followed by a reaction with an aldehyde of formula (XII)

HCO—$R^2$ (XII)

wherein $R^2$ is as defined herein, and, if desired, converting a compound of the formula (IB) obtained into a different compound of the formula (IB) or (IC), and/or converting an obtainable salt of a compound of the formula (IB) into a different salt thereof, and/or converting an obtainable free compound of the formula (IB) into a salt thereof, and/or separating an obtainable isomer of a compound of the formula (IB) from one or more different obtainable isomers of the formula (IB).

The invention also relates in a further aspect to a manufacturing process for a compound of formula (IC) or (IH) comprising step l: reacting a compound of formula (VIIA)

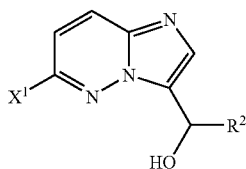
(VIIA)

wherein the substituents are as defined herein, with a reducing agent, such as a combination of hypophosphoric acid and iodine to provide a compound of formula (VIIB)

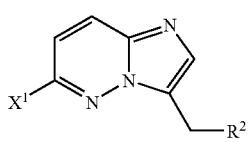
(VIIB)

wherein the substituents are as defined herein
and then
reacting said compound of formula (VIIB) with a compound of formula $R^1$-$A^1$-$X^2$ in analogy to step e to obtain a compound of formula (IC) or alternatively and preferably (IH), wherein A1=BOND.

The invention also relates in a further aspect to a manufacturing process for a compound of formula (ID) or (IJ) comprising step m: reacting a compound of formula (VIIA)

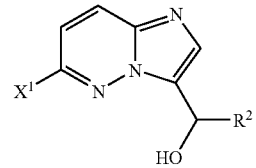
(VIIA)

wherein the substituents are as defined herein, with oxidizing agents, such as Dess-Martin periodinane or 2-iodoxybenzoic acid to obtain a compound of formula (IIX)

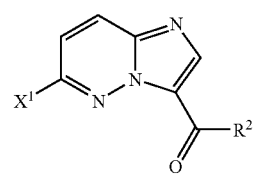
(IIX)

followed by step n: reacting the compound of formula (IIX) with a low alkyl magnesium Grignard reagent, such as methyl magnesium Grignard to obtain a compound of formula (VIIC)

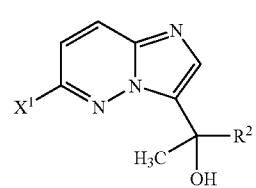
(VIIC)

followed by, step o: reacting the compound of formula (VIIC) with a reducing agent, such as a combination of hypophosphoric acid and iodine, or step p: reacting the compound of formula (VIIC) with an inorganic acid to obtain a compound of formula (XV)

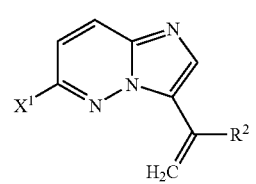
(XV)

followed by step q: reacting the obtained compound of formula (XV) with a reducing agent, such hydrogen in the presence of a hydrogenating catalyst, to obtain a compound of formula (VIID),

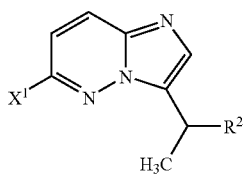
(VIID)

and then
reacting said compound of formula (VIID) with a compound of formula R¹-A¹-X² in analogy to step e to obtain a compound of formula (ID) or alternatively and preferably (IJ), wherein A1=BOND.

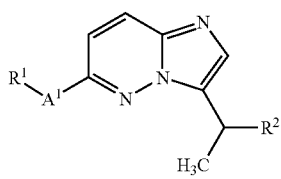
(ID)

The invention also relates in a further aspect to a manufacturing process for a compound of formula (IG) or (IK)

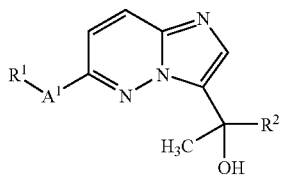
(IG)

comprising,
the reaction a compound of formula (VIIC)

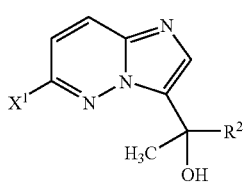
(VIIC)

with a compound of formula R¹-A¹-X² in analogy to step e wherein, the substituents are as defined herein, to obtain the compound of formula (IG) or alternatively and preferably, (IK) wherein A1=BOND.

The invention also relates in a further aspect to a manufacturing process for a compound of formula (I) comprising deprotection in step r by reacting a compound of formula (XVI)

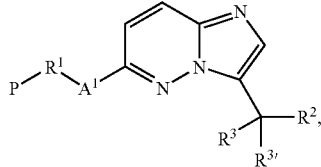
(XVI)

wherein P is a protecting group,
or formula (XVII)

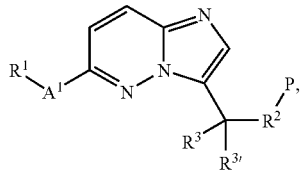
(XVII)

wherein P is a protecting group,
with an inorganic or strong organic acid to provide a compound of formula (I).

Reaction Conditions

Where temperatures are given hereinbefore or hereinafter, "about" has to be added, as minor deviations from the numeric values given, e.g. variations of ±10%, are tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates. Reaction aids, such as acids, bases or catalysts may be added in suitable amounts, as known in the field, required by a reaction and in line with generally known procedures.

Buchwald Reaction

This reaction, also known as Buchwald amination or Buchwald-Hartwig reaction is generally known in the field. This reaction is catalyzed by transition metals, in particular Cu or Pd complexes or salts; takes place in the presence of one or more basic compounds (such as an amine or an alkalialkoxide) and one or more diluents (such as polar aprotic diluents).

Suzuki Reaction

This reaction is generally known in the field. The Suzuki reaction is the organic reaction of an aryl- or vinyl-boronic acid with an aryl- or vinyl-halide catalyzed by a palladium complex.

Further details may be found in the examples.

Reduction

Carbonyl, hydroxy group reduction reactions are generally known. Typical condition suitable for the process as described herein are: carbonyl group reduction with sodium borohydride, e.g. as described in "Sodium Borohydride" in Encyclopedia of Reagents for Organic Synthesis (Ed: L. Paquette) 2004, J. Wiley & Sons, New York. Reduction of benzyl alcohols using triethylsilane in presence of TFA, eg as described in Tetrahedron Letters, 1993, 34, 1605-1608; or using a combination of hypophosphorous acid and iodine, e.g. as described in Tetrahedron Letters, 2001, 42, 831-833, the content of these documents is incorporated by reference.

Fluorination

Methods to convert carbonyl and hydroxy groups into the corresponding fluoro compounds are generally known. Typical conditions suitable for the process are described e.g. in J.

Org. Chem., 1986, 51, 3508-3513 or J. Am. Chem. Soc. 1984, 106, 4189-4192; the content of which is incorporated by reference.

Alkylation

Carbonyl groups may be converted in the corresponding alkylated hydroxyl group using a Grignard reaction. Typical conditions suitable for the process are described, e.g. in Synthesis, 1981, 585-604. Further, carbonyl groups may be converted in the corresponding dialkylated compounds using a multi-step protocol, e.g. as described in Chem. Ber., 1985, 118, 1050-1057. Furthermore, carbonyl groups may be converted in the corresponding ispiro cyclopropane compound in two steps by Wittig olefination, e.g. as described in Chem. Rev., 1989, 89, 863-927, and subsequent cyclopronation reaction, e.g. Simmons-Smith as described in Org. React., 2001, 58, 1-415; the content of the above documents is incorporated by reference.

Protecting Groups

If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I) into a different compound of the formula (I), protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below. The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Optional Reactions and Conversions

A compound of the formula (I) may be converted into a different compound of the formula (I). For example, in a compound of the formula (I) wherein $R^1$ or especially $R^4$ carries an amino or amino-$C_1$-$C_7$-alkyl substituent, the amino can be converted into acylamino, e.g. $C_1$-$C_7$-alkanoylamino or $C_1$-$C_7$-alkanesulfonylamino, by reaction with a corresponding $C_1$-$C_7$-alkanoylhalogenide or $C_1$-$C_7$-alkanesulfonylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

In a compound of the formula (I) wherein $R^1$ or especially $R^4$ carries a cyano substituent, the cyano may be converted to an aminomethyl group, e.g. by hydrogenation in the presence of an appropriate metal catalyst, such as Raney Nickel or Raney Cobalt, in an appropriate solvent, e.g. a lower alkanol, such as methanol and/or ethanol, for example at temperatures in the range from −20 to 50° C., e.g. at about room temperature.

In a compound of the formula (I) wherein $R^1$ or especially $R^4$ carries a carboxyl (COOH) substituent, the latter can be converted into an amide group, e.g. an N—$C_1$-$C_7$-alkyl-carbamoyl group, by reaction with the corresponding amine, e.g. in the presence of a coupling agent, that forms a preferred reactive derivative of the carboxyl group in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methylpropenyl)-dimethylamine. For review of some other possible coupling agents, see e.g. Klauser; Bodansky, *Synthesis* (1972), 453-463. The reaction mixture is preferably stirred at a temperature of between approximately −20 and 50° C., especially between 0° C. and 30° C., e.g. at room temperature.

In a compound of the formula (I) wherein $R^1$ or especially $R^4$ carries two vicinal amino groups, the two nitrogen atoms of the two amino groups can be bridged by a —CH=group (thus forming, together with the two carbon atoms that bind the original amino groups and the bond between them, an 1H-imidazolo ring annelated to $R^1$ or $R^4$; for example, (vicinal diamino)-phenyl can be converted into benzoimidazolyl according to this method. The reaction preferably takes place by first reacting the compound of the formula (I) carrying the two vicinal amino groups with formic acid, e.g. in the presence of a coupling agent as mentioned in the preceding paragraph, such as EDC hydrochloride, a base, such as N,N-dimethylaminopyridine (DMAP) and preferably an appropriate solvent, such as methylene chloride, e.g. at temperatures in the range from −20 to 50° C., e.g. at about room temperature, thus converting one (especially a para-positioned) of the vicinal amino groups into a formylamino group. In a second step, the amino and formylamino group are then reacted to —N=C—N— by heating in the presence of an acid, especially acetic acid, e.g. at temperatures in the range from 50 to 110° C., for example at about 100° C.

Salts of a compound of formula (I) with a salt-forming group may be prepared in a manner known per se. Acid addition salts of compounds of formula (I) may thus be obtained by treatment with an acid or with a suitable anion exchange reagent. A salt with two acid molecules (for example a dihalogenide of a compound of formula (I)) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula (I). Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula (I) itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates (and are thus useful in the preparation of corresponding starting materials).

Starting Materials:

The starting materials of the formulae II, III, V, VII, IIX, IX, XI and XIII, as well as other starting materials mentioned herein, e.g. below, can be prepared according to or in analogy to methods that are known in the art, are known in the art and/or are commercially available. Novel starting materials, as well as processes for the preparation thereof, are likewise an embodiment of the present invention. In the preferred embodiments, such starting materials are used and the reaction chosen are selected so as to enable the preferred compounds to be obtained.

In the starting materials (including intermediates), which may also be used and/or obtained as salts where appropriate and expedient, the substituents are preferably as defined for a compound of the formula (I).

In particular, the invention also relates to a compound of formula (II), (XI) and (XIII)

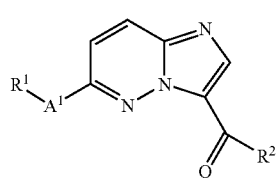

(II)

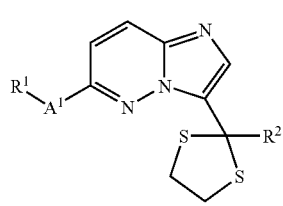

(XI)

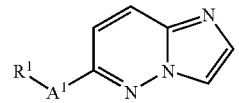

(XIII)

wherein in each case the substituents are as defined in formula (I) and to manufacturing processes thereof.

A compound of formula (II) is obtainable by reacting a compound of formula (V)

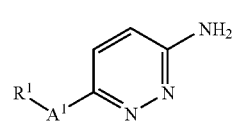

(V)

wherein the substituents are as defined herein, first with N,N-dimethylformamide dimethylacetal (step c in scheme 1) followed by reaction with a compound of formula (IV)

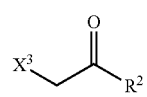

(IV)

wherein $R^2$ is as defined herein and $X^3$ represents a lewving group, in particular a halogen such as chloro, optionally in the presence of a diluent, optionally in the presence of a reaction aid.

A compound of formula (XI) is obtainable by a method as described above, step a1.

A compound of formula (XIII) is obtainable by converting a compound of formula (XV)

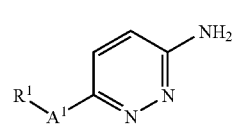

(XV)

wherein $R^1$ and $A^1$ are as defined herein, with chloroacetaldehyde, optionally in the presence of a diluent, optionally in the presence of a reaction aid.

Compounds of formula (XV) are known, and may be obtained by substitution reaction or Suzuki reaction of the corresponding chloro-pyrimidineaminde.

The following examples illustrate the invention without limiting the scope thereof. In the examples provided, temperatures are measured in degrees Celsius. Unless otherwise indicated, the reactions take place at rt. Further, if not indicated otherwise, the analytical HPLC conditions are as follows:

Conditions 1 and 2:

The flow is 2 mL/min of acetonitrile and water (both with 0.1% TFA)

0-2.2 min: 5% to 95% of acetonitrile 2.2-2.7 min: 95% of acetonitrile

The gradient is the same in conditions 1 and 2. Only the column changes.

Conditions 1: column Atlantis T3 3 µm 4.6×30 mm from Waters.

Conditions 2: column Sunfire C18 3.5 μm 2.1×2.0 IS from Waters.
Conditions 3:
The flow is 2 mL/min of acetonitrile and water (both with 0.1% formic acid)
0-8.0 min: 2% to 100% of acetonitrile
8.0-10.0 min: 100% of acetonitrile
Column: Chromolith Performance, RP-18e 4.6×100 mm from Merck
Precolumn: Chromolith Performance, RP-18e 4.6×5 mm from Merck
Conditions 4:
The flow is 1.2 mL/min of Eluents A and B
Eluent A: 2500 mL Water, 5 mL ortho-Phosphoric acid 85%, 50 mL Tetramethylammonium hydroxide solution 10%.
Eluent B: 500 mL Water, 2.5 mL ortho-Phosphoric acid 85%, 25 mL Tetramethylammonium hydroxide solution 10%, 2000 mL Acetonitrile
0-6.67 min: 0% to 95% of eluent B
6.67-10 min: 95% eluent B
Column: CC 7013 Nucleosil 100-3 C-18 from Macherey-Nagel
Precolumn: CC 8/3 Nucleosil 100-3 C18 from Macherey-Nagel
Oven temperature: 45° C.
Conditions 5.6 and 7:
Eluant A: Water with 0.1% trifluoroacetic acid
Eluant B: Acetonitrile with 0.1% trifluoroacetic acid
Column temperature: 45° C.
Conditions 5: The flow is 3 mL/min of eluents A and B
0-4 min: 5% to 100% of acetonitrile
Column: SunFire C18 20×4.6 mm, 3.5 μm, reverse phase
Conditions 6: The flow is 2 mL/min of eluents A and B
0-min: 5% to 100% of acetonitrile
Column: XTerra MS C18 50×4.6 mm, 5 μm, reverse phase
Conditions 7: The flow is 3 mL/min of eluents A and B
0-3 min: 1% to 35% of acetonitrile
3-3.3 min: 35% to 100% of acetonitrile
Column: SunFire C18 20×4.6 mm, 3.5 μm, reverse phase
Conditions 8:
The flow is 2 mL/min of acetonitrile and water (both with 0.1% TFA)
0-4.5 min: 2% to 100% acetonitrile
4.5-5.5 min: 100% of acetonitrile.
Column: Chromolith Performance RP-18e 100×4.6 from Merck
Conditions 9:
The flow is 2 mL/min of acetonitrile and water (+0.1% TFA)
0-0.5 min: 2% of acetonitrile
0.5-2.9 min: 2% to 100% of acetonitrile
2.9-3.2 min: 100% of acetonitrile
Column: Sunfire C18 3.5 μm 2.1×2.0 IS from Waters
Conditions 10:
The flow is 2 mL/min of acetonitrile and water (±0.1% TFA)
0-2.7 min: 5% to 50% of acetonitrile
2.7-2.9 min: 50% to 95% of acetonitrile
2.9-3.3 min: 95% of acetonitrile
Column: Atlantis T3 3 μm 4.6×30 mm from Waters.
Conditions 11:
The flow is 1.4 mL/min of acetonitrile and water (±0.05% TFA)
0-8 min: 5% to 95% of acetonitrile
Column: CC 70/3 Nucleosil 100-3 C-18 from Macherey-Nagel
Precolumn: CC 8/3 Nucleosil 100-3 C18 from Macherey-Nagel
Column temperature: 45° C.
Conditions 12:
System: Agilent 1100 Series with Waters Micromass ZQ
Column: XBridge C18, 3×30 mm, 2.5 micron
Flow Rate: 1.4-2.4 mL/min
Eluent A: $H_2O$, containing 5% acetonitrile and 0.8% HCOOH
Eluent B: acetonitrile, containing 0.6% HCOOH
Gradient: 0-2.9 min: 1% to 95% of B
Conditions 13:
The flow is 2 mL/min of acetonitrile and water (±0.1% TFA)
0-8.0 min: 2% to 100% of acetonitrile
8.0-10.0 min: 100% of acetonitrile
Column: Chromolith Performance, RP-18e 4.6×100 mm from Merck In the following examples, the abbreviations given below are used:

| | |
|---|---|
| AIBN | α,α'-azo-isobutyronitrile |
| atm. | atmosphere |
| BINAP | 2,2'-Bis-diphenylphosphanyl-[1,1']binaphthalenyl |
| Bn | benzyl |
| Boc | tert-butoxycarbonyl |
| CDI | 1,1'-carbonyldiimidazol |
| DAST | diethylaminosulfur trifluoride |
| DCM | dichloromethane |
| DME | 1,2-dimethoxyethane |
| DMF | N,N-dimethylformamide |
| DMSO | dimethyl sulfoxide |
| eq. | equivalent(s) |
| h | hour(s) |
| HATU | 2-(1H-7-Azabenzotriazol-1-yl)-1,1,3,3-tetramethyluronium hexafluorophosphate |
| HPLC | High Performance Liquid Chromatography |
| HV | high vacuum |
| Isolute | Isolute ® HM-N by International Solvent Technology Ltd., U.K. |
| LAH | lithium aluminium hydride |
| LCMS | liquid chromatography coupled with mass spectrometry |
| LDA | lithium diisopropylamide |
| mL | milliliter(s) |
| min | minute(s) |
| MPLC | Medium Pressure Liquid Chormatography |
| MS-ES | electrospray mass spectrometry |
| MW | microwave |
| NBS | N-Bromosuccinimide |
| n-BuLi | n-Butyllithium |
| NMP | N-Methylpyrrolidinone |
| $PdCl_2(dppf)$ | 1,1-Bis(diphenylphosphino)ferrocenedichloropalladiunn (II) |
| $Pd_2(dba)_3$ | Tris(dibenzylideneacetone)dipalladium (0) |
| PL | PolymerLabs (cartridge supplier) |
| RM | reaction mixture |
| $R_f$ | ratio of fronts in TLC |
| SPE | Solid Phase Extraction |
| rt | room temperature |
| TBAF | tetrabutylammonium fluoride |
| TBME | methyl tert-butyl ether |
| TFA | trifluoroacetic acid |
| THF | tetrahydrofuran |
| TLC | thin layer chromatography |
| $t_R$ | retention time |
| UV | Ultraviolet. |

SYNTHESIS OF ALDEHYDE INTERMEDIATES

Intermediates A and B:

5-Fluoro-quinoline-6-carbaldehyde (A) and 7-fluoro-quinoline-6-carbaldehyde (B)

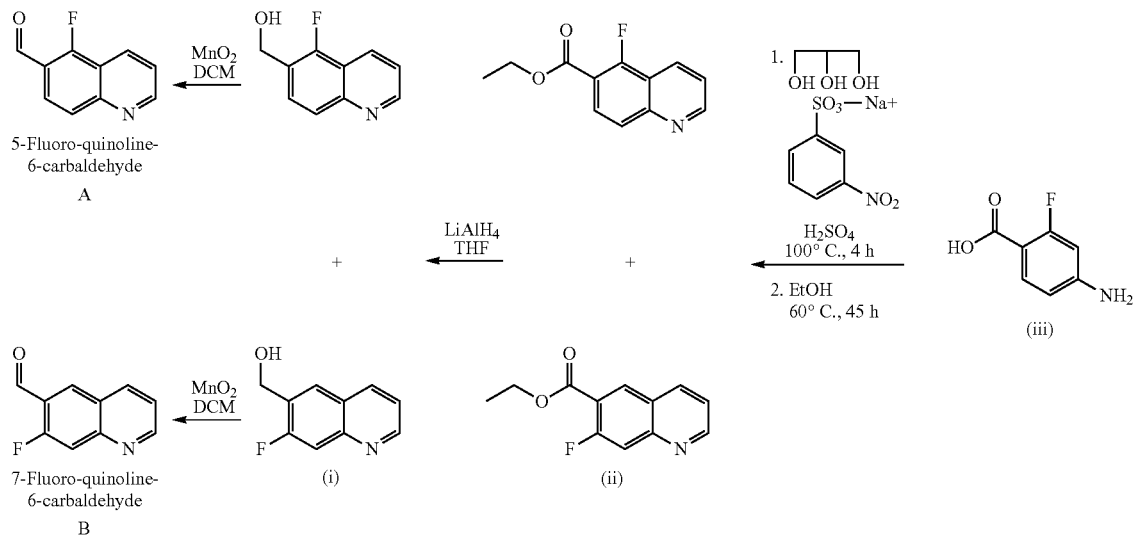

The title compounds were each obtained from the treatment of the corresponding regioisomer (i) dissolved in DCM, with 10 eq. $MnO_2$ at rt. After 16 h stirring, the black solid waw filtered off over celite and the solvent was removed to obtain a white solid. 5-Fluoro-quinoline-6-carbaldehyde (A) ($t_R$ 0.9 min (conditions 1), MH+=176, $^1$H-NMR in DMSO-d6: 10.47 (s, 1H); 9.13 (s, 1H); 8.70 (d, 1H); 8.05 (t, 1H); 7.97 (d, 1H); 7.75 (dd, 1H)) or 7-Fluoro-quinoline-6-carbaldehyde (B) ($t_R$ 0.5 min (conditions 1), MH+=176, $^1$H-NMR in DMSO-d6: 10.31 (s, 1H); 9.05 (s, 1H); 8.66 (d, 1H); 8.63 (d, 1H); 7.91 (d, 1H); 7.64 (dd, 1H)).

(5-Fluoro-quinolin-6-yl)-methanol and (7-fluoro-quinolin-6-yl)-methanol (i)

A mixture of regioisomers (ii) (792 mg, 3.6 mmol) was dissolved in THF (7.5 mL) under nitrogen and cooled down to 0° C. with an ice-water bath. Then a solution of $LiAlH_4$ (1 M in THF, 4.3 mL) was added slowly. The precipitate formed was filtered off and the filtrate was concentrated. The residue was purified by MPLC eluting with a DCM/MeOH gradient to afford (5-fluoro-quinolin-6-yl)-methanol as a yellow solid pure at 79% by 1H-NMR ($t_R$ 0.3 min (conditions 1), MH+=178) and a white solid as (7-fluoro-quinolin-6-yl)-methanol ($t_R$ 0.3 min (conditions 1), MH+=178).

5-Fluoro-quinoline-6-carboxylic acid ethyl ester and 7-fluoro-quinoline-6-carboxylic acid ethyl ester (ii)

To a suspension of 4-Amino-2-fluoro-benzoic acid (iii) (1 g, 6.38 mmol) in sulfuric acid 75% (15 mL) were added glycerol anhydrous (2.108 mL, 28.72 mmol) and sodium 3-nitrosulfonate (2.93 g, 12.8 mmol). The mixture was stirred at 100° C. for 4 h. It was then cooled down to 60° C. and EtOH was added. The mixture was then stirred at 60° C. for 45 h. The solution was poured into ice-water mixture and then basified with saturated aqueous ammonium hydroxide.

It was extracted twice with EtOAc. The organic phases were joined and washed with brine, dried over $Na_2SO_4$ and concentrated. The residue was purified by MPLC eluting with a DCM/MeOH gradient to afford a yellow oil as a mixture (1:1) of 5-fluoro-quinoline-6-carboxylic acid ethyl ester and 7-fluoro-quinoline-6-carboxylic acid ethyl ester ($t_R$ 1.3 min and $t_R$ 1.1 min (conditions 1), MH+=220).

Intermediates C and D

5-Chloro-quinoline-6-carbaldehyde (C) and 7-chloro-quinoline-6-carbaldehyde (D)

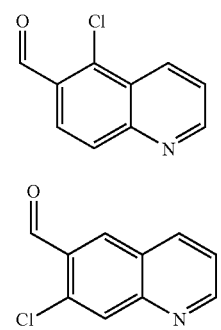

5-Chloro-quinoline-6-carbaldehyde (C) ($t_R$ 1.6 min (conditions 1), MH+=192, $^1$H-NMR in DMSO-d6: 10.60 (s, 1H); 9.14 (s, 1H); 8.836 (d, 1H); 8.20 (s, 2H); 7.82 (dd, 1H)) or 7-chloroquinoline-6-carbaldehyde (D) ($t_R$ 1.5 min (conditions 1), MH+=192, $^1$H-NMR in DMSO-d6: 10.44 (s, 1H); 9.05 (d, 1H); 8.64 (m, 2H); 8.20 (s, 1H); 7.67 (dd, 1H)) were obtained analogously to 5-fluoro-quinoline-6-carbaldehyde (A) and 7-fluoro-quinoline-6-carbaldehyde (B), by replacing fluoro derivative regioisomers (i) with chloro derivative regioisomers ($i_a$)

(5-Chloro-quinolin-6-yl)-methanol and (7-chloro-quinolin-6-yl)-methanol (i$_a$)

The title compounds were obtained analogously to fluoro derivative regioisomers (i) by replacing fluoro derivatives regioisomers (ii) with chloro derivatives regioisomers (ii$_a$). (5-Chloro-quinolin-6-yl)-methanol (t$_R$ 1.0 min (conditions 1), MH+=194) and (7-fluoro-quinolin-6-yl)-methanol (t$_R$ 0.9 min (conditions 1), MH+=194).

5-Chloro-quinoline-6-carboxylic acid ethyl ester and 7-Chloro-quinoline-6-carboxylic acid ethyl ester (ii$_b$)

The title compounds were obtained analogously to fluoro derivative regioisomers (ii) by replacing 4-amino-2-fluoro-benzoic acid (iii) with 4-amino-2-chloro-benzoic acid (iii$_a$). Mixture (2:1) of 5-chloro-quinoline-6-carboxylic acid ethyl ester and 7-chloro-quinoline-6-carboxylic acid ethyl ester (t$_R$ 1.8 min and t$_R$ 1.7 min (conditions 1), MH+=236).

Intermediate E

6-Fluoro-1H-indazole-5-carbaldehyde

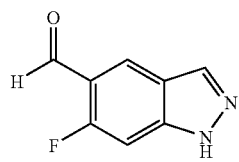 [SMILES: O=Cc1cc2cn[nH]c2cc1F]

A solution of 5-bromo-6-fluoro-1H-indazole (3 g, 13.95 mmol) in THF (10 mL) was added to a suspension of NaH (3.38 g, 141 mmol) in THF (100 mL) over 10 min at 0° C. The RM was cooled to −70° C. then the s-Buli solution (1.4 M, 19 mL) was added slowly over 20 min. It was stirred at this temperature for 45 min. A solution of DMF (6.18 mL, 80 mmol) in THF (10 mL) was added over 15 min at −70° C. and the RM was then warmed up to rt over 1 h 30. The reaction was quenched with 100 mL of 1 N HCl. The RM was extracted twice with EtOAc. Then the organics were joined and washed with brine, dried over Na$_2$SO$_4$ and the solvent was removed. The residue was triturated for 1 h with Et$_2$O. The precipitate formed was filtered off and identified as the desired aldehyde. The filtrate was left in the freezer over night and a second batch of the product was filtered off to afford the title compound as a light yellow solid (t$_R$ 0.7 min (conditions 2), MH+=165, $^1$H-NMR in DMSO-d6: 13.50 (s, 1H); 10.15 (s, 1H); 8.39 (d, 1H); 8.32 (s, 1H); 7.45 (d, 1H)).

Intermediate F 5,7-Difluoro-quinoline-6-carbaldehyde

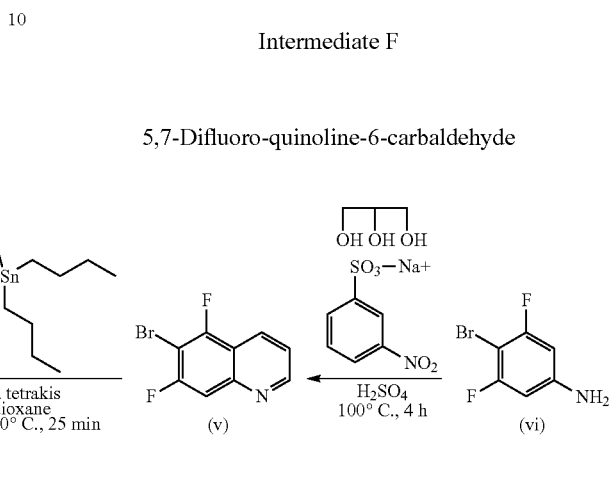

5,7-Difluoro-6-vinyl-quinoline (iv) (614 mg, 3.21 mmol) was dissolved in dioxane (1.7 mL) and water (0.6 mL). 2,6-lutidine (0.761 mL, 6.42 mmol), sodium periodate (2.75 g, 12.85 mmol) and osmium tetroxide (653 mg, 0.064 mmol) were added to the previous solution. The RM was stirred at rt for 15 min. A precipitate was formed. Water was added to the RM and it was extracted twice with EtOAc. The organics were joined and washed with brine, dried over Na$_2$SO$_4$ and the solvent was removed. The residue was purified by MPLC with Hexane and EtOAc to give the title compound as a white solid (t$_R$ 1.2 min (conditions 2), MH+=244, $^1$H-NMR in DMSO-d6: 10.36 (s, 1H); 9.15 (s, 1H); 8.65 (d, 1H); 7.79 (d, 1H); 7.69 (dd, 1H)).

5,7-Difluoro-6-vinyl-quinoline (iv)

6-Bromo-5,7-difluoro-quinoline (v) (1 g, 4.10 mmol), tetrakis(triphenylphosphine)palladium(0) (47 mg, 0.041 mmol) and tributyl(vinyl)tin (1.34 g, 4.10 mmol) were put together with dioxane (3.7 mL) in a microwave reactor and stirred for 25 min at 150° C. under microwave irradiations. The solvent was removed and the residue was purified by MPLC with hexane and EtOAc. The title compound was obtained as a colorless oil (t$_R$ 1.1 min (conditions 2), MH+=192).

6-Bromo-5,7-difluoro-quinoline (v)

Was obtained analogously to 5-fluoro-quinoline-6-carboxylic acid ethyl ester and 7-fluoro-quinoline-6-carboxylic acid ethyl ester (ii) in synthesis of Intermediates A and B by replacing 4-amino-2-fluoro-benzoic acid (iii) with 3,5-difluoro-4-bromoaniline (vi) and avoiding the esterification step with ethanol. The title compound was obtained as a brown solid ($t_R$ 0.8 min (conditions 2), MH+=194).

Intermediate G

7-Trifluoromethyl-quinoline-6-carbaldehyde

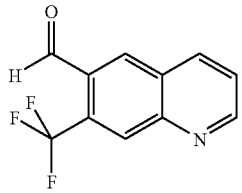 [SMILES: O=Cc1cc2cccnc2cc1C(F)(F)F]

The title compound was obtained in analogy to 7-fluoro-quinoline-6-carbaldehyde (Intermediate B) starting with 4-amino-2-trifluoromethyl-benzoic acid instead of 4-amino-2-fluoro-benzoic acid (iii) ($t_R$ 1.62 min (conditions 12), MH+=226 (LCMS), $^1$H-NMR in DMSO-d6: 10.30 (s, 1H); 9.22 (d, 1H); 8.90 (s, 1H); 8.75 (d, 1H); 8.52 (s, 1H); 7.75 (dd, 1H)).

Intermediate H

6-Fluoro-1-methyl-1H-indazole-5-carbaldehyde warm up to room temperature. After 30 min, the RM was basified with saturated aqueous NaHCO$_3$ solution and then extracted with EtOAc. The organic phase was washed with brine, dried over Na$_2$SO$_4$ and evaporated under vacuo. The residue was triturated with Et$_2$O. The precipitate formed was filtered off to give a yellow solid identified as the desired aldehyde ($t_R$ 0.79 min (conditions 2), MH+=179).

5-Bromo-4-fluoro-1-methyl-1H-indazole (vii)

To a suspension of NaH (1.637 g, 41 mmol) in THF (8 mL) was added dropwise a solution of 5-bromo-6-fluoro-1H-indazole (viii) (8 g, 37 mmol) in THF (8 mL). After 15 min, MeI (2.6 mL, 41 mmol) was added and the RM was stirred between 0° C. and 5° C. for 3 h. The reaction was quenched with a HCl 2 N solution and extracted with EtOAc. The organic phases were combined, washed with brine, dried over Na$_2$SO$_4$ and evaporated under vacuo. The 2 isomers formed were separated by MPLC with heptane and EtOAc to afford the title compound as a yellow solid ($t_R$ 1.4 min (conditions 2), MH+=229).

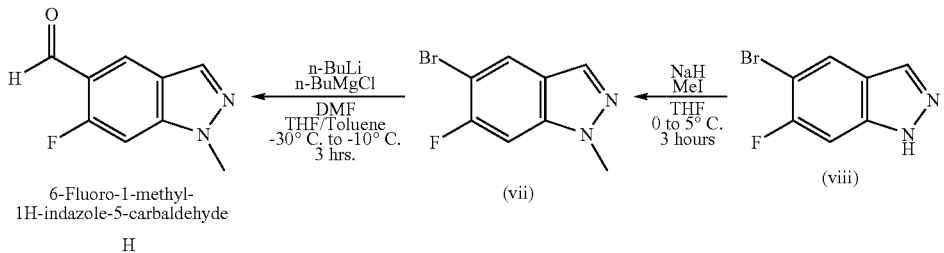

A 2 M solution of n-butyl magnesium chloride in THF (4.8 mL, 9.57 mmol) was added to toluene (34 mL) under nitrogen and cooled to −10° C. To this was added a 1.3 M solution of n-butyl lithium in hexane (12.2 mL, 19.5 mmol) and after 1 h, the RM was cooled to −30° C. To the RM was then added a solution of 5-bromo-6-fluoro-1-methyl-1H-indazole (vii) (4 g, 17.73 mmol) in THF (17 mL) and the reaction was warmed up to −10° C. After 1 h, DMF (8.23 mL, 106 mmol) was added and the RM was stirred at −10° C. for another 1 h. The reaction was quenched using 2 N HCl and was allowed to Intermediate I 4,6-Difluoro-1-methyl-1H-indazole-5-carbaldehyde

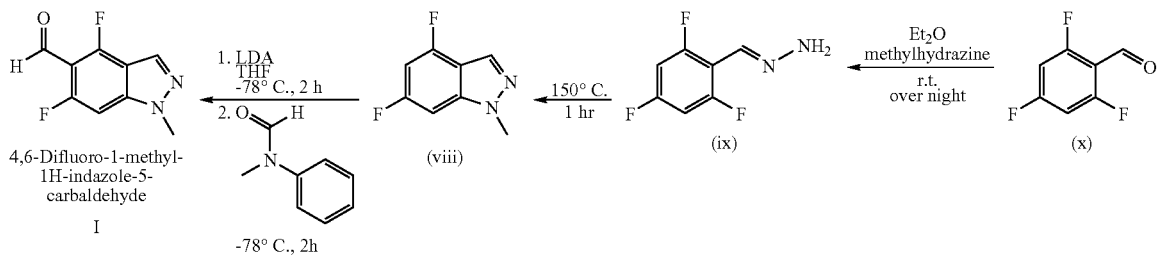

A solution of 4,6-difluoro-1-methyl-1H-indazole (viii) (168 mg, 1 mmol) in dry THF (1 mL) was added dropwise to a freshly prepared solution of LDA (n-BuLi 1.25 mL and diisopropylamine 0.285 mL, 2 mmol, in 10 mL THF) at −78° C. The solution was stirred at this temperature for 2 h, and then N-methylformanilide (0.247 mL, 2 mmol) was added dropwise at −70° C. After stirring 2 additional hours at −78° C. the RM was quenched with glacial acetic acid, diluted with water, and extracted twice with EtOAc. The combined organic phases were washed with brine, dried over Na$_2$SO$_4$ and the solvent was removed. The residue was purified (CombiFlash® Companion System®, with RediSep® silica gel column, n-hexane/EtOAc=95:5->50:50) to afford the title compound as a yellowish crystalline powder (t$_R$ 4.49 min (conditions 3), MH+=197, $^1$H-NMR in DMSO-d6: 10.2 (s, 1H); 8.42 (s, 1H); 7.61 (d, 1H); 4.04 (s, 3H)).

27.3 mmol) and the RM was stirred overnight. The solvent was evaporated and the solid residue was suspended in a mixture of pentane and EtOAc to afford after filtration the title compound as a bright yellow crystalline solid (t$_R$ 4.95 min (conditions 3), MH+=198.1).

Intermediate J 3-(2-Pyrrolidin-1-yl-ethyl)-3H-benzoimidazole-5-carbaldehyde

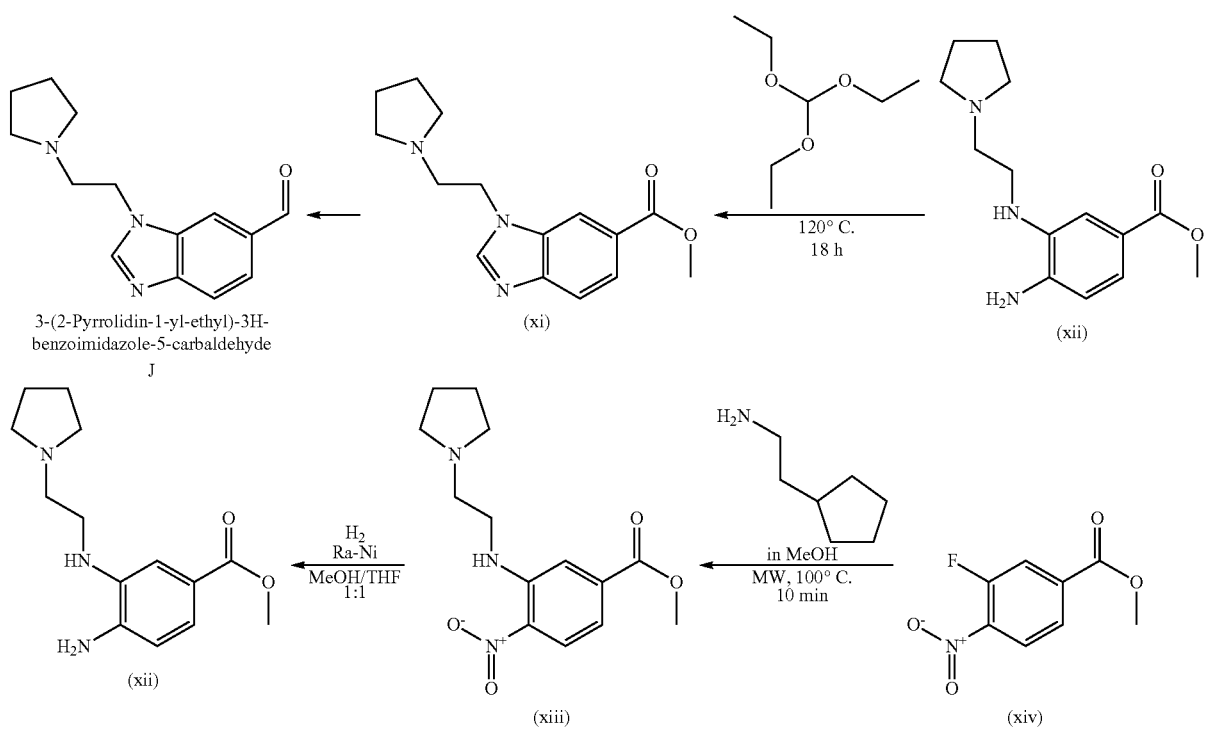

4,6-Difluoro-1-methyl-1H-indazole (viii)

The title compound was synthesized by following a procedure described in *Synthetic Communications*, 1997, 27(7), 1199-1207: [1-(2,4,6-trifluoro-phenyl)-meth-(E)-ylidene]-hydrazine (ix) (1.84 g, 9.8 mmol) was fused at 150° C. for 1 h. The residue was purified (CombiFlash® Companion System®, with RediSep® silica gel column, n-hexane/EtOAc=95:5->80:20) to afford the title compound as a yellow crystalline powder (t$_R$ 5.26 min (conditions 3), $^1$H-NMR in DMSO-d6: 8.17 (s, 1H); 7.45 (dt, 1H); 7.00 (td, 1H); 4.00 (s, 3H)).

[1-(2,4,6-Trifluoro-phenyl)-meth-(E)-ylidene]-hydrazine (ix)

2,4,6-Trifluoro-benzaldehyde (x) (4.5 g, 27.3 mmol) was dissolved in Et$_2$O, methylhydrazine was added (1.43 mL, The title compound was obtained in a similar manner as Intermediate A starting from 3-(2-pyrrolidin-1-yl-ethyl)-3H-benzoimidazole-5-carboxylic acid methyl ester (xi) instead of 5-fluoro-quinoline-6-carboxylic acid ethyl ester and 7-fluoro-quinoline-6-carboxylic acid ethyl ester (ii) (t$_R$ 1.62 min (conditions 8), MH+=244).

3-(2-Pyrrolidin-1-yl-ethyl)-3H-benzoimidazole-5-carboxylic acid methyl ester (xi)

4-Amino-3-(2-pyrrolidin-1-yl-ethylamino)-benzoic acid methyl ester (xii) (1.14 g, 4.33 mmol) and triethylorthoformate (20 mL, 120 mmol) were heated at 120° C. for 18 h before being evaporated to dryness. The residue was taken in EtOAc and aqueous saturated NaHCO$_3$. The aqueous layer was extracted 2 times with EtOAc. The combined organic layers were washed with brine, dried over Na$_2$SO$_4$, filtered and evaporated to dryness to afford the title compound as a brown oil (t$_R$ 1.83 min (conditions 8), MH+=274).

4-Amino-3-(2-pyrrolidin-1-yl-ethylamino)-benzoic acid methyl ester (xii)

4-Nitro-3-(2-pyrrolidin-1-yl-ethylamino)-benzoic acid methyl ester (xiii) (1.30 g, 4.42 mmol) was shaken in MeOH/

THF 1:1 (40 mL) in presence of Raney nickel under 1.1 bar H$_2$ at rt for 40 min. The catalyst was filtered off and washed with MeOH. The filtrate was evaporated to give the title compound as an oil (t$_R$ 2.05 min (conditions 8), MH+=264).

4-Nitro-3-(2-pyrrolidin-1-yl-ethylamino)-benzoic acid methyl ester (xiii)

3-Fluoro-4-nitro-benzoic acid methyl ester (xiv) (1.08 g, 5.41 mmol) and 2-pyrrolidin-1-yl-ethylamine (1.36 g, 11.9 mmol) in MeOH (19 mL) were stirred under microwave irradiation at 100° C. for 10 min. The RM was diluted with EtOAc and washed with aqueous saturated NaHCO$_3$ and brine, dried over Na$_2$SO$_4$, filtered and evaporated to dryness. The residue was dry loaded on silica gel and purified by chromatography with DCM and MeOH to yield the title product as an orange solid (t$_R$ 2.45 min (conditions 8), MH+=294).

Intermediate K

3-Methyl-3H-benzoimidazole-5-carbaldehyde

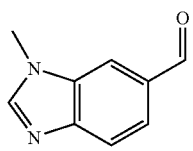

The title compound was synthesized in a similar manner as described for intermediate J using methyl amine solution in MeOH instead of 2-pyrrolidin-1-yl-ethylamine to react with 3-fluoro-4-nitro-benzoic acid methyl ester (xiv) (t$_R$ 1.56 min (conditions 8), MH+=161).

Intermediate L

7-Fluoro-imidazo[1,2-a]pyridine-6-carbaldehyde

To 7-fluoro-6-vinyl-imidazo[1,2-a]pyridine (xv) (94 mg, 0.58 mmol), sodium periodate (496 mg, 2.32 mmol) and 2,6-lutidine (0.135 mL, 1.16 mmol) in dioxane/water 3:1 (4.8 mL) was added in two portions a 2.5% solution of osmium tetroxyde in tert-butanol (2×0.728 mL, 2×0.058 mmol). The RM was stirred at rt for 19.5 h and at 50° C. for 24 h. The RM was diluted with aqueous saturated NaHCO$_3$ and extracted twice with EtOAc. The organic layers were washed with brine, dried over Na$_2$SO$_4$, filtered and evaporated to dryness. The residue was purified by chromatography with DCM and MeOH to yield the title product as a brown solid (TLC RF (DCM/MeOH 9: 1)=0.40, MH+=165).

7-Fluoro-4-vinyl-imidazo[1,2a]pyridine (xv)

To 4-fluoro-5-vinyl-pyridin-2-ylamine (xvi) (200 mg, 1.45 mmol) and NaHCO$_3$ (182 mg, 2.17 mmol) in EtOH (2 mL) was added a 55% aqueous solution of 2-chloroacetaldehyde (0.204 mL, 1.74 mmol). The RM was sealed and heated at 80° C. for 3 h. The RM was purified by preparative HPLC with acetonitrile and water (+0.1% TFA) to afford the title compound as a white solid (t$_R$ 1.84 min (conditions 8), MH+=163).

4-Fluoro-5-vinyl-pyridin-2-ylamine (xvi)

5-Bromo-4-fluoro-pyridin-2-ylamine mono HCl salt (xvii) (368 mg, 1.62 mmol), tributyl(vinyl)stannane (0.52 mL, 1.78 mmol) and palladium tetrakis(triphenylphosphine) (19 mg, 0.016 mmol) in dioxane (6 mL) under argon were heated under microwave irradiation at 120° C. for 45 min. Were then added tributyl(vinyl)stannane (0.2 mL, 0.685 mmol) and palladium tetrakis(triphenylphosphine) (7 mg, 0.006 mmol) and the RM was placed under argon and heated once more under microwave irradiation at 120° C. for 45 min. The RM was diluted with EtOAc and washed with brine, dried over Na$_2$SO$_4$, filtered and evaporated to dryness. The residue was purified by chromatography with hexane and EtOAc to yield the title product as a yellow solid (t$_R$ 1.76 min (conditions 8), MH+=139).

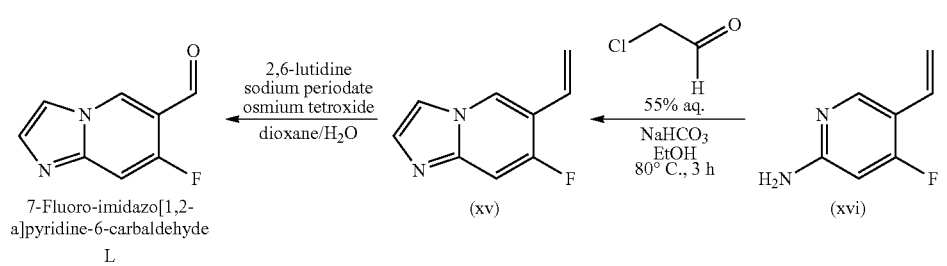

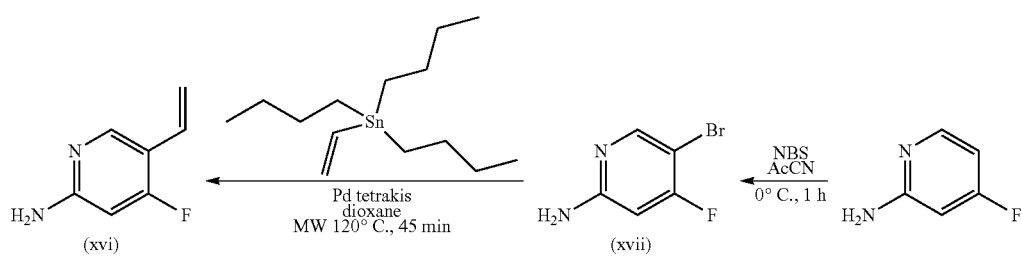

5-Bromo-4-fluoro-pyridin-2-ylamine mono HCl salt (xvii)

To mono HCl salt of 4-fluoro-pyridin-2-ylamine (xviii) (3 g, 20.2 mmol) in acetonitrile at 0° C. was added in 3 portions N-bromosuccinimide (3.59 g, 20.2 mmol) over 1.5 h. The RM was stirred 1 h at 0° C. and the precipitate was filtered and dried under vacuo to give the title compound as mono HCl salt ($t_R$ 1.61 min (conditions 8), MH+=191, 193).

EXAMPLE 1

(rac)-[6-(1-Methyl-1H-pyrazol-4-yl)-imidazo[1,2-b]pyridazin-3-yl]-quinolin-6-yl-methanol

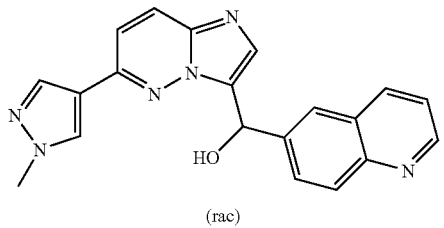 [SMILES: Cn1cc(-c2ccc3ncc(C(O)c4ccc5ncccc5c4)n3n2)cn1]

(rac)

A microwave tube was charged with rac-(6-Chloro-imidazo[1,2-b]pyridazin-3-yl)-quinolin-6-ylmethanol (Stage 1.1, 1.12 g, 3.60 mmol), 1-methyl-4-(4,4,5,5-tetramethyl-[1,3,2]dioxaborolan-2-yl)-1H-pyrazole (789 mg, 3.60 mmol), tetrakis-(triphenylphosphine)palladium (210 mg), 2M $Na_2CO_3$ (6.5 mL) and DME (11 mL). It was heated at 150° C. under microwave irradiation for 10 min. The RM was taken up with EtOAc and washed with 10% $Na_2CO_3$ and brine. The organic layer was dried over $Na_2SO_4$, filtered and concentrated in vacuo. The reside was purified by MPLC eluting with a DCM/MeOH gradient to afford the title compound as a brown solid ($t_R$ 1.0 min(conditions 1), MH+=357).

Stage 1.1

(rac)-(6-Chloro-imidazo[1,2-b]pyridazin-3-yl)-quinolin-6-yl-methanol

Sodium borohydride (103 mg, 2.62 mmol) was added to a solution of (6-chloro-imidazo[1,2-b]pyridazin-3-yl)-quinolin-6-yl-methanone (Stage 1.2, 1.62 g, 5.25 mmol) in ethanol (17 mL) and the solution was stirred at rt for 4 h. Water was then added and the mixture extracted with 9:1 DCM/MeOH. The organic extracts were dried, filtered and concentrated to afford the title compound as a brown solid ($t_R$ 1.0 min (conditions 1), MH+=311).

Stage 1.2

(6-Chloro-imidazo[1,2-b]pyridazin-3-yl)-quinolin-6-yl-methanone

A mixture of N'-(6-chloro-pyridazin-3-yl)-N,N-dimethyl-formamidine (Stage 1.6, 2 g, 10.8 mmol), 2-bromo-1-quinolin-6-yl-ethanone (Stage 1.3, 3.36 g, 10.8 mmol) and triethylamine (1.1 g, 10.8 mmol) was stirred under reflux for 90 min. The reaction was allowed to cool and water (100 mL) was then added. The resulting red precipitate was filtered off to afford the title compound as a red solid ($t_R$ 1.2 min(conditions 1), MH+=309).

Stage 1.3

2-Bromo-1-quinolin-6-yl-ethanone

Bromine (6.69 g, 132 mmol) was added to a warm (100° C.) solution of 1-quinolin-6-yl-ethanone (Stage 1.4, 18.8 g, 110 mmol) in acetic acid (50 mL). The mixture stirred at 100° C. for 45 min then cooled to rt. A precipitate was formed which was filtered off and washed with $Et_2O$. Drying under HV at 50° C. afforded the title compound as a brown solid ($t_R$ 1.3 min (conditions 1), MH+=251.8).

Stage 1.4

1-Quinolin-6-yl-ethanone

Methylmagnesium bromide (190 mL of a 1.4 M solution in toluene/THF 3:1, 270 mmol) was added over 35 min to a solution of quinoline-6-carboxylic acid methoxy-methyl-amide (Stage 1.5, 26 g, 120 mmol) in THF at 0° C. under nitrogen. The RM was stirred for 30 min at 0° C. and then allowed to warm up to rt. The RM was quenched with 1 M HCl and the THF removed under reduced pressure. The residue was taken up in EtOAc and the organic layer separated, dried and concentrated to give the title compound as a yellow solid ($t_R$ 1.0 min (conditions 1), MH+=172).

Stage 1.5

Quinoline-6-carboxylic acid methoxy-methyl-amide

CDI (25.8 g, 151 mmol) was added to a solution of 6-quinolinecarboxylic acid (25 g, 141 mmol) in DMF and the mixture stirred at rt for 10 min. N,O-dimethylhydroxylamine hydrochloride (14.1 g, 142 mmol) was added and the mixture stirred for an additional hour. Brine was then added and the mixture extracted with EtOAc. The organic extracts were dried, filtered and concentrated to give the title compound as a yellow oil ($t_R$ 0.2 min (conditions 2), MH+=217).

Stage 1.6

N'-(6-Chloro-pyridazin-3-yl)-N,N-dimethyl-formamidine

A mixture of 3-amino-6-chloropyridazine (6.39 g, 49.3 mmol) and N,N-dimethylformamide dimethyl acetal (7.67 mL, 54.3 mmol) was stirred under reflux for 75 min. Excess N,N-dimethyl-formamide dimethyl acetal was removed to afford the title compound as a beige solid ($t_R$ 1.0 min (conditions 1), MH+=185).

EXAMPLE 2

6-[6-(1-Methyl-1H-pyrazol-4-yl)-imidazo[1,2-b]pyridazin-3-ylmethyl]-quinoline

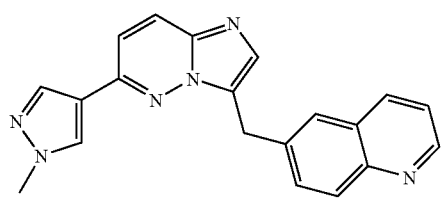 [SMILES: Cn1cc(-c2ccc3ncc(Cc4ccc5ncccc5c4)n3n2)cn1]

The title compound was synthesized like described in *Tetrahedron Letters*, 2001, 42, 831-833): iodine (207 mg, 0.82 mmol) and H₃PO₂ (0.44 mL of a 50% aqueous solution, 4.07 mmol) were added to a solution of (rac)-[6-(1-methyl-1H-pyrazol-4-yl)-imidazo[1,2-b]pyridazin-3-yl]-quinolin-6-yl-methanol (Example 1, 145 mg, 0.41 mmol) in acetic acid (1 mL). The RM was subjected to MW-irradiation at 150° C. for 30 min. The RM was diluted with water and extracted with EtOAc. The organic layer was separated and washed carefully with sat. K₂CO₃-sol then dried filtered and concentrated. Purification by HPLC and then liberation of the free base afforded the title compound as a white solid ($t_R$ 1.055 min (conditions 1), MH+=341.2, ¹H-NMR in DMSO-d6: 8.9 (d, 1H), 8.5 (s, 1H), 8.4 (d, 1H), 8.2 (d, 1H), 8.1 (s, 1H), 8.05 (s, 1H), 8.0 (d, 1H), 7.9 (d, 1H), 7.8 (s, 1H), 7.7 (d, 1H), 7.6 (dd, 1H), 4.6 (s, 2H), 4.0 (s, 3H)).

EXAMPLE 3

(rac)-(4-Methoxy-phenyl)-[6-(1-methyl-1H-pyrazol-4-yl)-imidazo[1,2-b]pyridazin-3-yl]-methanol

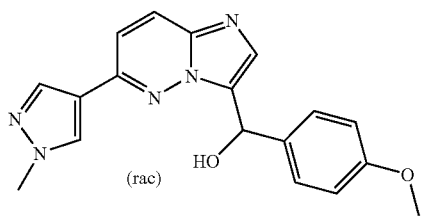 [SMILES: COc1ccc(C(O)c2cnc3ccc(-c4cnn(C)c4)nn23)cc1]

The title compound was prepared in analogy to the synthesis of compound of Stage 1.1, using (4-Methoxy-phenyl)-[6-(1-methyl-1H-pyrazol-4-yl)-imidazo[1,2-b]pyridazin-3-yl]-methanone (Stage 3.1) as starting material ($t_R$ 0.8 min (conditions 2), MH+=336).

Stage 3.1

(4-Methoxy-phenyl)-[6-(1-methyl-1H-pyrazol-4-yl)-imidazo[1,2-b]pyridazin-3-yl]-methanone The title compound was prepared in analogy to the synthesis of compound of Example 1, starting with (6-chloro-imidazo[1,2-b]pyridazin-3-yl)-(4-methoxy-phenyl)-methanone (Stage 3.2) ($t_R$ 1.1 min (conditions 2), MH+=334)

Stage 3.2

(6-Chloro-imidazo[1,2-b]pyridazin-3-yl)-(4-methoxy-phenyl)-methanone

The title compound was obtained in analogy to the synthesis of compound of Stage 1.2 using 2-bromo-1-(4-methoxy-phenyl)-ethanone ($t_R$ 2.93 min (conditions 8), MH+=288).

EXAMPLE 4

3-(4-methoxy-benzyl)-6-(1-methyl-1H-pyrazol-4-yl)-imidazo[1,2-b]pyridazine

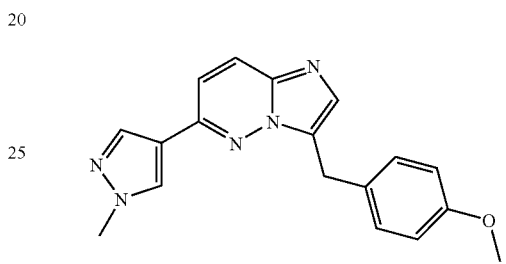

The compound 6-chloro-3-(4-methoxy-benzyl)-imidazo-[1,2-b]-pyridazine (Stage 4.1, 100 mg, 0.36 mmol) was introduced in a microwave reactor with 1-methyl-4-(4,4,5,5-tetramethyl-1,3,2-dioxaboran-2-yl)-1H-pyrazole (75 mg, 0.36 mmol) and dissolved in 1 mL of 2-dimethoxyethane. An aqueous solution of 2 M Na₂CO₃ (660 µL, 1.3 mmol) was added to this mixture and also tetrakis-(triphenylphosphine)-palladium (21 mg, 0.02 mmol). The RM was heated at 180° C. for 30 min under microwave irradiations. The reaction was taken up with EtOAc and washed with 10% Na₂CO₃ and brine. The organic layer was dried over Na₂SO₄ and the solvent was removed. The residue was purified by preparative HPLC with acetonitrile and water (+0.1% TFA). The white solid the title compound was obtained ($t_R$ 1.0 min (conditions 2), MH+=320).

Stage 4.1

6-Chloro-3-(4-methoxy-benzyl)-imidazo-[1,2-b]-pyridazine

The compound (6-chloro-imidazo[1,2-b]pyridazin-3-yl)-(4-methoxy-phenyl)-methanone (Stage 3.2, 2.04 g, 7.1 mmol) was suspended in ethanol (20 mL) with sodium borohydride (140 mg, 3.6 mmol) and stirred at rt for 7 h. Then water was added and the precipitate formed was filtered off. The yellow solid obtained was dried and then dissolved in TFA (50 mL). Triethylsilane (2.85 mL, 17.7 mmol) was added to the solution and it was stirred at rt for 30 min. the RM was poured into ice water. It was extracted with EtOAc and washed with aqueous 1 N sodium hydroxide solution then with brine. The organic layer was dried over Na₂SO₄ and concentrated. The residue was purified by chromatography with DCM and MeOH. The title compound was obtained As a white solid ($t_R$ 1.1 min (conditions 2), MH+=274).

EXAMPLE 5

4-[6-(1-Methyl-1H-pyrazol-4-yl)-imidazo[1,2-b]pyridazin-3-ylmethyl]-phenol

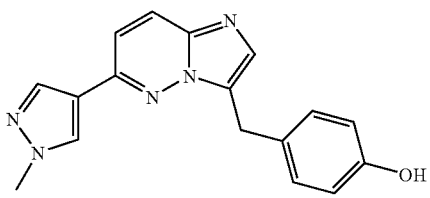 [SMILES: Cn1cc(-c2ccc3ncc(Cc4ccc(O)cc4)n3n2)cn1]

10% Palladium on carbon (49 mg) was added to a solution of 3-(4-benzyloxy-benzyl)-6-(1-methyl-1H-pyrazol-4-yl)-imidazo[1,2-b]pyridazine (Stage 5.1, 214 mg, 0.46 mmol) in ethanol and the resulting mixture was stirred under an atmosphere of hydrogen at rt for 24 h. The RM was filtered through Celite and concentrated in vacuo. Purification by HPLC afforded the title compound as a white solid ($t_R$ 0.8 min (conditions 2), MH+=306, $^1$H-NMR in CD$_3$OD: 8.4 (s, 1H), 8.2 (d, 1H), 8.1 (s, 1H), 8.0 (d, 1H), 7.7 (s, 1H), 7.2 (d, 2H), 6.8 (d, 2H), 4.3 (s, 2H), 4.0 (s, 3H)).

Stage 5.1

3-(4-Benzyloxy-benzyl)-6-(1-methyl-1H-pyrazol-4-yl)-imidazo[1,2-b]pyridazine

Sodium borohydride was added to a solution of (4-benzyloxy-phenyl)-[6-(1-methyl-1H-pyrazol-4-yl)-imidazo[1,2-b]pyridazin-3-yl]-methanone (Stage 5.2, 190 mg, 0.46 mmol) in ethanol (1.5 mL) and the reaction stirred for 16 h. Water was added to the reaction and the resulting solid was filtered off and dried under vacuum. The solid was dissolved in TFA (2 mL) and to this solution was added triethylsilane (0.18 mL, 1.16 mmol) and the mixture was stirred at rt for 30 min. Water was added and the mixture extracted with EtOAc. The EtOAc extract was dried, filtered and concentrated to give the title compound as red solid ($t_R$ 1.3 min (conditions 2), MH+=396).

Stage 5.2

(4-Benzyloxy-phenyl)-[6-(1-methyl-1H-pyrazol-4-yl)-imidazo[1,2-b]pyridazin-3-yl]-methanone By proceeding in a similar manner as Example 1 but using (4-benzyloxy-phenyl)-(6-chloro-imidazo[1,2-b]pyridazin-3-yl)-methanone (Stage 5.3, 600 mg, 1.65 mmol) instead of (rac)-(6-chloro-imidazo[1,2-b]pyridazin-3-yl)-quinolin-6-yl-methanol the title compound was obtained as a brown solid ($t_R$ 1.4 min (conditions 2), MH+=410).

Stage 5.3

(4-Benzyloxy-phenyl)-(6-chloro-imidazo[1,2-b]pyridazin-3-yl)-methanone

By proceeding in a similar manner (Stage 1.2) but using 1-(4-benzyloxy-phenyl)-2-bromo-ethanone (687 mg, 3.72 mmol) instead of 2-bromo-1-quinolin-6-yl-ethanone the title compound was obtained as a black solid ($t_R$ 1.6 min (conditions 2), MH+=364).

EXAMPLE 6

6-{Difluoro-[6-(1-methyl-1H-pyrazol-4-yl)-imidazo[1,2-b]pyridazin-3-yl]-methyl}-quinoline

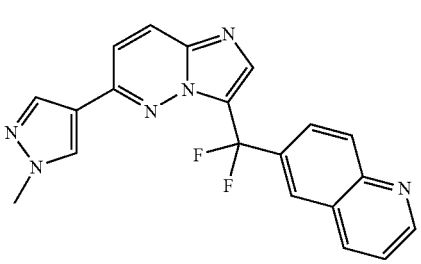 [SMILES: Cn1cc(-c2ccc3ncc(C(F)(F)c4ccc5ncccc5c4)n3n2)cn1]

A microwave tube was charged with 6-[(6-chloro-imidazo[1,2-b]pyridazin-3-yl)-difluoro-methyl]-quinoline (Stage 6.1, 10 mg, 0.03 mmol), 1-methyl-4-(4,4,5,5-tetramethyl-[1,3,2]dioxaborolan-2-yl)-1H-pyrazole (10 mg, 0.045 mmol), tetrakis-(triphenylphosphine)palladium (1.7 mg), 2M Na$_2$CO$_3$ (0.054 mL) and DME (1 mL). It was heated at 150° C. under microwave irradiation for 20 min. The RM was taken up with EtOAc (2 mL) and washed with 10% Na$_2$CO$_3$ and brine. The organic layer was dried over Na$_2$SO$_4$, filtered and concentrated in vacuo. The residue was purified by HPLC to afford the title compound as a brown solid ($t_R$ 1.379 min (conditions 1), MH+=376.8, $^1$H-NMR in DMSO-d6: 9.00 (m, 1H); 8.65 (d, 1H); 8.52 (s, 1H); 8.30 (s, 1H); 8.21 (d, 1H); 8.14 (d, 1H); 7.99 (m, 2H); 7.87 (s, 1H); 7.66 (m, 2H); 3.86 (s, 3H)).

Stage 6.1

6-[(6-Chloro-imidazo[1,2-b]pyridazin-3-yl)-difluoro-methyl]-quinoline

DAST (0.059 mL, 0.45 mmol) was added to a solution of N-bromosuccinimide (32 mg, 0.18 mmol) in DCM (1.5 mL) at rt under nitrogen. A solution of 6-[2-(6-chloro-imidazo[1,2-b]pyridazin-3-yl)-[1,3]dithiolan-2-yl]-quinoline (Stage 6.2, 35 mg, 0.09 mmol) in DCM (0.5 mL) was then added and the RM stirred at rt for one hour. The RM was then partitioned between water and EtOAc. The organic layer was dried, filtered and concentrated to give the title compound as a yellow oil ($t_R$ 1.532 min (conditions 1), MH+=330.8).

Stage 6.2

6-[2-(6-Chloro-imidazo[1,2-b]pyridazin-3-yl)-[1,3]dithiolan-2-yl]-quinoline

Boron trifluoride acetic acid complex (0.062 mL, 0.16 mmol) was added to a solution of 6-chloro-imidazo[1,2-b]pyridazin-3-yl)-quinolin-6-yl-methanone (Stage 1.2, 50 mg, 0.16 mmol) in 1,2-ethanedithiol (0.17 mL, 2.1 mmol) under an N$_2$ atmosphere. The RM was heated to 60° C. for 2 h then allowed to cool to rt. The RM was diluted with EtOAc and washed 2× with sat. NaHCO$_3$-sol., 1M NaOH and brine. The organic phase was then dried, filtered and concentrated under reduced pressure. The residue was then purified by HPLC to afford the title compound as a red solid ($t_R$ 1.138 min (conditions 1), MH+=384.8).

EXAMPLE 7

6-[6-(1-Piperidin-4-yl-1H-pyrazol-4-yl)-imidazo[1,2-b]pyridazin-3-ylmethyl]-quinoline

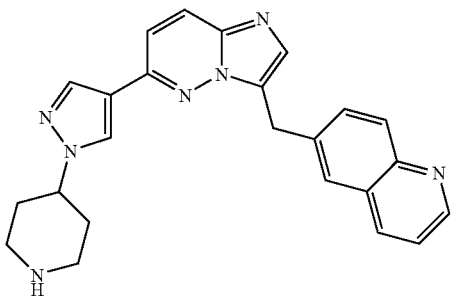 [SMILES: c1cnc2ccc(Cc3cnc4ccc(-c5cnn(C6CCNCC6)c5)nn34)cc2c1]

The title compound was prepared in analogy to the synthesis of compound of Example 2, using tert-butyl 4-(4-(4,4,5-trimethyl-1,3,2-dioxaborolan-2-yl)-1H-pyrazol-1-yl)piperidine-1-carboxylate and with an additional deprotection step before final reduction ($t_R$ 1.0 min (conditions 1), MH+=410).

EXAMPLE 8

3-Benzofuran-5-ylmethyl-6-(1-methyl-1H-pyrazol-4-yl)-imidazo[1,2-b]pyridazine

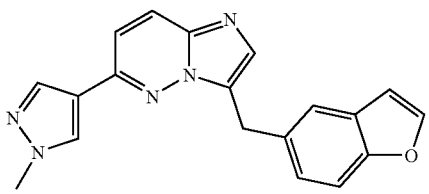 [SMILES: Cn1cc(-c2ccc3ncc(Cc4ccc5occc5c4)n3n2)cn1]

The title compound was prepared in analogy to the synthesis of compound of Example 2 using the crude benzylique alcohol inter-mediate obtained in further analogy to the synthesis of compound of Stage 9.1 starting with compound of Stage 8.1 and 1-benzofuran-5-carbaldehyde ($t_R$ 1.5 min (conditions 2), MH+=330, $^1$H-NMR in DMSO-d6: 8.5 (s, 1H); 8.3 (d, 1H); 8.2 (s, 1H); 7.9 (d, 1H); 7.8 (m, 2H); 7.7 (s, 1H); 7.5 (d, 1H); 7.3 (d, 1H); 6.9 (d, 1H); 4.4 (s, 2H); 3.9 (s, 3H)).

Stage 8.1

3-Bromo-6-(1-methyl-1h-pyrazol-4-yl)-imidazo[1,2-b]pyridazine 6-(1-Methyl-1H-pyrazol-4-yl)-imidazo[1,2-b]pyridazine (Stage 8.2, 2.22 g, 11.1 mmol) was dissolved in DMF (33 mL) and cooled down to 0° C. with an ice-water bath. Then N-bromo-succinimide (2.3 g, 12.3 mmol) was added and the RM was stirred at the same temperature for 1 h45. It was then taken up with EtOAc and washed with a saturated solution of NaHCO3 and brine. The organic layer was dried over Na2SO4 and the solvent was removed. The residue was triturated with Et2O and the precipitate was filtered off to afford the title compound as a yellow solid ($t_R$ 1.3 min (conditions 2), MH+=278).

Stage 8.2

6-(1-Methyl-1H-pyrazol-4-yl)-imidazo[1,2-b]pyridazine 6-(1-Methyl-1H-pyrazol-4-yl)-pyridazin-3-ylamine (Stage 8.3, 2.41 g, 13.8 mmol) was dissolved in EtOH (18 mL). Chloroacetaldehyde 55% in H2O (1.61 mL, 13.8 mmol) and NaHCO3 (2.3 g, 27.5 mmol) were added. The RM was stirred at 80° C. for 5 h. The solvent was removed and a solution of 5% NaHCO3 was added. The mixture was extracted twice with DCM/MeOH (9/1). The combined organic phases were washed with brine, dried over Na2SO4, and the solvent was removed to afford the title compound as a black solid ($t_R$ 1.0 min (conditions 2), MH+=200).

Stage 8.3

6-(1-Methyl-1H-pyrazol-4-yl)-pyridazin-3-ylamine

3-Amino-6-chloropyridazine (7.76 g, 59.9 mmol) was introduced in a round bottom flask with 1-methyl-4-(4,4,5,5-tetramethyl-1,3,2-dioxaboran-2-yl)-1H-pyrazole (13.1 g, 59.9 mmol) and dissolved in 2-dimethoxyethane (160 mL). An aqueous solution of 2 M Na2CO3 (110 mL, 220 mmol) was added to this mixture and also tetrakis-(triphenylphosphine)-palladium (3.5 g, 2.99 mmol). The RM was refluxed for 26 h under nitrogen. Then was taken up with EtOAc and washed with 1N NaOH and brine. The organic layer was dried over Na2SO4 and the solvent was removed. The residue was triturated with Et2O to afford the title compound as a yellow solid ($t_R$ 0.9 min (conditions 2), MH+=176).

EXAMPLE 9

(rac)-Imidazo[1,2-a]pyridin-6-yl-[6-(1-methyl-1H-pyrazol-4-yl)-imidazo[1,2-b]pyridazin-3-yl]-methanol

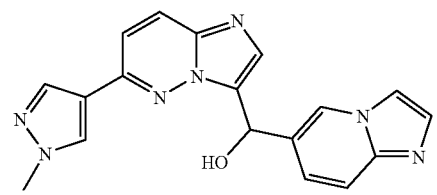 [SMILES: Cn1cc(-c2ccc3ncc(C(O)c4ccc5nccn5c4)n3n2)cn1]

A microwave tube was charged under argon atm. with (rac)-(6-chloro-imidazo[1,2-b]pyridazin-3-yl)-imidazo[1,2-a]pyridin-6-yl-methanol (Stage 9.1, 89.9 mg, 0.3 mmol), 1-methyl-4-(4,4,5,5-tetramethyl-[1,3,2]dioxaborolan-2-yl)-1H-pyrazole (62.4 mg, 0.3 mmol), Pd(PPh3)2Cl2 (6.3 mg) and 2 M K2CO3 (0.405 mL) and DME (1 mL). The mixture was heated at 80° C. for 3 h. The RM was taken up with DCM and washed with NaCl solution. After filtration of both layers, the solid part was dissolved in MeOH and evaporated to dryness. The residue was stirred in EtOAc and filtered to give the pure title compound. The organic layer of the first filtrate was dried over Na2SO4, filtered and concentrated in vacuo. The residue was purified by flash chromatography (Combi-Flash® Companion System®, with RediSep® silica gel column, DCM/MeOH=95:5—>80:20) to afford a second batch of the title compound (t$_R$ 2.57 min (conditions 3), MH+=346.2)

Stage 9.1

(rac)-(6-chloro-imidazo[1,2-b]pyridazin-3-yl)-imidazo[1,2-a]pyridin-6-yl-methanol Ethyl magnesium bromide (3 M in Et$_2$O, 333 µL, 1 mmol) was added to a solution of 3-bromo-6-chloro-imidazo[1,2-b]pyridazine (116 mg, 0.5 mmol) in THF (5 mL) at rt. The RM was stirred for 30 min and imidazo[1,2-a]pyridine-6-carbaldehyde (154 mg, 2 mmol) in THF (3 mL) was added dropwise. After 1 h the RM was extracted with a solution of NH$_4$Cl and EtOAc. The combined organic phases were dried over Na$_2$SO$_4$, concentrated under reduced pressure, and purified by flash chromatography (CombiFlash® Companion System®, with RediSep® silica gel column, Hexane/EtOAc=95:5->0:100) to afford the title compound as a yellowish crystalline compound (t$_R$ 2.72 min (conditions 3), MH+=300.2).

EXAMPLE 10

3-Imidazo[1,2-a]pyridin-6-ylmethyl-6-(1-methyl-1H-pyrazol-4-yl)-imidazo[1,2-b]pyridazine

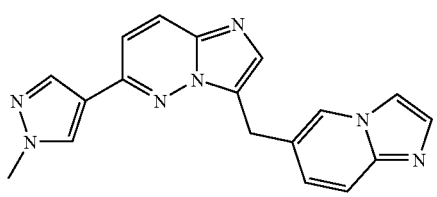 [SMILES: Cn1cc(-c2ccc3ncc(Cc4ccc5nccn5c4)n3n2)cn1]

Iodine (50.8 mg, 0.2 mmol) and H$_3$PO$_2$ (0.11 mL of a 50% aqueous solution, 1.0 mmol) were added to a solution of (rac)-Imidazo[1,2-a]pyridin-6-yl-[6-(1-methyl-1H-pyrazol-4-yl)imidazo[1,2-b]pyridazin-3-yl]-methanol (Example 9, 34.5 mg, 0.1 mmol) in acetic acid (0.5 mL). The RM was heated at 150° C. for 1 h. The RM was diluted with water and extracted with EtOAc. The organic layer was separated and washed with 10% Na$_2$CO$_3$-sol then dried on Na$_2$SO$_4$, filtered and concentrated. Combined aqueous layers were completely neutralized and again extracted with DCM containing little MeOH. Organic layers were evaporated and both crudes from the two extractions were purified together by flash chromatography (CombiFlash® Companion System®, with RediSep® silica gel column, DCM/MeOH=95:5->80:20). The fractions containing the product were evaporated and the residue taken in EtOAc and pentane, filtered and dried under high vacuum to afford the title compound as beige crystals (t$_R$ 2.70 min (conditions 3), MH+=330.2, $^1$H-NMR in DMSO-d6: 8.58 (s, 1H); 8.44 (s, 1H); 8.12 (s, 1H); 8.08 (d, 1H); 7.90 (s, 1H); 7.62 (s, 1H); 7.54-7.44 (m, 3H); 7.22 (d, 1H); 4.31 (s, 2H); 3.90 (s, 3H)).

EXAMPLE 11

(rac)-[6-(1-Methyl-1H-pyrazol-4-yl)-imidazo[1,2-b]pyridazin-3-yl]-quinoxalin-6-yl-methanol

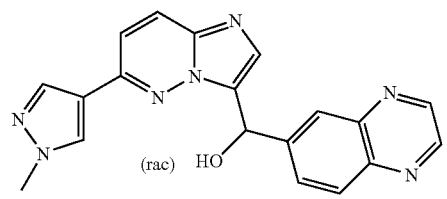 [SMILES: Cn1cc(-c2ccc3ncc(C(O)c4ccc5nccnc5c4)n3n2)cn1]

The title compound was prepared in analogy to the compound of Example 9 starting with compound of Stage 11.1 (t$_R$ 3.18 min (conditions 3), MH+=358.2).

Stage 11.1

(rac)-(6-Chloro-imidazo[1,2-b]pyridazin-3-yl)-quinoxalin-6-yl-methanol

The title compound was prepared in analogy to the compound of Stage 9.1 using quinoxaline-6-carbaldehyde as starting material (t$_R$ 5.42 min (conditions 4), MH+=311.9).

EXAMPLE 12

3-Benzothiazol-6-ylmethyl-6-(1-methyl-1H-pyrazol-4-yl)-imidazo[1,2-b]pyridazine

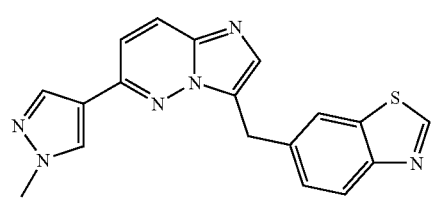 [SMILES: Cn1cc(-c2ccc3ncc(Cc4ccc5ncsc5c4)n3n2)cn1]

The title compound was prepared in analogy to the compound of Example 8, using benzothiazole-6-carbaldehyde as starting material (t$_R$ 1.3 min (conditions 2), MH+=347, $^1$H-NMR in DMSO-d6: 9.3 (s, 1H); 8.5 (s, 1H); 8.3 (d, 1H);

8.2 (s, 1H); 8.1 (s, 1H); 8.0 (d, 1H); 7.9 (s, 1H); 7.8 (d, 1H); 8.6 (d, 1H); 4.3 (s, 2H); 3.9 (s, 3H)).

EXAMPLE 13

3-(2-Methyl-benzothiazol-6-ylmethyl)-6-(1-methyl-1H-pyrazol-4-yl)-imidazo[1,2-b]pyridazine

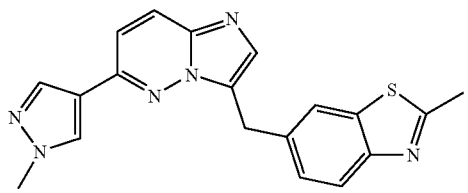 [SMILES: Cc1nc2ccc(Cc3cnc4ccc(-c5cnn(C)c5)nn34)cc2s1]

The title compound was prepared in analogy to the compound of Example 8, using 2-methylbenzothiazole-6-carbaldehyde as starting material ($t_R$ 1.4 min (conditions 2), MH+=361, $^1$H-NMR in DMSO-d6: 8.5 (s, 1H); 8.3 (d, 1H); 8.2 (s, 1H); 8.1 (s, 1H); 7.9 (s, 1H); 7.8 (m, 2H); 7.5 (d, 1H); 4.5 (s, 2H); 3.9 (s, 3H)).

EXAMPLE 14

(6-Chloro-imidazo[1,2-b]pyridazin-3-yl)-quinoline

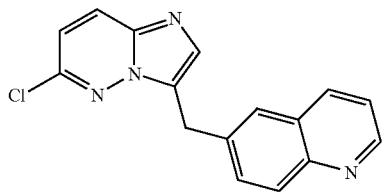 [SMILES: Clc1ccc2ncc(Cc3ccc4ncccc4c3)n2n1]

H$_3$PO$_2$ (28.8 mL of a 50% aqueous solution, 263 mmol) was added to a solution of (rac)-(6-chloro-imidazo[1,2-b]pyridazin-3-yl)-quinolin-6-yl-methanol (Stage 1.1, 10.89 g, 35.0 mmol) in acetic acid (272 mL) at 80° C. Iodine (13.34 g, 52.6 mmol) was then added and the RM was stirred at 110° C. for 90 min. The RM was cooled down to rt and acetic acid was removed. The residue was taken up in water and DCM. A 2 N NaOH solution was then added until pH=11. The organic layer was then separated and washed with water (2×). The aqueous layer was further extracted with DCM (3×). The combined organic layer was then dried, filtered and concentrated. The residue crystallized in EtOAc. The resulting solid was purified by flash chromatography (Flashmaster, with a 50 g silica gel column, TBME/MeOH: 97:3→84:16). The solid crystallized again in EtOAc/Et$_2$O. It was filtered and dried under vacuum to afford the title compound as a white solid ($t_R$ 4.72 min (conditions 4), MH+=295.0, $^1$H-NMR in DMSO-d6: 8.86 (m, 1H); 8.30 (m, 1H); 8.23 (d, 1H); 7.98 (d, 1H); 7.82 (m, 1H); 7.72 (m, 2H); 7.50 (dd, 1H); 7.35 (d, 1H); 4.52 (s, 2H)).

EXAMPLE 15

2-Chloro-4-(3-quinolin-6-ylmethyl-imidazo[1,2-b]pyridazin-6-yl)-benzamide

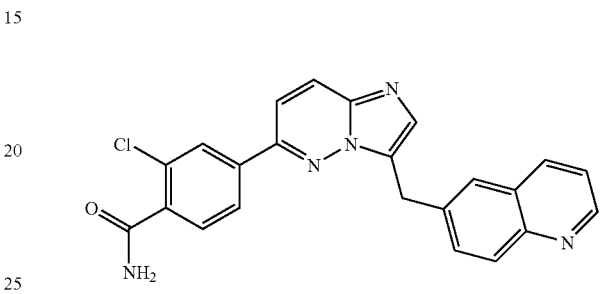

A microwave tube was charged with (6-chloro-imidazo[1,2-b]pyridazin-3-yl)-quinoline (Example 14, 150 mg, 0.509 mmol), 4-carbamoyl-3-chlorophenyboronic acid (304 mg, 1.527 mmol), DME (1.6 mL) and DMF (250 µL). 2 M Na$_2$CO$_3$ (763 µL, 1.527 mmol) was then added, followed by tetrakis-(triphenylphosphine)-palladium (21 mg, 0.025 mmol). The RM was heated at 90° C. for 24 h. The cool reaction mixture was poured in DCM, filtered through a Celite pad and washed with water. The organic layer was dried over Na$_2$SO$_4$, filtered and concentrated in vacuo. While concentrating some crystals appeared. The crystals were filtered off and dried to afford the title compound as a beige solid ($t_R$ 4.28 min (conditions 4), MH+=414.4, $^1$H-NMR in DMSO-d6: 8.85 (m, 1H); 8.32 (m, 1H); 8.24 (d, 1H); 8.11 (m, 1H); 8.07 (dd, 1H); 7.97 (m, 3H); 7.86 (d, 1H); 7.80 (s, 1H); 7.78 (dd, 1H); 7.70 (s, 1H); 7.61 (d, 1H); 7.51 (dd, 1H); 4.63 (s, 2H)).

EXAMPLE 16-71

The following compounds were prepared according to the procedure of Example 15 starting with the appropriate boronic acid or ester and using the appropriate purification method: crystallization, preparative LCMS or flash chromatography.

| Ex | Structure | Name | $t_R$ (min) Conditions | MH+ |
|---|---|---|---|---|
| 16 | 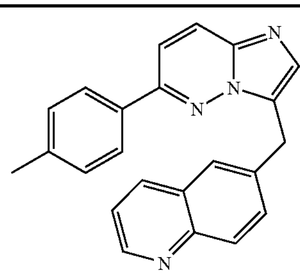 | 6-(6-p-Tolyl-imidazo[1,2-b]pyridazin-3-ylmethyl)-quinoline | 6.27 Conditions 4 | 351.0 |

| Ex | Structure | Name | $t_R$ (min) Conditions | MH+ |
|---|---|---|---|---|
| 17 | 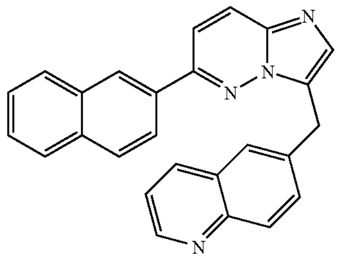 [SMILES: c1ccc2cc(-c3ccc4ncc(Cc5ccc6ncccc6c5)n4n3)ccc2c1] | 6-(6-Naphthalen-2-yl-imidazo[1,2-b]pyridazin-3-ylmethyl)-quinoline | 7.16 Conditions 4 | 387.0 |
| 18 | 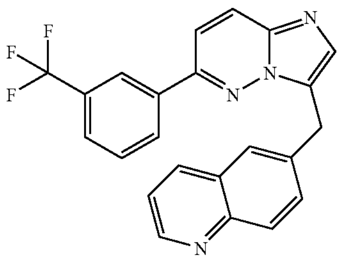 [SMILES: FC(F)(F)c1cccc(-c2ccc3ncc(Cc4ccc5ncccc5c4)n3n2)c1] | 6-[6-(3-Trifluoromethyl-phenyl)-imidazo[1,2-b]pyridazin-3-ylmethyl]-quinoline | 2.55 Conditions 6 | 404.9 |
| 19 | 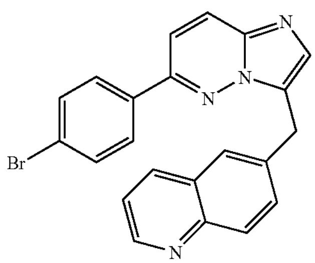 | 6-[6-(4-Bromo-phenyl)-imidazo[1,2-b]pyridazin-3-ylmethyl]-quinoline | 2.53 Conditions 6 | 414.8 |
| 20 | 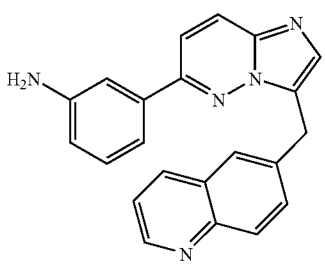 [SMILES: Nc1cccc(-c2ccc3ncc(Cc4ccc5ncccc5c4)n3n2)c1] | 3-(3-Quinolin-6-ylmethyl-imidazo[1,2-b]pyridazin-6-yl)-phenylamine | 4.24 Conditions 4 | 352.0 |
| 21 | 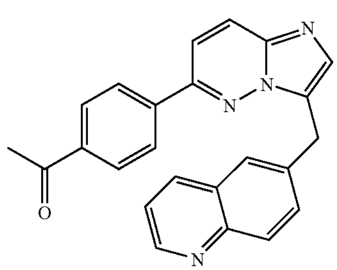 [SMILES: CC(=O)c1ccc(-c2ccc3ncc(Cc4ccc5ncccc5c4)n3n2)cc1] | 1-[4-(3-Quinolin-6-ylmethyl-imidazo[1,2-b]pyridazin-6-yl)-phenyl]-ethanone | 2.00 Conditions 6 | 378.9 |
| 22 | 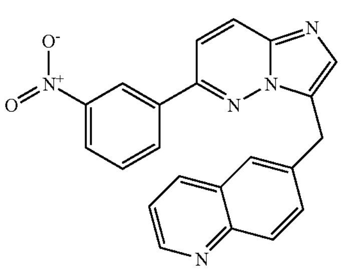 [SMILES: O=[N+]([O-])c1cccc(-c2ccc3ncc(Cc4ccc5ncccc5c4)n3n2)c1] | 6-[6-(3-Nitro-phenyl)-imidazo[1,2-b]pyridazin-3-ylmethyl]-quinoline | 2.12 Conditions 6 | 381.9 |

| Ex | Structure | Name | t$_R$ (min) Conditions | MH+ |
|---|---|---|---|---|
| 23 | 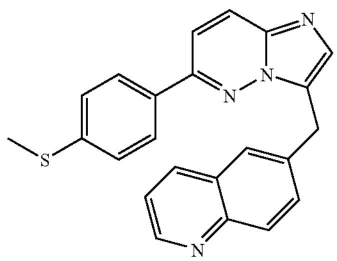 [SMILES: CSc1ccc(-c2ccc3ncc(Cc4ccc5ncccc5c4)n3n2)cc1] | 6-[6-(4-Methylsulfanyl-phenyl)-imidazo[1,2-b]pyridazin-3-ylmethyl]-quinoline | 2.44 Conditions 6 | 382.9 |
| 24 | 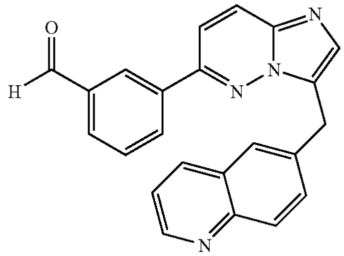 [SMILES: O=Cc1cccc(-c2ccc3ncc(Cc4ccc5ncccc5c4)n3n2)c1] | 3-(3-Quinolin-6-ylmethyl-imidazo[1,2-b]pyridazin-6-yl)-benzaldehyde | 1.83/1.91 Conditions 6 | 365.0 |
| 25 | 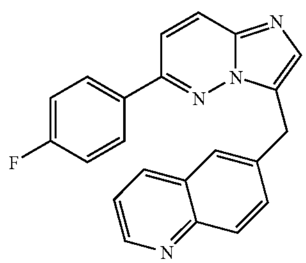 [SMILES: Fc1ccc(-c2ccc3ncc(Cc4ccc5ncccc5c4)n3n2)cc1] | 6-[6-(4-Fluoro-phenyl)-imidazo[1,2-b]pyridazin-3-ylmethyl]-quinoline | 2.16 Conditions 6 | 355.0 |
| 26 | 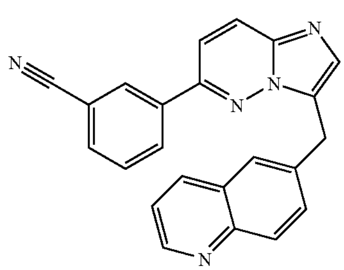 [SMILES: N#Cc1cccc(-c2ccc3ncc(Cc4ccc5ncccc5c4)n3n2)c1] | 3-(3-Quinolin-6-ylmethyl-imidazo[1,2-b]pyridazin-6-yl)-benzonitrile | 1.98 Conditions 6 | 361.9 |
| 27 | 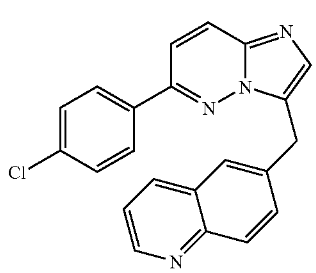 [SMILES: Clc1ccc(-c2ccc3ncc(Cc4ccc5ncccc5c4)n3n2)cc1] | 6-[6-(4-Chloro-phenyl)-imidazo[1,2-b]pyridazin-3-ylmethyl]-quinoline | 2.43 Conditions 6 | 370.9 |

| Ex | Structure | Name | t$_R$ (min) Conditions | MH+ |
|---|---|---|---|---|
| 28 | 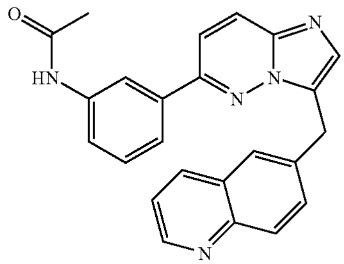 [SMILES: CC(=O)Nc1cccc(-c2ccc3ncc(Cc4ccc5ncccc5c4)n3n2)c1] | N-[3-(3-Quinolin-6-ylmethyl-imidazo[1,2-b]pyridazin-6-yl)-phenyl]-acetamide | 2.13 Conditions 6 | 393.9 |
| 29 | 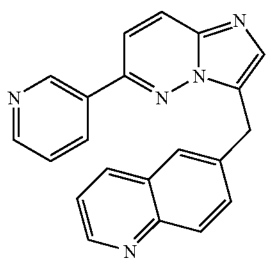 | 6-(6-Pyridin-3-yl-imidazo[1,2-b]pyridazin-3-ylmethyl)-quinoline | 1.23 Conditions 6 | 338.0 |
| 30 | 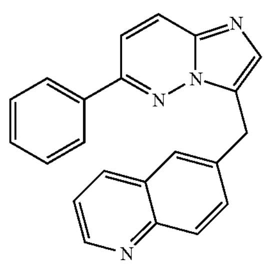 [SMILES: c1ccc(-c2ccc3ncc(Cc4ccc5ncccc5c4)n3n2)cc1] | 6-(6-Phenyl-imidazo[1,2-b]pyridazin-3-ylmethyl)-quinoline | 2.07 Conditions 6 | 337.0 |
| 31 | 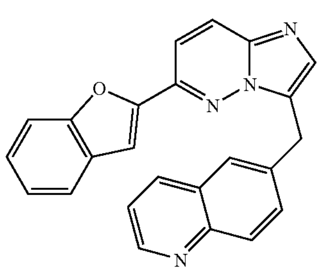 [SMILES: c1cnc2ccc(Cc3cnc4ccc(-c5cc6ccccc6o5)nn34)cc2c1] | 6-(6-Benzofuran-2-yl-imidazo[1,2-b]pyridazin-3-ylmethyl)-quinoline | 2.50 Conditions 6 | 376.9 |
| 32 | 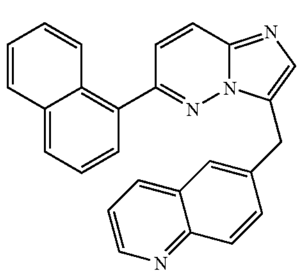 [SMILES: c1cnc2ccc(Cc3cnc4ccc(-c5cccc6ccccc56)nn34)cc2c1] | 6-(6-Naphthalen-1-yl-imidazo[1,2-b]pyridazin-3-ylmethyl)-quinoline | 2.53 Conditions 6 | 386.9 |

| Ex | Structure | Name | $t_R$ (min) Conditions | MH+ |
|---|---|---|---|---|
| 33 | 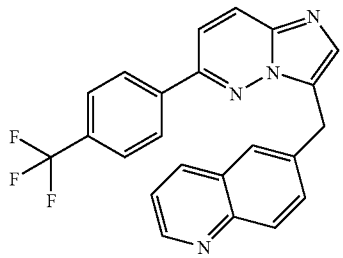 [SMILES: FC(F)(F)c1ccc(-c2ccc3ncc(Cc4ccc5ncccc5c4)n3n2)cc1] | 6-[6-(4-Trifluoromethyl-phenyl)-imidazo[1,2-b]pyridazin-3-ylmethyl]-quinoline | 2.71 Conditions 6 | 404.9 |
| 34 | 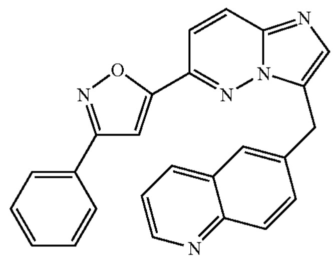 [SMILES: c1ccc(-c2cc(-c3ccc4ncc(Cc5ccc6ncccc6c5)n4n3)on2)cc1] | 6-[6-(3-Phenyl-isoxazol-5-yl)-imidazo[1,2-b]pyridazin-3-ylmethyl]-quinoline | 2.77 Conditions 6 | 403.9 |
| 35 | 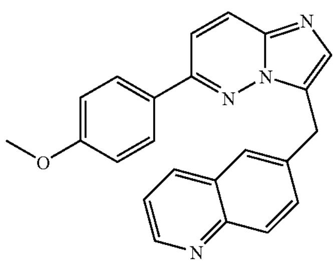 [SMILES: COc1ccc(-c2ccc3ncc(Cc4ccc5ncccc5c4)n3n2)cc1] | 6-[6-(4-Methoxy-phenyl)-imidazo[1,2-b]pyridazin-3-ylmethyl]-quinoline | 2.17 Conditions 6 | 367.0 |
| 36 | 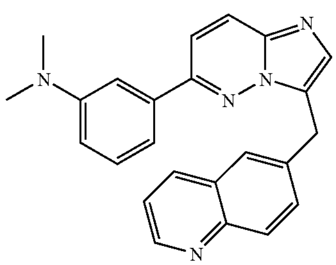 [SMILES: CN(C)c1cccc(-c2ccc3ncc(Cc4ccc5ncccc5c4)n3n2)c1] | Dimethyl-[3-(3-quinolin-6-ylmethyl-imidazo[1,2-b]pyridazin-6-yl)-phenyl]-amine | 1.63/1.73 Conditions 6 | 380.0 |
| 37 | 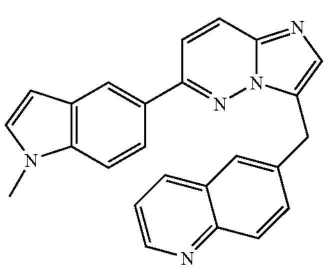 [SMILES: Cn1ccc2cc(-c3ccc4ncc(Cc5ccc6ncccc6c5)n4n3)ccc21] | 6-[6-(1-Methyl-1H-indol-5-yl)-imidazo[1,2-b]pyridazin-3-ylmethyl]-quinoline | 2.37 Conditions 6 | 390.0 |
| 38 | 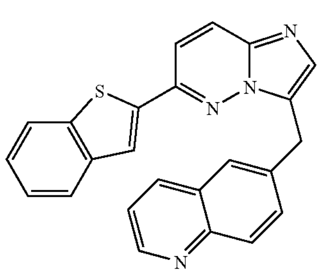 | 6-(6-Benzo[b]thiophen-2-yl-imidazo[1,2-b]pyridazin-3-ylmethyl)-quinoline | 2.62 Conditions 6 | 392.9 |

| Ex | Structure | Name | t_R (min) Conditions | MH+ |
|---|---|---|---|---|
| 39 | 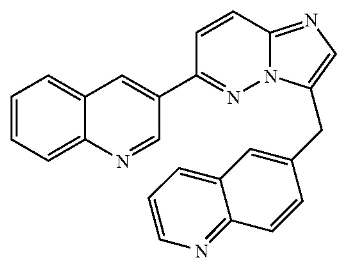 [SMILES: c1cnc2ccc(Cc3cnc4ccc(-c5cnc6ccccc6c5)nn34)cc2c1] | 6-(6-Quinolin-3-yl-imidazo[1,2-b]pyridazin-3-ylmethyl)-quinoline | 1.89 Conditions 6 | 387.9 |
| 40 | 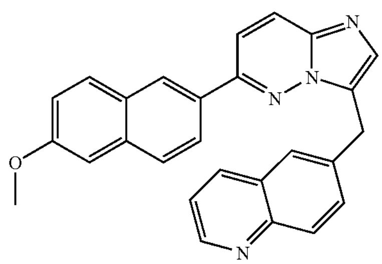 [SMILES: COc1ccc2cc(-c3ccc4ncc(Cc5ccc6ncccc6c5)n4n3)ccc2c1] | 6-[6-(6-Methoxy-naphthalen-2-yl)-imidazo[1,2-b]pyridazin-3-ylmethyl]-quinoline | 2.71 Conditions 6 | 416.9 |
| 41 | 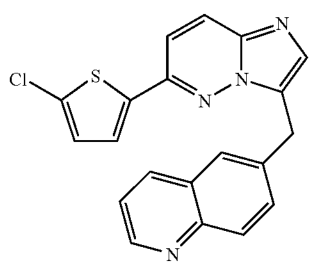 [SMILES: Clc1ccc(-c2ccc3ncc(Cc4ccc5ncccc5c4)n3n2)s1] | 6-[6-(5-Chloro-thiophen-2-yl)-imidazo[1,2-b]pyridazin-3-ylmethyl]-quinoline | 2.42 Conditions 6 | 376.9 |
| 42 | 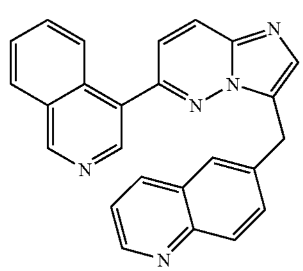 [SMILES: c1cnc2ccc(Cc3cnc4ccc(-c5cncc6ccccc56)nn34)cc2c1] | 6-(6-Isoquinolin-4-yl-imidazo[1,2-b]pyridazin-3-ylmethyl)-quinoline | 1.51/1.60 Conditions 6 | 387.9 |
| 43 | 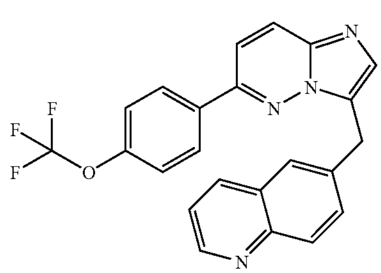 [SMILES: FC(F)(F)Oc1ccc(-c2ccc3ncc(Cc4ccc5ncccc5c4)n3n2)cc1] | 6-[6-(4-Trifluoromethoxy-phenyl)-imidazo[1,2-b]pyridazin-3-ylmethyl]-quinoline | 2.79 Conditions 6 | 420.9 |

| Ex | Structure | Name | t$_R$ (min) Conditions | MH+ |
|---|---|---|---|---|
| 44 | 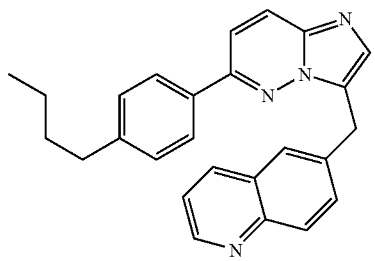 [SMILES: CCCCc1ccc(-c2ccc3ncc(Cc4ccc5ncccc5c4)n3n2)cc1] | 6-[6-(4-Butyl-phenyl)-imidazo[1,2-b]pyridazin-3-ylmethyl]-quinoline | 3.19 Conditions 6 | 393.0 |
| 45 | 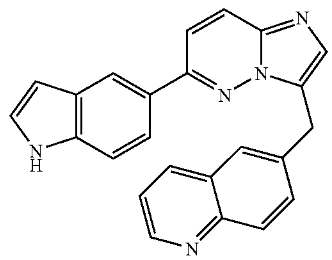 [SMILES: c1cnc2ccc(Cc3cnc4ccc(-c5ccc6[nH]ccc6c5)nn34)cc2c1] | 6-[6-(1H-Indol-5-yl)-imidazo[1,2-b]pyridazin-3-ylmethyl]-quinoline | 2.08 Conditions 6 | 376.0 |
| 46 | 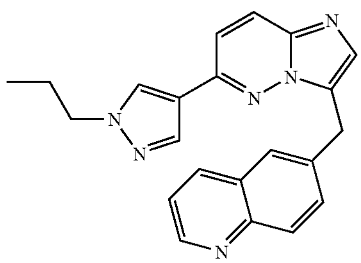 [SMILES: CCCn1cc(-c2ccc3ncc(Cc4ccc5ncccc5c4)n3n2)cn1] | 6-[6-(1-Propyl-1H-pyrazol-4-yl)-imidazo[1,2-b]pyridazin-3-ylmethyl]-quinoline | 1.93 Conditions 6 | 369.0 |
| 47 | 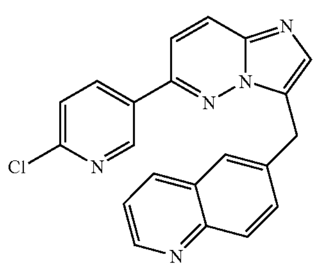 [SMILES: Clc1ccc(-c2ccc3ncc(Cc4ccc5ncccc5c4)n3n2)cn1] | 6-[6-(6-Chloro-pyridin-3-yl)-imidazo[1,2-b]pyridazin-3-ylmethyl]-quinoline | 1.96 Conditions 6 | 371.9 |
| 48 | 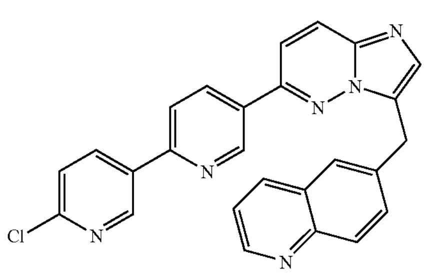 [SMILES: Clc1ccc(-c2ccc(-c3ccc4ncc(Cc5ccc6ncccc6c5)n4n3)cn2)cn1] | 6'-Chloro-5-(3-quinolin-6-ylmethyl-imidazo[1,2-b]pyridazin-6-yl)-[2,3']bipyridinyl | 2.40 Conditions 6 | 448.8 |

| Ex | Structure | Name | t_R (min) Conditions | MH+ |
|---|---|---|---|---|
| 49 | 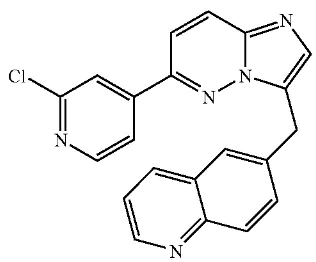 | 6-[6-(2-Chloro-pyridin-4-yl)-imidazo[1,2-b]pyridazin-3-ylmethyl]-quinoline | 1.92 Conditions 6 | 371.9 |
| 50 | 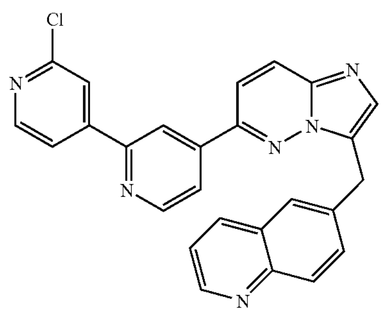 [SMILES: Clc1cc(-c2cc(-c3ccc4ncc(Cc5ccc6ncccc6c5)n4n3)ccn2)ccn1] | 2'-Chloro-4-(3-quinolin-6-ylmethyl-imidazo[1,2-b]pyridazin-6-yl)-[2,4']bipyridinyl | 2.42 Conditions 6 | 448.8 |
| 51 | 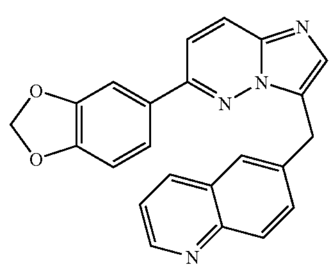 [SMILES: c1cnc2ccc(Cc3cnc4ccc(-c5ccc6c(c5)OCO6)nn34)cc2c1] | 6-(6-Benzo[1,3]dioxol-5-yl-imidazo[1,2-b]pyridazin-3-ylmethyl)-quinoline | 2.10 Conditions 6 | 380.9 |
| 52 | 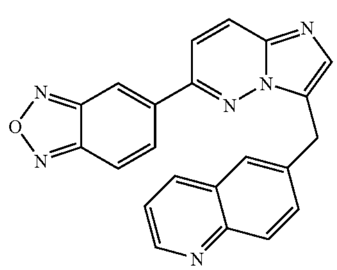 [SMILES: c1cnc2ccc(Cc3cnc4ccc(-c5ccc6nonc6c5)nn34)cc2c1] | 6-(6-Benzo[1,2,5]oxadiazol-5-yl-imidazo[1,2-b]pyridazin-3-ylmethyl)-quinoline | 6.31 Conditions 4 | 378.9 |
| 53 | 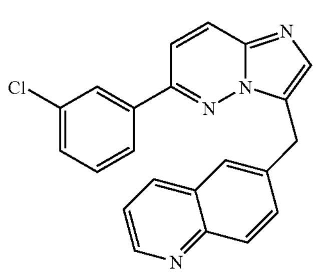 [SMILES: Clc1cccc(-c2ccc3ncc(Cc4ccc5ncccc5c4)n3n2)c1] | 6-[6-(3-Chloro-phenyl)-imidazo[1,2-b]pyridazin-3-ylmethyl]-quinoline | 2.40 Conditions 6 | 370.9 |

-continued

| Ex | Structure | Name | t_R (min) Conditions | MH+ |
|---|---|---|---|---|
| 54 | 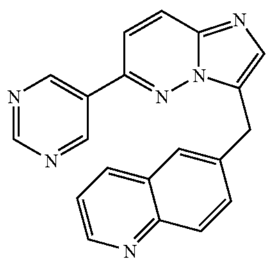 [SMILES: c1cnc2ccc(Cc3cnc4ccc(-c5cncnc5)nn34)cc2c1] | 6-(6-Pyrimidin-5-yl-imidazo[1,2-b]pyridazin-3-ylmethyl)-quinoline | 4.03 Conditions 4 | 339.1 |
| 55 | 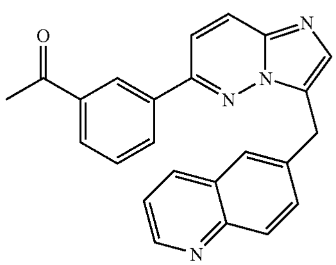 [SMILES: CC(=O)c1cccc(-c2ccc3ncc(Cc4ccc5ncccc5c4)n3n2)c1] | 1-[3-(3-Quinolin-6-ylmethyl-imidazo[1,2-b]pyridazin-6-yl)-phenyl]-ethanone | 5.39 Conditions 4 | 379.3 |
| 56 | 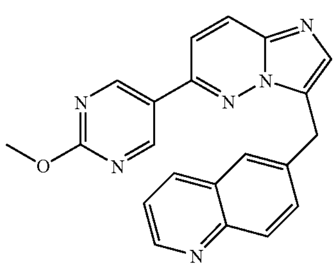 [SMILES: COc1ncc(-c2ccc3ncc(Cc4ccc5ncccc5c4)n3n2)cn1] | 6-[6-(2-Methoxy-pyrimidin-5-yl)-imidazo[1,2-b]pyridazin-3-ylmethyl]-quinoline | 4.55 Conditions 4 | 369.4 |
| 57 | 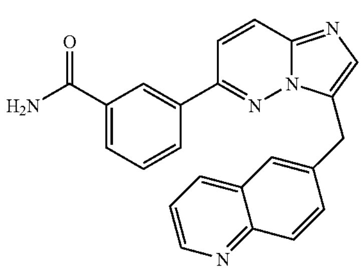 [SMILES: NC(=O)c1cccc(-c2ccc3ncc(Cc4ccc5ncccc5c4)n3n2)c1] | 3-(3-Quinolin-6-ylmethyl-imidazo[1,2-b]pyridazin-6-yl)-benzamide | 4.06 Conditions 4 | 380.3 |
| 58 | 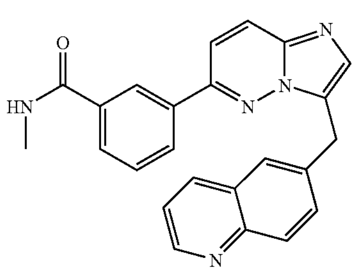 [SMILES: CNC(=O)c1cccc(-c2ccc3ncc(Cc4ccc5ncccc5c4)n3n2)c1] | N-Methyl-3-(3-quinolin-6-ylmethyl-imidazo[1,2-b]pyridazin-6-yl)-benzamide | 1.72 Conditions 6 | 394.0 |

| Ex | Structure | Name | t$_R$ (min) Conditions | MH+ |
|---|---|---|---|---|
| 59 | 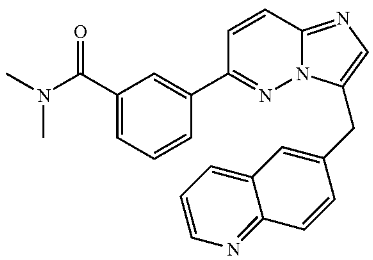 [SMILES: CN(C)C(=O)c1cccc(-c2ccc3ncc(Cc4ccc5ncccc5c4)n3n2)c1] | N,N-Dimethyl-3-(3-quinolin-6-6-ylmethyl-imidazo[1,2-b]pyridazin-6-yl)-benzamide | 1.81 Conditions 6 | 408.0 |
| 60 | 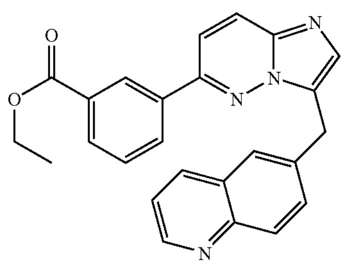 [SMILES: CCOC(=O)c1cccc(-c2ccc3ncc(Cc4ccc5ncccc5c4)n3n2)c1] | 3-(3-Quinolin-6-ylmethyl-imidazo[1,2-b]pyridazin-6-yl)-benzoic acid ethyl ester | 2.53 Conditions 6 | 409.0 |
| 61 | 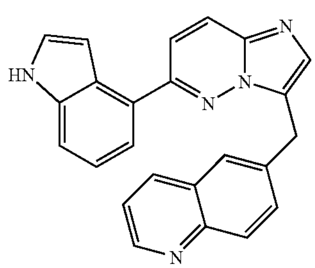 [SMILES: c1cnc2ccc(Cc3cnc4ccc(-c5cccc6[nH]ccc56)nn34)cc2c1] | 6-[6-(1H-Indol-4-yl)-imidazo[1,2-b]pyridazin-3-ylmethyl]-quinoline | 2.01 Conditions 6 | 376.0 |
| 62 | 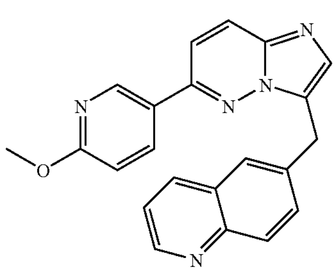 | 6-[6-(6-Methoxy-pyridin-3-yl)-imidazo[1,2-b]pyridazin-3-ylmethyl]-quinoline | 1.96 Conditions 6 | 368.1 |
| 63 | 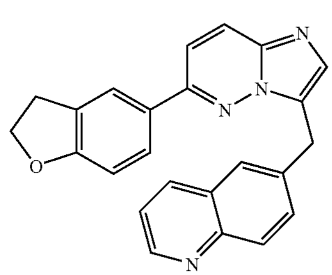 | 6-[6-(2,3-Dihydro-benzofuran-5-yl)-imidazo[1,2-b]pyridazin-3-ylmethyl]-quinoline | 2.22 Conditions 6 | 379.0 |
| 64 | 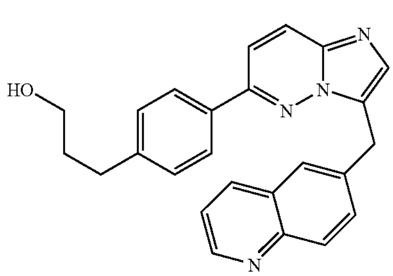 [SMILES: OCCCc1ccc(-c2ccc3ncc(Cc4ccc5ncccc5c4)n3n2)cc1] | 3-[4-(3-Quinolin-6-ylmethyl-imidazo[1,2-b]pyridazin-6-yl)-phenyl]-propan-1-ol | 2.00 Conditions 6 | 395.0 |

-continued

| Ex | Structure | Name | t_R (min) Conditions | MH+ |
|---|---|---|---|---|
| 65 | 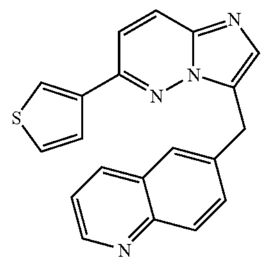 [SMILES: c1cnc2ccc(Cc3cnc4ccc(-c5ccsc5)nn34)cc2c1] | 6-(6-Thiophen-3-yl-imidazo[1,2-b]pyridazin-3-ylmethyl)-quinoline | 2.01 Conditions 6 | 343.0 |
| 66 | 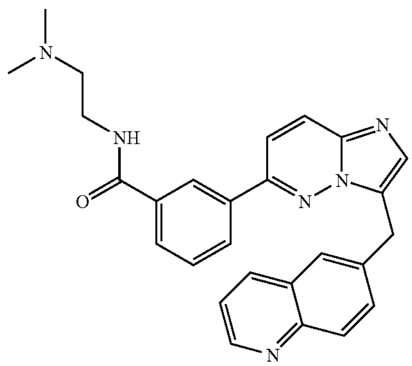 [SMILES: CN(C)CCNC(=O)c1cccc(-c2ccc3ncc(Cc4ccc5ncccc5c4)n3n2)c1] | N-(2-Dimethylamino-ethyl)-3-(3-quinolin-6-ylmethyl-imidazo[1,2-b]pyridazin-6-yl)-benzamide | 1.48 Conditions 6 | 451.1 |
| 67 | 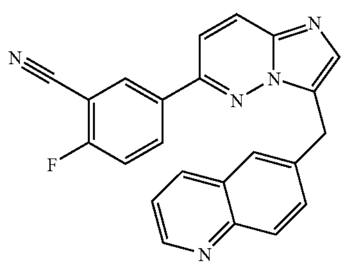 [SMILES: N#Cc1cc(-c2ccc3ncc(Cc4ccc5ncccc5c4)n3n2)ccc1F] | 2-Fluoro-5-(3-quinolin-6-ylmethyl-imidazo[1,2-b]pyridazin-6-yl)-benzonitrile | 2.21 Conditions 6 | 380.1 |
| 68 | 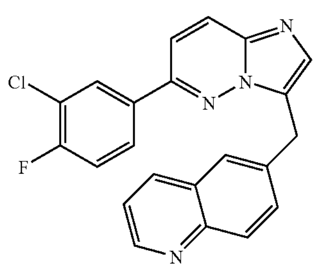 [SMILES: Fc1ccc(-c2ccc3ncc(Cc4ccc5ncccc5c4)n3n2)cc1Cl] | 6-[6-(3-Chloro-4-fluoro-phenyl)-imidazo[1,2-b]pyridazin-3-ylmethyl]-quinoline | 2.54 Conditions 6 | 389.0 |
| 69 | 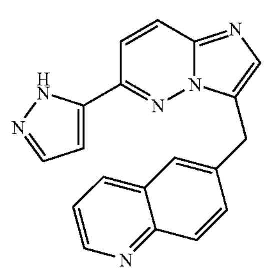 [SMILES: c1cnc2ccc(Cc3cnc4ccc(-c5ccn[nH]5)nn34)cc2c1] | 6-[6-(2H-Pyrazol-3-yl)-imidazo[1,2-b]pyridazin-3-ylmethyl]-quinoline | 1.39/1.51 Conditions 6 | 327.1 |

| Ex | Structure | Name | $t_R$ (min) Conditions | MH+ |
|---|---|---|---|---|
| 70 | 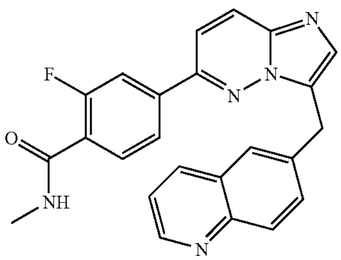 [SMILES: CNC(=O)c1ccc(-c2ccc3ncc(Cc4ccc5ncccc5c4)n3n2)cc1F] | 2-Fluoro-N-methyl-4-(3-quinolin-6-ylmethyl-imidazo[1,2-b]pyridazin-6-yl)-benzamide | 1.76 Conditions 6 | 412.3 |
| 71 | 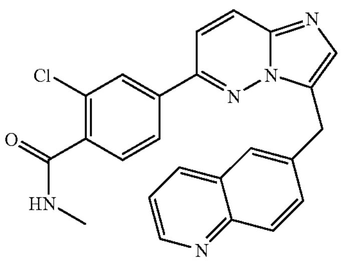 [SMILES: CNC(=O)c1ccc(-c2ccc3ncc(Cc4ccc5ncccc5c4)n3n2)cc1Cl] | 2-Chloro-N-methyl-4-(3-quinolin-6-ylmethyl-imidazo[1,2-b]pyridazin-6-yl)-benzamide | 1.73 Conditions 6 | 428.3 |

EXAMPLE 72

3-(3-Quinolin-6-ylmethyl-imidazo[1,2-b]pyridazin-6-yl)-benzoic acid

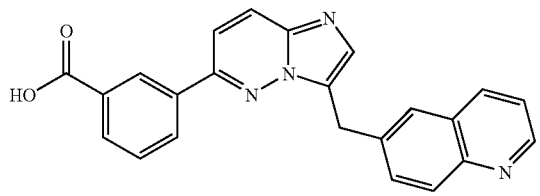 [SMILES: O=C(O)c1cccc(-c2ccc3ncc(Cc4ccc5ncccc5c4)n3n2)c1]

The title compound was prepared in analogy to the compound of Example 15 starting with 3-(4,4,5,5-Tetramethyl-[1,3,2]dioxaborolan-2-yl)-benzoic acid ethyl ester, using PdCl$_2$(dppf)/CH$_2$Cl$_2$ (1/1) as catalyst and with an additional ester deprotection step afterwards ($t_R$ 3.14 min (conditions 11), MH+=380.9).

EXAMPLE 73

5-(3-Quinolin-6-ylmethyl-imidazo[1,2-b]pyridazin-6-yl)-pyridin-2-ol

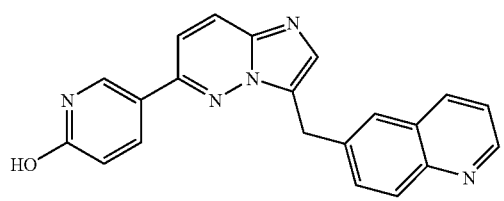 [SMILES: Oc1ccc(-c2ccc3ncc(Cc4ccc5ncccc5c4)n3n2)cn1]

Boron tribromide (1364 mg, 5.44 mmol) was added to a suspension of 6-[6-(6-Methoxypyridin-3-yl)-imidazo[1,2-b]pyridazin-3-ylmethyl]-quinoline (Example 62, 200 mg, 0.544 mmol) in DCM (5 mL) at −78° C. The RM was stirred at −78° C. for 15 min and then allowed to reach rt. It was then stirred at rt for 68 h. The RM was filtered and the obtained solid was purified by reverse phase chromatography (water 0.1% TFA/acetonitrile +0.1% TFA). The resulting oil precipitated in TBME/MeOH to afford the title compound as a white powder ($t_R$ 4.21 min (conditions 4), MH+=354.3, $^1$H-NMR in DMSO-d6: 9.00 (m, 1H); 8.58 (m, 1H); 8.31 (m, 2H); 8.19 (dd, 1H); 8.05 (m, 4H); 7.92 (dd, 1H); 7.70 (dd, 1H); 6.54 (d, 1H); 4.65 (s, 2H)).

EXAMPLE 74

6-Chloro-3-imidazo[1,2-a]pyridin-6-ylmethyl-imidazo[1,2-b]pyridazine

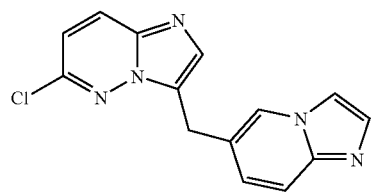 [SMILES: Clc1ccc2ncc(Cc3ccc4nccn4c3)n2n1]

The title compound was prepared in analogy to the compound of Stage 14 using compound of Stage 9.1 as starting material ($t_R$ 4.62 min (conditions 4), MH+=284.1, $^1$H-NMR in DMSO-d6: 8.42 (s, 1H); 8.23 (d, 1H); 7.90 (s, 1H); 7.72 (s, 1H); 7.52 (m, 2H); 7.36 (d, 1H); 7.20 (dd, 1H); 4.32 (s, 2H)).

EXAMPLE 75

2-(3-Imidazo[1,2-a]pyridin-6-ylmethyl-imidazo[1,2-b]pyridazin-6-ylamino)-ethanol

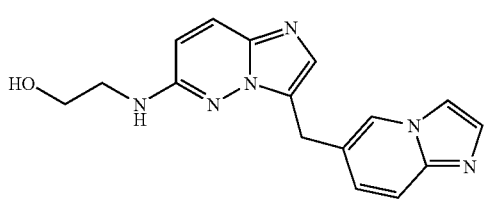 [SMILES: OCCNc1ccc2ncc(Cc3ccc4nccn4c3)n2n1]

Ethanolamine (277 µL, 4.55 mmol) was added to a solution of (6-Chloro-3-imidazo[1,2-a]pyridin-6-ylmethyl-imidazo[1,2-b]pyridazine (Example 74, 65 mg, 0.228 mmol) and KF (67 mg, 1.138 mmol) in NMP (1.5 mL). The RM was stirred at 180° C. for 2 h. The mixture was diluted with EtOAc and washed with 1 M Na$_2$CO$_3$ (1×) and water (3×). The aqueous layer was extracted with EtOAc (×2). The combined organic layer was dried over Na$_2$SO$_4$, filtered and concentrated. The aqueous phase was further extracted with DCM (4×). The organic layer was then dried over Na$_2$SO$_4$, filtered and concentrated. The combined residues were purified by preparative LCMS to afford the title compound as a yellow oil (t$_R$ 2.62 min (conditions 4), MH+=309.1, $^1$H-NMR in DMSO-d6: 8.84 (s, 1H); 8.28 (d, 1H); 8.16 (d, 1H); 7.95 (m, 3H); 7.86 (s, 1H); 7.72 (m, 1H); 7.16 (d, 1H); 4.40 (s, 2H); 3.52 (t, 2H); 3.32 (m, 2H)).

EXAMPLE 76

[(R)-1-(3-Imidazo[1,2-a]pyridin-6-ylmethyl-imidazo[1,2-b]pyridazin-6-yl)-pyrrolidin-3-yl]-dimethyl-amine

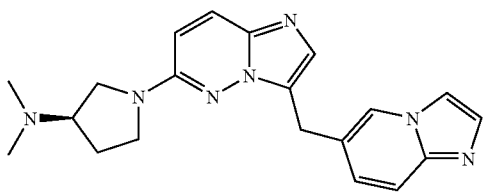 [SMILES: CN(C)[C@@H]1CCN(c2ccc3ncc(Cc4ccc5nccn5c4)n3n2)C1]

The title compound was prepared in analogy to the compound of Example 75 using dimethyl(R)-pyrrolidin-3-yl-amine as starting material (t$_R$ 0.93 min (conditions 7), MH+=362.1, $^1$H-NMR in DMSO-d6: 8.48 (s, 1H); 7.86 (s, 1H); 7.76 (d, 1H); 7.52 (s, 1H); 7.46 (d, 1H); 7.37 (s, 1H); 7.19 (d, 1H); 6.78 (d, 1H); 4.17 (s, 2H); 3.63 (m, 2H); 3.35 (m, 1H); 3.16 (m, 1H); 2.78 (m, 1H); 2.18 (m, 7H); 1.81 (m, 1H)).

EXAMPLE 77

(rac)-(6-Isobutylamino-imidazo[1,2-b]pyridazin-3-yl)-quinolin-6-yl-methanol

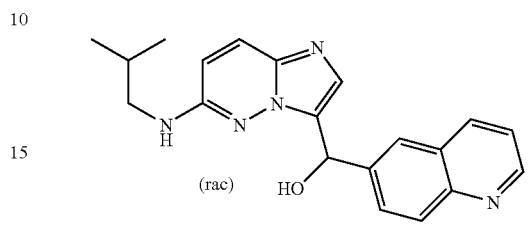

(rac)-(6-chloro-imidazo[1,2-b]pyridazin-3-yl)-quinolin-6-yl-methanol (Stage 1.1, 80 mg, 0.257 mmol) and KF (30 mg, 0.515 mmol) were suspended in NMP (2 mL). Isobutylamine (129 µL, 1.287 mmol) was then added and the RM was stirred at 160° C. for 7 h. The mixture was diluted with TBME and washed with water (3×). The aqueous layer was then extracted with TBME (3×). The combined layers were dried over Na$_2$SO$_4$, filtered and concentrated. The residue was purified by flash chromatography (Flashmaster) to afford the title compound as a yellow foam (t$_R$ 4.11 min (conditions 4), MH+=348.0, $^1$H-NMR in DMSO-d6: 8.86 (m, 1H); 8.32 (m, 1H); 8.02 (m, 1H); 7.94 (d, 1H); 7.80 (m, 1H); 7.61 (d, 1H); 7.51 (dd, 1H); 7.31 (s, 1H); 6.88 (t, 1Ht); 6.61 (d, 1H); 6.24 (m, 1H); 6.12 (d, 1H); 2.98 (m, 2H); 1.82 (m, 1H); 0.86 (m, 6H)).

EXAMPLE 78 sec-Butyl-(3-quinolin-6-ylmethyl-imidazo[1,2-b]pyridazin-6-yl)-amine

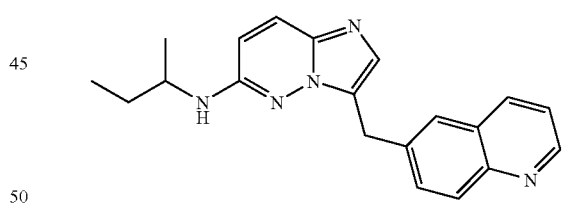

6-(6-Chloro-imidazo[1,2-b]pyridazin-3-ylmethyl)-quinoline (Example 14, 70 mg, 0.237 mmol), KF (70 mg, 1.187 mmol) and sec-butylamine (484 µL, 4.75 mmol) were suspended in NMP (1 mL). The RM was stirred at 180° C. for 29 h. The mixture was diluted with EtOAc and washed with 1 M Na$_2$CO$_3$ (×1) and water (×2). The aqueous was further extracted with EtOAc (2×). The combined organic layer was dried over Na$_2$SO$_4$, filtered and concentrated. The residue was purified by flash chromatography (Flashmaster) and then crystallized in Et$_2$O to afford the title compound as a beige solid (t$_R$ 4.28 min (conditions 4), MH+ 332.3, $^1$H-NMR in DMSO-d6: 8.83 (m, 1H); 8.25 (m, 1H); 7.92 (d, 1H); 7.83 (m, 1H); 7.70 (m, 1H); 7.61 (d, 1H); 7.48 (dd, 1H); 7.32 (s, 1H); 6.66 (d, 1H); 6.56 (d, 1H); 4.34 (s, 2H); 3.70 (m, 1H); 1.46 (m, 2H); 1.07 (d, 3H); 0.80 (t, 3H)).

EXAMPLE 79-118

The following compounds are prepared according to the procedure of Example 78 starting with the appropriate amine, imidazole, phenol or thiol.

| EX | Structure | Name | $t_R$ (min) Conditions | MH+ |
|---|---|---|---|---|
| 79 | 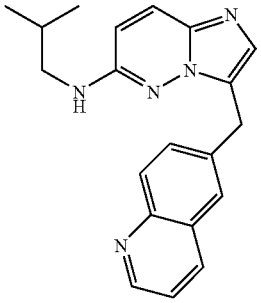 [SMILES: CC(C)CNc1ccc2ncc(Cc3ccc4ncccc4c3)n2n1] | Isobutyl-(3-quinolin-6-ylmethyl-imidazo[1,2-b]pyridazin-6-yl)-amine | 4.47 Conditions 4 | 332.0 |
| 80 | 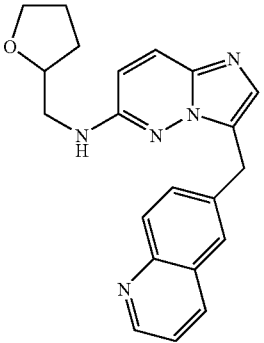 [SMILES: c1cnc2ccc(Cc3cnc4ccc(NCC5CCCO5)nn34)cc2c1] | (3-Quinolin-6-ylmethyl-imidazo[1,2-b]pyridazin-6-yl)-(tetrahydro-furan-2-ylmethyl)-amine | 3.63 Conditions 4 | 360.3 |
| 81 | 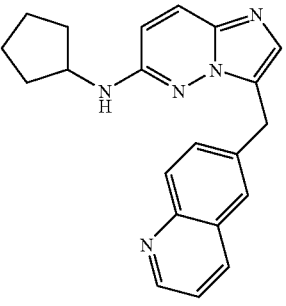 [SMILES: c1cnc2ccc(Cc3cnc4ccc(NC5CCCC5)nn34)cc2c1] | Cyclopentyl-(3-quinolin-6-ylmethyl-imidazo[1,2-b]pyridazin-6-yl)-amine | 4.45 Conditions 4 | 344.2 |
| 82 | 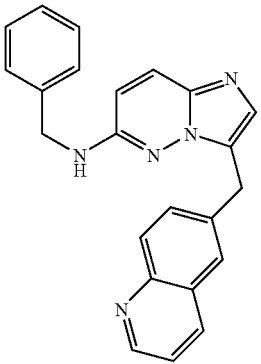 [SMILES: c1ccc(CNc2ccc3ncc(Cc4ccc5ncccc5c4)n3n2)cc1] | Benzyl-(3-quinolin-6-ylmethyl-imidazo[1,2-b]pyridazin-6-yl)-amine | 4.24 Conditions 4 | 366.2 |

| EX | Structure | Name | t_R (min) Conditions | MH+ |
|---|---|---|---|---|
| 83 | 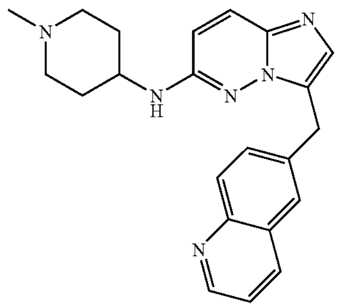 [SMILES: CN1CCC(Nc2ccc3ncc(Cc4ccc5ncccc5c4)n3n2)CC1] | (1-Methyl-piperidin-4-yl)-(3-quinolin-6-ylmethyl-imidazo[1,2-b]pyridazin-6-yl)-amine | 3.12 Conditions 4 | 373.3 |
| 84 | 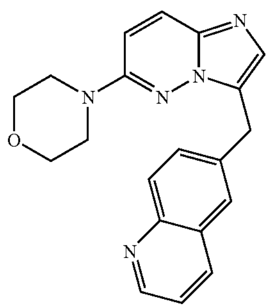 [SMILES: c1cnc2ccc(Cc3cnc4ccc(N5CCOCC5)nn34)cc2c1] | 6-(6-Morpholin-4-yl-imidazo[1,2-b]pyridazin-3-ylmethyl)-quinoline | 3.42 Conditions 4 | 346.2 |
| 85 | 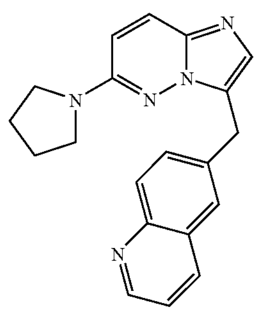 [SMILES: c1cnc2ccc(Cc3cnc4ccc(N5CCCC5)nn34)cc2c1] | 6-(6-Pyrrolidin-1-yl-imidazo[1,2-b]pyridazin-3-ylmethyl)-quinoline | 4.10 Conditions 4 | 330.2 |
| 86 | 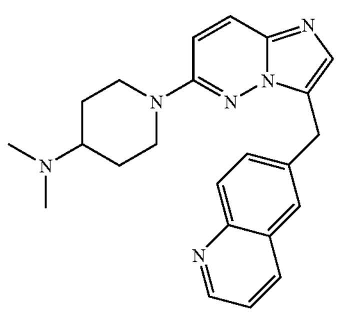 [SMILES: CN(C)C1CCN(c2ccc3ncc(Cc4ccc5ncccc5c4)n3n2)CC1] | Dimethyl-[1-(3-quinolin-6-ylmethyl-imidazo[1,2-b]pyridazin-6-yl)-piperidin-4-yl]-amine | 2.78 Conditions 4 | 387.4 |
| 87 | 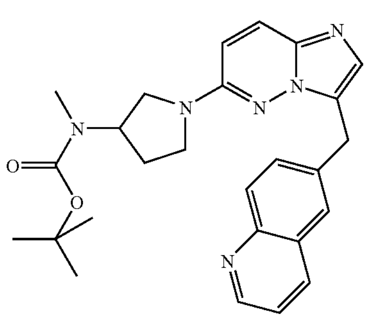 [SMILES: CN(C(=O)OC(C)(C)C)C1CCN(c2ccc3ncc(Cc4ccc5ncccc5c4)n3n2)C1] | Methyl-[1-(3-quinolin-6-ylmethyl-imidazo[1,2-b]pyridazin-6-yl)-pyrrolidin-3-yl]-carbamic acid tert-butyl ester | 5.08 Conditions 4 | 459.5 |

| EX | Structure | Name | $t_R$ (min) Conditions | MH+ |
|---|---|---|---|---|
| 88 | 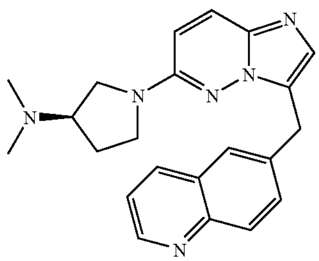 [SMILES: CN(C)[C@@H]1CCN(c2ccc3ncc(Cc4ccc5ncccc5c4)n3n2)C1] | Dimethyl-[(R)-1-(3-quinolin-6-ylmethyl-imidazo[1,2-b]pyridazin-6-yl)-pyrrolidin-3-yl]-amine | 3.09 Conditions 4 | 373.3 |
| 89 | 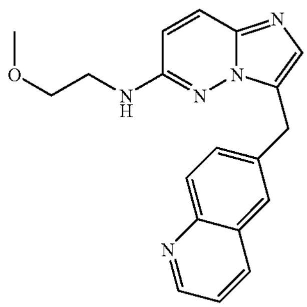 [SMILES: COCCNc1ccc2ncc(Cc3ccc4ncccc4c3)n2n1] | (2-Methoxy-ethyl)-(3-quinolin-6-ylmethyl-imidazo[1,2-b]pyridazin-6-yl)-amine | 3.52 Conditions 4 | 334.2 |
| 90 | 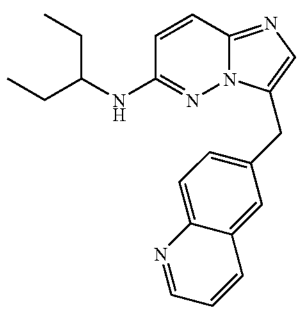 [SMILES: CCC(CC)Nc1ccc2ncc(Cc3ccc4ncccc4c3)n2n1] | (1-Ethyl-propyl)-(3-quinolin-6-ylmethyl-imidazo[1,2-b]pyridazin-6-yl)-amine | 4.79 Conditions 4 | 346.2 |
| 91 | 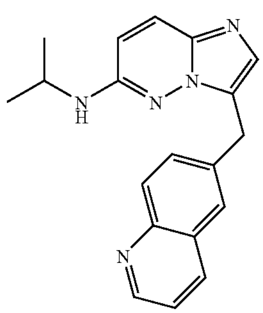 [SMILES: CC(C)Nc1ccc2ncc(Cc3ccc4ncccc4c3)n2n1] | Isopropyl-(3-quinolin-6-ylmethyl-imidazo[1,2-b]pyridazin-6-yl)-amine | 4.09 Conditions 4 | 318.2 |
| 92 | 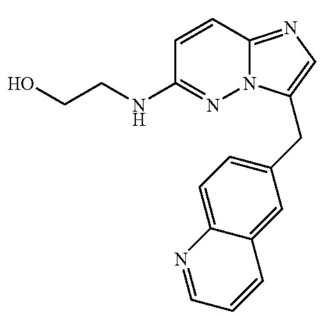 [SMILES: OCCNc1ccc2ncc(Cc3ccc4ncccc4c3)n2n1] | 2-(3-Quinolin-6-ylmethyl-imidazo[1,2-b]pyridazin-6-ylamino)-ethanol | 3.03 Conditions 4 | 320.1 |

| EX | Structure | Name | t_R (min) Conditions | MH+ |
|---|---|---|---|---|
| 93 | 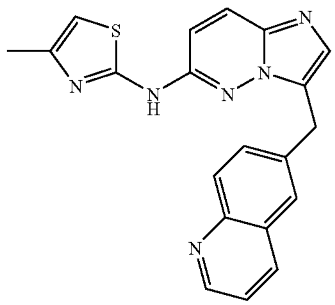 [SMILES: Cc1csc(Nc2ccc3ncc(Cc4ccc5ncccc5c4)n3n2)n1] | 4-Methyl-thiazol-2-yl)-(3-quinolin-6-ylmethyl-imidazo[1,2-b]pyridazin-6-yl)-amine | 4.49 Conditions 4 | 373.1 |
| 94 | 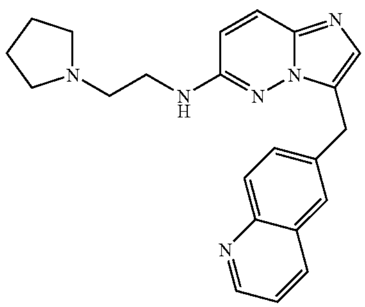 [SMILES: c1cnc2ccc(Cc3cnc4ccc(NCCN5CCCC5)nn34)cc2c1] | (2-Pyrrolidin-1-yl-ethyl)-(3-quinolin-6-ylmethyl-imidazo[1,2-b]pyridazin-6-yl)-amine | 3.26 Conditions 4 | 373.4 |
| 95 | 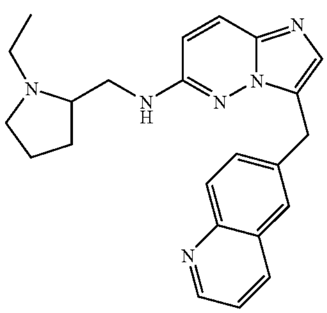 [SMILES: CCN1CCCC1CNc1ccc2ncc(Cc3ccc4ncccc4c3)n2n1] | (1-Ethyl-pyrrolidin-2-ylmethyl)-(3-quinolin-6-ylmethyl-imidazo[1,2-b]pyridazin-6-yl)-amine | 3.29 Conditions 4 | 387.4 |
| 96 | 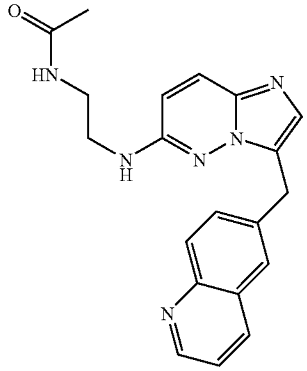 [SMILES: CC(=O)NCCNc1ccc2ncc(Cc3ccc4ncccc4c3)n2n1] | N-[2-(3-Quinolin-6-ylmethyl-imidazo[1,2-b]pyridazin-6-ylamino)-ethyl]-acetamide | 3.05 Conditions 4 | 361.2 |

| EX | Structure | Name | t_R (min) Conditions | MH+ |
|---|---|---|---|---|
| 97 | 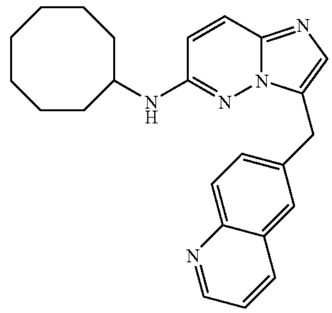 [SMILES: c1cnc2ccc(Cc3cnc4ccc(NC5CCCCCCC5)nn34)cc2c1] | Cyclooctyl-(3-quinolin-6-ylmethyl-imidazo[1,2-b]pyridazin-6-yl)-amine | 5.73 Conditions 4 | 386.4 |
| 98 | 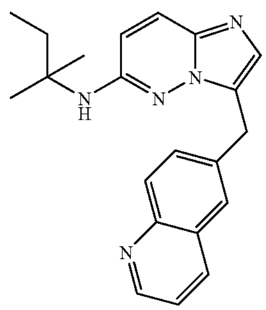 [SMILES: CCC(C)(C)Nc1ccc2ncc(Cc3ccc4ncccc4c3)n2n1] | (1,1-Dimethyl-propyl)-(3-quinolin-6-ylmethyl-imidazo[1,2-b]pyridazin-6-yl)-amine | 4.67 Conditions 4 | 346.2 |
| 99 | 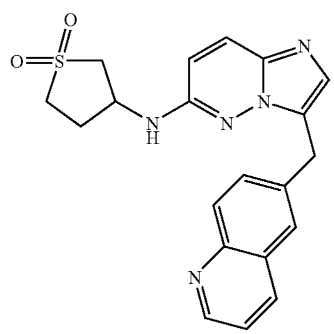 [SMILES: O=S1(=O)CCC(Nc2ccc3ncc(Cc4ccc5ncccc5c4)n3n2)C1] | 1,1-Dioxo-tetrahydro-1lambda*6*-thiophen-3-yl)-(3-quinolin-6-ylmethyl-imidazo[1,2-b]pyridazin-6-yl)-amine | 3.10 Conditions 4 | 394.2 |
| 100 | 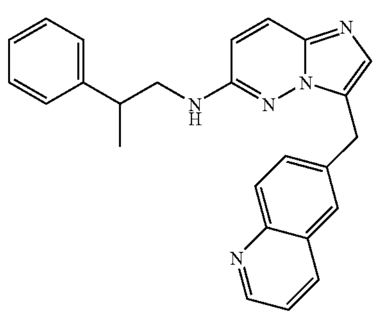 [SMILES: CC(CNc1ccc2ncc(Cc3ccc4ncccc4c3)n2n1)c1ccccc1] | (2-Phenyl-propyl)-(3-quinolin-6-ylmethyl-imidazo[1,2-b]pyridazin-6-yl)-amine | 5.08 Conditions 4 | 394.4 |
| 101 | 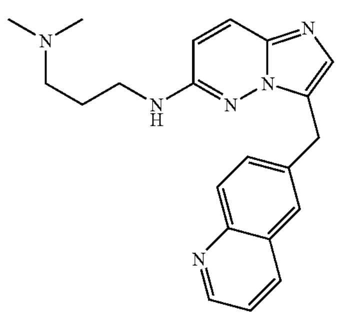 [SMILES: CN(C)CCCNc1ccc2ncc(Cc3ccc4ncccc4c3)n2n1] | N,N-Dimethyl-N'-(3-quinolin-6-ylmethyl-imidazo[1,2-b]pyridazin-6-yl)-propane-1,3-diamine | 3.08/3.23 Conditions 4 | 361.3 |

| EX | Structure | Name | t_R (min) Conditions | MH+ |
|---|---|---|---|---|
| 102 | 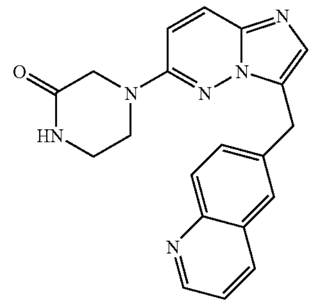 [SMILES: O=C1CN(c2ccc3ncc(Cc4ccc5ncccc5c4)n3n2)CCN1] | 4-(3-Quinolin-6-ylmethyl-imidazo[1,2-b]pyridazin-6-yl)-piperazin-2-one | 3.43 Conditions 4 | 359.2 |
| 103 | 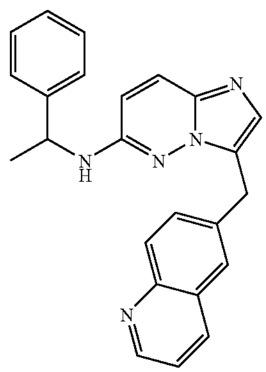 [SMILES: CC(Nc1ccc2ncc(Cc3ccc4ncccc4c3)n2n1)c1ccccc1] | (1-Phenyl-ethyl)-(3-quinolin-6-ylmethyl-imidazo[1,2-b]pyridazin-6-yl)-amine | 4.66 Conditions 4 | 380.4 |
| 104 | 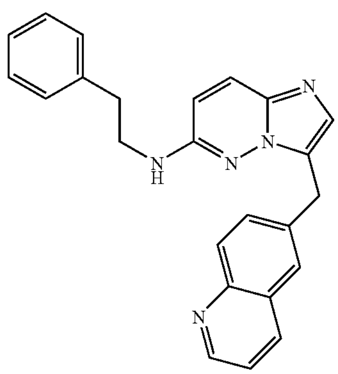 [SMILES: c1ccc(CCNc2ccc3ncc(Cc4ccc5ncccc5c4)n3n2)cc1] | Phenethyl-(3-quinolin-6-ylmethyl-imidazo[1,2-b]pyridazin-6-yl)-amine | 4.77 Conditions 4 | 380.3 |
| 105 | 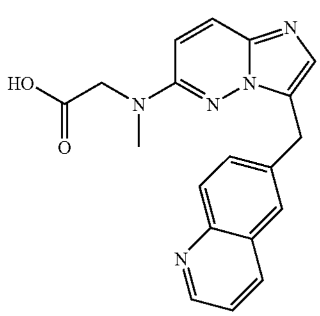 [SMILES: CN(CC(=O)O)c1ccc2ncc(Cc3ccc4ncccc4c3)n2n1] | [Methyl-(3-quinolin-6-ylmethyl-imidazo[1,2-b]pyridazin-6-yl)-amino[-acetic acid | 3.44 Conditions 4 | 348.1 |

-continued

| EX | Structure | Name | t_R (min) Conditions | MH+ |
|---|---|---|---|---|
| 106 | 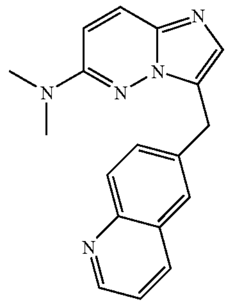 [SMILES: CN(C)c1ccc2ncc(Cc3ccc4ncccc4c3)n2n1] | Dimethyl-(3-quinolin-6-ylmethyl-imidazo[1,2-b]pyridazin-6-yl)-amine | 3.69 Conditions 4 | 304.2 |
| 107 | 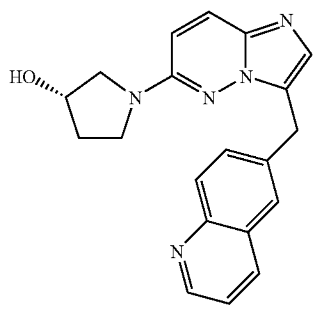 [SMILES: O[C@H]1CCN(c2ccc3ncc(Cc4ccc5ncccc5c4)n3n2)C1] | (S)-1-(3-Quinolin-6-ylmethyl-imidazo[1,2-b]pyridazin-6-yl)-pyrrolidin-3-ol | 3.60 Conditions 4 | 346.2 |
| 108 | 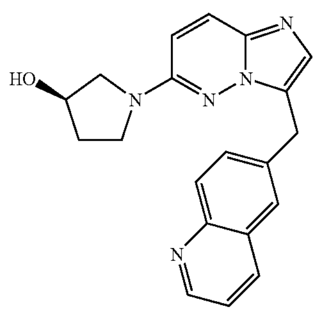 [SMILES: O[C@@H]1CCN(c2ccc3ncc(Cc4ccc5ncccc5c4)n3n2)C1] | (R)-1-(3-Quinolin-6-ylmethyl-imidazo[1,2-b]pyridazin-6-yl)-pyrrolidin-3-ol | 4.65/4.71 Conditions 4 | 346.2 |
| 109 | 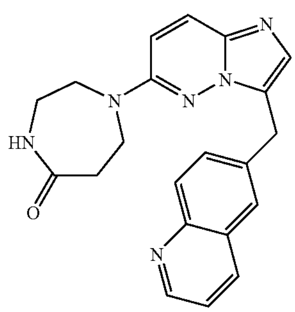 [SMILES: O=C1CCN(c2ccc3ncc(Cc4ccc5ncccc5c4)n3n2)CCN1] | 1-(3-Quinolin-6-ylmethyl-imidazo[1,2-b]pyridazin-6-yl)-[1,4]diazepan-5-one | 4.59 Conditions 4 | 373.4 |
| 110 | 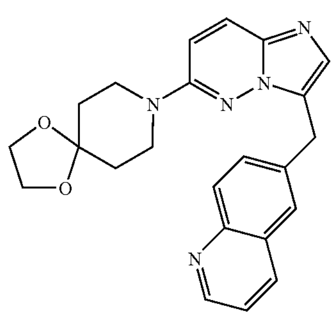 [SMILES: c1cnc2ccc(Cc3cnc4ccc(N5CCC6(CC5)OCCO6)nn34)cc2c1] | 6-[6-(1,4-Dioxa-8-aza-spiro[4.5]dec-8-yl)-imidazo[1,2-b]pyridazin-3-ylmethyl]-quinoline | 1.86 Conditions 6 | 402.0 |

| EX | Structure | Name | t$_R$ (min) Conditions | MH+ |
|---|---|---|---|---|
| 111 | 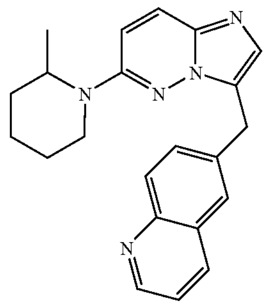 [SMILES: CC1CCCCN1c1ccc2ncc(Cc3ccc4ncccc4c3)n2n1] | 6-[6-(2-Methyl-piperidin-1-yl)-imidazo[1,2-b]pyridazin-3-ylmethyl]-quinoline | 2.29 Conditions 6 | 358.2 |
| 112 | 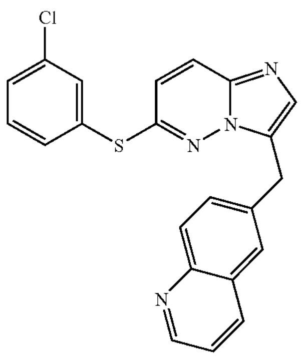 [SMILES: Clc1cccc(Sc2ccc3ncc(Cc4ccc5ncccc5c4)n3n2)c1] | 6-[6-(3-Chloro-phenylsulfanyl)-imidazo[1,2-b]pyridazin-3-ylmethyl]-quinoline | 6.95 Method 4 | 403.1 |
| 113 | 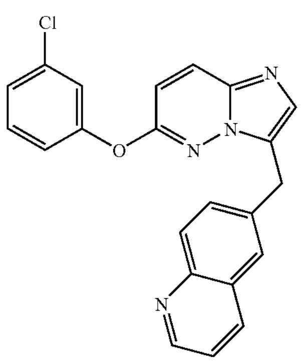 [SMILES: Clc1cccc(Oc2ccc3ncc(Cc4ccc5ncccc5c4)n3n2)c1] | 6-[6-(3-Chloro-phenoxy)-imidazo[1,2-b]pyridazin-3-ylmethyl]-quinoline | 6.34 Conditions 4 | 387.1 |
| 114 | 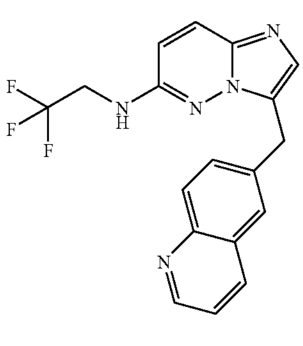 [SMILES: FC(F)(F)CNc1ccc2ncc(Cc3ccc4ncccc4c3)n2n1] | (3-Quinolin-6-ylmethyl-imidazo[1,2-b]pyridazin-6-yl)-(2,2,2-trifluoro-ethyl)-amine | 3.82 Conditions 4 | 358.3 |

| EX | Structure | Name | t_R (min) Conditions | MH+ |
|---|---|---|---|---|
| 115 | 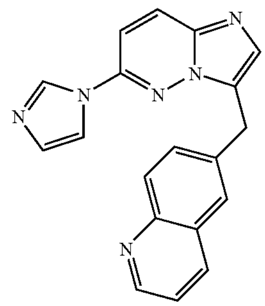 [SMILES: c1cnc2ccc(Cc3cnc4ccc(-n5ccnc5)nn34)cc2c1] | 6-(6-Imidazol-1-yl-imidazo[1,2-b]pyridazin-3-ylmethyl)-quinoline | 3.66 Conditions 4 | 327.1 |
| 116 | 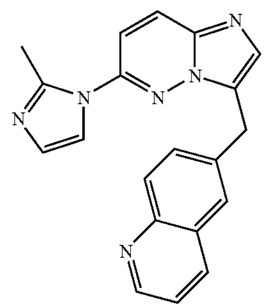 [SMILES: Cc1nccn1-c1ccc2ncc(Cc3ccc4ncccc4c3)n2n1] | 6-[6-(2-Methyl-imidazol-1-yl)-imidazo[1,2-b]pyridazin-3-ylmethyl]-quinoline | 3.10 Conditions 4 | 341.4 |
| 117 | 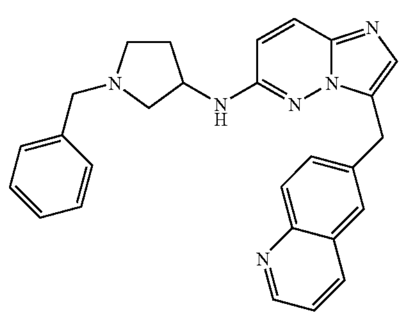 [SMILES: c1ccc(CN2CCC(Nc3ccc4ncc(Cc5ccc6ncccc6c5)n4n3)C2)cc1] | (1-Benzyl-pyrrolidin-3-yl)-(3-quinolin-6-ylmethyl-imidazo[1,2-b]pyridazin-6-yl)-amine | 3.56 Conditions 4 | 435.4 |
| 118 | 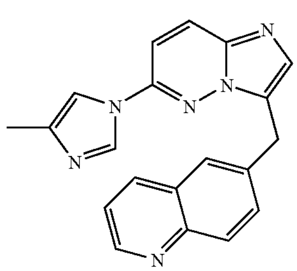 [SMILES: Cc1cn(-c2ccc3ncc(Cc4ccc5ncccc5c4)n3n2)cn1] | 6-[6-(4-Methyl-imidazol-1-yl)-imidazo[1,2-b]pyridazin-3-ylmethyl]-quinoline | 1.18/1.29 Conditions 6 | 341.4 |

EXAMPLE 119

(rac)-Methyl-[1-(3-quinolin-6-yl methyl-imidazo[1,2-b]pyridazin-6-yl)-pyrrolidin-3-yl]-amine

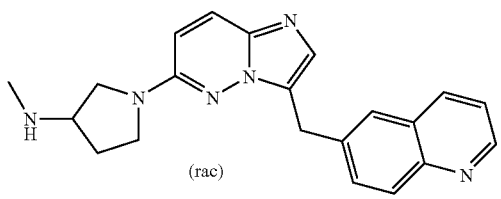 [SMILES: CNC1CCN(c2ccc3ncc(Cc4ccc5ncccc5c4)n3n2)C1]

(rac)

(rac)-Methyl-[1-(3-quinolin-6-ylmethyl-imidazo[1,2-b]pyridazin-6-yl)-pyrrolidin-3-yl]-carbamic acid tert-butyl ester (Example 87, 105 mg, 0.231 mmol) was dissolved in DCM (5 mL) and TFA (2 mL). The RM was stirred at rt for 1.5 h. A basic work up (1 M $Na_2CO_3$) followed by a crystallization in $Et_2O$ afforded the title compound as white crystals ($t_R$ 2.46 min (conditions 4), MH+=359.2, $^1$H-NMR in DMSO-d6: 8.83 (m, 1H); 8.28 (d, 1H); 7.93 (d, 1H); 7.88 (s, 1H); 7.75 (d, 2H); 7.48 (dd, 1H); 7.39 (s, 1H); 6.74 (d, 1H); 4.37 (s, 2H); 3.46 (m, 3H); 3.23 (m, 2H); 2.27 (s, 3H); 2.07 (m, 1H); 1.80 (m, 1H)).

EXAMPLE 120

1-(3-Quinolin-6-ylmethyl-imidazo[1,2-b]pyridazin-6-yl)-piperidin-4-one

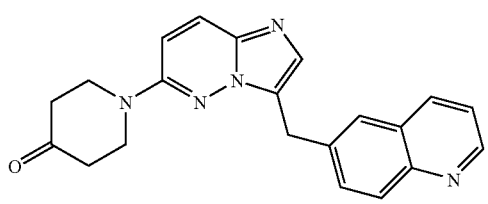 [SMILES: O=C1CCN(c2ccc3ncc(Cc4ccc5ncccc5c4)n3n2)CC1]

6-[6-(1,4-Dioxa-8-aza-spiro[4.5]dec-8-yl)-imidazo[1,2-b]pyridazin-3-yl methyl]-quinoline (Example 110, 132 mg, 0.329 mmol) was dissolved in THF (493 μL). A 2 M HCl solution (493 μL) was then added and the RM was stirred at rt for 22 h and then at 40° C. for 3 h. A basic work up ($KHCO_3$) followed by a crystallization in $Et_2O$/isopropanol afforded the title compound as white crystals ($t_R$ 1.33/1.48 min (conditions 6), MH+=358.1, $^1$H-NMR in DMSO-d6: 8.84 (m, 1H); 8.29 (m, 1H); 7.90 (m, 3H); 7.72 (m, 1H); 7.49 (m, 2H); 7.22 (d, 1H); 4.42 (s, 2H); 3.85 (m, 4H); 2.35 (m, 4H)).

EXAMPLE 121

(3-Chloro-phenyl)-(3-quinolin-6-ylmethyl-imidazo[1,2-b]pyridazin-6-yl)-amine

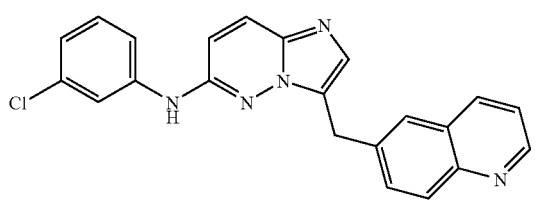 [SMILES: Clc1cccc(Nc2ccc3ncc(Cc4ccc5ncccc5c4)n3n2)c1]

NaH (34 mg, 0.85 mmol) was suspended in NMP (1.5 mL) under argon. 3-Chloroaniline (108 μL, 1.017 mmol) was added and the RM was heated to 85° C. After 10 min, 6-(6-chloro-imidazo[1,2-b]pyridazin-3-ylmethyl)-quinoline (Example 14, 100 mg, 0.339 mmol) was added and the RM was stirred at 85° C. for 1 h. The mixture was then heated to 160° C. for 10 min. The mixture was diluted with EtOAc and washed with water (3×). The aqueous layer was extracted with EtOAc (3×). The combined organic layers were dried over $Na_2SO_4$, filtered and concentrated. The residue was purified by flash chromatography (Flashmaster) and crystallized in $Et_2O$ to afford the title compound as a yellow solid ($t_R$ 4.99 min (conditions 4), MH+=386.1, $^1$H-NMR in DMSO-d6: 9.57 (s, 1H); 8.82 (m, 1H); 7.93 (m, 3H); 7.86 (m, 1H); 7.71 (m, 1H); 7.56 (s, 1H); 7.47 (dd, 1H); 7.43 (m, 1H); 7.25 (t, 1H); 6.99 (m, 1H); 6.85 (d, 1H); 4.50 (s, 2H)).

EXAMPLE 122

Phenyl-(3-quinolin-6-ylmethyl-imidazo[1,2-b]pyridazin-6-yl)-amine

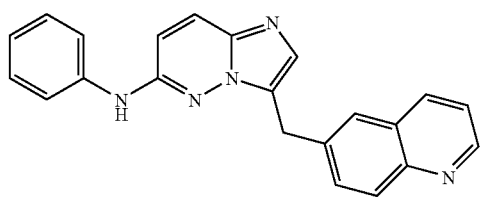 [SMILES: c1ccc(Nc2ccc3ncc(Cc4ccc5ncccc5c4)n3n2)cc1]

The title compound was prepared in analogy to the compound of Example 121 using aniline as starting material instead of 3-chloroaniline and with a preparative LCMS purification instead of a flash chromatography ($t_R$ 4.30 min (conditions 4), MH+=352.3, $^1$H-NMR in DMSO-d6: 8.91 (m, 1H); 8.36 (m, 1H); 8.17 (d, 1H); 8.08 (s, 1H); 8.03 (d, 1H);

7.96 (m, 1H); 7.79 (m, 1H); 7.58 (dd, 1H); 7.50 (m, 2H); 7.35 (d, 1H); 7.25 (t, 2H); 7.01 (t, 1H); 4.59 (s, 2H)).

EXAMPLE 123

6-(6-ethoxy-imidazo[1,2-b]pyridazin-3-ylmethyl)-quinoline

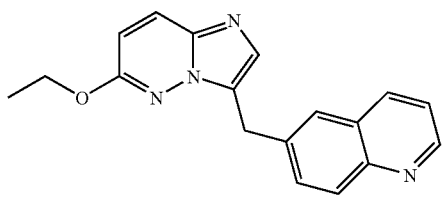 [SMILES: CCOc1ccc2ncc(Cc3ccc4ncccc4c3)n2n1]

6-(6-Chloro-imidazo[1,2-b]pyridazin-3-ylmethyl)-quinoline (Example 14, 112 mg, 0.380 mmol) was suspended in EtOH (1 mL). 2 M NaOH (950 µL, 1.900 mmol) was added and the RM was stirred at 80° C. for 1 h. The mixture was neutralized with 2 M HCl until pH=6 and then concentrated. The residue was diluted with DCM and the obtained solution was dried over $Na_2SO_4$, filtered and concentrated. The residue was crystallized in $Et_2O$ and small amount of isopropanol. The resulting solid was purified by flash chromatography (Flashmaster, with a 20 g silica gel column, TBME/MeOH: 100:0→85:15) and crystallized again in $Et_2O$ to afford the title compound as a yellow solid ($t_R$ 1.67 min (conditions 6), MH+=305.2, $^1$H-NMR in DMSO-d6: 8.85 (m, 1H); 8.30 (m, 1H); 7.95 (m, 2H); 7.89 (m, 1H); 7.75 (m, 1H); 7.56 (s, 1H); 7.50 (dd, 1H); 6.80 (d, 1H); 4.44 (s, 2H); 4.35 (q, 2H); 1.31 (t, 3H)).

EXAMPLE 124

6-[6-((R)-3-fluoro-pyrrolidin-1-yl)-imidazo[1,2-b]pyridazin-3-ylmethyl]-quinoline

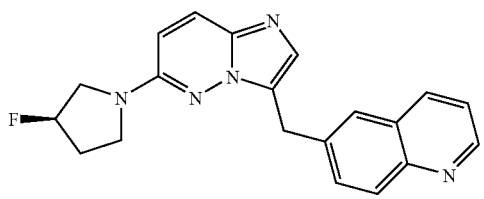 [SMILES: F[C@@H]1CCN(c2ccc3ncc(Cc4ccc5ncccc5c4)n3n2)C1]

6-(6-Chloro-imidazo[1,2-b]pyridazin-3-ylmethyl)-quinoline (Example 14, 100 mg, 0.339 mmol), (R)-(−)-3-fluoropyrrolidine hydrochloride (220 mg, 1.696 mmol) and KF (99 mg, 1.696 mmol) were suspended in NMP (1.5 mL). N-Ethyldiisopropylamine (296 µL, 1.696 mmol) was then added and the RM was stirred at 170° C. for 4 h. The mixture was diluted with EtOAc and extracted with 1 M HCl (3×). The aqueous layer was washed with TBME (2×) and then adjusted to pH 10 with 2 M NaOH. The solution was extracted with DCM (3×). The organic layer was washed with water (2×), dried over sodium, filtered and concentrated. The residue was purified by flash chromatography (Flashmaster) and triturated in DCM to afford the title compound as a yellow foam ($t_R$ 4.14 min (conditions 4), MH+=348.5, $^1$H-NMR in DMSO-d6: 8.84 (m, 1H); 8.29 (m, 1H); 7.93 (m, 2H); 7.81 (d, 1H); 7.76 (m, 1H); 7.49 (dd, 1H); 7.43 (s, 1H); 6.81 (d, 1H); 5.46 (m, 1H); 4.38 (s, 2H); 3.62 (m, 4H); 2.20 (m, 2H)).

EXAMPLE 125

6-[6-((S)-3-Fluoro-pyrrolidin-1-yl)-imidazo[1,2-b]pyridazin-3-ylmethyl]-quinoline

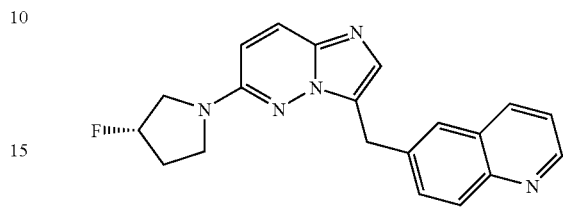

The title compound was prepared in analogy to the compound of Example 124 using (S)-(+)-3-fluoropyrrolidine hydrochloride as starting material instead of (R)-(−)-3-fluoropyrrolidine hydrochloride ($t_R$ 3.89 min (conditions 4), MH+=348.2, $^1$H-NMR in DMSO-d6: 8.84 (m, 1H); 8.29 (m, 1H); 7.92 (m, 2H); 7.81 (d, 1H); 7.75 (m, 1H); 7.49 (dd, 1H); 7.43 (s, 1H); 6.81 (d, 1H); 5.46 (m, 1H); 4.38 (s, 2H); 3.62 (m, 4H); 2.21 (m, 2H)).

EXAMPLE 126

(4-Piperidin-1-ylmethyl-phenyl)-(3-quinolin-6-ylmethyl-imidazo[1,2-b]pyridazin-6-yl)-amine

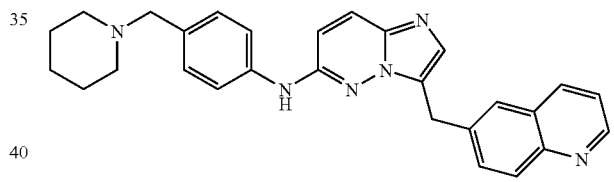

6-(6-Chloro-imidazo[1,2-b]pyridazin-3-ylmethyl)-quinoline (Example 14, 101 mg, 0.343 mmol), rac-BINAP (13 mg, 0.021 mmol) and $Pd_2(dba)_3$ (6 mg, 0.007 mmol) were charged into a vial under argon. Toluene (1.5 mL) was then added, followed by KOtBu (119 mg, 1.028 mmol). Toluene (1.5 mL) was added again and at last 3-(piperidin-1-ylmethyl)aniline (134 mg, 0.685 mmol). The RM was stirred at 115° C. for 45 min. It was then diluted with EtOAc and extracted with 2 M HCl (3×). The aqueous was washed with EtOAc (×2) and then adjusted to pH 10 with 2 M NaOH. The solution was extracted with EtOAc (×3). The organic layer was dried over $Na_2SO_4$, filtered and concentrated. The residue was purified by flash chromatography (Flashmaster) and then by prep-LCMS to afford the title compound as a yellow solid ($t_R$ 3.47 min (conditions 4), MH+=449.5, $^1$H-NMR in DMSO-d6: 8.91 (m, 1H); 8.33 (m, 1H); 8.21 (d, 1H); 8.01 (m, 2H); 7.89 (s, 1H); 7.80 (m, 1H); 7.70 (m, 1H); 7.55 (m, 2H); 7.35 (m, 2H); 7.16 (d, 1H); 4.62 (s, 2H); 4.19 (m, 2H); 3.29 (d, 2H); 2.79 (m, 2H); 1.75 (d, 2H); 1.60 (m, 3H); 1.29 (m, 1H)).

EXAMPLE 127-141

The following compounds were prepared according to the procedure of Example 126 starting with the appropriate aromatic amine.

| Ex | structure | Name | t$_R$ (min) Conditions | MH+ |
|---|---|---|---|---|
| 127 | 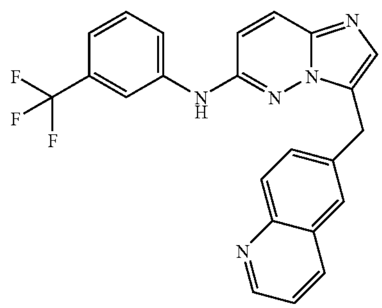 [SMILES: FC(F)(F)c1cccc(Nc2ccc3ncc(Cc4ccc5ncccc5c4)n3n2)c1] | (3-Quinolin-6-ylmethyl-imidazo[1,2-b]pyridazin-6-yl)-(3-trifluoromethyl-phenyl)-amine | 5.48 Conditions 4 | 420.4 |
| 128 | 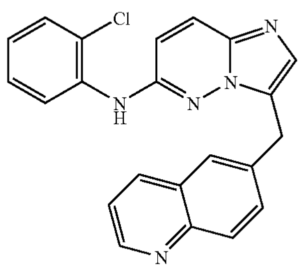 [SMILES: Clc1ccccc1Nc1ccc2ncc(Cc3ccc4ncccc4c3)n2n1] | (2-Chloro-phenyl)-(3-quinolin-6-ylmethyl-imidazo[1,2-b]pyridazin-6-yl)-amine | 4.64 Conditions 4 | 386.1 |
| 129 | 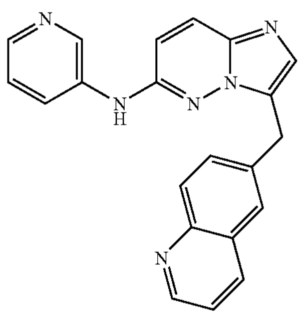 [SMILES: c1cncc(Nc2ccc3ncc(Cc4ccc5ncccc5c4)n3n2)c1] | Pyridin-3-yl-(3-quinolin-6-ylmethyl-imidazo[1,2-b]pyridazin-6-yl)-amine | 3.07 Conditions 4 | 353.2 |
| 130 | 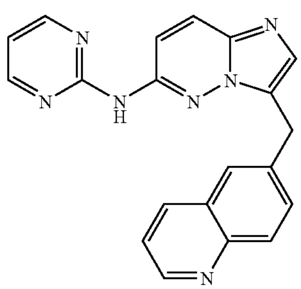 [SMILES: c1cnc(Nc2ccc3ncc(Cc4ccc5ncccc5c4)n3n2)nc1] | Pyrimidin-2-yl-(3-quinolin-6-ylmethyl-imidazo[1,2-b]pyridazin-6-yl)-amine | 3.67 Conditions 4 | 354.3 |
| 131 | 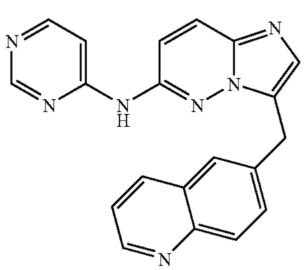 [SMILES: c1cnc2ccc(Cc3cnc4ccc(Nc5ccncn5)nn34)cc2c1] | Pyrimidin-4-yl-(3-quinolin-6-ylmethyl-imidazo[1,2-b]pyridazin-6-yl)-amine | 3.43 Conditions 4 | 354.2 |

| Ex | structure | Name | t_R (min) Conditions | MH+ |
|---|---|---|---|---|
| 132 | 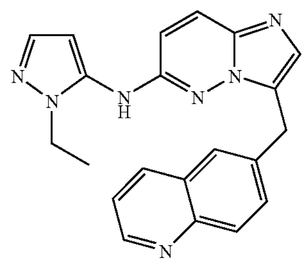 [SMILES: CCn1nccc1Nc1ccc2ncc(Cc3ccc4ncccc4c3)n2n1] | (2-Ethyl-2H-pyrazol-3-yl)-(3-quinolin-6-ylmethyl-imidazo[1,2-b]pyridazin-6-yl)-amine | 3.59 Conditions 4 | 370.3 |
| 133 | 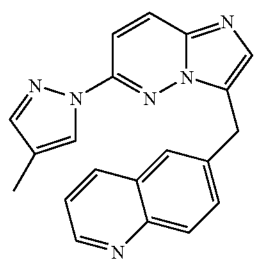 [SMILES: Cc1cnn(-c2ccc3ncc(Cc4ccc5ncccc5c4)n3n2)c1] | 7-[6-(4-Methyl-pyrazol-1-yl)-imidazo[1,2-b]pyridazin-3-ylmethyl]-quinoline | 5.54 Conditions 4 | 341.1 |
| 134 | 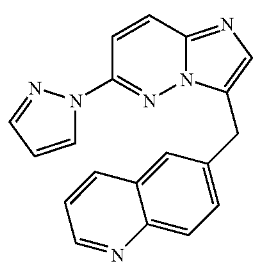 [SMILES: c1cnc2ccc(Cc3cnc4ccc(-n5cccn5)nn34)cc2c1] | 6-(6-Pyrazol-1-yl-imidazo[1,2-b]pyridazin-3-ylmethyl)-quinoline | 5.08 Conditions 4 | 327.2 |
| 135 | 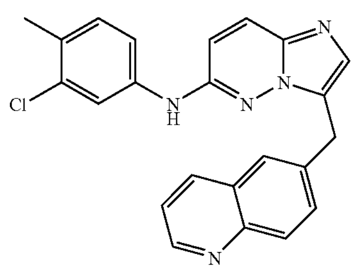 [SMILES: Cc1ccc(Nc2ccc3ncc(Cc4ccc5ncccc5c4)n3n2)cc1Cl] | (3-Chloro-4-methyl-phenyl)-(3-quinolin-7-ylmethyl-imidazo[1,2-b]pyridazin-6-yl)-amine | 5.46 Conditions 4 | 400.2 |
| 136 | 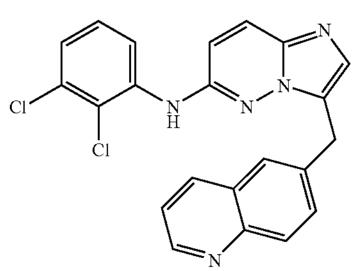 [SMILES: Clc1cccc(Nc2ccc3ncc(Cc4ccc5ncccc5c4)n3n2)c1Cl] | (2,3-Dichloro-phenyl)-(3-quinolin-6-ylmethyl-imidazo[1,2-b]pyridazin-6-yl)-amine | 5.41 Conditions 4 | 420.1 |

| Ex | structure | Name | t_R (min) Conditions | MH+ |
|---|---|---|---|---|
| 137 | 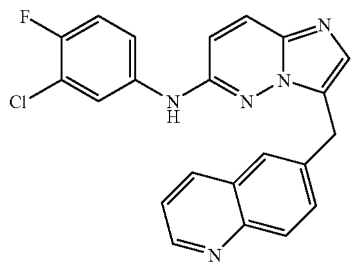 [SMILES: Fc1ccc(Nc2ccc3ncc(Cc4ccc5ncccc5c4)n3n2)cc1Cl] | (3-Chloro-4-fluoro-phenyl)-(3-quinolin-6-ylmethyl-imidazo[1,2-b]pyridazin-6-yl)-amine | 5.37 Conditions 4 | 404.1 |
| 138 | 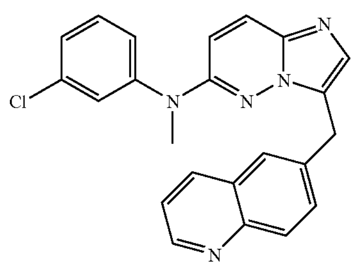 [SMILES: CN(c1cccc(Cl)c1)c1ccc2ncc(Cc3ccc4ncccc4c3)n2n1] | (3-Chloro-phenyl)-methyl-(3-quinolin-6-ylmethyl-imidazo[1,2-b]pyridazin-6-yl)-amine | 5.45 Conditions 4 | 400.2 |
| 139 | 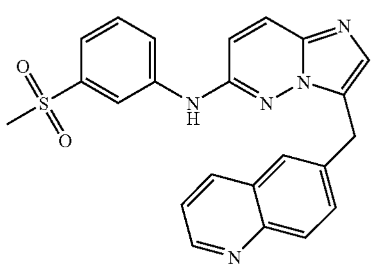 [SMILES: CS(=O)(=O)c1cccc(Nc2ccc3ncc(Cc4ccc5ncccc5c4)n3n2)c1] | (3-Methanesulfonyl-phenyl)-(3-quinolin-6-ylmethyl-imidazo[1,2-b]pyridazin-6-yl)-amine | 3.89 Conditions 4 | 430.3 |
| 140 | 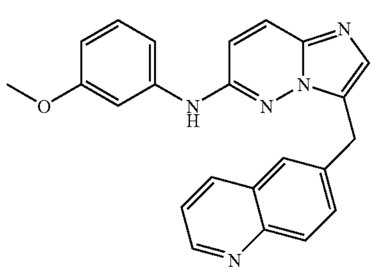 [SMILES: COc1cccc(Nc2ccc3ncc(Cc4ccc5ncccc5c4)n3n2)c1] | (3-Methoxy-phenyl)-(3-quinolin-6-ylmethyl-imidazo[1,2-b]pyridazin-6-yl)-amine | 4.39 Conditions 4 | 382.3 |
| 141 | 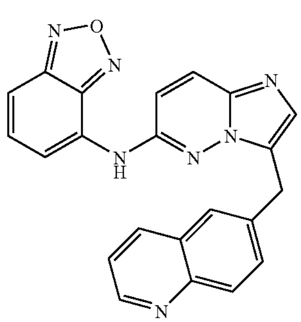 [SMILES: c1cnc2ccc(Cc3cnc4ccc(Nc5cccc6nonc56)nn34)cc2c1] | Benzo[1,2,5]oxadiazol-4-yl-(3-quinolin-7-ylmethyl-imidazo[1,2-b]pyridazin-6-yl)-amine | 4.56 Conditions 4 | 394.4 |

EXAMPLE 142

6-[(6-Chloro-imidazo[1,2-b]pyridazin-3-yl)-dideutero-methyl]-quinoline

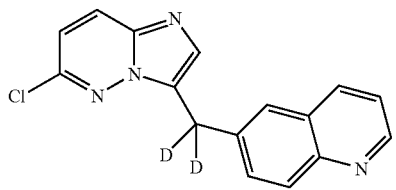 [SMILES: [2H]C([2H])(c1ccc2ncccc2c1)c1cnc2ccc(Cl)nn12]

(rac)-(6-Chloro-imidazo[1,2-b]pyridazin-3-yl)-deuteroquinolin-6-yl-methanol (Stage 142.1, 460 mg, 1.476 mmol) was suspended in acetic acid-d4. Hypophosphorous acid-d3 (1.51 mL, 14.8 mmol) was then added to the mixture at 90° C. Iodine (749 mg, 2.951 mmol) was finally added and the RM was stirred at reflux (116° C.) for 5 h. The mixture was cooled down to rt and acetic acid-d4 was removed under vacuo. The residue was dissolved with water and adjusted to pH 11-12 with 2 M NaOH. The solution was extracted with DCM (3×). The combined organic layers were washed with water (2×), dried over $Na_2SO_4$, filtered and concentrated. The residue was purified by flash chromatography (Flashmaster) to afford the title compound as an oil ($t_R$ 5.24 min (conditions 4), MH+=297.1).

Stage 142.1

(rac)-(6-Chloro-imidazo[1,2-b]pyridazin-3-yl)-deuteroquinolin-6-yl-methanol (6-Chloro-imidazo[1,2-b]pyridazin-3-yl)-quinolin-6-yl-methanone (Stage 1.2, 480 mg, 1.55 mmol) was suspended in EtOH (8 mL). $NaBD_4$ (33 mg, 0.777 mmol) was added to the suspension at rt under nitrogen. The RM was stirred at rt for 3 h. Deuteriumoxide was added to the mixture and the solution is extracted with DCM (3×). The organic layer was washed with water (×2), dried over $Na_2SO_4$, filtered and concentrated to afford the title compound as orange crystals ($t_R$ 4.81 min (conditions 4), MH+=311.9).

EXAMPLE 143

6{Dideutero-[6-(1-methyl-1H-pyrazol-4-yl)-imidazo[1,2-b]pyridazin-3-ylmethyl]}-quinoline The title compound was prepared in analogy to the compound of Example 15 using 6-[(6-chloro-imidazo[1,2-b]pyridazin-3-yl)-dideutero-methyl]-quinoline (Example 142) as starting material instead of (6-chloro-imidazo[1,2-b]pyridazin-3-yl)-quinoline (Example 14) and with purification by prep-LCMS instead of crystallization ($t_R$ 0.77 min (conditions 5), MH+=343.3, $^1$H-NMR in DMSO-d6: 8.98 (m, 1H); 8.56 (m, 2H); 8.33 (d, 1H); 8.18 (s, 1H); 8.13 (m, 1H); 8.04 (m, 2H); 7.95 (m, 1H); 7.89 (d, 1H); 7.67 (dd, 1H); 3.96 (s, 3H)).

EXAMPLE 144

2-Chloro-N-(2-pyrrolidin-1-yl-ethyl)-4-(3-quinolin-6-ylmethyl-imidazo[1,2-b]pyridazin-6-yl)benzamide

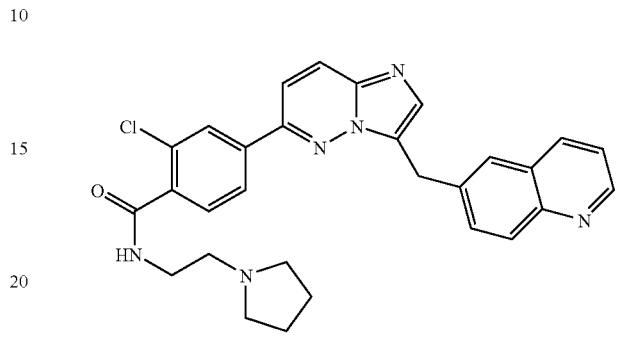

A flask was charged with (6-chloro-imidazo[1,2-b]pyridazin-3-yl)-quinoline (Example 14, 300 mg, 1.018 mmol), 3-chloro-4-(2-pyrrolidin-1-yl-ethylcarbamoyl)-boronic acid (Stage 144.1, 604 mg, 2.036 mmol), DME (6.4 mL) and DMF (1 mL). 2 M $Na_2CO_3$ (1.527 mL, 3.05 mmol) was then added, followed by Pd(dppf)/$CH_2Cl_2$ 1:1 (42 mg, 0.051 mmol). The RM was heated at 90° C. for 25 h. The cool RM was poured in DCM and washed with water (3×). The aqueous layers were combined and extracted with DCM (2×). The combined organic layer was dried over $Na_2SO_4$, filtered and concentrated in vacuo. The resulting oil was purified by flash chromatography (Flashmaster, with a 50 g silica gel column, TBME/(MeOH/NH3 9:1)=80:20 →60:40). The residue was crystallized with isopropanol/$Et_2O$ 2:8. The crystals were filtered off and dried to afford the title compound as a beige solid ($t_R$ 4.16 min (conditions 4), MH+=511.3, $^1$H-NMR in $CDCl_3$: 8.91 (m, 1H); 8,15 (m, 1H); 8.07 (m, 2H); 8.00 (m, 1H); 7.84 (m, 3H); 7.75 (dd, 1H); 7.72 (s, 1H); 7.46 (d, 1H); 7.41 (dd, 1H); 4.62 (s, 2H); 3.65 (m, 2H); 2.72 (m, 6H); 1.86 (m, 4H))

Stage 144.1

3-Chloro-4-(2-pyrrolidin-1-yl-ethylcarbamoyl)-boronic acid

4-Carboxy-3-chlorophenyboronic acid (500 mg, 2.495 mmol) was suspended in DCM (10 mL). Thionyl chloride (378 µL, 2.99 mmol) was then added and the suspension was heated to reflux. As the gas evolution was really weak, the solvent was exchange to DME (10 mL). The suspension was stirred at 75° C. for 6 h and the mixture was then cooled down to rt. Triethylamine (834 µL, 5.99 mmol) and 1-(2-aminoethyl)-pyrrolidine (377 µL, 2.99 mmol) were added and the RM was stirred for 30 min. The mixture was concentrated and the residue was poured in a 0.4 M HCl solution. The solution was washed with EtOAc (3×) and the combined organic layers were extracted with 2 M HCl (2×). The organic phase contained 87% of boronic acid (starting material). It was discarded. The aqueous was then neutralized to pH 7 with 2 M NaOH. Extraction with EtOAc only afforded 25 mg of the desired product as beige crystals. The aqueous layer was purified by reverse phase chromatography (Flashmaster, with a 65 g RP 18 column, MeOH/water=100:0→0:100) and lyophilized to afford the title compound as a beige solid ($t_R$ 2.58 min (conditions 4), MH+=297.2, $^1$H-NMR in DMSO-d6+ D$_2$O: 7.81 (m, 1H); 7.73 (m, 1H); 7.36 (d, 1H); 3.33 (t, 2H); 2.55 (t, 2H); 2.47 (m, 4H); 1.68 (m, 4H)).

EXAMPLE 145

6-[6-(3-Chloro-benzenesulfonyl)-imidazo[1,2-b]pyridazin-3-ylmethyl]-quinoline

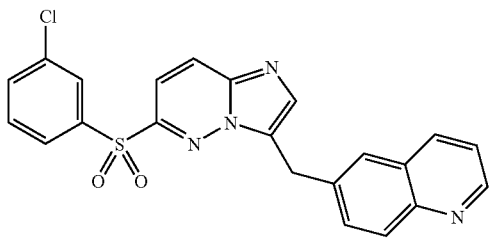 [SMILES: O=S(=O)(c1cccc(Cl)c1)c1ccc2ncc(Cc3ccc4ncccc4c3)n2n1]

6-[6-(3-Chloro-phenylsulfanyl)-imidazo[1,2-b]pyridazin-3-ylmethyl]-quinoline (Example 112, 100 mg, 0.248 mmol) and MoO$_3$ (1.7 mg, 0.012 mmol) were charged in a flask. EtOH (500 µL) was then added followed by H$_2$O$_2$ (107 µL, 1.241 mmol). The RM was heated to 80° C. and stirred for 8 h (mixture of desired product and over-oxydized product). The mixture was then poured into water and stirred with a NaHSO$_3$ solution. The solution was then extracted with DCM (2×). The resulting organic layers were combined, dried over Na$_2$SO$_4$, filtered and concentrated. The residue was separated from the side product by flash chromatography (Flashmaster, with a 4 g silica gel column, TBME/MeOH=100:0→60:40) and then crystallized in Et$_2$O to afford the title compound as yellow crystals (t$_R$ 5.70 min (conditions 4), MH+=435.1, $^1$H-NMR in DMSO-d6: 8.86 (m, 1H); 8.46 (d, 1H); 8.22 (m, 1H); 8.07 (s, 1H); 7.99 (m, 1H); 7.88 (m, 3H); 7.76 (m, 1H); 7.71 (m, 1H); 7.58 (m, 1H); 7.50 (m, 2H); 4.49 (s, 2H)).

EXAMPLE 146

7-Fluoro-6-{6-[1-(1-methyl-azetidin-3-yl)-1H-pyrazol-4-yl]-imidazo[1,2-b]pyridazin-3-yl methyl}-quinoline

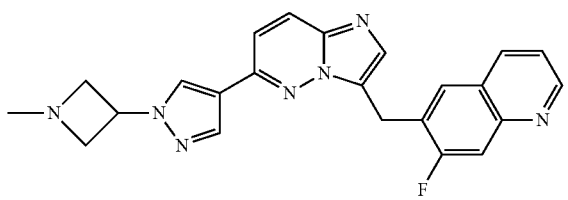 [SMILES: CN1CC(n2cc(-c3ccc4ncc(Cc5cc6cccnc6cc5F)n4n3)cn2)C1]

A flask was charged with MeOH (1 mL). 6-[6-(1-Azetidin-3-yl-1H-pyrazol-4-yl)-imidazo[1,2-b]pyridazin-3-ylmethyl]-7-fluoro-quinoline (Stage 146.1, 26 mg, 0.065 mmol), formaldehyde (9.7 µL, 0.130 mmol) and NaBH$_3$CN (20 mg, 0.325 mmol) were then added. The pH was adjusted to 5-6 with a drop of acetic acid and the RM was stirred at rt for 2 h. The mixture was then diluted with DCM, washed with NaHCO$_3$ and brine. The organic layer was dried over Na$_2$SO$_4$, filtered and concentrated. The residue was purified by flash chromatography (CombiFlash® Companion System®, with a 4 g RediSep® silica gel column, DCM/(DCM/MeOH 19:1)=100:0→0:100)). The residue crystallized in DCM. The solid was filtered off, and dissolved in EtOAc. The solution was washed again with NaHCO$_3$, dried over Na$_2$SO$_4$, filtered and concentrated to afford the title compound as a foam (t$_R$ 2.93 min (conditions 3), MH+=414.1, $^1$H-NMR in DMSO-d6: 8.85 (m, 1H); 8.60 (s, 1H); 8.35 (m, 1H); 8.09 (m, 3H); 7.77 (m, 1H); 7.58 (m, 2H); 7.47 (m, 1H); 5.01 (m, 1H); 4.55 (s, 2H); 3.71 (m, 2H); 3.40 (m, 2H); 2.34 (s, 3H))

Stage 146.1

6-[6-(1-Azetidin-3-yl-1H-pyrazol-4-yl)-imidazo[1,2-b]pyridazin-3-ylmethyl]-7-fluoro-quinoline Dioxane (5 mL) was charged in a flask. 3-{4-[3-(7-Fluoro-quinolin-6-ylmethyl)-imidazo[1,2-b]pyridazin-6-yl]-pyrazol-1-yl}-azetidine-1-carboxylic acid tert-butyl ester (Stage 146.2, 100 mg, 0.200 mmol) and HCl in dioxane (4 M solution, 500 µL, 2.002 mmol) were then added and the mixture was stirred at rt for 1 h. The RM was diluted with EtOAc/NaHCO$_3$. The organic layer was separated and washed with brine (2×) then dried over Na$_2$SO$_4$, filtered and concentrated. The residue was purified by flash chromatography (CombiFlash® Companion System®, with a 4 g RediSep® silica gel column, DCM/(DCM/MeOH 19:1)=100:0→0:100) and precipitated in Et$_2$O to afford the title compound as a foam (t$_R$ 2.87 min (conditions 3), MH+=400.1).

Stage 146.2

3-{4-[3-(7-Fluoro-quinolin-6-ylmethyl)-imidazo[1,2-b]pyridazin-6-yl]-pyrazol-1-yl}-azetidine-1-carboxylic acid tert-butyl ester A flask was charged with 6-(6-chloro-imidazo[1,2-b]pyridazin-3-ylmethyl)-7-fluoro-quinoline (Stage 173.1, 100 mg, 0.320 mmol), 3-[4-(4,4,5,5-tetramethyl-[1,3,2]dioxaborolan-2-yl)pyrazol-1-yl]-azetidine-1-carboxylic acid tert-butyl ester (Stage 146.3), 168 mg, 0.480 mmol), DME (2 mL), Pd(PPh$_3$)$_2$Cl$_2$ (11 mg, 0.05 mmol) and 2 M K$_2$CO$_3$ (432 µL, 0.863 mmol). The RM was heated at 95° C. for 2 h. The cool RM was diluted with EtOAc/NaHCO$_3$. The organic phase was separated and washed with brine (2×) then dried over Na$_2$SO$_4$, filtered and concentrated in vacuo. The residue was purified by flash chromatography (CombiFlash® Companion System®, with a 4 g RediSep®: silica gel column, DCM/(DCM/MeOH 19:1)=100:0→0:100) to afford the title compound as a foam (t$_R$ 4.33 min (conditions 3), MH+=500.1).

Stage 146.3

3-[4-(4,4,5,5-Tetramethyl-[1,3,2]dioxaborolan-2-yl)-pyrazol-1-yl]-azetidine-1-carboxylic acid tert-butyl ester The title compound was prepared as described in published patent application WO 2008148867:
To a solution of 1-BOC-3-hydroxyazetidine (1.0 g, 5.77 mmol), 4-dimethylaminopyridine (7 mg, 0.058 mmol) and triethylamine (0.880 mL, 6.35 mmol) in DCM (15 mL) cooled at 0° C. was added dropwise methanesulfonyl chloride (0.45 mL, 5.77 mmol). The RM was stirred 18 h at rt, diluted with DCM, washed with a solution of saturated NaHCO$_3$ and brine. The organic layer was dried over Na$_2$SO$_4$, filtered and the solvent was removed under reduced pressure. 3-Methanesulfonyloxy-azetidine-1-carboxylic acid tert-butyl ester obtained as an oil was used directly in the next step.
To a solution of 4-(4,4,5,5-tetramethyl-1,3,2-dioxaborolan-2-yl)-1H-pyrazole (1.4 g 5.57 mmol) in DMF (20 mL) stirred at 0° C. was added sodium hydride (55% in oil, 0.243 g, 5.57 mmol). After addition the mixture was stirred 1 h at rt, a solution of the above obtained 3-methanesulfonyloxy-azetidine-1-carboxylic acid tert-butyl ester (1.4 g, 5.57 mmol) in DMF (3 mL) was added. The RM was stirred 30 min at rt, and then 3 h at 95° C. After cooling at rt the mixture was poured in ice water and extracted with EtOAc. The combined organic phases were washed with a solution of saturated NaHCO₃ and brine. The organic layer was dried over Na₂SO₄, filtered and the solvent was removed under reduced pressure. The residue was purified by flash chromatography (with heptane and EtOAc as eluants) to afford the title compound as an oil ($t_R$ 4.33 min (conditions 3), MH+=350.1)

EXAMPLE 147

2-(4-{4-[3-(7-Fluoro-quinolin-6-ylmethyl)-imidazo[1,2-b]pyridazin-6-yl]-pyrazol-1-yl}-piperidin-1-yl)-ethanol

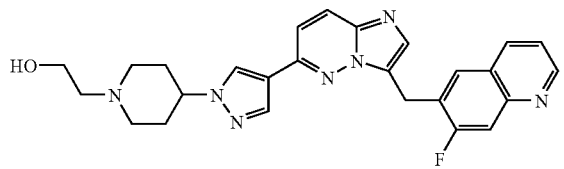 [SMILES: OCCN1CCC(n2cc(-c3ccc4ncc(Cc5cc6cccnc6cc5F)n4n3)cn2)CC1]

A flask was charged with THF (5 mL), 6-[6-(1-{1-[2-(tert-Butyl-dimethyl-silanyloxy)-ethyl]-piperidin-4-yl}-1H-pyrazol-4-yl)-imidazo[1,2-b]pyridazin-3-ylmethyl]-7-fluoro-quinoline (Stage 147.1, 96 mg, 0.164 mmol) and tetrabutylammonium fluoride (819 μL of a 1 M solution, 0.819 mmol). The mixture was stirred at rt for 2 h. The RM was diluted with EtOAc and washed with NaHCO₃ and brine. The organic layer was dried over Na₂SO₄, filtered and concentrated. The residue was purified by MPLC, then taken up in NaHCO₃ and extracted with DCM. The organic layer was dried over Na₂SO₄, filtered and concentrated to afford the title compound ($t_R$ 2.99 min (conditions 3), MH+=472.1, ¹H-NMR in DMSO-d6: 8.84 (m, 1H); 8.50 (s, 1H); 8.34 (m, 1H); 8.08 (m, 2H); 8.06 (m, 1H); 7.76 (d, 1H); 7.60 (s, 1H); 7.53 (d, 1H); 7.47 (m, 1H); 4.55 (s, 2H); 4.41 (t, 1H); 3.50 (m, 2H); 2.97 (m, 2H); 2.42 (t, 2H); 2.13 (m, 2H); 1.97 (m, 4H)).

Stage 147.1

6-[6-(1-{1-[2-(tert-Butyl-dimethyl-silanyloxy)-ethyl]-piperidin-4-yl}-1H-pyrazol-4-yl)-imidazo[1,2-b]pyridazin-3-ylmethyl]-7-fluoro-quinoline A mixture of 7-fluoro-6-[6-(1-piperidin-4-yl-1H-pyrazol-4-yl)-imidazo[1,2-b]pyridazin-3-ylmethyl]-quinoline (Example 180, 70 mg, 0.164 mmol), tert-butyldimethylsilyloxy-acetaldehyde (47 μL, 0.246 mmol) and NaBH₃CN (52 mg, 0.246 mmol) in MeOH (2 mL) was stirred at rt for 2 h. The pH was then adjusted to 5-6 with AcOH and the RM was stirred at rt for 2 h more. The mixture was diluted with DCM and washed with NaHCO₃ and brine. The organic layer was dried over Na₂SO₄, filtered and concentrated to afford the title compound as a foam ($t_R$ 4.27 min (conditions 3), MH+=586.1).

EXAMPLE 148

6-{6-[1-(1-Ethyl-piperidin-4-yl)-1H-pyrazol-4-yl]-imidazo[1,2-b]pyridazin-3-ylmethyl}-7-fluoro-quinoline

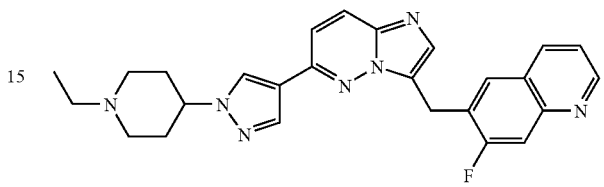

A mixture of 7-fluoro-6-[6-(1-piperidin-4-yl-1H-pyrazol-4-yl)-imidazo[1,2-b]pyridazin-3-ylmethyl]-quinoline (Example 180, 50 mg, 0.117 mmol) and ethyliodide (19 μL, 0.234 mmol) in dioxane (1 mL) was stirred at rt for 2 h. Cs₂CO₃ (19 mg, 0.059 mmol) was then added and the RM was stirred at rt for 5 h more. The mixture was diluted with EtOAc and washed with NaHCO₃ and brine. The organic layer was dried over Na₂SO₄, filtered and concentrated. The residue was purified by flash chromatography (CombiFlash® Companion System®, with a 4 g RediSep® silica gel column, DCM/(DCM/MeOH 9:1+NH₃)=100:0→0:100) to afford the title compound as a foam ($t_R$ 3.10 min (conditions 3), MH+=456.2, ¹H-NMR in DMSO-d6: 8.84 (m, 1H); 8.50 (s, 1H); 8.34 (m, 1H); 8.08 (m, 2H); 8.04 (d, 1H); 7.76 (d, 1H); 7.60 (s, 1H); 7.53 (d, 1H); 7.47 (dd, 1H); 4.55 (s, 2H); 4.18 (m, 1H); 2.96 (m, 2H); 2.35 (q, 2H); 1.97 (m, 6H); 1.01 (t, 3H)).

EXAMPLE 149

7-Fluoro-6-(6-{1-[1-(2,2,2-trifluoro-ethyl)-piperidin-4-yl]-1H-pyrazol-4-yl}-imidazo[1,2-b]pyridazin-3-ylmethyl)-quinoline

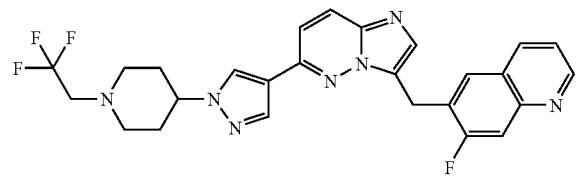 [SMILES: Fc1cc2ncccc2cc1Cc1cnc2ccc(-c3cnn(C4CCN(CC(F)(F)F)CC4)c3)nn12]

A mixture of 7-fluoro-6-[6-(1-piperidin-4-yl-1H-pyrazol-4-yl)-imidazo[1,2-b]pyridazin-3-ylmethyl]-quinoline (Example 180, 50 mg, 0.117 mmol), 2,2,2-trifluoroethyl methanesulfonate (55 μL, 0.468 mmol) and Cs₂CO₃ (76 mg, 0.234 mmol) in THF (1 mL) was stirred at 70° C. for 2 h. 2,2,2-trifluoroethyl methanesulfonate (69 μL, 0.585 mmol) was then added and the RM was stirred at reflux for 24 h. 2,2,2-trifluoroethyl methanesulfonate (69 μL, 0.585 mmol) was added again and the RM was stirred at reflux for 18 h more. The mixture was diluted with EtOAc and washed with NaHCO₃ and brine. The organic layer was dried over Na₂SO₄, filtered and concentrated. The residue was purified by flash chromatography (CombiFlash® Companion System®, with a 4 g RediSep® silica gel column, DCM/(DCM/

MeOH 19:1)=100:0→0:100) to afford the title compound (t_R 3.74 min (conditions 3), $^1$H-NMR in DMSO-d6: 8.85 (m, 1H); 8.54 (s, 1H); 8.34 (d, 1H); 8.07 (m, 3H); 7.77 (d, 1H); 7.61 (s, 1H); 7.54 (d, 1H); 7.47 (dd, 1H); 4.55 (s, 2H); 4.39 (m, 1H); 3.67 (m, 2H); 2.94 (m, 4H); 2.16 (m, 2H); 2.00 (m, 2H)).

EXAMPLE 150

3-(1H-Indazol-5-ylmethyl)-6-(1-methyl-1H-pyrazol-4-yl)-imidazo[1,2-b]pyridazine

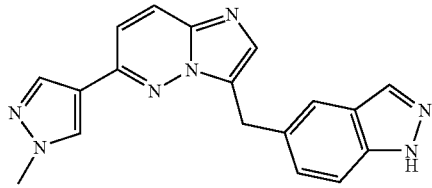 [SMILES: Cn1cc(-c2ccc3ncc(Cc4ccc5[nH]ncc5c4)n3n2)cn1]

The title compound was prepared in analogy to the synthesis of compound of Example 2 using (rac)-(1H-Indazol-5-yl)-[6-(1-methyl-1H-pyrazol-4-yl)-imidazo[1,2-b]pyridazin-3-yl]-methanol (Stage 150.1) as starting material (t_R 1.10 min (conditions 2), MH+=330).

Stage 150.1

(rac)-(1H-Indazol-5-yl)-[6-(1-methyl-1H-pyrazol-4-yl)-imidazo[1,2-b]pyridazin-3-yl]-methanol TBAF (1 M, 1 mL) was added to (rac)-[6-(1-Methyl-1H-pyrazol-4-yl)-imidazo[1,2-b]pyridazin-3-yl]-[2-(2-trimethylsilanyl-ethoxymethyl)-2H-indazol-5-yl]-methanol (Stage 150.2, 91 mg, 0.191 mmol) dissolved in THF (5 mL). The RM was heated at reflux for 1 h. After evaporation of the solvent, the residue was taken into EtOAc and washed with saturated aqueous sodium carbonate. The aqueous phase was again extracted 3 times with EtOAc and combined organic layers are dried on Na_2SO_4. After evaporation of the solvent, the crude was purified on preparative HPLC with acetonitrile and water (+0.1% TFA). The title compound was obtained from lyophilisation as a TFA salt (t_R 0.90 min (conditions 2), MH+=346).

Stage 150.2

(rac)-[6-(1-Methyl-1H-pyrazol-4-yl)-imidazo[1,2-b]pyridazin-3-yl]-[2-(2-trimethylsilanyl-ethoxymethyl)-2H-indazol-5-yl]-methanol.

(rac)-(6-Chloro-imidazo[1,2-b]pyridazin-3-yl)-[2-(2-trimethylsilanyl-ethoxymethyl)-2H-indazol-5-yl]-methanol (Stage 150.3, 134 mg, 0.296 mmol) was charged into a microwave vial together with DME (2 mL), 1-Methyl-4-(4,4,5,5-tetramethyl-[1,3,2]dioxaborolan-2-yl)-1H-pyrazole (173 mg, 0.815 mmol), followed by 2 M Na_2CO_3 (0.300 mL) and PdCl_2(PPh_3)_2 (20 mg). The RM was submitted to microwave irradiation at 150° C. for 30 min. After filtration and evaporation of the solvent, the residue was taken into EtOAc and washed with saturated aqueous sodium carbonate. The aqueous phase was again extracted 3 times with EtOAc. Combined organic layers were washed with brine and dried on Na_2SO_4. After evaporation of the solvent the crude was purified by flash chromatography (CombiFlash® Companion System®, with 12 g RediSep® silica gel column, DCM/MeOH=100:0->92:8) to afford the title compound (t_R 1.17 min (conditions 2), MH+=476)

Stage 150.3

(rac)-(6-Chloro-imidazo[1,2-b]pyridazin-3-yl)-[2-(2-trimethylsilanyl-ethoxymethyl)-2H-indazol-5-yl]-methanol The title compound was obtained analogously to (rac)-(6-chloro-imidazo[1,2-b]pyridazin-3-yl)imidazo[1,2-a]pyridin-6-yl-methanol (Stage 9.1) by replacing imidazo[1,2-a]pyridine-6-carbaldehyde with 2-(2-trimethylsilanyl-ethoxymethyl)-2H-indazole-5-carbaldehyde (Stage 150.4) (t_R 5.39 min (conditions 3), MH+=430).

Stage 150.4

2-(2-Trimethylsilanyl-ethoxymethyl)-2H-indazole-5-carbaldehyde

2H-Indazole-5-carbaldehyde (Stage 150.5, 770 mg, 5.27 mmol) was dissolved in THF (54 mL) and dicyclohexylmethylamine (1.37 mL, 6.32 mmol) was added. After dropwise addition of (2-chloromethoxy-ethyl)-trimethyl-silane (1.21 mL, 6.32 mmol), the RM was stirred for 48 h at rt. It was then taken into EtOAc and washed successively with 0.5 M aqueous NaOH solution and brine. The organic layer was dried on Na_2SO_4 and evaporated and the residue purified by flash chromatography (CombiFlash® Companion System®, with RediSep® silica gel column, n-hexane/EtOAc=100:0->70:30) to afford white crystals of the title compound (t_R 7.14 min (conditions 3), MH+=277).

Stage 150.5

2H-Indazole-5-carbaldehyde

5-Bromo-2H-indazole (2 g, 9.85 mmol) was dissolved in THF (50 mL) and cooled down to −40° C. n-BuLi in n-hexane (1.6 M, 15.4 mL) was added dropwise. After 15 min stirring, DMF (1.53 mL, 19.7 mmol) was added and the RM was stirred 30 min at −40° C. before warming up to rt. After 1 h, water was added (60 mL) and the mixture was extracted 3 times with EtOAc. Combined organic layers were washed with brine and dried on Na_2SO_4. After evaporation of the solvent the crude was purified by flash chromatography (CombiFlash® Companion System®, with 12 g RediSep® silica gel column, n-hexane/EtOAc=100:0->50:50) to afford the title compound (t_R 3.63 min (conditions 3), MH−=145).

EXAMPLE 151

(R)-[6-(1-Methyl-1H-pyrazol-4-yl)-imidazo[1,2-b]pyridazin-3-yl]-quinolin-6-yl-methanol

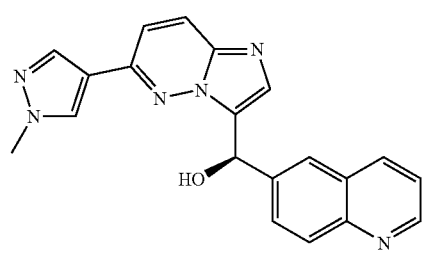 [SMILES: Cn1cc(-c2ccc3ncc([C@H](O)c4ccc5ncccc5c4)n3n2)cn1]

The title compound was obtained from the chiral separation of compound of Example 1 with a preparative HPLC on a Chiralcel OD (5×50 cm) column with a flow of 80 mL/min of n-hexane: EtOH:MeOH 60:35:5 (v/v). Oven 20° C., detection 210 nm ($t_R$ 24 min). ($t_R$ 1.0 min (conditions 1), MH+=357).

EXAMPLE 152

(S)-[6-(1-Methyl-1H-pyrazol-4-yl)-imidazo[1,2-b]pyridazin-3-yl]-quinolin-6-yl-methanol

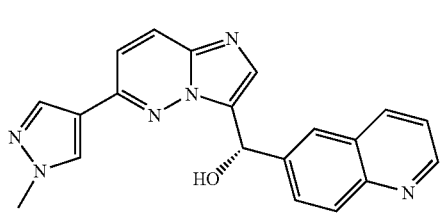 [SMILES: Cn1cc(-c2ccc3ncc([C@@H](O)c4ccc5ncccc5c4)n3n2)cn1]

The title compound was obtained from the chiral separation of compound of Example 1 with a Preparative HPLC on a Chiralcel OD (5×50 cm) column with a flow of 80 mL/min of n-hexane: EtOH:MeOH 60:35:5 (v/v) ($t_R$ 32 min). Oven 20° C., detection 210 nm. ($t_R$ 1.0 min (conditions 1), MH+=357).

EXAMPLE 153

(rac)-2,2,2-Trifluoro-N-(6-{hydroxy-[6-(1-methyl-1H-pyrazol-4-yl)-imidazo[1,2-b]pyridazin-3-yl]-methyl}-imidazo[1,2-a]pyridin-2-yl)-acetamide The title compound was obtained analogously to (rac)-(6-chloro-imidazo[1,2-b]pyridazin-3-yl)imidazo[1,2-a]pyridin-6-yl-methanol (Stage 9.1) by replacing imidazo[1,2-a]pyridine-6-carbaldehyde with 2,2,2-trifluoro-N-(6-formyl-imidazo[1,2-a]pyridin-2-yl)-acetamide (Stage 153.1) ($t_R$ 0.82 min (conditions 2), (MH+=457).

Stage 153.1

2,2,2-Trifluoro-N-(6-formyl-imidazo[1,2-a]pyridin-2-yl)-acetamide 2,2,2-Trifluoro-N-(6-iodo-imidazo[1,2-a]pyridin-2-yl)-acetamide (Stage 153.2, 1 g, 2.82 mmol) was dissolved in THF (15 mL) and cooled down to −40° C. under nitrogen atm. iPrMgCl in THF (2 M, 2.8 mL) was added dropwise. After 1 h stirring, cold DMF (0.65 mL, 8.46 mmol) in THF (1 mL) was added and the RM warmed up to −10° C. in 4 h. NH$_4$Cl solution was added and the mixture was extracted 3 times with EtOAc. Combined organic layers were washed with brine and dried on Na$_2$SO$_4$. After evaporation of the solvent the crude was purified by preparative HPLC with acetonitrile/water (with 0.1% TFA) to afford the title compound ($t_R$ 0.88 min (conditions 2), (MH+=258).

Stage 153.2

2,2,2-Trifluoro-N-(6-iodo-imidazo[1,2-a]pyridin-2-yl)-acetamide was obtained by following a literature procedure (*Synthesis,* 1998, 867) ($t_R$ 1.28 min (conditions 1), (MH+=356).

EXAMPLE 154

6-[1-(6-Chloro-imidazo[1,2-b]pyridazin-3-yl)-vinyl]-quinoline

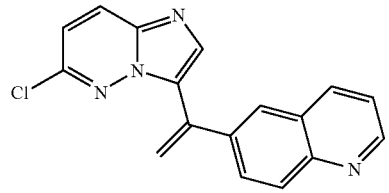 [SMILES: C=C(c1ccc2ncccc2c1)c1cnc2ccc(Cl)nn12]

(rac)-1-(6-Chloro-imidazo[1,2-b]pyridazin-3-yl)-1-quinolin-6-yl-ethanol (Stage 154.1, 50 mg, 0.154 mmol) was dissolved in acetic acid >99% (0.150 mL) and sulfuric acid conc. 98% (0.050 mL) and the mixture was heated to reflux for 1 h. After cooling down to rt, ice water was added. The mixture was basified with NaOH 1 N and extracted with EtOAc twice. Combined organic layers were washed with brine and dried on Na$_2$SO$_4$. After evaporation of the solvent the crude was purified by preparative HPLC with acetonitrile/water (with 0.1% TFA) to afford the title compound as a yellow solid ($t_R$ 1.10 min (conditions 1), (MH+=307).

Stage 154.1

(rac)-1-(6-Chloro-imidazo[1,2-b]pyridazin-3-yl)-1-quinolin-6-yl-ethanol (6-Chloro-imidazo[1,2-b]pyridazin-3-yl)-quinolin-6-yl-methanone (Stage 1.2, 500 mg, 1.62 mmol) was dissolved in anhydrous THF (10 mL) and cooled down to 0° C. Methylmagnesium bromide in toluene/THF (1.4 M, 1.27 mL) was slowly added and the RM was then warmed up to rt and stirred for 4 h. Water (2 mL) was added and the precipitate formed was filtered off. The filtrate was concentrated to give the title compound as a brown solid ($t_R$ 0.50 min (conditions 2), (MH+=325).

EXAMPLE 155

6-{1-[6-(1-Methyl-1H-pyrazol-4-yl)-imidazo[1,2-b]pyridazin-3-yl]-vinyl}-quinoline

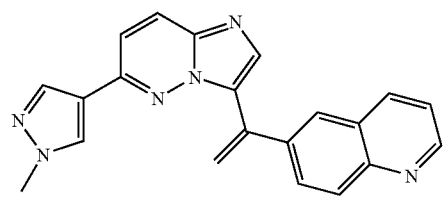 [SMILES: C=C(c1ccc2ncccc2c1)c1cnc2ccc(-c3cnn(C)c3)nn12]

6-[1-(6-Chloro-imidazo[1,2-b]pyridazin-3-yl)-vinyl]-quinoline (Example 154, 2.5 g, 8.15 mmol) was dissolved in DME (20 mL) under argon atm. 1-Methyl-4-(4,4,5,5-tetramethyl-[1,3,2]dioxaborolan-2-yl)-1H-pyrazole (2.54 g, 12.22 mmol) was added, followed by 2 M K₂CO₃ (11 mL) and PdCl₂(PPh₃)₂ (172 mg). The RM was stirred at 90° C. for 3 h. It was then taken into a mixture of EtOAc and brine and extracted. Organic phase was dried on Na₂SO₄. After evaporation of the solvent the crude was purified by column chromatography in silica gel with the eluent EtOAc/MeOH=9:1 then 4:1. The collected fractions containing product were concentrated and recrystallized from EtOAc/pentane. After a night drying under vacuo, the title compound was obtained as a beige powder ($t_R$ 3.65 min (conditions 3), MH+=353).

EXAMPLE 156

(rac)-6-{1-[6-(1-Methyl-1H-pyrazol-4-yl)-imidazo[1,2-b]pyridazin-3-yl]-ethyl}-1,2,3,4-tetrahydroquinoline

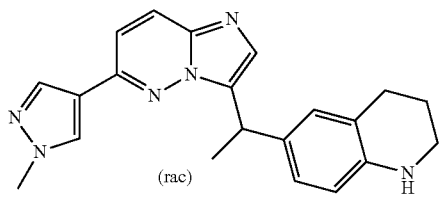 [SMILES: CC(c1ccc2c(c1)CCCN2)c1cnc2ccc(-c3cnn(C)c3)nn12]

6-{1-[6-(1-Methyl-1H-pyrazol-4-yl)-imidazo[1,2-b]pyridazin-3-yl]-vinyl}-quinoline (Example 155, 2.2 g, 6.24 mmol) was dissolved in ethanol (300 mL) and hydrogenated under H₂ atm. at rt in presence of Pd 15% C. After 10 h, the RM was filtered over Celite and the filtrate evaporated under vacuo. The residue was dried over night under vacuo and eluted on a silica gel column with EtOAc/MeOH=9:1 then 85:15 to afford, after evaporation of the solvent, crystals of the title compound ($t_R$ 3.24 min (conditions 3), MH+=359).

EXAMPLE 157

(rac)-6-{1-[6-(1-Methyl-1H-pyrazol-4-yl)-imidazo[1,2-b]pyridazin-3-yl]-ethyl}-quinoline

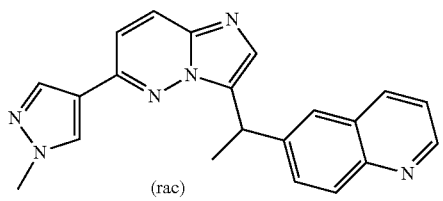 [SMILES: CC(c1ccc2ncccc2c1)c1cnc2ccc(-c3cnn(C)c3)nn12]

6-{1-[6-(1-Methyl-1H-pyrazol-4-yl)-imidazo[1,2-b]pyridazin-3-yl]-vinyl}-quinoline (Example 155, 2.2 g, 6.24 mmol) was dissolved in ethanol (300 mL) and hydrogenated under H₂ atm. at rt in presence of Pd/5% C. After 10 h, the RM was filtered over Celite and the filtrate evaporated under vacuo. The residue was dried over night under vacuo and eluted on a silica gel column with EtOAc/MeOH=9:1 then 85:15 to afford, after evaporation of the solvent, the title compound as a yellow foam ($t_R$ 3.21 min (conditions 3), MH+=355).

EXAMPLE 158

6-{(R)-1-[6-(1-Methyl-1H-pyrazol-4-yl)-imidazo[1,2-b]pyridazin-3-yl]-ethyl}-quinoline

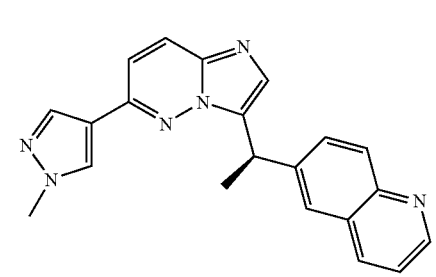 [SMILES: C[C@H](c1ccc2ncccc2c1)c1cnc2ccc(-c3cnn(C)c3)nn12]

The title compound was obtained from the chiral separation of compound of Example 157 with a preparative HPLC on a Chiralpak AD-H 5 um (20×250 mm) column with a flow of 15 mL/min of n-heptane:EtOH:MeOH 6:3:1 (v/v). Oven 20° C., detection 280 nm ($t_R$ 16.3 min). ($t_R$ 3.28 min (conditions 3), MH+=355, ¹H-NMR in DMSO-d6: 8.8 (dd, 1H); 8.33 (s, 1H); 8.31 (t, 1H); 8.04 (d, 1H); 7.98 (s, 2H); 7.92 (d, 1H); 7.78 (dd, 1H); 7.74 (s, 1H); 7.46 (dd, 1H); 7.44 (d, 1H); 4.82 (q, 1H ); 3.87 (s, 3H); 1.83 (d, 3H)).

EXAMPLE 159

6-{(S)-1-[6-(1-Methyl-1H-pyrazol-4-yl)-imidazo[1,2-b]pyridazin-3-yl]-ethyl}-quinoline

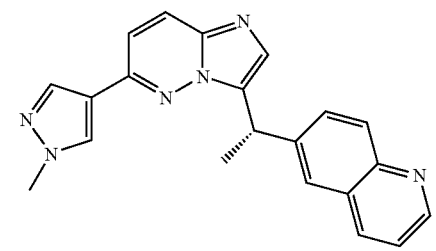 [SMILES: C[C@@H](c1ccc2ncccc2c1)c1cnc2ccc(-c3cnn(C)c3)nn12]

The title compound was obtained from the chiral separation of compound of Example 157 with a Preparative HPLC on a Chiralpak AD-H 5 um column (20×250 mm) with a flow of 15 mL/min of n-heptane:EtOH:MeOH 6:3:1 (v/v). Oven 20° C., detection 280 nm ($t_R$ 21.0 min). ($t_R$ 3.27 min (conditions 3), MH+=355, ¹H-NMR in DMSO-d6: 8.8 (dd, 1H), 8.33 (s, 1H), 8.31 (t, 1H), 8.04 (d, 1H), 7.98 (s, 2H), 7.92 (d, 1H), 7.78 (dd, 1H), 7.74 (s, 1H), 7.49 to 7.42 (m, 2H), 4.82 (q, 1H ), 3.87 (s, 3H), 1.83 (d, 3H)).

EXAMPLE 160

5-Fluoro-6-[6-(1-methyl-1H-pyrazol-4-yl)-imidazo[1,2-b]pyridazin-3-ylmethyl]-quinoline

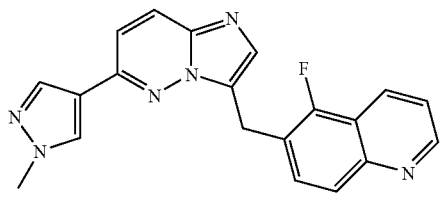 [SMILES: Cn1cc(-c2ccc3ncc(Cc4ccc5ncccc5c4F)n3n2)cn1]

The title compound was obtained by following synthesis described in Example 2 starting from (rac)-(5-fluoro-quinolin-6-yl)-[6-(1-methyl-1H-pyrazol-4-yl)-imidazo[1,2-b]pyridazin-3-yl]-methanol (Stage 160.1) ($t_R$ 1.0 min (conditions 1), (MH+=359).

Stage 160.1

(rac)-(5-Fluoro-quinolin-6-yl)-[6-(1-methyl-1H-pyrazol-4-yl)-imidazo[1,2-b]pyridazin-3-yl]-methanol was obtained analogously to Stage 9.1 by replacing 3-bromo-6-chloro-imidazo[1,2-b]pyridazine with 3-bromo-6-(1-methyl-1h-pyrazol-4-yl)-imidazo[1,2-b]pyridazine (Stage 8.1) and imidazo[1,2-a]pyridine-6-carbaldehyde with 5-fluoro-quinoline-6-carbaldehyde (Intermediate A) ($t_R$ 0.90 min (conditions 1), (MH+=375).

EXAMPLE 161

(rac)-(2-Amino-imidazo[1,2-a]pyridin-6-yl)-[6-(1-methyl-1H-pyrazol-4-yl)-imidazo[1,2-b]pyridazin-3-yl]-methanol

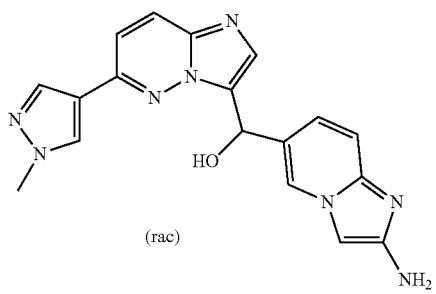 [SMILES: Cn1cc(-c2ccc3ncc(C(O)c4ccc5nc(N)cn5c4)n3n2)cn1]

(rac)-2,2,2-Trifluoro-N-(6-{hydroxy-[6-(1-methyl-1H-pyrazol-4-yl)-imidazo[1,2-b]pyridazin-3-yl]-methyl}-imidazo[1,2-a]pyridin-2-yl)-acetamide (Example 153, 120 mg, 0.263 mmol) was dissolved in THF/MeOH 1:1 (2 mL). $K_2CO_3$ was added (363 mg, 2.63 mmol) with water (1 mL) and the RM was heated over night at 90° C. After concentration under reduced pressure, the residue was purified by flash chromatography (CombiFlash® Companion System®, with 12 g RediSep® silica gel column, DCM/MeOH=8:2->DCM/MeOH/$H_2O$/ammonia=80:19:0.5: 0.5) to afford the title compound (MH+=361, $^1$H NMR in DMSO-d6: .8.5 (s, 1H); 8.4 (s, 1H); 8.1 (s, 1H); 8.0 (d, 1H); 7.6 (s, 1H); 7.5 (d, 1H), 7.1 (q, 2H), 7.0 (s, 1H); 6.2 (s, 2H); 5.0 (s, 2H); 3.9 (s, 3H)).

EXAMPLE 162

3-(1H-Benzoimidazol-5-ylmethyl)-6-(1-methyl-1H-pyrazol-4-yl)-imidazo[1,2-b]pyridazine

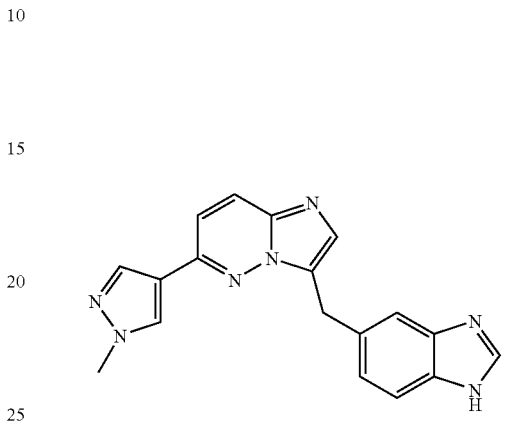

The title compound was obtained analogously to Example 2, starting from (rac)-(1H-benzoimidazol-5-yl)-[6-(1-methyl-1H-pyrazol-4-yl)-imidazo[1,2-b]pyridazin-3-yl]-methanol (Stage 162.1) ($t_R$ 0.7 min (conditions 2), (MH+=330).

Stage 162.1

(rac)-(1H-Benzoimidazol-5-yl)-[6-(1-methyl-1H-pyrazol-4-yl)-imidazo[1,2-b]pyridazin-3-yl]-methanol TBAF (1 M, 200 uL) was added to (rac)-[6-(1-Methyl-1H-pyrazol-4-yl)-imidazo[1,2-b]pyridazin-3-yl]-[1-(2-trimethylsilanyl-ethoxymethyl)-1H-benzoimidazol-5-yl]-methanol (Stage 162.2, 42 mg, 0.088 mmol) dissolved in THF (3 ml). The reaction mixture was heated at reflux for 1 h. After evaporation of the solvent, the residue was taken into EtOAc and washed with saturated aqueous sodium carbonate. The aqueous phase was again extracted with EtOAc (3×) and combined organic layers were dried on $Na_2SO_4$. After evaporation of the solvent, the title compound was obtained as an oil ($t_R$ 0.01 min (conditions 2), MH+=346).

Stage 162.2

(rac)-(1H-Benzoimidazol-5-yl)-[6-(1-methyl-1H-pyrazol-4-yl)-imidazo[1,2-b]pyridazin-3-yl]-methanol was obtained analogously to Stage 9.1 by replacing imidazo[1,2-a]pyridine-6-carbaldehyde with 1-(2-trimethylsilanyl-ethoxymethyl)-1H-benzoimidazole-5-carbaldehyde (Stage 162.3) ($t_R$ 1.02 min (conditions 2), (MH+=476).

Stage 162.3

1-(2-Trimethylsilanyl-ethoxymethyl)-1H-benzoimidazole-5-carbaldehyde was obtained analogously to Stage

EXAMPLE 163

6-{1-[6-(1-Methyl-1H-pyrazol-4-yl)-imidazo[1,2-b]pyridazin-3-yl]-cyclopropyl}-quinoline

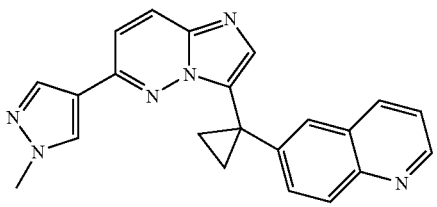 [SMILES: Cn1cc(-c2ccc3ncc(C4(c5ccc6ncccc6c5)CC4)n3n2)cn1]

NaH 60% (96 mg, 2.41 mmol) was introduced in a round bottom flask and placed under nitrogen. A solution of trimethylsulfoxonium chloride (372 mg, 2.84 mmol) in DMSO (4 mL) was added slowly at rt. It was stirred for 30 min until $H_2$ releasing was over. Then, a solution of 6-{1-[6-(1-methyl-1H-pyrazol-4-yl)-imidazo[1,2-b]pyridazin-3-yl]-vinyl}-quinoline (Example 155, 100 mg, 0.284 mmol) in DMSO (3 mL) was added dropwise. The RM was stirred for 1.5 h and then poured into 1 N NaOH. It was extracted twice with EtOAc and the organics were joined and washed with brine, dried over $Na_2SO_4$ and concentrated. The residue was again taken up in EtOAc and washed with water 4 times to take away remaining DMSO then washed with brine, dried over $Na_2SO_4$ and concentrated. It was purified by preparative HPLC with acetonitrile and water (+0.1% TFA) to give the title compound as a light yellow solid ($t_R$ 1.0 min (conditions 1), MH+=367).

EXAMPLE 164

(rac)-3-[1-(6-Fluoro-1H-indazol-5-yl)-ethyl]-6-(1-methyl-1H-pyrazol-4-yl)-imidazo[1,2-b]pyridazine

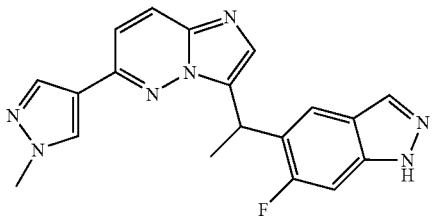 [SMILES: CC(c1cc2cn[nH]c2cc1F)c1cnc2ccc(-c3cnn(C)c3)nn12]

A mixture of (rac)-1-[6-Fluoro-2-(2-trimethylsilanyl-ethoxymethyl)-2H-indazol-5-yl]-1-[6-(1-methyl-1H-pyrazol-4-yl)-imidazo[1,2-b]pyridazin-3-yl]-ethanol and (rac)-1-[6-Fluoro-1-(2-trimethylsilanyl-ethoxymethyl)-1H-indazol-5-yl]-1-[6-(1-methyl-1H-pyrazol-4-yl)-imidazo[1,2-b]pyridazin-3-yl]-ethanol (Stage 164.1, 563 mg, 1.109 mmol), iodine (844 mg, 3.33 mmol), $H_3PO_2$ (1.815 mL of a 50% aqueous solution, 16.64 mmol) and acetic acid (9.5 mL) were introduced in a microwave tube and the mixture was subjected to MW-irradiation at 150° C. for 5 min. The solvent was removed and the residue was taken up with 1 N HCl and washed with EtOAc three times. The aqueous layer was basified with NaOH pellets and extracted twice with EtOAc. The organics were joined and washed with brine, dried over $Na_2SO_4$ and the solvent was removed. The title compound was obtained as a racemic mixture ($t_R$ 1.0 min (conditions 2), MH+=362).

Stage 164.1

A mixture of [6-fluoro-2-(2-trimethylsilanyl-ethoxymethyl)-2H-indazol-5-yl]-[6-(1-methyl-1H-pyrazol-4-yl)-imidazo[1,2-b]pyridazin-3-yl]-methanone and [6-fluoro-1-(2-trimethylsilanyl-ethoxymethyl)-1H-indazol-5-yl]-[6-(1-methyl-1H-pyrazol-4-yl)-imidazo[1,2-b]pyridazin-3-yl]-methanone (Stage 164.2, 840 mg, 1.709 mmol) was dissolved in anhydrous THF (13 mL) under nitrogen conditions and cooled down to 0° C. Methylmagnesium bromide in THF (1.4 M, 4.05 mL) was slowly added and the RM was then warmed up to rt and stirred for 6.5 h. The reaction was quenched with water and the RM taken up in EtOAc and washed with water and brine. The organic layer was dried over $Na_2SO_4$ and the solvent was removed. The residue was purified by chromatography with DCM and MeOH to give a mixture of (rac)-1-[6-fluoro-2-(2-trimethylsilanyl-ethoxymethyl)-2H-indazol-5-yl]-1-[6-(1-methyl-1H-pyrazol-4-yl)imidazo[1,2-b]pyridazin-3-yl]-ethanol and (rac)-1-[6-fluoro-1-(2-trimethylsilanyl-ethoxymethyl)-1H-indazol-5-yl]-1-[6-(1-methyl-1H-pyrazol-4-yl)-imidazo[1,2-b]pyridazin-3-yl]-ethanol as a brown oil ($t_R$ 1.3 min (conditions 2), MH+=508).

Stage 164.2

A mixture of (rac)-[6-Fluoro-2-(2-trimethylsilanyl-ethoxymethyl)-2H-indazol-5-yl]-[6-(1-methyl-1H-pyrazol-4-yl)-imidazo[1,2-b]pyridazin-3-yl]-methanol and (rac)-[6-Fluoro-1-(2-trimethylsilanyl-ethoxymethyl)-1H-indazol-5-yl]-[6-(1-methyl-1H-pyrazol-4-yl)-imidazo[1,2-b]pyridazin-3-yl]-methanol (Stage 164.3, 1.57 g, 3.18 mmol) was dissolved in DCM (15 mL) and Dess-Martin periodinane (1.349 g, 3.18 mmol) was added. The RM was stirred for 1 h at rt. It was then taken up with EtOAc and washed with 2.5 M NaOH twice and with brine. The organic layer was then dried over $Na_2SO_4$ and the solvent was removed. The residue was purified by MPLC with hexane and EtOAc to give a mixture of [6-fluoro-2-(2-trimethylsilanyl-ethoxymethyl)-2H-indazol-5-yl]-[6-(1-methyl-1H-pyrazol-4-yl)-imidazo[1,2-b]pyridazin-3-yl]-methanone and [6-fluoro-1-(2-trimethylsilanyl-ethoxymethyl)-1H-indazol-5-yl]-[6-(1-methyl-1H-pyrazol-4-yl)-imidazo[1,2-b]pyridazin-3-yl]-methanone as a brown solid ($t_R$ 1.6 min and 1.7 min (conditions 2), 492).

Stage 164.3

The mixture of (rac)-[6-fluoro-2-(2-trimethylsilanyl-ethoxymethyl)-2H-indazol-5-yl]-[6-(1-methyl-1H-pyrazol-4-yl)-imidazo[1,2-b]pyridazin-3-yl]-methanol and (rac)-[6-fluoro-1-(2-trimethylsilanyl-ethoxymethyl)-1H-indazol-5-yl]-[6-(1-methyl-1H-pyrazol-4-yl)-imidazo[1,2-b]pyridazin-3-yl]-methanol was obtained by following procedure of Stage 150.2 starting with a mixture of (rac)-(6-chloro-imidazo[1,2-b]pyridazin-3-yl)-[6-fluoro-1-(2-trimethylsilanyl-ethoxymethyl)-1H-indazol-5-yl]-methanol and (rac)-[6-fluoro-2-(2-trimethylsilanyl-ethoxymethyl)-2H-indazol-5-yl]-[6-(1-methyl-1H-pyrazol-4-yl)-imidazo[1,2-b]pyridazin-3-yl]-methanol (Stage 164.4), replacing $PdCl_2(PPh_3)_2$ with tetrakis-(triphenylphosphine)-palladium and MW-irradiation by a classical 80° C. heating overnight ($t_R$ 1.20 min for both (conditions 2), MH+=494).

Stage 164.4

The brown solid mixture of (rac)-(6-chloro-imidazo[1,2-b]pyridazin-3-yl)-[6-fluoro-1-(2-trimethylsilanyl-ethoxymethyl)-1H-indazol-5-yl]-methanol and (rac)-(6-chloro-imidazo[1,2-b]pyridazin-3-yl)-[6-fluoro-2-(2-trimethylsilanyl-ethoxymethyl)-2H-indazol-5-yl]-methanol was obtained analogously to Stage 150.3 starting from a mixture of 6-fluoro-1-(2-trimethylsilanyl-ethoxymethyl)-1H-indazole-5-carbaldehyde and 6-fluoro-2-(2-trimethylsilanyl-ethoxymethyl)-2H-indazole-5-carbaldehyde (Stage 164.5) ($t_R$ 1.40 min and 1.50 min (conditions 2).

Stage 164.5

The colorless oily mixture of 6-fluoro-1-(2-trimethylsilanyl-ethoxymethyl)-1H-indazole-5-carbaldehyde and 6-fluoro-2-(2-trimethylsilanyl-ethoxymethyl)-2H-indazole-5-carbaldehyde was obtained analogously to Stage 150.4 by starting from Intermediate E and replacing dicyclohexylmethylamine with NaH and letting it react 2 h before adding (2-Chloromethoxy -ethyl)-trimethyl-silane. The reaction was then quenched with water after 30 min. (MH+=295).

EXAMPLE 165

3-[(S)-1-(6-Fluoro-1H-indazol-5-yl)-ethyl]-6-(1-methyl-1H-pyrazol-4-yl)-imidazo[1,2-b]pyridazine

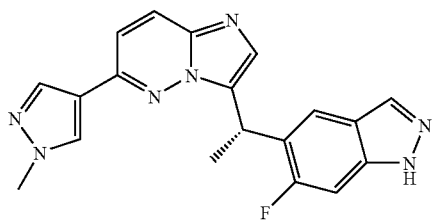 [SMILES: C[C@@H](c1cc2cn[nH]c2cc1F)c1cnc2ccc(-c3cnn(C)c3)nn12]

The title compound was obtained from the chiral separation of compound of Example 164 with a Preparative HPLC on a Chiralpak ADOOSC-JF004H (5×550 cm) column with a flow of 60 mL/min of EtOH:MeOH 60:40 (v/v). Oven 20° C., detection 210 nm ($t_R$ 35 min). ($t_R$ 1.0 min (conditions 2), MH+=362).

EXAMPLE 166

3-[(R)-1-(6-Fluoro-1H-indazol-5-yl)-ethyl]-6-(1-methyl-1H-pyrazol-4-yl)-imidazo[1,2-b]pyridazine

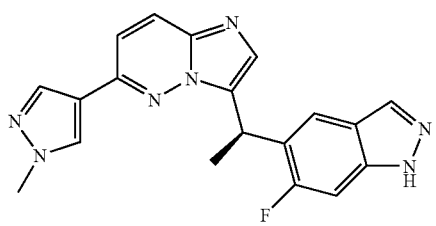 [SMILES: C[C@H](c1cc2cn[nH]c2cc1F)c1cnc2ccc(-c3cnn(C)c3)nn12]

The title compound was obtained from the chiral separation of compound of Example 164 with a Preparative HPLC on a Chiralpak ADOOSC-JF004H (5×550 cm) column with a flow of 60 mL/min of EtOH:MeOH 60:40 (v/v). Oven 20° C., detection 210 nm ($t_R$ 27 min). ($t_R$ 1.0 min (conditions 2), MH+=362).

EXAMPLE 167

3-(6-Fluoro-1H-indazol-5-ylmethyl)-6-(1-methyl-1H-pyrazol-4-yl)-imidazo[1,2-b]pyridazine

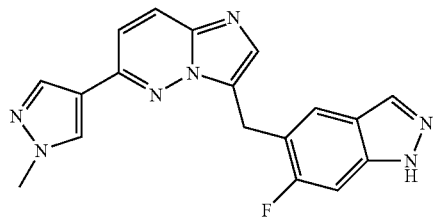 [SMILES: Cn1cc(-c2ccc3ncc(Cc4cc5cn[nH]c5cc4F)n3n2)cn1]

A mixture of (rac)-[6-fluoro-1-(2-trimethylsilanyl-ethoxymethyl)-1H-indazol-5-yl]-[6-(1-methyl-1H-pyrazol-4-yl)-imidazo[1,2-b]pyridazin-3-yl]-methanol and (rac)-[6-fluoro-2-(2-trimethylsilanyl-ethoxymethyl)-2H-indazol-5-yl]-[6-(1-methyl-1H-pyrazol-4-yl)-imidazo[1,2-b]pyridazin-3-yl]-methanol (Stage 164.3, 400 mg, 0.810 mmol), iodine (617 mg, 2.431 mmol) and $H_3PO_2$ (1.326 mL of a 50% aqueous solution, 12.16 mmol) were introduced in a microwave tube and the mixture was subjected to MW-irradiation at 150° C. for 5 min. The solvent was removed and the residue was taken up with 1 N HCl and washed with EtOAc three times. The aqueous layer was basified with NaOH pellets and extracted with EtOAc/MeOH (9:1) three times. The organics were joined and washed with brine, dried over $Na_2SO_4$ and the solvent was removed. The residue was purified by MPLC with DCM and MeOH to give the title compound as a light yellow solid ($t_R$ 0.90 min (conditions 2), MH+=348, $^1$H-NMR in DMSO-d6: 13.00 (s, 1H); 8.40 (s, 1H); 8.05 (m, 2H); 7.75 (d, 1H); 7.55 (m, 2H); 7.32 (d, 1H)).

EXAMPLE 168

(rac)-2,2,2-Trifluoro-1-[6-(1-methyl-1H-pyrazol-4-yl)-imidazo[1,2-b]pyridazin-3-yl]-1-quinolin-6-yl-ethanol

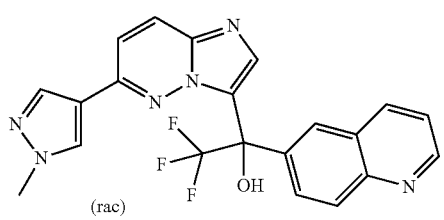 [SMILES: Cn1cc(-c2ccc3ncc(C(O)(c4ccc5ncccc5c4)C(F)(F)F)n3n2)cn1]

The title compound was obtained analogously to Example 1, starting from (rac)-(6-chloro-imidazo[1,2-b]pyridazin-3-yl)-2,2,2-trifluoro-1-quinolin-6-yl-ethanol (Stage 168.1) ($t_R$ 0.8 min (conditions 2), MH+=425).

Stage 168.1

(rac)-1-(6-Chloro-imidazo[1,2-b]pyridazin-3-yl)-2,2,2-trifluoro-1-quinolin-6-yl-ethanol (6-chloro-imidazo[1,2-b]pyridazin-3-yl)-quinolin-6-yl-methanone (Stage 1.2, 411 mg, 1.331 mmol) was dissolved in THF (1.5 mL) and DMF (1.5 mL) together with (trifluoromethyl)trimethylsilane (0.255 mL, 1.598 mmol) and the mixture was cooled down to 0° C. TBAF solution (1 M, 0.067 mL) was then added slowly. After 5 min, the RM was allowed to warm up to rt. After 24 h of stirring, it was warmed up to 50° C. and stirred for 24 h more. The reaction was then quenched with 1 N HCl. The precipitate formed was filtered off and identified as remaining pure starting material The solution was basified with pellets of NaOH. The second precipitate formed and filtered off was starting material as well. The aqueous layer was extracted twice with EtOAc and then the joined organics were washed with brine and dried over $Na_2SO_4$. After removing the solvent, the residue was purified by MPLC with DCM and MeOH to give the title compound as a brown solid ($t_R$ 0.8 min (conditions 2), MH+=379).

EXAMPLE 169

6-[6-(1-Methyl-1H-pyrazol-4-yl)-imidazo[1,2-b]pyridazin-3-ylmethyl]-7-trifluoromethyl-quinoline

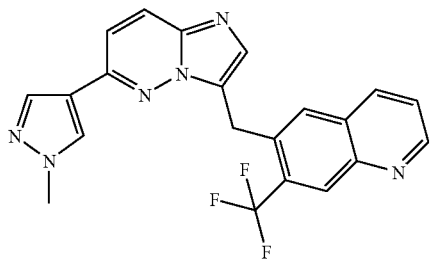 [SMILES: Cn1cc(-c2ccc3ncc(Cc4cc5cccnc5cc4C(F)(F)F)n3n2)cn1]

The title compound was obtained by analogy to Example 2 starting from (rac)-[6-(1-methyl-1H-pyrazol-4-yl)-imidazo[1,2-b]pyridazin-3-yl]-(7-trifluoromethyl-quinolin-6-yl)-methanol (Stage 169.1) ($t_R$ 1.41 min (conditions 12), MH+=409 (LCMS)).

Stage 169.1

(rac)-[6-(1-Methyl-1H-pyrazol-4-yl)-imidazo[1,2-b]pyridazin-3-yl]-(7-trifluoromethyl-quinolin-6-yl)-methanol was obtained in analogy to Example 1 starting from (rac)-(6-chloro-imidazo[1,2-b]pyridazin-3-yl)-(7-trifluoromethyl-quinolin-6-yl)-methanol (Stage 169.2) ($t_R$ 1.33 min (conditions 12), MH+=425 (LCMS))

Stage 169.2

(rac)-(6-Chloro-imidazo[1,2-b]pyridazin-3-yl)-(7-trifluoromethyl-quinolin-6-yl)-methanol 3-Bromo-6-chloro-imidazo[1,2-b]pyridazine (500 mg, 2.15 mmol) was dissolved THF (50 mL) and under nitrogen conditions, ethylmagnesium bromide solution (3 M, 0.860 mL) was added. The RM was stirred at rt for 30 min then a solution of 7-trifluoromethyl-quinoline-6-carbaldehyde (Intermediate G, 723 mg, 2.15 mmol) in THF was added. It was stirred at rt for 1 h. The solvent was removed and the residue was taken up with EtOAc and washed with water and brine. It was dried over $Na_2SO_4$ and the solvent was evaporated in vacuo. The residue was triturated with $Et_2O$ and the precipitate was filtered off. The title compound was obtained as a grey solid ($t_R$ 1.48 min (conditions 12), MH+=379).

EXAMPLE 170

5,7-Difluoro-6-[6-(1-methyl-1H-pyrazol-4-yl)-imidazo[1,2-b]pyridazin-3-ylmethyl]-quinoline

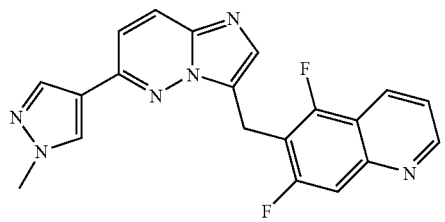 [SMILES: Cn1cc(-c2ccc3ncc(Cc4c(F)cc5ncccc5c4F)n3n2)cn1]

The title compound was obtained in analogy to Example 169 by replacing 7-trifluoromethyl-quinoline-6-carbaldehyde (Intermediate G) with 5,7-difluoro-quinoline-6-carbaldehyde (Intermediate E) ($t_R$ 0.9 min (conditions 2), MH+=377).

EXAMPLE 171

2-{4-[3-(5,7-Difluoro-quinolin-6-ylmethyl)-imidazo[1,2-b]pyridazin-6-yl]-pyrazol-1-yl}-ethanol

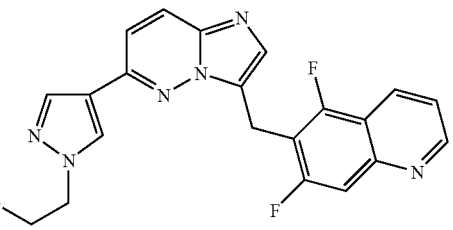

5,7-Difluoro-6-(6-{1-[2-(tetrahydro-pyran-2-yloxy)-ethyl]-1H-pyrazol-4-yl}-imidazo[1,2-b]pyridazin-3-ylmethyl)-quinoline (Stage 170.1, 82.2 mg, 0.168 mmol) was dissolved in DCM (2 mL) and a solution of 4 N HCl in dioxane (0.126 mL) was added. The RM was stirred at rt for 1 h and the solvent was removed. It was then taken up with EtOAc and washed with saturated $NaHCO_3$ and brine. The organic layer was dried over $Na_2SO_4$ and the solvent was removed. The residue was purified by preparative HPLC with acetonitrile and water (+0.1% TFA). The solvent was removed and the residue was diluted in MeOH. The solution was passed through an SPE cartridge of $HCO_3^-$ to remove the TFA salt. The filtrate was evaporated to give the free salt of the title compound ($t_R$ 0.8 min (conditions 2), MH+=407, $^1$H-NMR in DMSO-d6: 8.92 (dd, 1H); 8.51 (d, 1H); 8.38 (s, 1H); 8.06 (t, 2H); 7.72 (d, 1H); 7.59 (dd, 1H); 7.57 (s, 1H); 7.51 (d, 1H); 4.55 (s, 2H); 4.20 (t, 2H); 3.78-3.73 (m, 2H); 3.13 (s, 1H)).

Stage 171.1

5,7-Difluoro-6-(6-{1-[2-(tetrahydro-pyran-2-yloxy)-ethyl]-1H-pyrazol-4-yl}-imidazo[1,2-b]pyridazin-3-ylmethyl)-quinoline 6-(6-Chloro-imidazo[1,2-b]pyridazin-3-ylmethyl)-5,7-difluoro-quinoline (Stage 171.2, 90 mg, 0.272 mmol) was introduced in a microwave reactor together with 1-[2-(tetrahydro-pyran-2-yloxy)-ethyl]-4-(4,4,5,5-tetramethyl-[1,3,2]dioxaborolan-2-yl)-1H-pyrazole (Stage 171.4, 88 mg, 0.272 mmol), tetrakis-(triphenylphosphine)-palladium (15.72 mg), 2 M $Na_2CO_3$ (0.490 mL) and DME (0.9 mL). The mixture was heated at 150° C. under microwave irradiation for 30 min. The RM was taken up with EtOAc and washed with 10% $Na_2CO_3$ and brine. The organic layer was dried over $Na_2SO_4$, filtered and concentrated in vacuo. The residue was dissolved in MeOH and filtered through a cartridge of PL-Thiol to remove the palladium. The filtrate was then purified by preparative HPLC with acetonitrile and water (+0.1% TFA) to afford the title compound ($t_R$ 1.1 min (conditions 2), MH+=491).

Stage 171.2

6-(6-Chloro-imidazo[1,2-b]pyridazin-3-ylmethyl)-5,7-difluoro-quinoline (rac)-(6-Chloro-imidazo[1,2-b]pyridazin-3-yl)-(5,7-difluoro-quinolin-6-yl)-methanol (Stage 171.3, 200 mg, 0.577 mmol) was dissolved in acetic acid (4.93 mL) and introduced in a microwave reactor together with iodine (439 mg, 1.731 mmol) and $H_3PO_2$ (0.47 mL of a 50% aqueous solution, 8.65 mmol). The RM was stirred under microwave irradiations at 150° C. for 5 min. It was basified by a 2.5 M NaOH solution and extracted twice with EtOAc. The organics were joined and washed with brine, dried over $Na_2SO_4$ and the solvent was removed to afford the title compound as a beige solid ($t_R$ 1.0 min (conditions 2), MH+=331).

Stage 171.3

(rac)-(6-Chloro-imidazo[1,2-b]pyridazin-3-yl)-(5,7-difluoro-quinolin-6-yl)-methanol 3-Bromo-6-chloro-imidazo[1,2-b]pyridazine (4.40 g, 18.95 mmol) was suspended in THF (189 mL) and the ethyl-magnesium solution (3 M, 6.32 mL) was added slowly under nitrogen condition. The RM was stirred at rt for 15 min and the solution of 5,7-difluoro-quinoline-6-carbaldehyde (Intermediate F, 3.66 g, 18.95 mmol) was added. After 30 min, the reaction was quenched with 10% ammonium chloride. The precipitate was filtered off and a first part of the title compound was obtained as a white solid. The filtrate was concentrated and was taken up with 10% $NH_4Cl$. The precipitate was filtered off and was washed with EtOAc. A second part of the title compound was obtained as a brown solid ($t_R$ 0.8 min (conditions 2), MH+=347).

Stage 171.4

1-[2-(Tetrahydro-pyran-2-yloxy)-ethyl]-4-(4,4,5,5-tetramethyl-[1,3,2]dioxaborolan-2-yl)-1H-pyrazole This stage was prepared like described in patent application US 2007/0265272, p. 38 & 39: To a solution of 4-iodo-1-[2-(tetrahydro-pyran-2-yloxy)-ethyl]-1H-pyrazole (Stage 171.5, 7 g, 21.73 mmol) in anhydrous THF (55 mL) was added at 0° C. under argon iPrMgCl in THF (2 M, 21.73 mL) drop by drop. The RM was stirred at 0° C. for 1 h. Then 2-methoxy-4,4,5,5-tetramethyl-1,3,2-dioxaborolane (5.36 g, 32.6 mmol) was added at 0° C. and the solution was stirred at rt for 1 further hour. The RM was then quenched with 140 mL sat. aqueous $NH_4Cl$ and extracted with 3×150 mL EtOAc. The combined organic layers were washed with 70 mL sat. aqueous $NH_4Cl$, dried over $Na_2SO_4$, filtered and evaporated to dryness. The residue was purified by flash chromatography (4×20 cm, Hexane/EtOAc 5%-40%) to afford the title compound as a colorless oil ($t_R$ 3.20 min (conditions 8), MH+=323).

Stage 171.5

4-Iodo-1-[2-(tetrahydro-pyran-2-yloxy)-ethyl]-1H-pyrazole

In flask were introduced 4-iodopyrazole (10 g, 51.6 mmol), cesium carbonate (20.16 g, 61.9 mmol) and anhydrous DMF (98 mL). The suspension was stirred at rt for 5 min, before adding 2-(2-bromoethoxy)tetrahydro-2H-pyran (9.74 mL, 61.9 mmol) and heating at 70° C. for 17 h. Then the RM was quenched with 100 mL water and extracted with 3×120 mL EtOAc. The combined organic layers were washed with 3×100 mL water and 1×100 mL brine, before being dried over $Na_2SO_4$, filtered and evaporated to dryness. The residue was purified by flash chromatography (6×25 cm, Hexane/EtOAc 0%-30%) to afford the title compound as a colorless oil ($t_R$ 3.12 min (conditions 8), MH+=323).

EXAMPLE 172

5-Chloro-6-[6-(1-methyl-1H-pyrazol-4-yl)-imidazo[1,2-b]pyridazin-3-ylmethyl]-quinoline

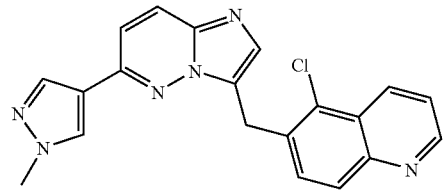 [SMILES: Cn1cc(-c2ccc3ncc(Cc4ccc5ncccc5c4Cl)n3n2)cn1]

The title compound was obtained in analogy to Example 169 by replacing 7-trifluoromethyl-quinoline-6-carbaldehyde (Intermediate G) by 5-chloro-quinoline-6-carbaldehyde (Intermediate C) ($t_R$ 2.38 min (conditions 8), MH+=375).

EXAMPLE 173

7-Fluoro-6-[6-(1-methyl-1H-pyrazol-4-yl)-imidazo[1,2-b]pyridazin-3-ylmethyl]-quinoline

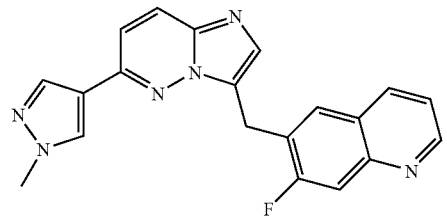 [SMILES: Cn1cc(-c2ccc3ncc(Cc4cc5cccnc5cc4F)n3n2)cn1]

The title compound was obtained by following procedure of Stage 150.2 starting from 6-(6-chloro-imidazo[1,2-b]pyridazin-3-ylmethyl)-7-fluoro-quinoline (Stage 173.1) and replacing $Na_2CO_3$ with $K_2CO_3$ and MW-irradiation by a classical 95° C. heating for 2 h ($t_R$ 3.41 min (conditions 3), MH+=359).

Stage 173.1

6-(6-Chloro-imidazo[1,2-b]pyridazin-3-ylmethyl)-7-fluoro-quinoline

The title compound was obtained from (rac)-(6-chloro-imidazo[1,2-b]pyridazin-3-yl)-(7-fluoro-quinolin-6-yl)-methanol (Stage 174.3) treated with iodine and $H_3PO_2$ in the conditions described in Example 2 ($t_R$ 4.41 min (conditions 3), MH+=313).

EXAMPLE 174

(rac)-1-(7-Fluoro-quinolin-6-yl)-1-[6-(1-methyl-1H-pyrazol-4-yl)-imidazo[1,2-b]pyridazin-3-yl]-ethanol

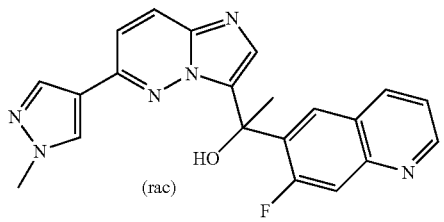 [SMILES: Cn1cc(-c2ccc3ncc(C(C)(O)c4cc5cccnc5cc4F)n3n2)cn1]

(rac)-1-(6-Chloro-imidazo[1,2-b]pyridazin-3-yl)-1-(7-fluoro-quinolin-6-yl)-ethanol (Stage 174.1, 51.4 mg, 0.15 mmol) was charged into a microwave vial together with DME (1 mL), 1-methyl-4-(4,4,5,5-tetramethyl-[1,3,2]dioxaborolan-2-yl)-1H-pyrazole (46.8 mg, 0.225 mmol), followed by 2 M $K_2CO_3$ (0.203 mL) and Pd(PPh$_3$)$_2$Cl$_2$ (3.2 mg). The RM was heated at 80-90° C. for 2 h. The RM was extracted with DCM and water. The organic phase was dried on $MgSO_4$. After evaporation of the solvent the crude was purified by flash chromatography (CombiFlash® Companion System®, with 4 g RediSep® silica gel column, EtOAc/MeOH=100:0->80:20) to afford, after recrystallisation in pentane/EtOAc, a beige powder of the title compound ($t_R$ 3.31 min (conditions 3), MH+=389, 1H-NMR in DMSO-d6: 8.86 (d, 1H); 8.64 (d, 2H); 8.03 (d, 1H); 7.83 (d, 2H); 7.57-7.49 (m, 2H); 7.42 (s, 1H); 7.38 (d, 2H); 6.26 (s, 1H); 3.68 (s, 3H); 2.14 (s, 3H)).

Stage 174.1

(rac)-1-(6-Chloro-imidazo[1,2-b]pyridazin-3-yl)-1-(7-fluoro-quinolin-6-yl)-ethanol (6-Chloro-imidazo[1,2-b]pyridazin-3-yl)-(7-fluoro-quinolin-6-yl)-methanone (Stage 174.2, 294 mg, 0.9 mmol) was dissolved in anhydrous THF (70 mL) at 40° C. and methylmagnesium bromide in Et$_2$O (3 M, 0.36 mL) was slowly added and the RM was then allowed to cool down to rt and stirred for 2 h. More methylmagnesium bromide in Et$_2$O (3 M, 0.5 mL) was added and the RM was stirred for 1 h more. It was then taken into DCM and 10% aqueous NaHCO$_3$ solution and extracted. The organic phase was dried on MgSO$_4$. After evaporation of the solvent the crude was purified by flash chromatography (CombiFlash® Companion System®, with RediSep® silica gel column, EtOAc/MeOH=100:0->90:10) to afford the title compound ($t_R$ 3.74 min (conditions 3), MH+=343, $^1$H-NMR in DMSO-d6: 8.87 (dd, 1H); 8.50 (d, 1H); 8.49 (d, 1H); 8.18 (d, 1H); 7.85 (s, 1H); 7.59 (d, 1H); 7.51 (dd, 1H); 7.23 (d, 1H); 6.33 (s, 1H); 2.13 (s, 3H))

Stage 174.2

(6-Chloro-imidazo[1,2-b]pyridazin-3-yl)-(7-fluoro-quinolin-6-yl)-methanone (rac)-(6-Chloro-imidazo[1,2-b]pyridazin-3-yl)-(7-fluoro-quinolin-6-yl)-methanol (Stage 174.3, 329 g, 1.0 mmol) was dissolved in acetone (40 mL) and 2-iodoxybenzoic acid (45%, 1.245 g, 2.0 mmol) was added. The RM was heated to reflux for 3 h (suspension). The acetone was then removed under reduced pressure and the residue was taken up with water and 2 M NaOH. The beige suspension was filtered, washed with water and dried overnight under vacuum to afford the title compound as a beige powder ($t_R$ 4.31 min (conditions 3), MH+=327, $^1$H-NMR in DMSO-d6: 9.03 (d, 1H); 8.53 (d, 1H); 8.49-8.41 (m, 2H); 8.39 (s, 1H); 7.90 (d, 1H); 7.74 (d, 1H); 7.62 (dd, 1H)).

Stage 174.3

(rac)-(6-Chloro-imidazo[1,2-b]pyridazin-3-yl)-(7-fluoro-quinolin-6-yl)-methanol

3-Bromo-6-chloro-imidazo[1,2-b]pyridazine (1.327 g, 5.71 mmol) was dissolved THF (40 mL) and under nitrogen conditions, it was cooled down to 0° C. and ethylmagnesium bromide solution (1 M, 6.85 mL) was added. The RM was stirred at rt for 30 min then a solution of 7-fluoro-quinoline-6-carbaldehyde (Intermediate B), (1.0 g, 5.71 mmol) in THF (20 mL) was added by 0° C. The RM was stirred at rt for 2 h. The solvent was partially removed by evaporation and water (40 mL) was added to the residual mash. After 1 h stirring, the crystallized product was filtered and dried overnight under vacuum to afford the title compound as a powder ($t_R$ 3.70 min (conditions 3), MH+=329, $^1$H-NMR in DMSO-d6: 8.90 (dd, 1H); 8.46 (d, 1H); 8.29-8.23 (m, 2H); 7.72 (d, 1H); 7.54-7.49 (m, 2H); 7.40 (d, 1H); 6.56-6.49 (m, 2H)).

EXAMPLE 175

(R)-1-(7-Fluoro-quinolin-6-yl)-1-[6-(1-methyl-1H-pyrazol-4-yl)-imidazo[1,2-b]pyridazin-3-yl]-ethanol

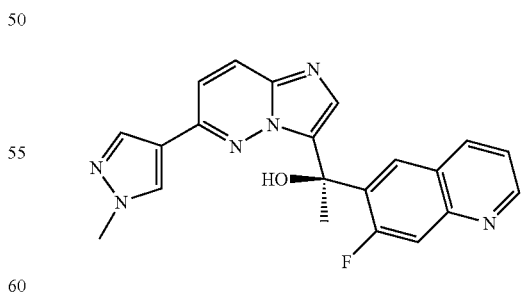

The title compound was obtained from the chiral separation of compound of Example 174 with a preparative HPLC on a on a Chiracel OJ (20 um) 10×50 cm column with a flow of 100-120 mL/min of n-hexane:EtOH 70:30 (v/v). Oven 20° C., detection 210 nm ($t_R$ 77.6) ($t_R$ 3.24 min (conditions 3), MH+=389 $^1$H-NMR in DMSO-d6: 8.86 (d, 1H); 8.64 (d, 2H);

8.03 (d, 1H); 7.83 (d, 2H); 7.57-7.49 (m, 2H); 7.42 (s, 1H); 7.38 (d, 2H); 6.26 (s, 1H); 3.68 (s, 3H); 2.14 (s, 3H)).

EXAMPLE 176

{4-[3-(7-Fluoro-quinolin-6-ylmethyl)-imidazo[1,2-b]pyridazin-6-yl]-pyrazol-1-yl}-acetonitrile

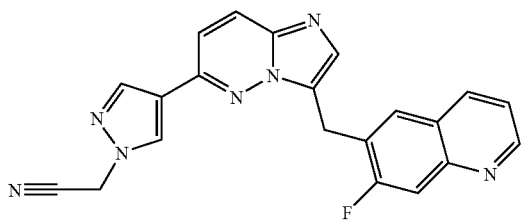 [SMILES: N#CCn1cc(-c2ccc3ncc(Cc4cc5cccnc5cc4F)n3n2)cn1]

The title compound was prepared in analogy to the compound of Example 231 using bromoacetonitrile instead of 1-(2-chlorethyl)pyrrolidine hydrochloride (t$_R$ 3.52 min (conditions 3), MH+=384.1).

EXAMPLE 177

(rac)-2-{4-[3-(1-Quinolin-6-yl-ethyl)-imidazo[1,2-b]pyridazin-6-yl]-pyrazol-1-yl}-ethanol

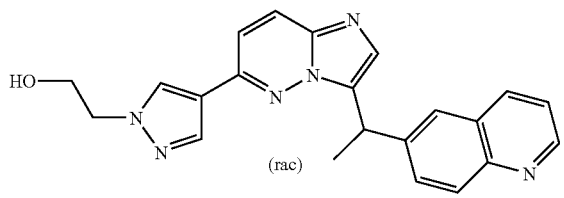 [SMILES: CC(c1ccc2ncccc2c1)c1cnc2ccc(-c3cnn(CCO)c3)nn12]

In a flask were introduced (rac)-6-[1-(6-{1-[2-(tetrahydro-pyran-2-yloxy)-ethyl]-1H-pyrazol-4-yl}-imidazo[1,2-b]pyridazin-3-yl)-ethyl]-quinoline (Stage 177.1, 147 mg, 0.33 mmol) and DCM (4 mL), before adding dropwise HCl in dioxane (4 N, 0.248 mL). The RM was stirred at rt for 1 h and was then blown off with nitrogen. The residue was dissolved in water/CH$_3$CN 1:1. The solution was basified with NaHCO$_3$ (ca. 0.5 g) before being concentrated. The white suspension was filtered and the cake was washed with water, before being dried under vacuum. The crude was dissolved in MeOH/water and purified by preparative HPLC (H$_2$O/CH$_3$CN/TFA 1000:0:1 to 750:250:1 in 20 min.). Collected fractions containing the product were put together and basified with NaHCO$_3$, before being concentrated. The resulting white suspension was filtered and the cake was washed with water, before being dried under high vacuum to give the title compound as a white solid (t$_R$ 1.83 min (conditions 8), MH+=360).

Stage 177.1

(rac)-6-[1-(6-{1-[2-(Tetrahydro-pyran-2-yloxy)-ethyl]-1H-pyrazol-4-yl}-imidazo[1,2-b]pyridazin-3-yl)-ethyl]-quinoline In a microwave vial were introduced under argon 1-[2-(tetrahydro-pyran-2-yloxy)-ethyl]-4-(4,4,5,5-tetramethyl-[1,3,2]dioxaborolan-2-yl)-1H-pyrazole (Stage 171.4, 85 mg, 0.262 mmol) and (rac)-6-[1-(6-chloro-imidazo[1,2-b]pyridazin-3-yl)-ethyl]-quinoline (Example 271, 54 mg, 0.175 mmol) with 1.2 mL DME. The solution was degassed with argon, before adding PdCl$_2$(PPh$_3$)$_2$ (4 mg) and 2 M K$_2$CO$_3$ (0.236 mL). The RM was then stirred at 90° C. for 4 h. It was then diluted with EtOAc and washed with sat. aqueous NaHCO$_3$ and brine. The organic layer was dried over Na$_2$SO$_4$, filtered and evaporated to dryness to give the title compound as a yellow oil (t$_R$ 2.36 min (conditions 8), MH+=469).

EXAMPLE 178

2-{4-[3-((R)-1-Quinolin-6-yl-ethyl)-imidazo[1,2-b]pyridazin-6-yl]-pyrazol-1-yl}-ethanol

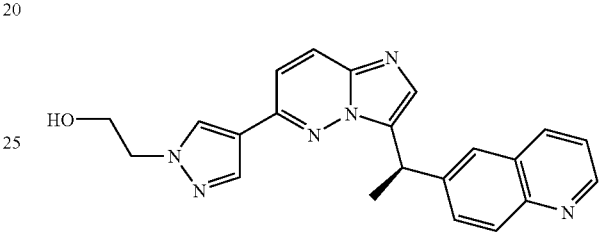

The title compound was obtained from the chiral separation of compound of Example 177 with a preparative HPLC on a on a Chirapak AD-H (1185) 0.46×25 cm column with a flow of 1 mL/min of n-heptane:EtOH:MeOH 60:25:15 (v/v). Oven 20° C., detection 220 nm. (t$_R$ 3.095 min (conditions 3), MH+=385, $^1$H-NMR in DMSO-d6: 8.80 (dd, 1H); 8.36 (s, 1H); 8.33 (d, 1H); 8.03 (d, 1H); 8.00-7.95 (m, 2H); 7.90 (d, 1H); 7.80-7.74 (m, 2H); 7.49-7.44 (m, 2H); 4.92 (t, 1H); 4.82 (q, 1H); 4.18 (t, 2H); 3.74 (q, 2H); 1.85 (d, 3H)).

EXAMPLE 179

2-{4-[3-((S)-1-Quinolin-6-yl-ethyl)-imidazo[1,2-b]pyridazin-6-yl]-pyrazol-1-yl}-ethanol

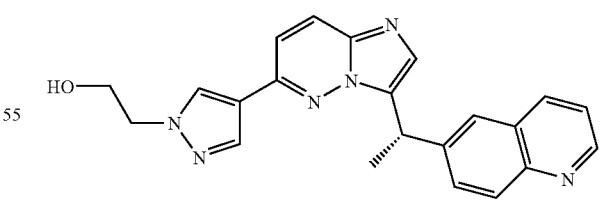

The title compound was obtained from the chiral separation of compound of Example 177 with a preparative HPLC on a on a Chirapak AD-H (1185) 0.46×25 cm column with a flow of 1 mL/min of n-heptane:EtOH:MeOH 60:25:15 (v/v). Oven 20° C., detection 220 nm. (t$_R$ 3.087 min (conditions 3), MH+=385, $^1$H-NMR in DMSO-d6: 8.80 (dd, 1H); 8.36 (s, 1H); 8.33 (d, 1H); 8.03 (d, 1H); 8.00-7.95 (m, 2H); 7.90 (d, 1H); 7.80-7.74 (m, 2H); 7.49-7.44 (m, 2H); 4.92 (t, 1H); 4.82 (q, 1H); 4.18 (t, 2H); 3.74 (q, 2H); 1.85 (d, 3H)).

EXAMPLE 180

7-Fluoro-6-[6-(1-piperidin-4-yl-1H-pyrazol-4-yl)-imidazo[1,2-b]pyridazin-3-ylmethyl]-quinoline

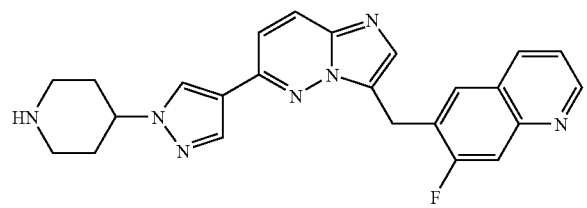 [SMILES: Fc1cc2ncccc2cc1Cc1cnc2ccc(-c3cnn(C4CCNCC4)c3)nn12]

4-{4-[3-(7-Fluoro-quinolin-6-ylmethyl)-imidazo[1,2-b]pyridazin-6-yl]-pyrazol-1-yl}-piperidine-1-carboxylic acid tert-butyl ester (Stage 180.1, 850 mg, 1.611 mmol) was stirred 1 h at rt in dioxane (15 mL) with HCl in dioxane (4 M, 4,03 mL). The RM was then basified with saturated NaHCO₃ aqueous sol. and the dioxane was evaporated. The resulting aqueous sol. was extracted 3 times with DCM containing 10% EtOH. Combined organic layers were dried and evaporated and the residue was purified by flash chromatography (CombiFlash® Companion System®, with RediSep® silica gel column, DCM/MeOH with ammonia=100:0->90:10) to afford the title compound ($t_R$ 3.04 min (conditions 3), MH+=428).

Stage 180.1

4-{4-[3-(7-Fluoro-quinolin-6-ylmethyl)-imidazo[1,2-b]pyridazin-6-yl]-pyrazol-1-yl}-piperidine-1-carboxylic acid tert-butyl ester A microwave tube was charged with 6-(6-chloro-imidazo[1,2-b]pyridazin-3-ylmethyl)-7-fluoro-quinoline (Stage 180.2, 500 mg, 1.599 mmol), 4-[4-(4,4,5,5-tetramethyl-[1,3,2]dioxaborolan-2-yl)-pyrazol-1-yl]-piperidine-1-carboxylic acid tert-butyl ester (prepared as described in published patent application WO 2007/066185 p. 9 & 10; 905 mg, 2.398 mmol), Pd(PPh₃)₂Cl₂ (56 mg), 2 M K₂CO₃ (2.158 mL) and DME (5 mL) and was heated at 90° C. for 2 h under stirring. The RM was extracted with EtOAc and aqueous NaHCO₃. The organic layer was dried and concentrated in vacuo. The reside was dried under vacuum (12 mbar) for 3 days to afford the title compound ($t_R$ 4.5 min (conditions 3), MH+=528)

Stage 180.2

6-(6-Chloro-imidazo[1,2-b]pyridazin-3-ylmethyl)-7-fluoro-quinoline

Iodine (3.09 g, 12.17 mmol) and H₃PO₂ (1.673 mL of a 50% aqueous solution, 30.4 mmol) are added to a solution of (rac)-(6-chloro-imidazo[1,2-b]pyridazin-3-yl)-(7-fluoroquinolin-6-yl)methanol (Stage 174.3, 2 g, 6.08 mmol) in acetic acid (20 mL). The RM was heated under stirring at 110° C. for 18 h. The RM was then evaporated and taken into DCM and washed with NaHCO₃ sol., and extracted with DCM/NaHCO₃ sol. The combined organic layer were dried and concentrated. The residue was stirred in acetone and filtered.

After 3 h drying under vacuum, it gave the title compound ($t_R$ 4.41 min (conditions 3), MH+=313).

EXAMPLE 181

7-Fluoro-6-{6-[1-(1-methyl-piperidin-4-yl)-1H-pyrazol-4-yl]-imidazo[1,2-b]pyridazin-3-ylmethyl}-quinoline

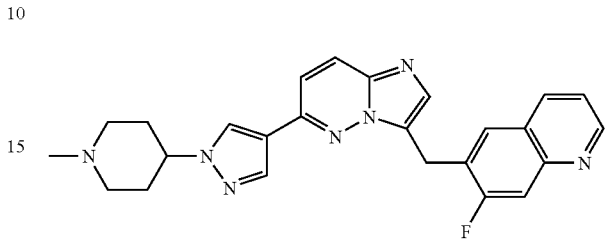

To abs. MeOH (6 mL) stirred at rt were added 7-fluoro-6-[6-(1-piperidin-4-yl-1H-pyrazol-4-yl)imidazo[1,2-b]pyridazin-3-ylmethyl]-quinoline (Example 180, 104 mg, 0.243 mmol), formaldehyde (0.034 mL, 1.216 mmol) and NaBH₃CN (76 mg, 1.216 mmol). The RM was then brought to pH 5-6 with addition of acetic acid and stirred at rt for 2 h. It was then taken into DCM and washed with saturated NaHCO₃ sol. The organic layer was then washed with brine, dried on Na₂SO₄, filtered and evaporated. A purification of the crude by flash chromatography (CombiFlash® Companion System®, with RediSep® silica gel column, DCM/MeOH with ammonia=100:0->90:10) gave the title compound ($t_R$ 3.07 min (conditions 3), MH+=442, ¹H-NMR in DMSO-d6: 8.82 (d, 1H); 8.49 (s, 1H); 8.33 (d, 1H); 8.10-8.01 (m, 3H), 7.76 (d, 1H); 7.59 (s, 1H); 7.53 (d, 1H); 7.46 (dd, 1H), 4.53 (s, 2H); 4.20-4.10 (m, 1H); 2.85 (d, 2H); 2.18 (s, 3H); 2.06-1.92 (m, 6H).

EXAMPLE 182

(rac)-2-(4-{3-[1-(5,7-Difluoro-quinolin-6-yl)-ethyl]-imidazo[1,2-b]pyridazin-6-yl}-pyrazol-1-yl)ethanol

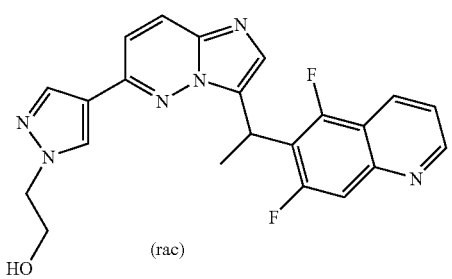 [SMILES: CC(c1c(F)cc2ncccc2c1F)c1cnc2ccc(-c3cnn(CCO)c3)nn12]

(rac)-6-[1-(6-Chloro-imidazo[1,2-b]pyridazin-3-yl)-ethyl]-5,7-difluoro-quinoline (Stage 182.1, 620 mg, 1.529 mmol) was dissolved in DME (5 mL) in a microwave reactor with 1-[2-(tetrahydro-pyran-2-yloxy)-ethyl]-4-(4,4,5,5-tetramethyl-[1,3,2]dioxaborolan-2-yl)-1H-pyrazole (Stage 171.4, 493 mg, 1.529 mmol) and a solution of 2 M Na₂CO₃ (2.75 mL). Then tetrakis(triphenylphosphine)-palladium (88 mg) was added and the RM was heated at 150° C. for 15 min under microwave irradiations. It was then taken up with EtOAc and washed with 10% Na₂CO₃ sol. and brine. The organic layer was dried over Na₂SO₄ and the solvent was removed. It was then dissolved in DCM (18 mL) and HCl in dioxane (4 N, 1.146 mL) was added. It was stirred at rt for 2 h. The solvent was removed and it was taken up in EtOAc/MeOH (9:1) and washed with water and brine. The organic layer was dried over Na₂SO₄ and the solvent was removed. The residue was triturated with Et₂O and the solid was filtered off. The yellow solid obtained was the pure racemate of the title compound (t$_R$ 1.1 min (conditions 2), MH+=421)
Stage 182.1

(rac)-6-[1-(6-Chloro-imidazo[1,2-b]pyridazin-3-yl)-ethyl]-5,7-difluoro-quinoline (rac)-1-(6-Chloro-imidazo[1,2-b]pyridazin-3-yl)-1-(5,7-difluoro-quinolin-6-yl)-ethanol (Stage 182.2, 570 mg, 1.58 mmol), iodine (1.203 g, 4.74 mmol) and H₃PO₂ (1.293 mL of a 50% aqueous solution, 23.7 mmol) were charged together with acetic acid (16 mL) in a microwave vial. The mixture was subjected to MW-irradiation at 150° C. for 5 min. It was then taken up with water and basified with NaOH (2.5 M). It was extracted with EtOAc twice and the organics were joined and washed with brine, dried over Na₂SO₄ and the solvent was removed. The title compound was obtained as a yellow solid (t$_R$ 1.1 min (conditions 2), MH+=346).
Stage 182.2

(rac)-1-(6-Chloro-imidazo[1,2-b]pyridazin-3-yl)-1-(5,7-difluoro-quinolin-6-yl)-ethanol (6-Chloro-imidazo[1,2-b]pyridazin-3-yl)-(5,7-difluoro-quinolin-6-yl)-methanone (Stage 182.3, 3.05 g, 8.41 mmol) was suspended in THF (65 mL) and the mixture was cooled down to 0° C. with an ice bath. Then the methylmagnesium bromide (1.4 M, 15.01 mL) was added slowly. The RM was stirred for 30 min and was then allowed to warm up to rt. After 2 h, it was quenched with a few mL of water. The solution was filtered. The solid residue was washed with water and the filtrate extracted with EtOAc twice. Then the organics were joined and washed with brine, dried over Na₂SO₄ and the solvent was removed. The crude was purified with DCM and MeOH by MPLC to give the title compound as a yellow solid (t$_R$ 0.9 min (conditions 2), MH+=361).
Stage 182.3

(6-Chloro-imidazo[1,2-b]pyridazin-3-yl)-(5,7-difluoro-quinolin-6-yl)-methanone (rac)-(6-Chloro-imidazo[1,2-b]pyridazin-3-yl)-(5,7-difluoro-quinolin-6-yl)-methanol (Stage 182.4, 3.0 g, 8.65 mmol) was dissolved in DCM (87 mL) and Dess-Martin periodinane (4.40 g, 10.38 mmol) was added. The RM was stirred for 3 h at rt. The solvent was removed and the residue was then taken up with EtOAc and washed with 2.5 M NaOH and with brine. The organic layer was then dried over Na₂SO₄ and the solvent was removed to give the title compound as a brown solid (t$_R$ 1.2 min (conditions 2), MH+=345).
Stage 182.4

(rac)-(6-Chloro-imidazo[1,2-b]pyridazin-3-yl)-(5,7-difluoro-quinolin-6-yl)-methanol 3-Bromo-6-chloro-imidazo[1,2-b]pyridazine (4.40 g, 18.95 mmol) was dissolved in THF (189 mL) and under nitrogen conditions, ethylmagnesium bromide solution (3 M, 6.32 mL) was added slowly. The RM was stirred at rt for 15 min then a solution of 5,7-difluoro-quinoline-6-carbaldehyde (Intermediate F, 3.66 g, 18.95 mmol) in THF was added. It was stirred at rt for 30 min. The reaction was quenched with 10% NH₄Cl. The precipitate was filtered off and a first part of the title compound was obtained as a white solid. The filtrate was concentrated and was taken up with 10% NH₄Cl. The precipitate was filtered off and was washed with EtOAc. A second part of the title compound was obtained as a brown solid (t$_R$ 0.8 min (conditions 2), MH+=347).

EXAMPLE 183

2-(4-{3-[(R)-1-(5,7-Difluoro-quinolin-6-yl)-ethyl]-imidazo[1,2-b]pyridazin-6-yl}-pyrazol-1-yl)ethanol

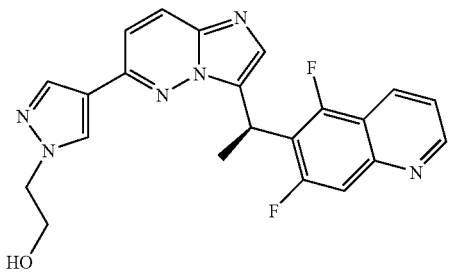 [SMILES: C[C@H](c1c(F)cc2ncccc2c1F)c1cnc2ccc(-c3cnn(CCO)c3)nn12]

The title compound was obtained as a yellow solid from the chiral separation of compound of Example 182 with a Preparative HPLC on a Chiralpak AD-H (20×250 mm) 5 µm column with a flow of 7 mL/min of n-Heptane : EtOH 20:80 (v/v). Oven 20° C., detection 220 nm (t$_R$ 13 min). (t$_R$ 1.50 min (conditions 9), MH+=421, ¹H-NMR in DMSO-d6: 8.90 (d, 1H); 8.44 (d, 1H); 8.24 (s, 1H); 8.04 (d, 1H); 7.83 (d, 2H); 7.67 (d, 1H); 7.56 (dd, 1H); 7.46 (d, 1H); 5.10 (d, 1H); 4.95 (t, 1H); 4.14 (t, 2H); 3.71 (q, 2H); 1.92 (d, 3H)).

EXAMPLE 184

2-(4-{3-[(S)-1-(5,7-Difluoro-quinolin-6-yl)-ethyl]-imidazo[1,2-b]pyridazin-6-yl}-pyrazol-1-yl)ethanol

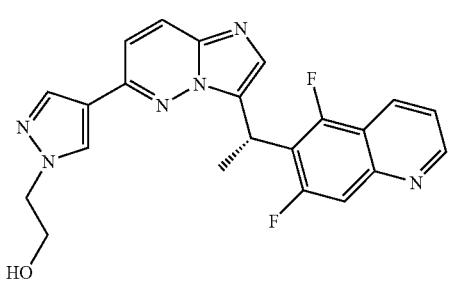 [SMILES: C[C@@H](c1c(F)cc2ncccc2c1F)c1cnc2ccc(-c3cnn(CCO)c3)nn12]

The title compound was obtained as a yellow solid from the chiral separation of compound of Example 182 with a Preparative HPLC on a Chiralpak AD-H (20×250 mm) 5 µm column with a flow of 7 mL/min of n-Heptane : EtOH 20:80 (v/v). Oven 20° C., detection 220 nm (t$_R$ 18 min). (t$_R$ 1.49 min (conditions 9), MH+=421, ¹H-NMR in DMSO-d6: 8.90 (d, 1H); 8.44 (d, 1H); 8.24 (s, 1H); 8.04 (d, 1H); 7.83 (d, 2H);

7.67 (d, 1H); 7.56 (dd, 1H); 7.46 (d, 1H); 5.10 (d, 1H); 4.95 (t, 1H); 4.14 (t, 2H); 3.71 (q, 2H); 1.92 (d, 3H)).

EXAMPLE 185

(rac)-2-(4-{3-[1-(3-Methyl-3H-benzoimidazol-5-yl)-ethyl]-imidazo[1,2-b]pyridazin-6-yl}-pyrazol-1-yl)-ethanol

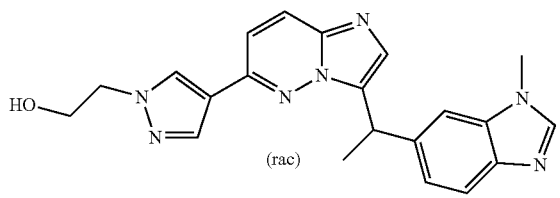 [SMILES: CC(c1ccc2ncn(C)c2c1)c1cnc2ccc(-c3cnn(CCO)c3)nn12]

(rac)-3-[1-(3-Methyl-3H-benzoimidazol-5-yl)-ethyl]-6-{1-[2-(tetrahydro-pyran-2-yloxy)-ethyl]-1H-pyrazol-4-yl}-imidazo[1,2-b]pyridazine (Stage 185.1, 600 mg, 1.018 mmol) was dissolved in DCM (10 mL) and MeOH (2.5 mL). HCl in dioxane (4 N, 1.272 mL) was added and the RM was stirred 1 h at rt. The solvent was totally evaporated and the residue taken in water /acetonitrile. It was basified with NaHCO₃. the mixture was cooled down with dry ice and sonicated to afford a suspension. It was filtered and collected, and dried under high vacuum overnight to afford the title compound as a white solid ($t_R$ 2.04 min (conditions 8), MH+=388, 1H-NMR in DMSO-d6: 8.39 (s, 1H); 8.07 (d, 2H); 8.01 (d, 1H); 7.69 (s, 1H); 7.61 (s, 1H); 7.51 (d, 1H); 7.47 (d, 1H); 7.23 (d, 1H); 4.95 (t, 1H); 4.76 (q, 1H); 4.18 (t, 2H); 3.78 (s, 3H); 3.75 (q, 2H); 1.79 (d, 3H)).

Stage 185.1

(rac)-3-[1-(3-Methyl-3H-benzoimidazol-5-yl)-ethyl]-6-{1-[2-(tetrahydro-pyran-2-yloxy)-ethyl]-1H-pyrazol-4-yl}-imidazo[1,2-b]pyridazine (rac)-6-Chloro-3-[1-(3-methyl-3H-benzoimidazol-5-yl)-ethyl]-imidazo[1,2-b]pyridazine (Stage 185.2, 525 mg, 1.381 mmol) was introduced in a microwave reactor together with 1-[2-(tetrahydro-pyran-2-yloxy)-ethyl]-4-(4,4,5,5-tetramethyl-[1,3,2]dioxaborolan-2-yl)-1H-pyrazole (Stage 171.4, 667 mg, 2.071 mmol) and DME (9 mL). The mixture was purged with Argon for 5 min. Pd(PPh₃)₂Cl₂ (38.8 mg) and 2 M K₂CO₃ (1.864 mL) were added and the mixture was flushed with Argon before being sealed. It was then heated at 90° C. for 4,5 h. The RM was diluted with EtOAc and washed with water, brine, dried over Na₂SO₄, filtered and evaporated. The residue was purified by flash chromatography (CombiFlash® Companion System®, with 40 g RediSep® silica gel column, DCM/MeOH=100:0->92:8 in 25 min). The collected fractions containing product were evaporated and the residue was dried under vacuum to afford the title compound as an oil ($t_R$ 2.39 min (conditions 8), MH+=472).

Stage 185.2

(rac)-6-Chloro-3-[1-(3-methyl-3H-benzoimidazol-5-yl)-ethyl]-imidazo[1,2-b]pyridazine In a microwave vial, (rac)-1-(6-chloro-imidazo[1,2-b]pyridazin-3-yl)-1-(3-methyl-3H-benzoimidazol-5-yl)-ethanol (Stage 185.3, 650 mg, 1.507 mmol) was dissolved in AcOH (15 mL) under Argon. Iodine (1.148 g, 4.52 mmol) and H₃PO₂ (1.233 mL of a 50% aqueous solution, 11.3 mmol) were added and the mixture was submitted to MW-irradiation at 150° C. for 10 min. The mixture was diluted with water. It was basified until pH 5 with NaOH 10 M and then saturated NaHCO₃ sol. until pH 7-8. It was then extracted with EtOAc one time. The organic phase was washed with brine, dried over Na₂SO₄, filtered and evaporated. It was then dried under vacuum overnight to afford the title compound as a foam ($t_R$ 2.12 min (conditions 8), MH+=312).

Stage 185.3

(rac)-1-(6-Chloro-imidazo[1,2-b]pyridazin-3-yl)-1-(3-methyl-3H-benzoimidazol-5-yl)-ethanol (6-Chloro-imidazo[1,2-b]pyridazin-3-yl)-(3-methyl-3H-benzoimidazol-5-yl)-methanone (Stage 185.4, 560 mg, 1.796 mmol) was dissolved in THF (50 mL) with heating under Argon. The solution was let to cool down and methylmagnesium bromide (3 M, 0.719 mL) was added. The mixture was stirred at rt for 1 h. To complete the reaction, more methylmagnesium bromide (3 M, 0.30 mL) was added and the RM was stirred 30 min longer. It was then diluted with EtOAc and washed with a saturated NaHCO₃ sol. The aqueous phase was extracted twice with EtOAc. The combined organics were washed with brine, dried over Na₂SO₄, filtered and evaporated. The residue was dried under vacuum overnight to afford the title compound as an off white foam ($t_R$ 1.84 min (conditions 8), MH+=328).

Stage 185.4

(6-Chloro-imidazo[1,2-b]pyridazin-3-yl)-(3-methyl-3H-benzoimidazol-5-yl)-methanone (rac)-(6-Chloro-imidazo[1,2-b]pyridazin-3-yl)-(3-methyl-3H-benzoimidazol-5-yl)-methanol (Stage 185.5, 1.03 g, 3.22 mmol) was suspended in DCM (30 mL). Dess-Martin periodinane (1.688 g, 3.86 mmol) was added and the mixture was stirred at rt for 1.5 h. The mixture was evaporated to dryness and the residue was taken in 1 M NaOH and sonicated. After 15 min of stirring, it was filtered. The precipitate was dried under vacuum overnight to afford the title compound ($t_R$ 2.18 min (conditions 8), MH+=312)

Stage 185.5

(rac)-(6-Chloro-imidazo[1,2-b]pyridazin-3-yl)-(3-methyl-3H-benzoimidazol-5-yl)-methanol 3-Bromo-6-chloro-imidazo[1,2-b]pyridazine (850 mg, 3.47 mmol) was dissolved in THF (50 mL) under Argon. Ethylmagnesium bromide solution (1 M, 3.47 mL) was added and the mixture was stirred at rt for 20 min. Then 3-methyl-3H-benzoimidazole-5-carbaldehyde in THF (10 mL) was slowly added and the mixture was stirred at rt for 18 h. The mixture was quenched with water and NaHCO₃. It was extracted with EtOAc twice and some MeOH to dissolve the solids. The combined organic layers were washed with brine, dried over Na₂SO₄, filtered and evaporated. The residue was purified by flash chromatography (CombiFlash® Companion System®, with 40 g RediSep® silica gel column, DCM/MeOH=100:0->94:6 in 25 min then up to 11% MeOH). The collected fractions containing product were evaporated and

EXAMPLE 186

2-(4-{3-[(R)-1-(3-Methyl-3H-benzoimidazol-5-yl)-ethyl]-imidazo[1,2-b]pyridazin-6-yl}-pyrazol-1-yl)-ethanol

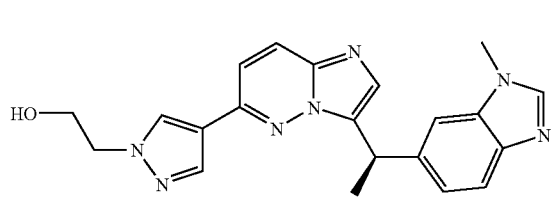 [SMILES: C[C@H](c1ccc2ncn(C)c2c1)c1cnc2ccc(-c3cnn(CCO)c3)nn12]

The title compound was obtained from the chiral separation of compound of Example 185 with a preparative HPLC on a Chiralpak ADoosC-JF004 (5×50 cm) column with a flow of 100 mL/min of n-heptane:EtOH 40:60 (v/v). Oven 20° C., detection 220 nm ($t_R$ 19.0 min). ($t_R$ 2.84 min (conditions 3), MH+=388, 1H-NMR in DMSO-d6: 8.39 (s, 1H); 8.07 (d, 2H); 8.01 (d, 1H); 7.69 (s, 1H); 7.61 (s, 1H); 7.51 (d, 1H); 7.47 (d, 1H); 7.23 (d, 1H); 4.95 (t, 1H); 4.76 (q, 1H); 4.18 (t, 2H); 3.78 (s, 3H); 3.75 (q, 2H); 1.79 (d, 3H)).

EXAMPLE 187

2-(4-{3-[(S)-1-(3-Methyl-3H-benzoimidazol-5-yl)-ethyl]-imidazo[1,2-b]pyridazin-6-yl}-pyrazol-1-yl)-ethanol

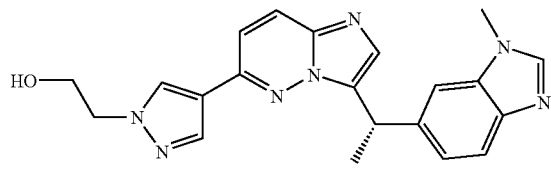 [SMILES: C[C@@H](c1ccc2ncn(C)c2c1)c1cnc2ccc(-c3cnn(CCO)c3)nn12]

The title compound was obtained from the chiral separation of compound of Example 185 with a preparative HPLC on a Chiralpak ADoosC-JF004 (5×50 cm) column with a flow of 100 mL/min of n-heptane:EtOH 40:60 (v/v). Oven 20° C., detection 220 nm ($t_R$ 39.3 min). ($t_R$ 2.84 min (conditions 3), MH+=388, 1H-NMR in DMSO-d6: 8.39 (s, 1H); 8.07 (d, 2H); 8.01 (d, 1H); 7.69 (s, 1H); 7.61 (s, 1H); 7.51 (d, 1H); 7.47 (d, 1H); 7.23 (d, 1H); 4.95 (t, 1H); 4.76 (q, 1H); 4.18 (t, 2H); 3.78 (s, 3H); 3.75 (q, 2H); 1.79 (d, 3H)).

EXAMPLE 188

(rac)-2-(4-{3-[1-(5-Chloro-quinolin-6-yl)-ethyl]-imidazo[1,2-b]pyridazin-6-yl}-pyrazol-1-yl)ethanol

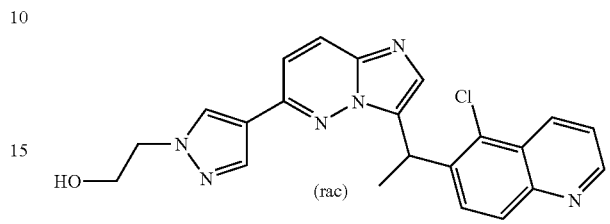

The title compound was obtained in analogy to Example 185 by replacing 3-methyl-3H-benzoimidazole-5-carbaldehyde in Stage 185.5 with 5-chloro-quinoline-6-carbaldehyde (Intermediate C) ($t_R$ 2.33 min (conditions 8), MH+=419).

EXAMPLE 189

(rac)-2-{4-[3-(1-Imidazo[1,2-a]pyridin-6-yl-ethyl)-imidazo[1,2-b]pyridazin-6-yl]-pyrazol-1-yl}-ethanol

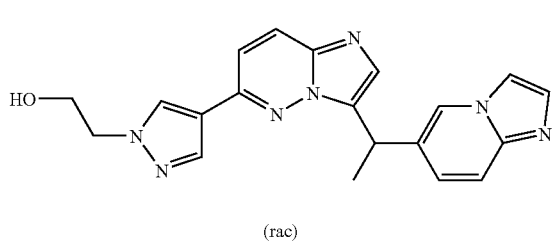 [SMILES: CC(c1ccc2nccn2c1)c1cnc2ccc(-c3cnn(CCO)c3)nn12]

The title compound was obtained in analogy to Example 185 by replacing 3-methyl-3H-benzoimidazole-5-carbaldehyde in Step 185.5 with imidazo[1,2-a]pyridine-6-carbaldehyde ($t_R$ 2.73 min (conditions 3), MH+=374).

EXAMPLE 190

(rac)-2-(4-{3-[1-(2H-Indazol-5-yl)-ethyl]-imidazo[1,2-b]pyridazin-6-yl}-pyrazol-1-yl)-ethanol

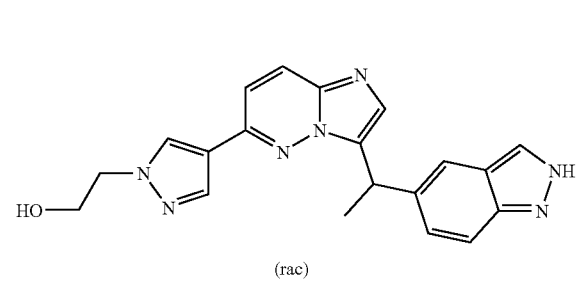 [SMILES: CC(c1ccc2n[nH]cc2c1)c1cnc2ccc(-c3cnn(CCO)c3)nn12]

The title compound was obtained in analogy to Example 185 by replacing 3-methyl-3H-benzoimidazole-5-carbaldehyde in Step 185.5 with 2-(2-trimethylsilanyl-ethoxymethyl)-2H-indazole-5-carbaldehyde (Stage 150.4). An additional reprotection of the indazole group was needed on the chlorine intermediate before the Suzuki coupling as it was cleaved in the alkylation conditions of Stage 185.2. This was done analogously to Stage 150.4 but at rt ($t_R$ 3.42 min (conditions 3), MH+=374).

EXAMPLE 191

(rac)-5,7-Difluoro-6-{1-[6-(1-methyl-1H-pyrazol-4-yl)-imidazo[1,2-b]pyridazin-3-yl]-ethyl}-quinoline

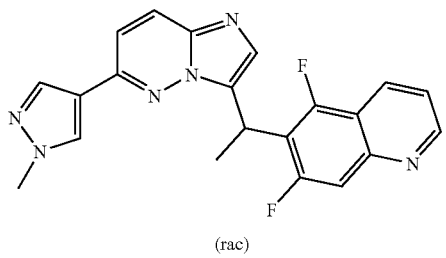 [SMILES: CC(c1c(F)cc2ncccc2c1F)c1cnc2ccc(-c3cnn(C)c3)nn12]

(rac)

Iodine (723 mg, 2.85 mmol) and $H_3PO_2$ (0.777 mL, 14.25 mmol) were added to a solution of (rac)-1-(5,7-difluoro-quinolin-6-yl)-1-[6-(1-methyl-1H-pyrazol-4-yl)-imidazo[1,2-b]pyridazin-3-yl]-ethanol (Stage 191.1, 386 mg, 0.950 mmol) in acetic acid (8 mL). The RM was subjected to MW-irradiation at 150° C. for 5 min. The RM was neutralized with 2.5 M NaOH solution and extracted twice with EtOAc. The organics were joined and washed with brine, then dried over $Na_2SO_4$ and the solvent was removed. The residue was triturated with $Et_2O$ and the precipitate was filtered off to afford the title compound a yellow solid ($t_R$ 0.95 min (conditions 2), MH+=391, 1H-NMR in DMSO-d6: 8.90 (d, 1H); 8.49 (d, 1H); 8.18 (s, 1H); 8.04 (d, 1H); 7.81 (s, 1H); 7.67 (d, 1H); 7.56 (dd, 1H); 7.42 (d, 1H); 5.10 (q, 1H); 3.85 (s, 3H); 1.91 (d, 3H)).

Stage 191.1

(rac)-1-(5,7-Difluoro-quinolin-6-yl)-1-[6-(1-methyl-1H-pyrazol-4-yl)-imidazo[1,2-b]pyridazin-3-yl]-ethanol (5,7-Difluoro-quinolin-6-yl)-[6-(1-methyl-1H-pyrazol-4-yl)-imidazo[1,2-b]pyridazin-3-yl]-methanone (Stage 191.2, 666 mg, 1.706 mmol) was dissolved in THF (13 mL) and the mixture was cooled down to 0° C. with an ice bath. A solution of methylmagnesium bromide (1.4 M, 3.05 mL) was added slowly. The RM was stirred at 0° C. for 15 min then it was warmed up to rt. After 4 h stirring, more methylmagnesium bromide (1.4 M, 1.0 mL) was added and after 1 h stirring, the reaction was quenched with a few mL of water. The RM was mixed with 10% $Na_2CO_3$ solution and the aqueous layer was extracted with EtOAc. The organics were joined and washed with brine, dried over $Na_2SO_4$ and the solvent was removed. The residue was triturated with $Et_2O$ and the yellow solid was filtered off to give the title compound ($t_R$ 1.28 min (conditions 12), MH+=407).

Stage 191.2

(5,7-Difluoro-quinolin-6-yl)-[6-(1-methyl-1H-pyrazol-4-yl)-imidazo[1,2-b]pyridazin-3-yl]-methanone (rac)-(5,7-Difluoro-quinolin-6-yl)-[6-(1-methyl-1H-pyrazol-4-yl)-imidazo[1,2-b]pyridazin-3-yl]-methanol (Stage 191.3, 1.0 g, 2.55 mmol) was dissolved in DCM (25.5 mL) and Dess-Martin periodinane (1.621 g, 3.82 mmol) was added. The RM was stirred for 1 h at rt and then 2.5 M NaOH solution was added. The RM was extracted with EtOAc/MeOH (9:1) twice. The organics were joined and washed with brine, dried over $Na_2SO_4$ and the solvent was removed. The residue was purified by MPLC with DCM and MeOH to afford a light yellow solid as the title compound ($t_R$ 1.2 min (conditions 2), MH+=391)

Stage 191.3

(rac)-(5,7-Difluoro-quinolin-6-yl)-[6-(1-methyl-1H-pyrazol-4-yl)-imidazo[1,2-b]pyridazin-3-yl]-methanol (rac)-(6-Chloro-imidazo[1,2-b]pyridazin-3-yl)-(5,7-difluoro-quinolin-6-yl)-methanol (Stage 171.3, 1.8 g, 5.19 mmol) was introduced in a microwave reactor together with 1-Methyl-4-(4,4,5,5-tetramethyl-[1,3,2]dioxaborolan-2-yl)-1H-pyrazole (1.08 g, 5.19 mmol), tetrakis(triphenylphosphine)-palladium (300 mg, 0.26 mmol), 2 M $Na_2CO_3$ (9.34 mL) and DME (20 mL). The mixture was heated at 150° C. under microwave irradiation for 50 min. The RM was taken up with EtOAc and washed with 10% $Na_2CO_3$ and brine. The organic layer was dried over $Na_2SO_4$, filtered and concentrated in vacuo. The residue was triturated with $Et_2O$ and the precipitate was filtered off to give the title compound as a black solid ($t_R$ 0.8 min (conditions 2), MH+=393)

EXAMPLE 192

5,7-Difluoro-6-{(S)-1-[6-(1-methyl-1H-pyrazol-4-yl)-imidazo[1,2-b]pyridazin-3-yl]-ethyl}-quinoline

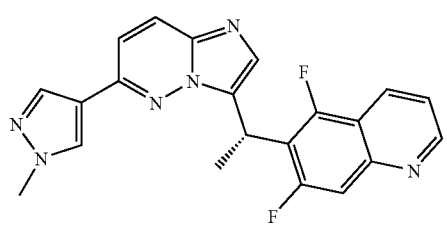 [SMILES: C[C@@H](c1c(F)cc2ncccc2c1F)c1cnc2ccc(-c3cnn(C)c3)nn12]

The title compound was obtained from the chiral separation of compound of Example 191 using a preparative HPLC on a Chiralpak AD 20 um, 50×500 mm column with a flow of 70 mL/min of EtOH. Oven 20° C., detection 220 nm ($t_R$ 38 min). ($t_R$ 0.95 min (conditions 2), MH+=391, 1H-NMR in DMSO-d6: 8.90 (d, 1H); 8.49 (d, 1H); 8.18 (s, 1H); 8.04 (d, 1H); 7.81 (s, 1H); 7.67 (d, 1H); 7.56 (dd, 1H); 7.42 (d, 1H); 5.10 (q, 1H); 3.85 (s, 3H); 1.91 (d, 3H)).

EXAMPLE 193

5,7-Difluoro-6-{(R)-1-[6-(1-methyl-1H-pyrazol-4-yl)-imidazo[1,2-b]pyridazin-3-yl]-ethyl}-quinoline

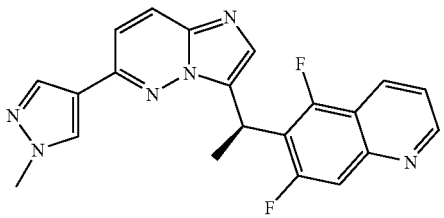 [SMILES: C[C@H](c1c(F)cc2ncccc2c1F)c1cnc2ccc(-c3cnn(C)c3)nn12]

The title compound was obtained from the chiral separation of compound of Example 191 using a preparative HPLC on a Chiralpak AD 20 um, 50×500 mm column with a flow of 70 mL/min of EtOH. Oven 20° C., detection 220 nm ($t_R$ 23 min). ($t_R$ 0.96 min (conditions 2), MH+=391, 1H-NMR in DMSO-d6: 8.90 (d, 1H); 8.49 (d, 1H); 8.18 (s, 1H); 8.04 (d, 1H); 7.81 (s, 1H); 7.67 (d, 1H); 7.56 (dd, 1H); 7.42 (d, 1H); 5.10 (q, 1H); 3.85 (s, 3H); 1.91 (d, 3H)).

EXAMPLE 194

3-[(S)-1-(6-Fluoro-1-methyl-1H-indazol-5-yl)-ethyl]-6-(1-methyl-1H-pyrazol-4-yl)-imidazo[1,2-b]pyridazine

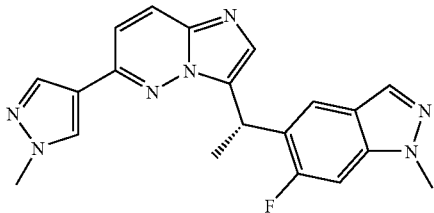 [SMILES: C[C@@H](c1cc2cnn(C)c2cc1F)c1cnc2ccc(-c3cnn(C)c3)nn12]

3-[(S)-1-(6-Fluoro-1H-indazol-5-yl)-ethyl]-6-(1-methyl-1H-pyrazol-4-yl)-imidazo[1,2-b]pyridazine (Example 165, 23 mg, 0.065 mmol) was dissolved in DMF (0.374 mL) and cooled down to 0° C. under nitrogen conditions. NaH (3.82 mg, 0.095 mmol) was added and the RM was stirred at 0° C. for 30 min. Then methyliodide (10.84 mg, 0.076 mmol) was introduced. The RM was allowed to warm up to rt and stirred for 2.5 h, then it was quenched with water. It was extracted twice with EtOAc. The organics were joined and washed with brine, dried over $Na_2SO_4$. The solvent was removed and the residue was purified by preparative HPLC with acetonitrile and water (+0.1% TFA). The acetonitrile was removed and the aqueous solution was basified with 5% $NaHCO_3$. It was extracted twice with EtOAc and then the organics were joined and washed with brine. It was dried over $Na_2SO_4$ and the solvent was removed. The residue was triturated with pentane and the precipitate was filtered off to afford the title compound as a white solid ($t_R$ 1.0 min (conditions 2), MH+=376, 1H-NMR in DMSO-d6: 8.30 (s, 1H); 8.06 (d, 1H); 7.94 (s, 2H); 7.67 (s, 1H); 7.59 (d, 1H); 7.54 (d, 1H); 7.46 (d, 1H); 4.95 (q, 1H); 3.95 (s, 3H); 3.88 (s, 3H); 1.77 (d, 3H)).

EXAMPLE 195

3-[(S)-1-(2H-Indazol-5-yl)-ethyl]-6-(1-methyl-1H-pyrazol-4-yl)-imidazo[1,2-b]pyridazine

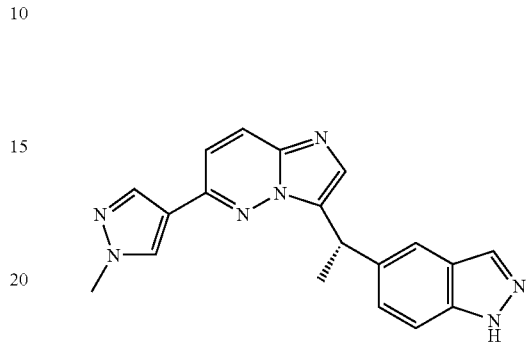

To a solution of (rac)-1-[6-(1-Methyl-1H-pyrazol-4-yl)-imidazo[1,2-b]pyridazin-3-yl]-1-[2-(2-trimethylsilanyl-ethoxymethyl)-2H-indazol-5-yl]-ethanol (Stage 195.1, 194 mg, 0.396 mmol) in acetic acid (2.2 mL) were added iodine (201 mg, 0.792 mmol) and $H_3PO_2$ (0.436 mL of a 50% aqueous solution, 3.96 mmol). The mixture was then heated to 150° C. for 30 min. After cooling down to rt, the acetic acid was removed in vacuo and the residue was diluted with water and 10% $Na_2CO_3$-solution. The precipitate was filtered and washed with water and dried under vacuum overnight to afford the racemate. The mixture was then separated with a Preparative HPLC on a Chiralpak ADOOSC-JF004 (2.5×20 cm) column with a flow of 80 mL/min of n-heptane:EtOH:MeOH 70:25:10 (v/v). Oven 20° C., detection 210 nm ($t_R$ 41.3 min) to afford the title compound as a pure enantiomere ($t_R$ 3.64 min (conditions 3), MH+=344, 1H-NMR in DMSO-d6: 12.90 (s, 1H); 8.29 (s, 1H); 8.03-7.95 (m, 3H); 7.71 (s, 1H); 7.66 (s, 1H); 7.44-7.33 (m, 3H); 4.73 (q, 1H); 3.87 (s, 3H); 1.77 (d, 3H)).

Stage 195.1

(rac)-1-[6-(1-Methyl-1H-pyrazol-4-yl)-imidazo[1,2-b]pyridazin-3-yl]-1-[2-(2-trimethylsilanyl-ethoxymethyl)-2H-indazol-5-yl]-ethanol To a solution of (rac)-1-(6-chloro-imidazo[1,2-b]pyridazin-3-yl)-1-[2-(2-trimethylsilanyl-ethoxymethyl)-2H-indazol-5-yl]-ethanol (Stage 195.2, 400 mg, 0.901 mmol) in DME (4 mL) degassed with argon was added 1-methyl-4-(4,4,5,5-tetramethyl-[1,3,2]dioxaborolan-2-yl)-1H-pyrazole (281 mg, 1.351 mmol), followed by 2 M $K_2CO_3$ (1.216 mL) and $PdCl_2(PPh_3)_2$ (19 mg). The RM was heated at 80° C. for 5 h. It was then taken into EtOAc and brine and extracted. Combined organic layers were dried over $Na_2SO_4$ and evaporated. The residue was purified by flash chromatography (CombiFlash® Companion System®, with RediSep® silica gel column, EtOAc/MeOH=100:0->80:20) to afford the title compound ($t_R$ 4.56 min (conditions 3), MH+=490).

Stage 195.2

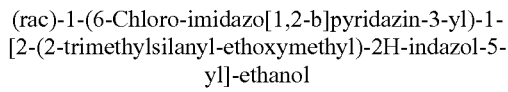
(rac)-1-(6-Chloro-imidazo[1,2-b]pyridazin-3-yl)-1-[2-(2-trimethylsilanyl-ethoxymethyl)-2H-indazol-5-yl]-ethanol To a solution of (6-Chloro-imidazo[1,2-b]pyridazin-3-yl)-[2-(2-trimethylsilanyl-ethoxymethyl)-2H-indazol-5-yl]-methanone (Stage 195.3, 539 mg, 1.259 mmol) in THF (50 mL) was added dropwise at rt a solution of methylmagnesium bromide in Et$_2$O (3 M, 0.462 mL). After 30 min stirring, the RM was taken into EtOAc and washed with a 10% NaHCO$_3$ solution and then with brine. The organic layer was dried over Na$_2$SO$_4$ and the solvent was evaporated. The residue was purified by flash chromatography (CombiFlash® Companion System®, with RediSep® silica gel column, n-hexane/EtOAc=95:5->0:100) to afford after recrystallisation in pentane with a little EtOAc the title compound as a light yellowish powder (t$_R$ 5.6 min (conditions 3), MH+=444).

Stage 195.3

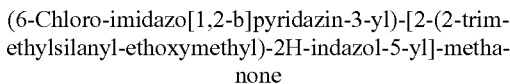
(6-Chloro-imidazo[1,2-b]pyridazin-3-yl)-[2-(2-trimethylsilanyl-ethoxymethyl)-2H-indazol-5-yl]-methanone (rac)-(6-Chloro-imidazo[1,2-b]pyridazin-3-yl)-[2-(2-trimethylsilanyl-ethoxymethyl)-2H-indazol-5-yl]-methanol (Stage 195.4, 580 mg, 1.349 mmol) was dissolved in acetone (40 mL) and heated 1 h to reflux together with 2-iodoxybenzoic acid (1.133 g, 4.05 mmol). The RM was cooled down to rt and the acetone was removed under reduced pressure. The residue was mixed with 2 M NaOH solution and extracted with EtOAc. The combined organic layers were dried over Na$_2$SO$_4$ and the solvent was evaporated. The residue was purified by flash chromatography (CombiFlash® Companion System®, with RediSep® silica gel column, n-hexane/EtOAc=50:50->0:100) to afford the title compound as a light brown foam (t$_R$ 7.11 min (conditions 3), MH+=428).

Stage 195.4

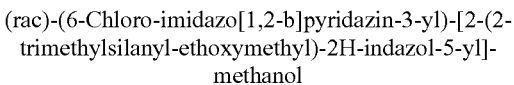
(rac)-(6-Chloro-imidazo[1,2-b]pyridazin-3-yl)-[2-(2-trimethylsilanyl-ethoxymethyl)-2H-indazol-5-yl]-methanol To a solution of 3-bromo-6-chloro-imidazo[1,2-b]pyridazine (465 mg, 2.0 mmol) in THF (60 mL) was added dropwise at rt a solution of ethylmagnesium bromide in Et$_2$O (3 M, 1.0 mL). The temperature rose slightly (up to 27° C.) and the RM was stirred 15 min. Then a solution of 2-(2-trimethylsilanyl-ethoxymethyl)-2H-indazole-5-carbaldehyde (Stage 150.4, 829 mg, 3.00 mmol) in THF (8 mL) was added dropwise and the RM was then stirred 2 h at rt. The RM was then taken into a solution of NH$_4$Cl and extracted with EtOAc. Combined organic layers were washed with brine, dried over Na$_2$SO$_4$ and the solvent was removed. The residue was purified by flash chromatography (CombiFlash® Companion System®, with RediSep® silica gel column, n-hexane/EtOAc=95:5->0:100) to afford the title compound as a light brown thick oil (t$_R$ 5.35 min (conditions 3), MH+=430).

EXAMPLE 196

3-[(S)-1-(1-Methyl-1H-indazol-5-yl)-ethyl]-6-(1-methyl-1H-pyrazol-4-yl)-imidazo[1,2-b]pyridazine

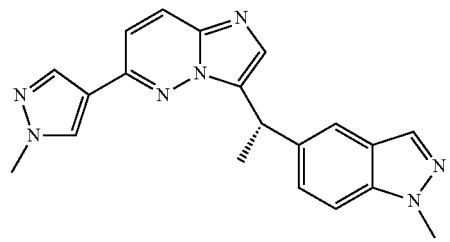 [SMILES: C[C@@H](c1ccc2c(cnn2C)c1)c1cnc2ccc(-c3cnn(C)c3)nn12]

To a mixture of NaH (4.8 mg, 0.1 mmol) in THF (0.5 mL) cooled to 0° C. was added (3-[(S)-1-(2H-indazol-5-yl)-ethyl]-6-(1-methyl-1H-pyrazol-4-yl)-imidazo[1,2-b]pyridazine (Example 195, 34.3 mg, 0.10 mmol). The RM was allowed to warm up to rt and stirred 15 min. Then it was cooled down again and methyliodide (21.3 mg, 0.150 mmol) was added dropwise. The RM was allowed to warm up to rt and stirred for 5 h. It was then taken into DCM and brine, extracted, and the organics were joined dried over MgSO$_4$. The solvent was removed and the residue was purified by flash chromatography (CombiFlash® Companion System®, with RediSep® silica gel column, 0 to 20% MeOH in EtOAc) to afford the title compound after evaporation of the solvent and drying of the material under vacuum (t$_R$ 3.72 min (conditions 3), MH+=358, 1H-NMR in DMSO-d6: 8.35 (s, 1H); 8.03 (d, 1H); 8.00 (s, 1H); 7.94 (s, 1H); 7.73 (s, 1H); 7.70 (s, 1H); 7.52 (d, 1H); 7.45 (d, 1H); 7.43 (d, 1H); 4.73 (q, 1H); 4.74 (s, 3H); 3.89 (s, 3H); 1.77 (d, 3H)).

EXAMPLE 197

6-{Difluoro-[6-(1-piperidin-4-yl-1H-pyrazol-4-yl)-imidazo[1,2-b]pyridazin-3-yl]-methyl}-quinoline

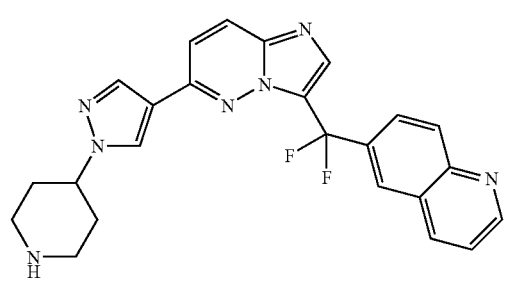 [SMILES: FC(F)(c1ccc2ncccc2c1)c1cnc2ccc(-c3cnn(C4CCNCC4)c3)nn12]

The title compound was obtained in analogy to Stage 180.1 by replacing 6-(6-chloro-imidazo[1,2-b]pyridazin-3-ylmethyl)-7-fluoro-quinoline with 6-[(6-chloro-imidazo[1,2-b]pyridazin-3-yl)-difluoro-methyl]-quinoline (Stage 6.1) and with an additional final Boc-deprotection in DCM with TFA ($t_R$ 1.24 min (conditions 1), MH+=446).

EXAMPLE 198

{4-[3-(5,7-Difluoro-quinolin-6-ylmethyl)-imidazo[1,2-b]pyridazin-6-yl]-pyrazol-1-yl}-acetonitrile

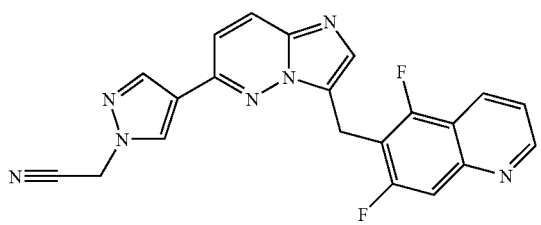 [SMILES: N#CCn1cc(-c2ccc3ncc(Cc4c(F)cc5ncccc5c4F)n3n2)cn1]

The title compound was prepared in analogy to the compound of Example 176 using 5,7-difluoro-6-[6-(1H-pyrazol-4-yl)-imidazo[1,2-b]pyridazin-3-ylmethyl]-quinoline (Example 263) instead of 6-(6-chloro-imidazo[1,2-b]pyridazin-3-ylmethyl)-7-fluoro-quinoline ($t_R$ 3.28 min (conditions 13), MH+=402).

EXAMPLE 199

6-(1-Methyl-1H-pyrazol-4-yl)-3-(1H-pyrrolo[2,3-b]pyridin-3-ylmethyl)-imidazo[1,2-b]pyridazine

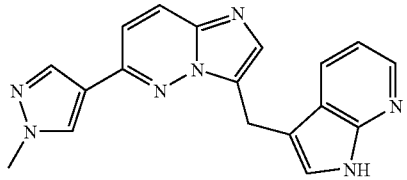 [SMILES: Cn1cc(-c2ccc3ncc(Cc4c[nH]c5ncccc45)n3n2)cn1]

Iodine (412.5 mg, 1.617 mmol) and $H_3PO_2$ (0.880 mL of a 50% aqueous solution, 8.1 mmol) were added to a solution of (rac)-(1-benzenesulfonyl-1H-pyrrolo[2,3-b]pyridin-3-yl)-[6-(1-methyl-1H-pyrazol-4-yl)-imidazo[1,2-b]pyridazin-3-yl]-methanol (Stage 199.1, 262 mg, 0.539 mmol) in acetic acid (3.2 mL). The RM was heated at 150° C. for 30 min under microwave irradiations. The solvent was removed. After purification by preparative HPLC with acetonitrile and water (+0.1% TFA), the fraction containing the product was lyophilized to give a TFA salt of the title compound ($t_R$ 1.1 min (conditions 1), MH+=330).

Stage 199.1

(rac)-(1-Benzenesulfonyl-1H-pyrrolo[2,3-b]pyridin-3-yl)-[6-(1-methyl-1H-pyrazol-4-yl)imidazo[1,2-b]pyridazin-3-yl]-methanol 3-Bromo-6-(1-methyl-1H-pyrazol-4-yl)-imidazo[1,2-b]pyridazine (Example 8.1, 150 mg, 0.539 mmol) was dissolved in THF (15 mL) under Nitrogen. Ethylmagnesium bromide solution (3 M, 0.360 mL) was added and the mixture was stirred at rt for 30 min. Then 1-benzenesulfonyl-1H-pyrrolo[2,3-b]pyridine-3-carbaldehyde (Stage 199.2, 173 mg, 0.539 mmol) in THF (2 mL) was slowly added and the mixture was stirred at rt for 3.5 h. The mixture was quenched with 10% $NH_4Cl$ solution. It was extracted with EtOAc twice. The combined organic layers was washed with brine, dried over $Na_2SO_4$, filtered and evaporated. The title compound was obtained as a yellow solid ($t_R$ 1.4 min (conditions 1), MH+=486).

Stage 199.2

1-Benzenesulfonyl-1H-pyrrolo[2,3-b]pyridine-3-carbaldehyde

1H-Pyrrolo[2,3-b]pyridine-3-carbaldehyde (200 mg, 1.368 mmol) was dissolved in DCM (8 mL). Then tetra-n-butylammonium hydrogen sulfate (48.4 mg, 0.137 mmol), benzensulfonyl chloride (0.176 mL, 1.37 mmol) and NaOH 50% (0.263 mL, 3.3 mmol) were added. The RM was stirred at rt for 1 h. Water was added and it was extracted with DCM twice. The combined organic layers was washed with brine and dried over $Na_2SO_4$, filtered and evaporated to afford the title compound as a light yellow solid ($t_R$ 2.0 min (conditions 1), MH+=287).

EXAMPLE 200

3-(3-Methyl-3H-benzoimidazol-5-ylmethyl)-6-(1-methyl-1H-pyrazol-4-yl)-imidazo[1,2-b]pyridazine

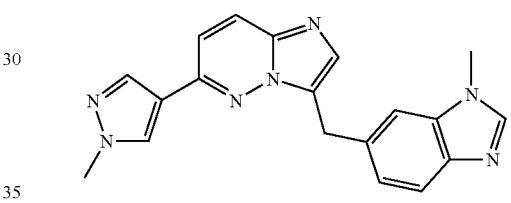

The title compound was obtained in a similar manner as described in Example 8 from the intermediate (rac)-(3-methyl-3H-benzoimidazol-5-yl)-[6-(1-methyl-1H-pyrazol-4-yl)imidazo[1,2-b]pyridazin-3-yl]-methanol (200.1) ($t_R$ 1.83 min (conditions 8), MH+=360) and using 3-methyl-3H-benzoimidazole-5-carbaldehyde (Intermediate K) ($t_R$ 2.04 min (conditions 8), MH+=344).

EXAMPLE 201

6-(1-Methyl-1H-pyrazol-4-yl)-3-[3-(2-pyrrolidin-1-yl-ethyl)-3H-benzoimidazol-5-ylmethyl]-imidazo[1,2-b]pyridazine

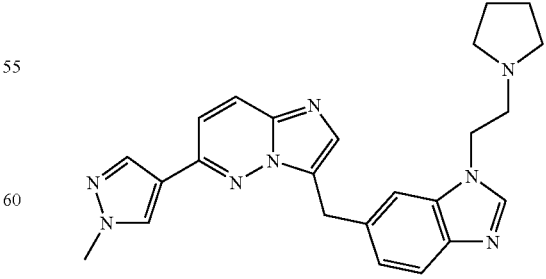

The title compound was obtained in a similar manner as described in Example 8 from the intermediate (rac)-[6-(1-methyl-1H-pyrazol-4-yl)-imidazo[1,2-b]pyridazin-3-yl]-[3-

(2-pyrrolidin-1-yl-ethyl)-3H-benzoimidazol-5-yl]-methanol (201.1) (t$_R$ 1.84 min (conditions 8), MH+=443) and using 3-(2-pyrrolidin-1-yl-ethyl)-3H-benzoimidazole-5-carbaldehyde (Intermediate J) (t$_R$ 2.00 min (conditions 8), MH+=427).

EXAMPLE 202

3-Fluoro-4-[6-(1-methyl-1H-pyrazol-4-yl)-imidazo[1,2-b]pyridazin-3-ylmethyl]-phenol

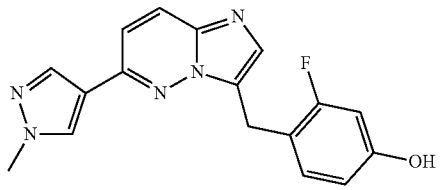 [SMILES: Cn1cc(-c2ccc3ncc(Cc4ccc(O)cc4F)n3n2)cn1]

The title compound was obtained in a similar manner as described in Example 8 using 2-fluoro-4-methoxy-benzaldehyde (t$_R$ 2.36 min (conditions 8), MH+=324).

EXAMPLE 203

3-(4-Bromo-2-fluoro-benzyl)-6-(1-methyl-1H-pyrazol-4-yl)-imidazo[1,2-b]pyridazine

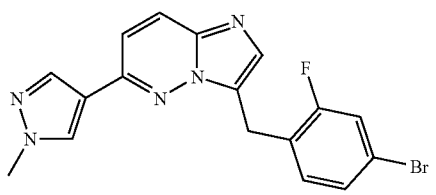 [SMILES: Cn1cc(-c2ccc3ncc(Cc4ccc(Br)cc4F)n3n2)cn1]

The title compound was obtained in a similar manner as described in Example 8 using 4-bromo-2-fluoro-benzaldehyde (t$_R$ 2.86 min (conditions 8), MH+=386, 388).

EXAMPLE 204

3-(2,4-Difluoro-benzyl)-6-(1-methyl-1H-pyrazol-4-yl)-imidazo[1,2-b]pyridazine

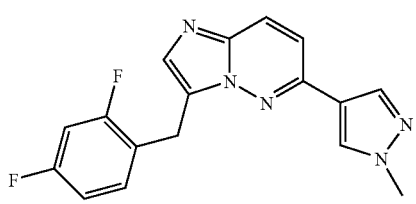 [SMILES: Cn1cc(-c2ccc3ncc(Cc4ccc(F)cc4F)n3n2)cn1]

The title compound was obtained in a similar manner as described in Example 8 using 2,4-difluoro-benzaldehyde (t$_R$ 2.69 min (conditions 8), MH+=326).

EXAMPLE 205

3-(7-Fluoro-imidazo[1,2-a]pyridin-6-ylmethyl)-6-(1-methyl-1H-pyrazol-4-yl)-imidazo[1,2-b]pyridazine

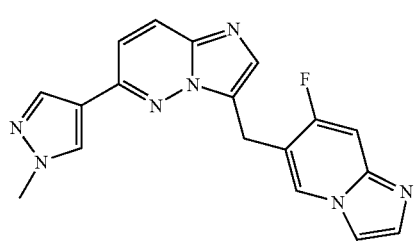 [SMILES: Cn1cc(-c2ccc3ncc(Cc4cn5ccnc5cc4F)n3n2)cn1]

The title compound was obtained in a similar manner as described in Example 8 using 7-fluoro-imidazo[1,2-a]pyridine-6-carbaldehyde (intermediate L) (t$_R$ 1.99 min (conditions 8), MH+=348).

EXAMPLE 206

(rac)-3-[1-(3-Methyl-3H-benzoimidazol-5-yl)-ethyl]-6-(1-methyl-1H-pyrazol-4-yl)-imidazo[1,2-b]pyridazine

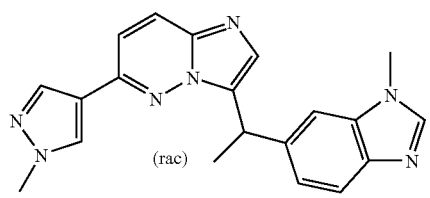 [SMILES: CC(c1ccc2ncn(C)c2c1)c1cnc2ccc(-c3cnn(C)c3)nn12]

The title compound was obtained in a similar manner as described in Example 164 using (rac)-(3-methyl-3H-benzoimidazol-5-yl)-[6-(1-methyl-1H-pyrazol-4-yl)-imidazo[1,2-b]pyridazin-3-yl]-methanol (200.1) (t_R 2.28 min (conditions 8), MH+=358).

EXAMPLE 207

(rac)-6-(1-Methyl-1H-pyrazol-4-yl)-3-{1-[3-(2-pyrrolidin-1-yl-ethyl)-3H-benzoimidazol-5-yl]-ethyl}-imidazo[1,2-b]pyridazine

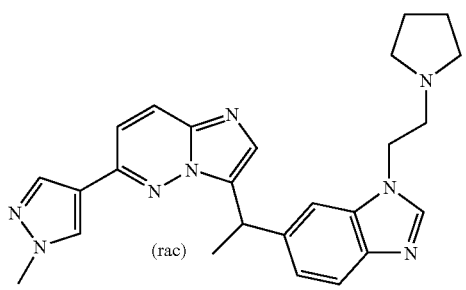 [SMILES: CC(c1ccc2ncn(CCN3CCCC3)c2c1)c1cnc2ccc(-c3cnn(C)c3)nn12]

The title compound was obtained in a similar manner as described in Example 164 using (rac)-[6-(1-methyl-1H-pyrazol-4-yl)-imidazo[1,2-b]pyridazin-3-yl]-[3-(2-pyrrolidin-1-yl-ethyl)-3H-benzoimidazol-5-yl]-methanol (201.1) (t_R 2.06 min (conditions 8), MH+=441).

EXAMPLE 208

3-Quinolin-6-ylmethyl-imidazo[1,2-b]pyridazine-6-carbonitrile

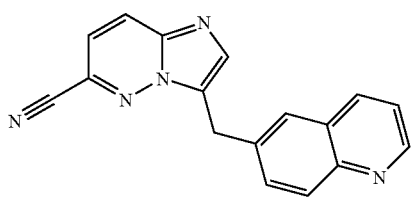 [SMILES: N#Cc1ccc2ncc(Cc3ccc4ncccc4c3)n2n1]

(6-Chloro-imidazo[1,2-b]pyridazin-3-yl)-quinoline (Example 14) (50 mg, 0.17 mmol) and CuCN (23 mg, 0.26 mmol) in 0.5 mL NMP were heated under microwave irradiation at 230° C. for 9.5 h. The RM was diluted with EtOAc and washed with aqueous saturated NaHCO_3 and brine, dried over Na_2SO_4, filtered and evaporated to dryness. The residue was purified by preparative HPLC with acetonitrile and water (+0.1% TFA) to yield the title compound as a yellow solid (t_R 2.16 min (conditions 8), MH+=286).

EXAMPLE 209

3-Quinolin-6-ylmethyl-imidazo[1,2-b]pyridazine-6-carboxamide

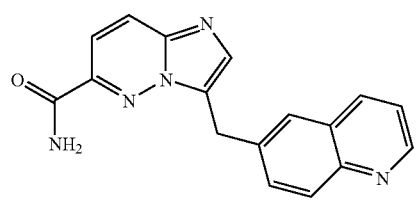 [SMILES: NC(=O)c1ccc2ncc(Cc3ccc4ncccc4c3)n2n1]

The title compound was obtained in a similar manner as described for Example 208 with a prolonged heating in presence of moisture (t_R 1.70 min (conditions 8), MH+=304).

EXAMPLE 210

2-[4-(3-Quinolin-6-ylmethyl-imidazo[1,2-b]pyridazin-6-yl)-pyrazol-1-yl]-ethanol

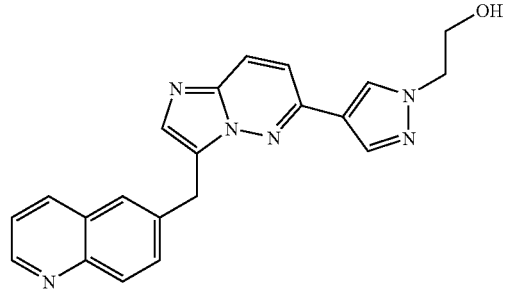 [SMILES: OCCn1cc(-c2ccc3ncc(Cc4ccc5ncccc5c4)n3n2)cn1]

The title compound was prepared in analogy to the compound of Stage 171 using 6-(6-{1-[2-(tetrahydro-pyran-2-yloxy)-ethyl]-1H-pyrazol-4-yl}-imidazo[1,2-b]pyridazin-3-ylmethyl)quinoline (Stage 236.2) instead of 5,7-difluoro-6-(6-{1-[2-(tetrahydro-pyran-2-yloxy)-ethyl]-1H-pyrazol-4-yl}-imidazo[1,2-b]pyridazin-3-ylmethyl)-quinoline (Stage 170.1) (t_R 1.94 min (8), MH+=371.1, $^1$H-NMR in DMSO-d6: 8.81 (m, 1H); 8.42 (s, 1H); 8.30 (d, 1H); 8.09 (s, 1H); 8.06 (d, 1H); 7.95 (m, 2H); 7.77 (m, 1H); 7.62 (s, 1H); 7.52 (d, 1H); 7.47 (dd, 1H); 4.94 (t, 1H); 4.52 (s, 2H); 4.20 (t, 2H); 3.76 (m, 2H)).

Stage 210.1

6-(6-{1-[2-(tetrahydro-pyran-2-yloxy)-ethyl]-1H-pyrazol-4-yl}-imidazo[1,2-b]pyridazin-3-ylmethyl)-quinoline

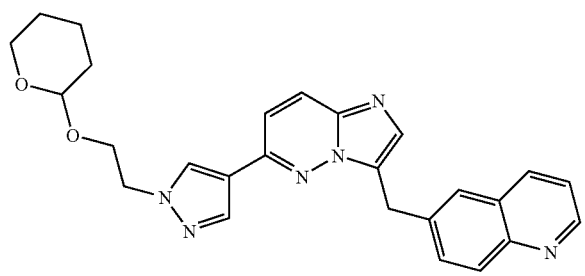 [SMILES: c1cnc2ccc(Cc3cnc4ccc(-c5cnn(CCOC6CCCCO6)c5)nn34)cc2c1]

6-(6-Chloro-imidazo[1,2-b]pyridazin-3-ylmethyl)-quinoline (Example 14, 500 mg, 1.679 mmol) was introduced in a microwave reactor together with 1-[2-(tetrahydro-pyran-2-yloxy)ethyl]-4-(4,4,5,5-tetramethyl-[1,3,2]dioxaborolan-2-yl)-1H-pyrazole (Stage 171.4, 812 mg, 2.52 mmol) and DME (10 mL). The solution was degassed with argon before adding Pd(PPh$_3$)$_2$Cl$_2$ (36 mg, 0.051 mmol) and 2 M K$_2$CO$_3$ (2.267 mL, 4.53 mmol). The mixture was stirred at 90° C. for 5.5 h. The RM was taken up with EtOAc and washed with NaHCO$_3$ and brine. The organic layer was dried over Na$_2$SO$_4$, filtered and concentrated in vacuo to afford a first batch of the desired product as a brownish oil (80% pure). 10% of the residue was dissolved in DCM and purified by flash chromatography (DCM/MeOH=100:0→93.5:6.5) to afford the title compound as a brownish oil (t$_R$ 2.30 min (8), MH+=455.1).

EXAMPLE 211

6-[6-(1-Ethyl-1H-pyrazol-4-yl)-imidazo[1,2-b]pyridazin-3-ylmethyl]-quinoline

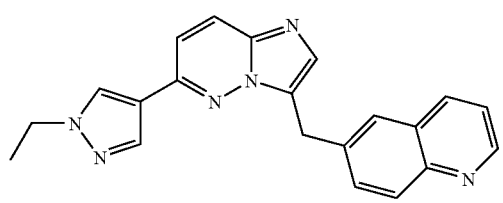 [SMILES: CCn1cc(-c2ccc3ncc(Cc4ccc5ncccc5c4)n3n2)cn1]

The title compound was obtained in a similar manner as described for Example 15 using 1-ethyl-4-(4,4,5,5-tetramethyl-[1,3,2]dioxaborolan-2-yl)-1H-pyrazole instead of 4-carbamoyl-3-chlorophenyboronic acid (t$_R$ 2.16 min (conditions 8), MH+=355).

EXAMPLE 212

6-[6-(1H-Pyrazol-4-yl)-imidazo[1,2-b]pyridazin-3-ylmethyl]-quinoline

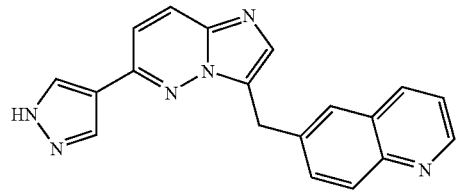 [SMILES: c1cnc2ccc(Cc3cnc4ccc(-c5cn[nH]c5)nn34)cc2c1]

The title compound was obtained in a similar manner as described for Example 15 using 4-(4,4,5,5-tetramethyl-[1,3,2]dioxaborolan-2-yl)-pyrazole-1-carboxylic acid tert-butyl ester; the Boc protecting group being cleaved under the reaction conditions (t$_R$ 1.94 min (conditions 8), MH+=327).

EXAMPLE 213

3-Quinolin-6-ylmethyl-imidazo[1,2-b]pyridazine-6-carboxylic acid ethylamide

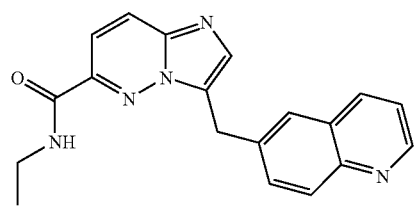 [SMILES: CCNC(=O)c1ccc2ncc(Cc3ccc4ncccc4c3)n2n1]

3-Quinolin-6-ylmethyl-imidazo[1,2-b]pyridazine-6-carbonitrile (Example 208; 43 mg, 0.15 mmol) in a 1 M aqueous solution of NaOH (1.8 mL, 1.8 mmol) was heated under microwave irradiation at 200° C. for 30 min. The RM was quenched with a 2 M aqueous solution of HCl (0.9 mL, 1.8 mmol) and diluted with MeOH and filtered over Celite. The filtrate is evaporated and dry under vacuo. The residue was suspended in DCM (3 mL) and cooled at 0° C. Were added DMF (0.01 mL) and, slowly, oxalyl chloride (0.055 mL, 0.65 mmol). The RM was allowed to reach rt and stirred at this temperature for 45 min. The RM was dropped in a 2 M solution of ethylamine in MeOH (6 mL). The RM was stirred at rt for 5 min before being evaporated to dryness and the residue quenched with aqueous saturated NaHCO$_3$ and diluted with EtOAc. The aqueous layer was extracted with EtOAc and the combined organic layers were washed with brine and dried over Na$_2$SO$_4$, filtered and evaporated. The residue was purified by preparative HPLC with acetonitrile and water (+0.1% TFA) to yield the title compound as light yellow solid (t$_R$ 1.96 min (conditions 8), MH+=332).

EXAMPLE 214

3-Quinolin-6-ylmethyl-imidazo[1,2-b]pyridazine-6-carboxylic acid methylamide

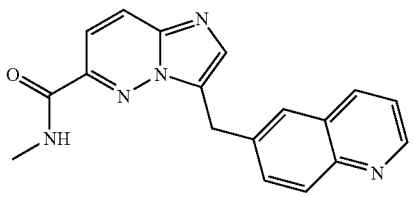 [SMILES: CNC(=O)c1ccc2ncc(Cc3ccc4ncccc4c3)n2n1]

The title compound was obtained in a similar manner as described for Example 213 using a methylamine solution (t$_R$ 1.85 min (conditions 8), MH+=318).

EXAMPLE 215

2-[4-(3-Imidazo[1,2-a]pyridin-6-ylmethyl-imidazo[1,2-b]pyridazin-6-yl)-pyrazol-1-yl]-ethanol

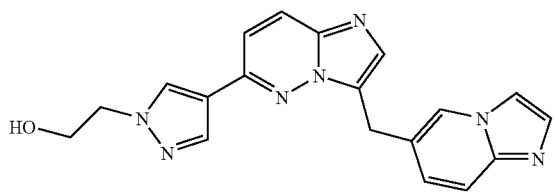 [SMILES: OCCn1cc(-c2ccc3ncc(Cc4ccc5nccn5c4)n3n2)cn1]

The title compound was obtained in a similar manner as described for Example 210 using 6-chloro-3-imidazo[1,2-a]pyridin-6-ylmethyl-imidazo[1,2-b]pyridazine (Example 74) (t$_R$ 1.83 min (conditions 8), MH+=360).

EXAMPLE 216

2-[4-(3-Imidazo[1,2-a]pyridin-6-ylmethyl-imidazo[1,2-b]pyridazin-6-yl)-pyrazol-1-yl]-ethanol

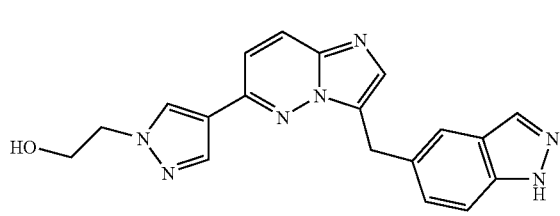 [SMILES: OCCn1cc(-c2ccc3ncc(Cc4ccc5[nH]ncc5c4)n3n2)cn1]

The title compound was obtained in a similar manner as described for Example 7 using 1-[2-(tetrahydro-pyran-2-yloxy)-ethyl]-4-(4,4,5,5-tetramethyl-[1,3,2]dioxaborolan-2-yl)-1H-pyrazole (Stage 171.4) and (rac)-(6-chloro-imidazo[1,2-b]pyridazin-3-yl)-[2-(2-trimethylsilanyl-ethoxymethyl)-2H-indazol-5-yl]-methanol (Stage 150.3) (t$_R$ 2.23 min (conditions 8), MH+=360).

EXAMPLE 217

2-{4-[3-(3-Methyl-3H-benzoimidazol-5-ylmethyl)-imidazo[1,2-b]pyridazin-6-yl]-pyrazol-1-yl}-ethanol

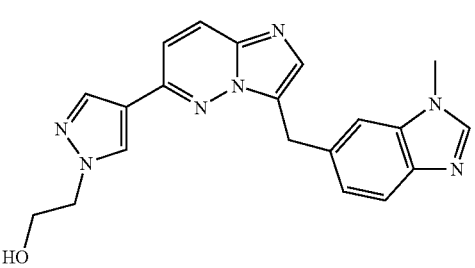 [SMILES: Cn1cnc2ccc(Cc3cnc4ccc(-c5cnn(CCO)c5)nn34)cc21]

The title compound was obtained in a similar manner as described for Example 210 using 6-chloro-3-(3-methyl-3H-benzoimidazol-5-ylmethyl)-imidazo[1,2-b]pyridazine (Stage 217.1) (t$_R$ 1.96 min (conditions 8), MH+=374).

Stage 217.1

6-Chloro-3-(3-methyl-3H-benzoimidazol-5-ylmethyl)-imidazo[1,2-b]pyridazine was obtained in a similar manner as described in Example 14 starting from (rac)-(6-chloro-imidazo[1,2-b]pyridazin-3-yl)-(3-methyl-3H-benzoimidazol-5-yl)-methanol (Stage 217.2) (t$_R$ 2.03 min (conditions 8), MH+=298).

Stage 217.2

(rac)-(6-Chloro-imidazo[1,2-b]pyridazin-3-yl)-(3-methyl-3H-benzoimidazol-5-yl)-methanol was obtained in a similar manner as described in Stage 164.5 starting from 3-methyl-3H-benzoimidazole-5-carbaldehyde (Intermediate K) (t$_R$ 1.78 min (conditions 8), MH+=314)

EXAMPLE 218

2-(4-{3-[3-(2-Pyrrolidin-1-yl-ethyl)-3H-benzoimidazol-5-ylmethyl]-imidazo[1,2-b]pyridazin-6-yl}-pyrazol-1-yl)-ethanol

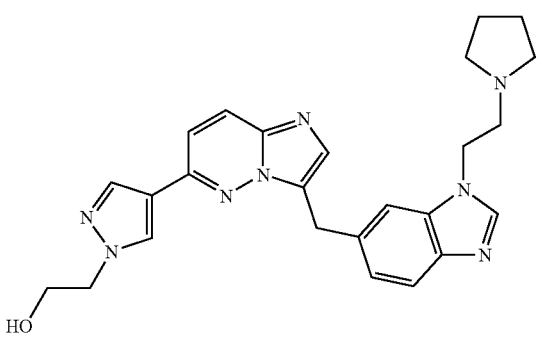 [SMILES: OCCn1cc(-c2ccc3ncc(Cc4ccc5ncn(CCN6CCCC6)c5c4)n3n2)cn1]

The title compound was obtained in a similar manner as described for Example 217 starting from 3-(2-pyrrolidin-1- yl-ethyl)-3H-benzoimidazole-5-carbaldehyde (Intermediate J) ($t_R$ 1.91 min (conditions 8), MH+=457).

EXAMPLE 219

3-Fluoro-4-{6-[1-(2-hydroxy-ethyl)-1H-pyrazol-4-yl]-imidazo[1,2-b]pyridazin-3-ylmethyl}-phenol

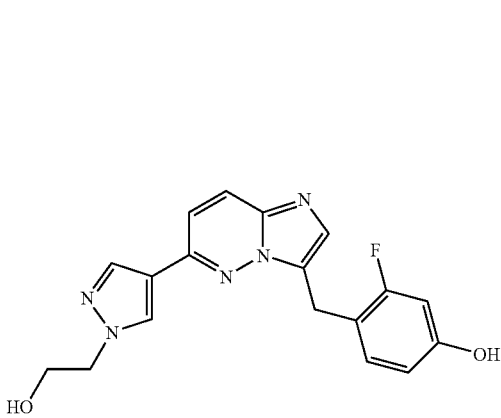 [SMILES: OCCn1cc(-c2ccc3ncc(Cc4ccc(O)cc4F)n3n2)cn1]

The title compound was obtained in a similar manner as described for Example 10 starting from (rac)-(2-fluoro-4-methoxy-phenyl)-(6-{1-[2-(tetrahydro-pyran-2-yloxy)-ethyl]-1H-pyrazol-4-yl}-imidazo[1,2-b]pyridazin-3-yl)-methanol (Stage 219.1) ($t_R$ 2.26 min (conditions 8), MH+=354).

Stage 219.1

(rac)-(2-Fluoro-4-methoxy-phenyl)-(6-{1-[2-(tetrahydro-pyran-2-yloxy)-ethyl]-1H-pyrazol-4-yl}-imidazo[1,2-b]pyridazin-3-yl)-methanol was obtained in a similar manner as Example 9 starting from 2-fluoro-4-methoxy-benzaldehyde ($t_R$ 2.72 min (conditions 8), MH+=468).

EXAMPLE 220

4-{6-[1-(2-Hydroxy-ethyl)-1H-pyrazol-4-yl]-imidazo[1,2-b]pyridazin-3-ylmethyl}-phenol

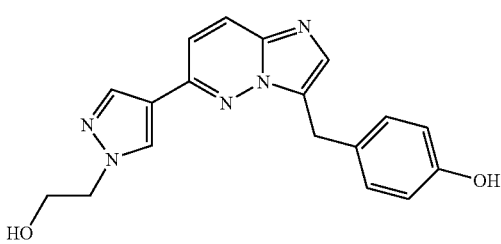 [SMILES: OCCn1cc(-c2ccc3ncc(Cc4ccc(O)cc4)n3n2)cn1]

The title compound was obtained in a similar manner as described for Example 171 starting from 4-methoxybenzaldehyde ($t_R$ 2.16 min (conditions 8), MH+=336).

EXAMPLE 221

(rac)-4-(1-{6-[1-(2-Hydroxy-ethyl)-1H-pyrazol-4-yl]-imidazo[1,2-b]pyridazin-3-yl}-ethyl)-phenol

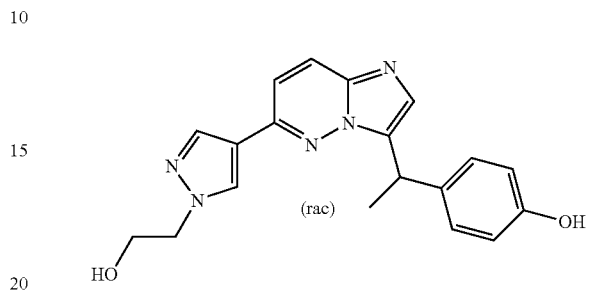

The title compound was obtained in a similar manner as described for Example 185 starting from 4-methoxybenzaldehyde ($t_R$ 2.27 min (conditions 8), MH+=350).

EXAMPLE 222

(rac)-4-{1-[6-(1-Methyl-1H-pyrazol-4-yl)-imidazo[1,2-b]pyridazin-3-yl]-ethyl}-phenol

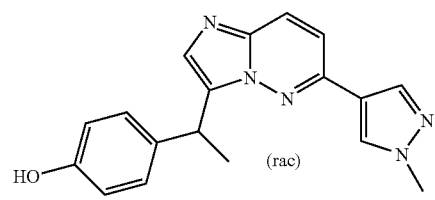 [SMILES: CC(c1ccc(O)cc1)c1cnc2ccc(-c3cnn(C)c3)nn12]

The title compound was obtained in a similar manner as described for Example 221 using 1-methyl-4-(4,4,5,5-tetramethyl-[1,3,2]dioxaborolan-2-yl)-1H-pyrazole and without final HCl deprotection step treatment ($t_R$ 2.41 min (conditions 8), MH+=320).

EXAMPLE 223

(rac)-5-Chloro-6-{1-[6-(1-piperidin-4-yl-1H-pyrazol-4-yl)-imidazo[1,2-b]pyridazin-3-yl]-ethyl}-quinoline

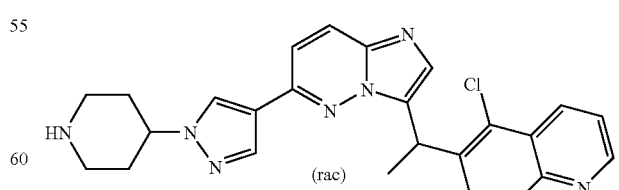

The title compound was obtained in a similar manner as described in Example 182 using 4-[4-(4,4,5,5-tetramethyl-[1,3,2]dioxaborolan-2-yl)-pyrazol-1-yl]-piperidine-1-carboxylic acid tert-butyl ester (see Stage 180.1) and starting from 5-chloro-quinoline-6-carbaldehyde (Intermediate C) ($t_R$ 2.25 min (conditions 8), MH+=458).

EXAMPLE 224

5-Chloro-6-(1-{6-[1-(1-methyl-piperidin-4-yl)-1H-pyrazol-4-yl]-imidazo[1,2-b]pyridazin-3-yl}-ethyl)-quinoline

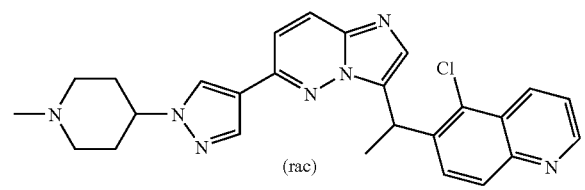 [SMILES: CC(c1ccc2ncccc2c1Cl)c1cnc2ccc(-c3cnn(C4CCN(C)CC4)c3)nn12]

To (rac)-5-chloro-6-{1-[6-(1-piperidin-4-yl-1H-pyrazol-4-yl)-imidazo[1,2-b]pyridazin-3-yl]-ethyl}-quinoline (131 mg, 0.287 mmol), a 37% aqueous solution of formaldehyde (0.107 mL, 1.434 mmol) and 85% sodium cyanoborohydride (106 mg, 1.434 mmol) in MeOH (5 mL) was added acetic acid to adjust pH at 5-6. The RM was stirred at rt for 2.5 h, filtered and purified by preparative HPLC with acetonitrile and water (+0.1% TFA) to yield the title compound as a white foam ($t_R$ 2.29 min (conditions 8), MH+=472).

EXAMPLE 225

(rac)-5-Chloro-6-{1-[6-(1-methyl-1H-pyrazol-4-yl)-imidazo[1,2-b]pyridazin-3-yl]-ethyl}-quinoline

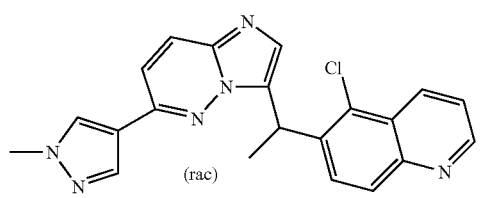 [SMILES: CC(c1ccc2ncccc2c1Cl)c1cnc2ccc(-c3cnn(C)c3)nn12]

The title compound was obtained in a similar manner as described for Example 164 using (rac)-(6-chloro-imidazo[1,2-b]pyridazin-3-yl)-(5-chloro-quinolin-6-yl)-methanol (Stage 225.1) ($t_R$ 2.48 min (conditions 8), MH+=389).

Stage 225.1

(rac)-(6-Chloro-imidazo[1,2-b]pyridazin-3-yl)-(5-chloro-quinolin-6-yl)-methanol was obtained in a similar manner as described for the compound of Stage 9.1 starting from 5-chloroquinoline-6-carbaldehyde (Intermediate C) ($t_R$ 2.26 min (conditions 8), MH+=345).

EXAMPLE 226

2-{4-[3-(5-Chloro-quinolin-6-ylmethyl)-imidazo[1,2-b]pyridazin-6-yl]-pyrazol-1-yl}-ethanol

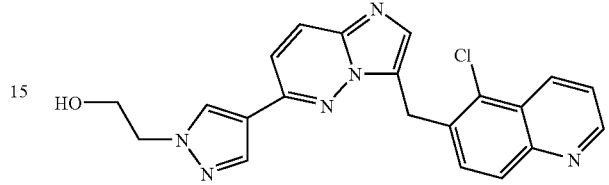

The title compound was obtained in a similar manner as described for Example 180 using 1-[2-(tetrahydro-pyran-2-yloxy)-ethyl]-4-(4,4,5,5-tetramethyl-[1,3,2]dioxaborolan-2-yl)-1H-pyrazole (Stage 171.4) and starting from (rac)-(6-chloro-imidazo[1,2-b]pyridazin-3-yl)-(5-chloro-quinolin-6-yl)-methanol (stage 225.1) ($t_R$ 2.23 min (conditions 8), MH+=405).

EXAMPLE 227

5-Chloro-6-[6-(1-piperidin-4-yl-1H-pyrazol-4-yl)-imidazo[1,2-b]pyridazin-3-ylmethyl]-quinoline

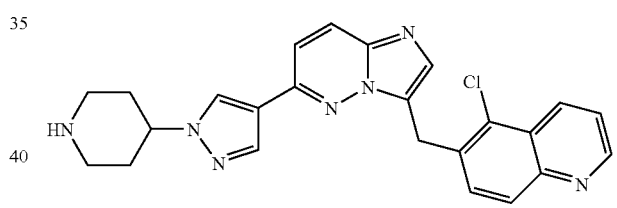

The title compound was obtained in a similar manner as described for Example 226 using 4-[4-(4,4,5,5-tetramethyl-[1,3,2]dioxaborolan-2-yl)-pyrazol-1-yl]-piperidine-1-carboxylic acid tert-butyl ester (see Stage 180.1) ($t_R$ 2.15 min (conditions 8), MH+=444).

EXAMPLE 228

5-Chloro-6-{6-[1-(1-methyl-piperidin-4-yl)-1H-pyrazol-4-yl]-imidazo[1,2-b]pyridazin-3-ylmethyl}-quinoline

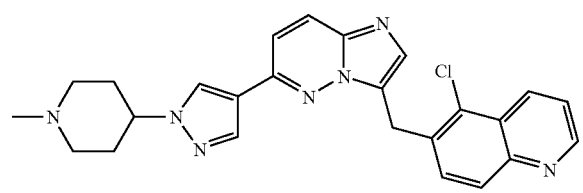 [SMILES: CN1CCC(n2cc(-c3ccc4ncc(Cc5ccc6ncccc6c5Cl)n4n3)cn2)CC1]

The title compound was obtained in a similar manner as described for Example 224 starting from 5-chloro-6-[6-(1- piperidin-4-yl-1H-pyrazol-4-yl)-imidazo[1,2-b]pyridazin-3-ylmethyl]-quinoline (Example 227) (t$_R$ 2.21 min (conditions 8), MH+=458).

EXAMPLE 229

(rac)-(3-Methyl-3H-benzoimidazol-5-yl)-[6-(1-methyl-1H-pyrazol-4-yl)-imidazo[1,2-b]pyridazin-3-yl]-methanol

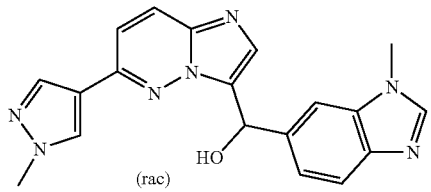 [SMILES: Cn1cc(-c2ccc3ncc(C(O)c4ccc5ncn(C)c5c4)n3n2)cn1]

The title compound is compound of Stage 200.1.

EXAMPLE 230

1-(4-{4-[3-(7-Fluoro-quinolin-6-ylmethyl)-imidazo[1,2-b]pyridazin-6-yl]-pyrazol-1-yl}-piperidin-1-yl)-ethanone

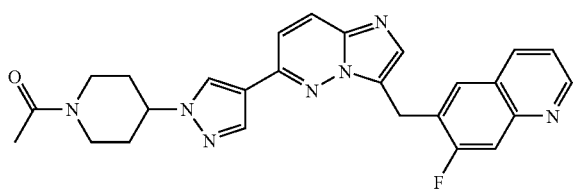 [SMILES: CC(=O)N1CCC(n2cc(-c3ccc4ncc(Cc5cc6cccnc6cc5F)n4n3)cn2)CC1]

7-Fluoro-6-[6-(1-piperidin-4-yl-1H-pyrazol-4-yl)-imidazo[1,2-b]pyridazin-3-ylmethyl]-quinoline (Example 180, 50 mg, 0.117 mmol) and triethylamine (33 µL, 0.234 mmol) were dissolved in THF (1 mL). Acetyl chloride (9 mg, 0.117 mmol) was then added dropwise and the mixture was stirred at rt for 2 h. The mixture was diluted with EtOAc and washed with NaHCO$_3$ and brine. The organic layer was dried over Na$_2$SO$_4$, filtered and concentrated. The residue was purified by flash chromatography (CombiFlash® Companion System®, with a 4 g RediSep® silica gel column, DCM/(DCM/MeOH 9:1+NH$_3$)=100:0→0:100) to afford the title compound as a foam (t$_R$ 3.50 min (conditions 3), MH+=470.2, $^1$H-NMR in DMSO-d6: 8.84 (m, 1H); 8.51 (s, 1H); 8.34 (m, 1H); 8.09 (m, 2H); 8.04 (d, 1H); 7.76 (d, 1H); 7.60 (s, 1H); 7.53 (d, 1H); 7.47 (dd, 1H); 4.55 (s, 2H); 4.48 (m, 2H); 3.92 (m, 1H); 3.21 (m, 1H); 2.72 (m, 1H); 2.04 (m, 5H); 1.89 (m, 1H); 1.75 (m, 1H)).

EXAMPLE 231

7-Fluoro-6-{6-[1-(2-pyrrolidin-1-yl-ethyl)-1H-pyrazol-4-yl]-imidazo[1,2-b]pyridazin-3-ylmethyl}-quinoline

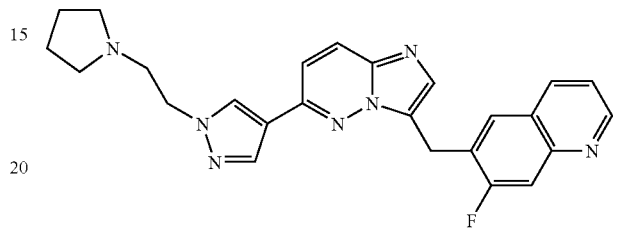

A mixture of 7-fluoro-6-[6-(1H-pyrazol-4-yl)-imidazo[1,2-b]pyridazin-3-ylmethyl]-quinoline (Example 251, 50 mg, 0.145 mmol), 1-(2-chlorethyl)pyrrolidine hydrochloride (25 mg, 0.145 mmol) and Cs$_2$CO$_3$ (99 mg, 0.305 mmol) in DMF (1 mL) was stirred at 95° C. for 18 h. The mixture was diluted with EtOAc and washed with NaHCO$_3$ and brine. The organic layer was dried over Na$_2$SO$_4$, filtered and concentrated. The residue was purified by flash chromatography (CombiFlash® Companion System®, with a 4 g RediSep® silica gel column, DCM/(DCM/MeOH 19:1)=100:0→0:100) to afford the title compound as a foam (t$_R$ 3.06 min (conditions 3), MH+=442.2, $^1$H-NMR in DMSO-d6: 8.84 (m, 1H); 8.44 (s, 1H); 8.34 (d, 1H); 8.08 (m, 2H); 8.03 (d, 1H); 7.76 (d, 1H); 7.61 (s, 1H); 7.52 (d, 1H); 7.46 (dd, 1H); 4.54 (s, 2H); 4.26 (t, 2H); 2.83 (m, 2H); 2.44 (m, 4H); 1.62 (m, 4H)).

EXAMPLE 232

7-Fluoro-6-{6-[1-(2-morpholin-4-yl-ethyl)-1H-pyrazol-4-yl]-imidazo[1,2-b]pyridazin-3-ylmethyl}-quinoline

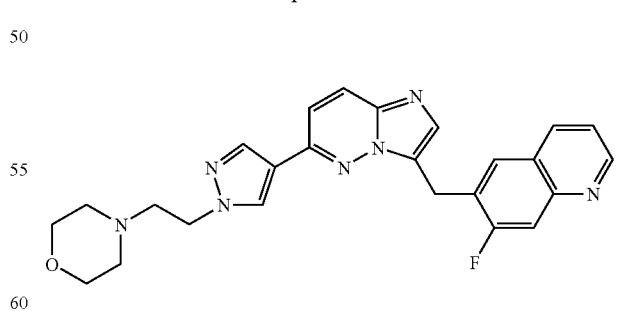

The title compound was prepared in analogy to the compound of Example 231 using 2-chlorethyl-morpholine hydrochloride instead of 1-(2-chlorethyl)pyrrolidine hydrochloride and with a second flash chromatography purification afterwards (t$_R$ 3.04 min (conditions 3), MH+=458.2, $^1$H-NMR in DMSO-d6: 8.84 (m, 1H); 8.44 (s, 1H); 8.33 (d, 1H); 8.09 (m, 2H); 8.01 (d, 1H); 7.76 (d, 1H); 7.62 (m, 1H); 7.52 (d, 1H); 7.46 (dd, 1H); 4.54 (s, 2H); 4.28 (t, 2H); 3.50 (m, 4H); 2.72 (m, 2H); 2.39 (m, 4H)).

EXAMPLE 233

7-Fluoro-6-(6-{1-[2-(2-methoxy-ethoxy)-ethyl]-1H-pyrazol-4-yl}-imidazo[1,2-b]pyridazin-3-ylmethyl)-quinoline

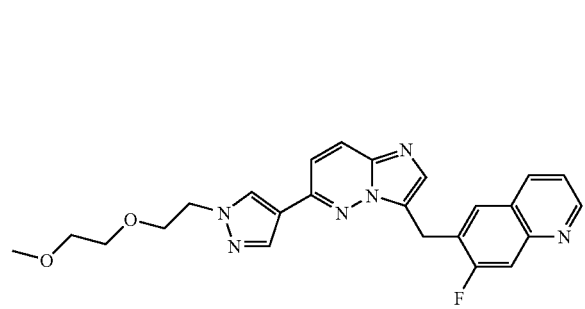 [SMILES: COCCOCCn1cc(-c2ccc3ncc(Cc4cc5cccnc5cc4F)n3n2)cn1]

A mixture of 6-(6-chloro-imidazo[1,2-b]pyridazin-3-ylmethyl)-7-fluoro-quinoline (Stage 173.1, 50 mg, 0.160 mmol), 1-[2-(2-methoxy-ethoxy)-ethyl]-4-(4,4,5,5-tetramethyl-[1,3,2]dioxaborolan-2-yl)-1H-pyrazole (Stage 233.1, 47 mg, 0.160 mmol), Pd(PPh$_3$)$_2$Cl$_2$ (6 mg, 0.008 mmol) and 2 M K$_2$CO$_3$ (216 μL, 0.432 mmol) in DME (1 mL) was stirred at 95° C. for 1 h. The mixture was diluted with EtOAc and washed with NaHCO$_3$ and brine. The organic layer was dried over Na$_2$SO$_4$, filtered and concentrated. The residue was purified twice by flash chromatography (CombiFlash® Companion System®, with a 4 g RediSep® silica gel column, DCM/(DCM/MeOH 19:1)=100:0→0:100) to afford the title compound as a foam (t$_R$ 3.56 min (conditions 3), MH+=447.1, $^1$H-NMR in DMSO-d6: 8.84 (m, 1H); 8.42 (s, 1H); 8.33 (d, 1H); 8.08 (m, 2H); 8.01 (d, 1H); 7.76 (d, 1H); 7.61 (s, 1H); 7.52 (d, 1H); 7.46 (dd, 1H); 4.55 (s, 2H); 4.31 (t, 2H); 3.79 (t, 2H); 3.50 (m, 2H); 3.36 (m, 2H); 3.15 (s, 3H)).

Stage 233.1

1-[2-(2-Methoxy-ethoxy)-ethyl]-4-(4,4,5,5-tetramethyl-[1,3,2]dioxaborolan-2-yl)-1H-pyrazole A mixture of 4-(4,4,5,5-tetramethyl-[1,3,2]dioxaborolan-2-yl)-1H-pyrazole (500 mg, 2.58 mmol), 1-(2-bromoethoxy)-2-methoxy-ethane (566 mg, 3.09 mmol) and Cs$_2$CO$_3$ (840 mg, 2.58 mmol) in DMF (5 mL) was stirred at 95° C. for 18 h. The mixture was diluted with EtOAc and washed with water and brine. The organic layer was dried over Na$_2$SO$_4$, filtered and concentrated to afford the title compound as an oil. (MH+=297.1, $^1$H-NMR in CDCl$_3$: 7.77 (m, 1 or 2H) 4.31 (t, 2H); 3.85 (t, 2H); 3.54 (m, 2H); 3.48 (m, 2H); 3.35 (s, 3H); 1.31 (s, 12H)).

EXAMPLE 234

7-Fluoro-6-{6-[1-(2-methoxy-ethyl)-1H-pyrazol-4-yl]-imidazo[1,2-b]pyridazin-3-ylmethyl}-quinoline The title compound was prepared in analogy to the compound of Example 233 using 1-(2-methoxy-ethyl)-4-(4,4,5,5-tetramethyl-[1,3,2]dioxaborolan-2-yl)-1H-pyrazole (Stage 234.1) instead of 1-[2-(2-methoxy-ethoxy)-ethyl]-4-(4,4,5,5-tetramethyl-[1,3,2]dioxaborolan-2-yl)-1H-pyrazole, with a reaction time of 5 h and only one purification by flash chromatography (t$_R$ 3.54 min (conditions 3), MH+=403.2, $^1$H-NMR in DMSO-d6: 8.84 (m, 1H); 8.42 (s, 1H); 8.34 (d, 1H); 8.09 (m, 2H); 8.03 (d, 1H); 7.76 (d, 1H); 7.61 (m, 1H); 7.54 (d, 1H); 7.46 (dd, 1H); 4.55 (s, 2H); 4.32 (t, 2H); 3.70 (t, 2H); 3.22 (s, 3H)).

Stage 234.1

1-(2-Methoxy-ethyl)-4-(4,4,5,5-tetramethyl-[1,3,2]dioxaborolan-2-yl)-1H-pyrazole was prepared in analogy to the compound of Stage 234.1 using 1-bromo-2-methoxy-ethane instead of 1-(2-bromo-ethoxy)-2-methoxy-ethane. (MH+=253.2, $^1$H-NMR in CDCl$_3$: 7.77 (m, 2H); 4.29 (t, 2H); 3.74 (t, 2H); 3.31 (s, 3H); 1.31 (s, 12H)).

EXAMPLE 235

6-{6-[1-(2-Azetidin-1-yl-ethyl)-1H-pyrazol-4-yl]-imidazo[1,2-b]pyridazin-3-ylmethyl}-quinoline The title compound was prepared in analogy to the compound of Example 236 using azetidine instead of pyrrolidine ($t_R$ 2.62 min (conditions 3), MH+=410.2).

EXAMPLE 236

6-{6-[1-(2-Pyrrolidin-1-yl-ethyl)-1H-pyrazol-4-yl]-imidazo[1,2-b]pyridazin-3-ylmethyl}-quinoline

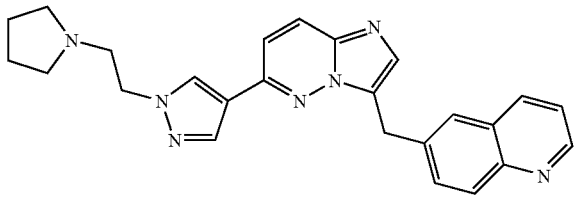 [SMILES: c1cnc2ccc(Cc3cnc4ccc(-c5cnn(CCN6CCCC6)c5)nn34)cc2c1]

A mixture of 2-[4-(3-quinolin-6-ylmethyl-imidazo[1,2-b]pyridazin-6-yl)-pyrazol-1-yl]-ethanol (Example 210, 74 mg, 0.200 mmol), triethylamine (61 µL, 0.440 mmol) and mesylchloride (33 µL, 0.420 mmol) in THF (10 mL) was stirred at rt for 24 h. Pyrrolidine (6 eq.) was then added and the mixture was stirred at 60° C. for 48 h. The mixture was diluted with DCM and washed with NaHCO$_3$ 10% and brine. The organic layer was dried over Na$_2$SO$_4$, filtered and concentrated. The residue was purified by flash chromatography (CombiFlash® Companion System®, with a 4 g RediSep® silica gel column, DCM/(MeOH+NH$_3$)=95:5→80:20) to afford the title compound ($t_R$ 2.70 min (conditions 3), MH+=424.3)

EXAMPLE 237

Methyl-{2-[4-(3-quinolin-6-ylmethyl-imidazo[1,2-b]pyridazin-6-yl)-pyrazol-1-yl]-ethyl}-amine

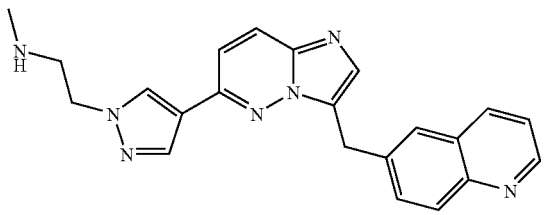 [SMILES: CNCCn1cc(-c2ccc3ncc(Cc4ccc5ncccc5c4)n3n2)cn1]

The title compound was prepared in analogy to the compound of Example 236 using a 2 M solution of methylamine in MeOH instead of pyrrolidine ($t_R$ 2.61 min (conditions 3), MH+=384.3, $^1$H-NMR in DMSO-d6: 8.82 (m, 1H); 8.56 (s, 1H); 8.32 (m, 1H); 8.19 (s, 2H); 8.11 (d, 1H); 7.94 (m, 2H); 7.78 (m, 1H); 7.66 (s, 1H); 7.54 (d, 1H); 7.48 (dd, 1H); 4.53 (m, 4H); 3.40 (t, 2H); 2.55 (s, 3H)).

EXAMPLE 238

6-{6-[1-(1-Methyl-piperidin-4-yl)-1H-pyrazol-4-yl]-imidazo[1,2-b]pyridazin-3-ylmethyl}-quinoline

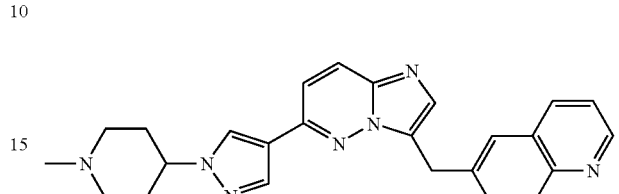

The title compound was obtained in analogy to Example 181, using 6-[6-(1-piperidin-4-yl-1H-pyrazol-4-yl)-imidazo[1,2-b]pyridazin-3-ylmethyl]-quinoline (Example 7) instead of 7-fluoro-6-[6-(1-piperidin-4-yl-1H-pyrazol-4-yl)-imidazo[1,2-b]pyridazin-3-ylmethyl]-quinoline ($t_R$ 2.68 min (conditions 3), MH+=424.2).

EXAMPLE 239

6-((S)-1-{6-[1-(1-Methyl-piperidin-4-yl)-1H-pyrazol-4-yl]-imidazo[1,2-b]pyridazin-3-yl}-ethyl)quinoline

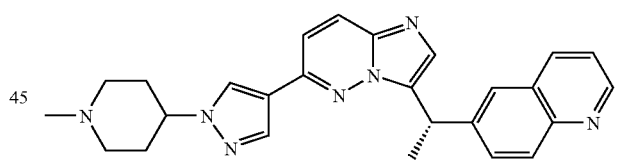

The title compound was obtained in analogy to Example 181, using 6-{(S)-1-[6-(1-piperidin-4-yl-1H-pyrazol-4-yl)-imidazo[1,2-b]pyridazin-3-yl]-ethyl}-quinoline (Stage 239.1) instead of 7-fluoro-6-[6-(1-piperidin-4-yl-1H-pyrazol-4-yl)-imidazo[1,2-b]pyridazin-3-ylmethyl]-quinoline ($t_R$ 2.84 min (conditions 3), MH+=438.2).

Stage 239.1

6-{(S)-1-[6-(1-Piperidin-4-yl-1H-pyrazol-4-yl)-imidazo[1,2-b]pyridazin-3-yl]-ethyl}-quinoline was obtained in analogy to Example 180 (Stage 180.1), starting with 6-[(S)-1-(6-chloro-imidazo[1,2-b]pyridazin-3-yl)-ethyl]-quinoline (Example 273) instead of 6-(6-chloro-imidazo[1,2-b]pyridazin-3-ylmethyl)-7-fluoro-quinoline (t_R 2.80 min (conditions 3), MH+=424.2).

EXAMPLE 240

6-{(S)-1-[6-(1H-Pyrazol-4-yl)-imidazo[1,2-b]pyridazin-3-yl]-ethyl}-quinoline

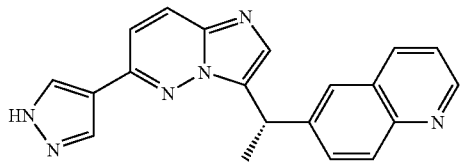 [SMILES: C[C@@H](c1ccc2ncccc2c1)c1cnc2ccc(-c3cn[nH]c3)nn12]

The title compound was obtained in analogy to Example 180 starting with 6-[(S)-1-(6-chloro-imidazo[1,2-b]pyridazin-3-yl)-ethyl]-quinoline (Example 273) instead of 6-(6-chloro-imidazo[1,2-b]pyridazin-3-ylmethyl)-7-fluoro-quinoline (Stage 180.2) and 1-tertbutoxycarbonyl-1H-pyrazole-4-boronic acid pinacol ester instead of 4-[4-(4,4,5,5-tetramethyl -[1,3,2]dioxaborolan-2-yl)-pyrazol-1-yl]-piperidine-1-carboxylic acid tert-butyl ester (t_R 2.97 min (conditions 3), MH+=341.2).

EXAMPLE 241

7-Chloro-6-[6-(1-methyl-1H-pyrazol-4-yl)-imidazo[1,2-b]pyridazin-3-ylmethyl]-quinoline

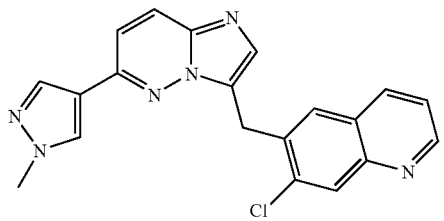 [SMILES: Cn1cc(-c2ccc3ncc(Cc4cc5cccnc5cc4Cl)n3n2)cn1]

The title compound was obtained in analogy to Example 173, starting with 7-chloro-6-(6-chloro-imidazo[1,2-b]pyridazin-3-ylmethyl)-quinoline (Stage 241.2) instead of 6-(6-chloro-imidazo[1,2-b]pyridazin-3-ylmethyl)-7-fluoro-quinoline (t_R 3.71 min (conditions 3), MH+=375.1).

Stage 241.1

7-Chloro-6-(6-chloro-imidazo[1,2-b]pyridazin-3-ylmethyl)-quinoline was obtained in analogy to Stage 173.1, starting with (rac)-(6-chloro-imidazo[1,2-b]pyridazin-3-yl)-(7-chloro-quinolin-6-yl)-methanol (Stage 241.2) instead of (rac)-(6-chloro-imidazo[1,2-b]pyridazin-3-yl)-(7-fluoro-quinolin-6-yl)-methanol (t_R 4.94 min (conditions 3), MH+=329.1).

Stage 241.2

(rac)-Chloro-imidazo[1,2-b]pyridazin-3-yl)-(7-chloro-quinolin-6-yl)-methanol was obtained in analogy to Stage 174.3, starting with 7-chloro-quinoline-6-carbaldehyde (Intermediate D) instead of 7-fluoro-quinoline-6-carbaldehyde (t_R 4.01 min (conditions 3), MH+=345.0).

EXAMPLE 242

7-Chloro-6-[6-(1-ethyl-1H-pyrazol-4-yl)-imidazo[1,2-b]pyridazin-3-ylmethyl]-quinoline

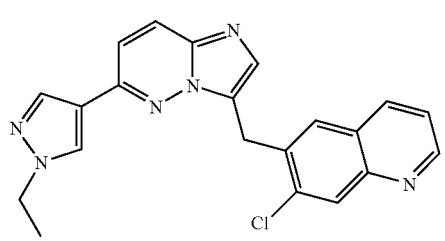 [SMILES: CCn1cc(-c2ccc3ncc(Cc4cc5cccnc5cc4Cl)n3n2)cn1]

The title compound was obtained in analogy to Example 241, replacing 1-methyl-4-(4,4,5,5-tetramethyl-[1,3,2]dioxaborolan-2-yl)-1H-pyrazole with 1-ethyl-4-(4,4,5,5-tetramethyl-[1,3,2]dioxaborolan-2-yl)-1H-pyrazole (t_R 3.71 min (conditions 3), MH+=375.1).

EXAMPLE 243

2-{4-[3-(7-Chloro-quinolin-6-ylmethyl)-imidazo[1,2-b]pyridazin-6-yl]-pyrazol-1-yl}-ethanol

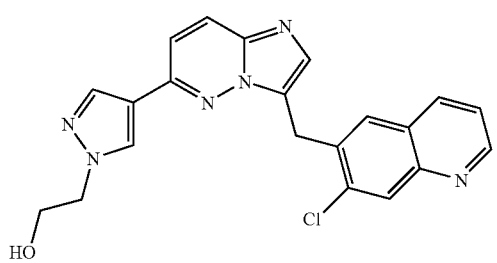 [SMILES: OCCn1cc(-c2ccc3ncc(Cc4cc5cccnc5cc4Cl)n3n2)cn1]

The title compound was prepared in analogy to Example 254, by replacing 6-(6-chloro-imidazo[1,2-b]pyridazin-3-ylmethyl)-7-fluoro-quinoline by 7-chloro-6-(6-chloro-imidazo

[1,2-b]pyridazin-3-ylmethyl)-quinoline (Stage 241.1) at Stage 254.1 ($t_R$ 3.38 min (conditions 3), MH+=405.1).

EXAMPLE 244

4-{4-[3-(5,7-Difluoro-quinolin-6-yl methyl)-imidazo[1,2-b]pyridazin-6-yl]-pyrazol-1-yl}-piperidine-1-carboxylic acid tert-butyl ester

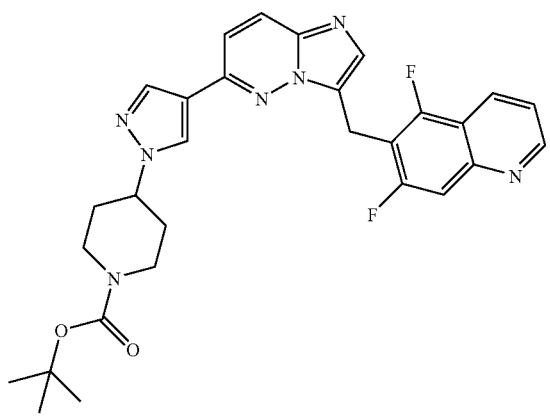 [SMILES: CC(C)(C)OC(=O)N1CCC(n2cc(-c3ccc4ncc(Cc5c(F)cc6ncccc6c5F)n4n3)cn2)CC1]

6-(6-Chloro-imidazo[1,2-b]pyridazin-3-ylmethyl)-5,7-difluoro-quinoline (Stage 171.2, 264 mg, 0.798 mmol) was dissolved in DME (2.5 mL) in a microwave reactor with 4-[4-(4,4,5,5-tetramethyl-[1,3,2]dioxaborolan-2-yl)-pyrazol-1-yl]-piperidine-1-carboxylic acid tert-butyl ester (see Stage 180.1, 301 mg, 0.798 mmol), and a solution of 2 M Na$_2$CO$_3$ (1.44 mL). Then tetrakis-(triphenylphosphine)-palladium (46.1 mg, 0.040 mmol) was added and the RM was heated at 150° C. for 5 min under microwave irradiations. It was then taken up with EtOAc and washed with 10% Na$_2$CO$_3$ sol. and brine. The organic layer was dried over Na$_2$SO$_4$ and the solvent was removed. The residue was purified by flash chromatography (CombiFlash® Companion System®, with RediSep® silica gel column, 0 to 20% MeOH in DCM) to afford after evaporation of the solvent the title compound as a pale yellow solid ($t_R$ 1.3 min (conditions 2), MH+=546).

EXAMPLE 245

5,7-Difluoro-6-[6-(1-piperidin-4-yl-1H-pyrazol-4-yl)-imidazo[1,2-b]pyridazin-3-ylmethyl]-quinoline

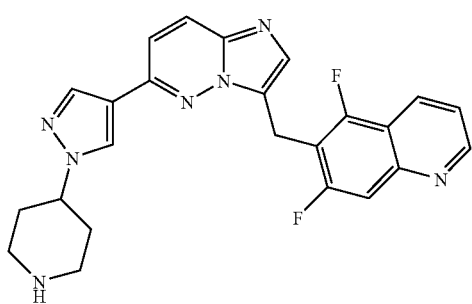 [SMILES: Fc1cc2ncccc2c(F)c1Cc1cnc2ccc(-c3cnn(C4CCNCC4)c3)nn12]

4-{4-[3-(5,7-Difluoro-quinolin-6-ylmethyl)-imidazo[1,2-b]pyridazin-6-yl]-pyrazol-1-yl}-piperidine-1-carboxylic acid tert-butyl ester (Example 244, 219 mg, 0.401 mmol) was dissolved in DCM (3 mL) with TFA (0.619 mL, 8.03 mmol). The RM was stirred at rt for 1 h 15 min and it was quenched with ice water. It was extracted with EtOAc twice. The combined organic layers was washed with brine and dried over Na$_2$SO$_4$. It was filtered and the solvent was removed. The residue was purified by preparative HPLC with acetonitrile and water (+0.1% TFA). The fractions were joined and the acetonitrile was removed. The aqueous solution was basified with 5% NaHCO$_3$ solution and was extracted with EtOAc twice. Combined organic layers was washed with brine and dried over Na$_2$SO$_4$. It was filtered to afford after evaporation of the solvent the title compound as a white solid ($t_R$ 0.8 min (conditions 2), MH+=446).

EXAMPLE 246

5,7-Difluoro-6-{6-[1-(1-methyl-piperidin-4-yl)-1H-pyrazol-4-yl]-imidazo[1,2-b]pyridazin-3-ylmethyl}-quinoline

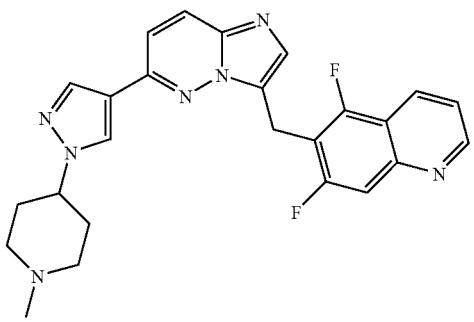 [SMILES: CN1CCC(n2cc(-c3ccc4ncc(Cc5c(F)cc6ncccc6c5F)n4n3)cn2)CC1]

5,7-Difluoro-6-[6-(1-piperidin-4-yl-1H-pyrazol-4-yl)-imidazo[1,2-b]pyridazin-3-ylmethyl]-quinoline (Example 245, 40 mg, 0.090 mmol) was dissolved in MeOH (1.5 mL) with formaldehyde (0.034 mL, 0.449 mmol) and sodium cyanoborohydride (33.2 mg, 0.449 mmol). The RM was stirred at rt for 2 h. Water was added and it was extracted with EtOAc twice. Combined organic layers were washed with brine and dried over Na$_2$SO$_4$, filtered and the solvent was removed. The residue was purified by preparative HPLC with acetonitrile and water (+0.1% TFA). The fractions were joined and lyophilized. The residue was dissolved in MeOH and it was passed through an SPE cartridge of HCO$_3^-$ to remove the TFA salt. The filtrate was evaporated to give the free salt of the title compound ($t_R$ 0.8 min (conditions 2), MH+=460).

EXAMPLE 247

(rac)-(5-Fluoro-quinolin-6-yl)-[6-(1-methyl-1H-pyrazol-4-yl)-imidazo[1,2-b]pyridazin-3-yl]-methanol

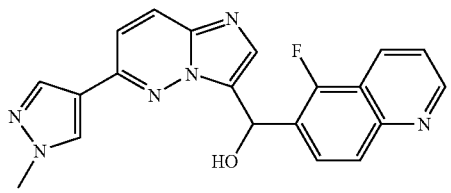

The title compound is compound of Stage 160.1.

EXAMPLE 248

(rac)-7-Fluoro-quinolin-6-yl)-[6-(1-methyl-1H-pyrazol-4-yl)-imidazo[1,2-b]pyridazin-3-yl]-methanol

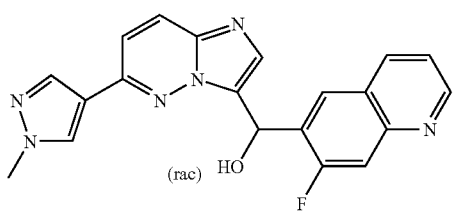 [SMILES: Cn1cc(-c2ccc3ncc(C(O)c4cc5cccnc5cc4F)n3n2)cn1]

The title compound was prepared in analogy to Example 9 using (rac)-(6-chloro-imidazo[1,2-b]pyridazin-3-yl)-(7-fluoro-quinolin-6-yl)-methanol (Stage 174.3) instead of (rac)-(6-chloro-imidazo[1,2-b]pyridazin-3-yl)-imidazo[1,2-a]pyridin-6-yl-methanol (Stage 9.1) ($t_R$ 3.20 min (conditions 3), MH+=375.1).

EXAMPLE 249

(rac)-[6-(1-Ethyl-1H-pyrazol-4-yl)-imidazo[1,2-b]pyridazin-3-yl]-(7-fluoro-quinolin-6-yl)methanol

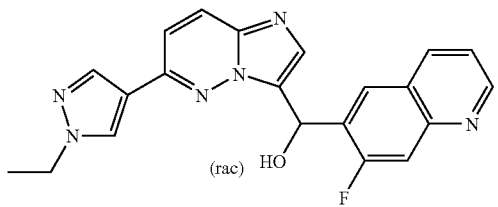 [SMILES: CCn1cc(-c2ccc3ncc(C(O)c4cc5cccnc5cc4F)n3n2)cn1]

The title compound was prepared in analogy to Example 9 using (rac)-(6-chloro-imidazo[1,2-b]pyridazin-3-yl)-(7-fluoro-quinolin-6-yl)-methanol (Stage 174.3) instead of (rac)-(6-chloro-imidazo[1,2-b]pyridazin-3-yl)-imidazo[1,2-a]pyridin-6-yl-methanol (Stage 9.1) and 1-ethyl-4-(4,4,5,5-tetramethyl-[1,3,2]dioxaborolan-2-yl)-1H-pyrazole instead of 1-methyl-4-(4,4,5,5-tetramethyl-[1,3,2]dioxaborolan-2-yl)-1H-pyrazole ($t_R$ 3.38 min (conditions 3), MH+=389.2).

EXAMPLE 250

6-[6-(1-Ethyl-1H-pyrazol-4-yl)-imidazo[1,2-b]pyridazin-3-ylmethyl]-7-fluoro-quinoline

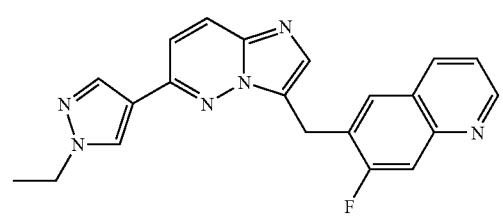 [SMILES: CCn1cc(-c2ccc3ncc(Cc4cc5cccnc5cc4F)n3n2)cn1]

The title compound was prepared in analogy to Example 173 using 1-ethyl-4-(4,4,5,5-tetramethyl-[1,3,2]dioxaborolan-2-yl)-1H-pyrazole instead of 1-methyl-4-(4,4,5,5-tetramethyl-[1,3,2]dioxaborolan-2-yl)-1H-pyrazole ($t_R$ 3.65 min (conditions 3), MH+=373.1).

EXAMPLE 251

7-Fluoro-6-[6-(1H-pyrazol-4-yl)-imidazo[1,2-b]pyridazin-3-ylmethyl]-quinoline

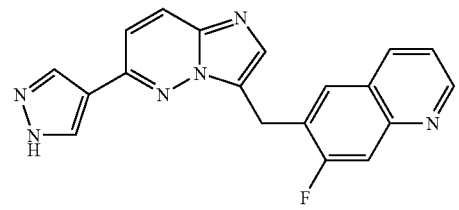 [SMILES: Fc1cc2ncccc2cc1Cc1cnc2ccc(-c3cn[nH]c3)nn12]

A mixture of 6-(6-chloro-imidazo[1,2-b]pyridazin-3-ylmethyl)-7-fluoro-quinoline (Stage 173.1, 50 mg, 0.160 mmol), 4-(4,4,5,5-tetramethyl-[1,3,2]dioxaborolan-2-yl)-pyrazole-1-carboxylic acid tert-butyl ester (70.5 mg, 0.240 mmol), Pd(PPh$_3$)$_2$Cl$_2$ (5.61 mg) and 2 M K$_2$CO$_3$ (0.216 mL, 0.423 mmol) in DME (1 mL) was stirred at 90° C. for 3 h. The Boc protecting group felt off during the course of the reaction. The mixture was diluted with EtOAc/NaHCO$_3$ and extracted with EtOAc. The combined organic phases were dried over Na$_2$SO$_4$, filtered, evaporated to dryness and the residue was purified by flash chromatography (CombiFlash® Companion System®, with RediSep® silica gel column, DCM/DCM/

MeOH 19:1=100:0->0:100) to afford the title compound (t$_R$ 3.22 min (conditions 3), MH+=345.1).

EXAMPLE 252

(rac)-(7-Fluoro-quinolin-6-yl)-[6-(1H-pyrazol-4-yl)-imidazo[1,2-b]pyridazin-3-yl]-methanol

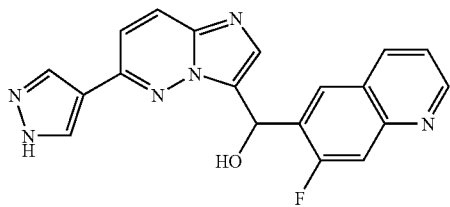 [SMILES: OC(c1cc2cccnc2cc1F)c1cnc2ccc(-c3cn[nH]c3)nn12]

The title compound was prepared in analogy to Example 251 using (rac)-(6-chloro-imidazo[1,2-b]pyridazin-3-yl)-(7-fluoro-quinolin-6-yl)-methanol (Stage 174.3) instead of 6-(6-chloro-imidazo[1,2-b]pyridazin-3-ylmethyl)-7-fluoro-quinoline (Stage 173.1) (t$_R$ 3.98 min (conditions 3), MH+=361.1).

EXAMPLE 253

(rac)-7-Fluoro-6-{1-[6-(1-methyl-1H-pyrazol-4-yl)-imidazo[1,2-b]pyridazin-3-yl]-ethyl}-quinoline

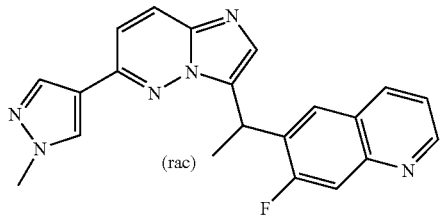 [SMILES: CC(c1cc2cccnc2cc1F)c1cnc2ccc(-c3cnn(C)c3)nn12]

The title compound was prepared in analogy to Stage 255.1 using 1-methyl-4-(4,4,5,5-tetramethyl-[1,3,2]dioxaborolan-2-yl)-1H-pyrazole instead of [2-(tetrahydro-pyran-2-yloxy)ethyl]-4-(4,4,5,5-tetramethyl-[1,3,2]dioxaborolan-2-yl)-1H-pyrazole (t$_R$ 3.65 min (conditions 3), MH+=373.1).

EXAMPLE 254

2-{4-[3-(7-Fluoro-quinolin-6-ylmethyl)-imidazo[1,2-b]pyridazin-6-yl]-pyrazol-1-yl}-ethanol

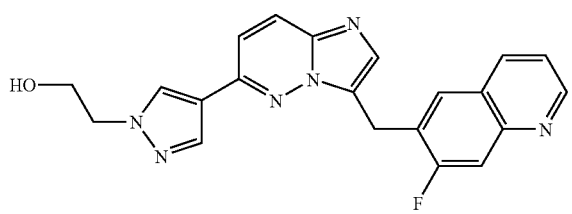 [SMILES: OCCn1cc(-c2ccc3ncc(Cc4cc5cccnc5cc4F)n3n2)cn1]

To a solution of 7-fluoro-6-(6-{1-[2-(tetrahydro-pyran-2-yloxy)-ethyl]-1H-pyrazol-4-yl}-imidazo[1,2-b]pyridazin-3-ylmethyl)-quinoline (Stage 254.1, 72 mg, 0.152 mmol) in DCM (2 mL) stirred at rt was added a solution of HCl in dioxane (4 M, 0.381 mL). The RM was stirred 1 h at rt, during this time the product precipitated as an oil. The supernatant DCM was discarded, the residue was taken in EtOAc and washed with a solution of 10% NaHCO$_3$. The organic phase was dried over Na$_2$SO$_4$ and concentrated under reduced pressure. The residue was purified by flash chromatography (CombiFlash® Companion System®, with RediSep® silica gel column, DCM/DCM/MeOH 19:1=100:0->0:100) to afford the title compound as a off white powder (t$_R$ 3.20 min (conditions 3), MH+=389.1, $^1$H-NMR in DMSO-d6: 8.82 (d, 1H), 8.42 (s, 1H); 8.33 (d, 2H); 8.12-8.05 (m, 2H); 8.02 (d, 1H); 7.76 (d, 1H); 7.58 (s, 1H); 7.52 (d, 1H); 7.49-7.43 (m, 1H); 4.97 (t, 1H); 4.54 (s, 2H); 4.18 (t, 2H); 3.72 (q, 2H)).

Stage 254.1

7-Fluoro-6-(6-{1-[2-(tetrahydro-pyran-2-yloxy)-ethyl]-1H-pyrazol-4-yl}-imidazo[1,2-b]pyridazin-3-ylmethyl)-quinoline A solution of [2-(tetrahydro-pyran-2-yloxy)-ethyl]-4-(4,4,5,5-tetramethyl-[1,3,2]dioxaborolan-2-yl)-1H-pyrazole (Stage 171.4, 77 mg, 0.240 mmol), 6-(6-chloro-imidazo[1,2-b]pyridazin-3-ylmethyl)-7-fluoro-quinoline (Stage 173.1, 55 mg, 0.160 mmol), PdCl$_2$(PPh$_3$)$_2$ (5.6 mg) and 2 M K$_2$CO$_3$ (0.216 mL) in DME (0.5 mL was stirred at 90° C. for 2 h under argon atmosphere. The RM was then diluted with EtOAc and washed with saturated aqueous NaHCO$_3$ and brine. The organic layer was dried over Na$_2$SO$_4$, filtered, evaporated to dryness and the residue was purified (CombiFlash® Companion System®, with RediSep® silica gel column, DCM/DCM/MeOH 9:1=100:0->0:100) to afford the title compound (t$_R$ 3.97 min (conditions 3), MH+=473.1).

EXAMPLE 255

(rac)-2-(4-{3-[1-(7-Fluoro-quinolin-6-yl)-ethyl]-imidazo[1,2-b]pyridazin-6-yl}-pyrazol-1-yl)ethanol

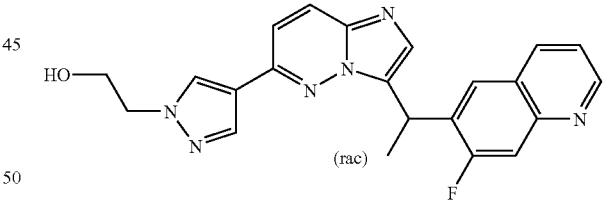

To a solution of (rac)-7-fluoro-6-[1-(6-{1-[2-(tetrahydropyran-2-yloxy)-ethyl]-1H-pyrazol-4-yl}-imidazo[1,2-b]pyridazin-3-yl)-ethyl]-quinoline (Stage 255.1, 49 mg, 0.101 mmol) in DCM (3 mL) stirred at rt was added a solution of HCl in dioxane (4 M, 0.252 mL). The RM was stirred 1 h at rt, during this time the product precipitated as an oil. The residue was taken in DCM and water, then neutralized with a solution of 10% NaHCO$_3$ and extracted with DCM. The combined organic phase was dried over MgSO$_4$ and concentrated under reduced pressure. The residue was purified by flash chromatography (CombiFlash® Companion System®, with RediSep® silica gel column, EtOAc/MeOH (1% NH$_3$)=100:0->80:20) to afford the title compound as a white crystalline powder (t$_R$ 3.40 min (conditions 3), MH+=403.3, $^1$H-NMR in DMSO-d6: 8.81 (d, 1H), 8.35-8.28 (m, 2H); 8.05 (d, 1H);

7.95-7.88 (m, 2H), 7.76 (d, 1H); 7.72 (s, 1H); 7.49 (d, 1H); 7.46-7.40 (m, 1H); 5.03 (q, 1H); 4.92 (t, 1H); 4.15 (t, 2H); 3.72 (q, 2H); 2.83 (d, 3H)).

Stage 255.1

(rac)-7-Fluoro-6-[1-(6-{1-[2-(tetrahydro-pyran-2-yloxy)-ethyl]-1H-pyrazol-4-yl}-imidazo[1,2-b]pyridazin-3-yl)-ethyl]-quinoline To a solution of [2-(tetrahydro-pyran-2-yloxy)-ethyl]-4-(4,4,5,5-tetramethyl-[1,3,2]dioxaborolan-2-yl)-1H-pyrazole (Stage 171.4, 72.5 mg, 0.225 mmol), (rac)-6-[1-(6-chloro-imidazo[1,2-b]pyridazin-3-yl)-ethyl]-7-fluoro-quinoline (Stage 255.2, 49 mg, 0.15 mmol), and 2 M $K_2CO_3$ (0.203 mL) in DME (1 mL) stirred at 80-90° C. under argon atmosphere was added $PdCl_2(PPh_3)_2$ (3.2 mg). After 1.5 h and cooling to rt the RM was taken-up in DCM and water, the aqueous phase was extracted with DCM, the combined organic layers were dried over $MgSO_4$, filtered, evaporated to dryness and the residue was purified by flash chromatography (CombiFlash® Companion System®, with RediSep® silica gel column, DCM/MeOH=100:0->80:20) to afford the title compound as a white solid ($t_R$ 4.14 min (conditions 3), MH+=487.2).

Stage 255.2

(rac)-6-[1-(6-Chloro-imidazo[1,2-b]pyridazin-3-yl)-ethyl]-7-fluoro-quinoline

To a solution of (rac)-1-(6-chloro-imidazo[1,2-b]pyridazin-3-yl)-1-(7-fluoro-quinolin-6-yl)ethanol (Stage 174.1, 200 mg, 0.584 mmol) in acetic acid (3.2 mL) were added iodine (296 mg, 1.167 mmol) and $H_3PO_2$ (0.642 mL of a 50% aqueous solution, 5.84 mmol). The RM was heated at 150° C. for 30 min. After cooling down to rt the acetic acid was evaporated under reduced pressure, water was added and the solution was neutralized with a solution of 10% $NaHCO_3$. The product which precipitated was extracted with DCM, the combined organic phase were dried over $MgSO_4$, filtered, evaporated to dryness and the residue was purified by flash chromatography (CombiFlash® Companion System®, with RediSep® silica gel column, hexane/EtOAc=50:50->0:100) to afford the title compound as a offwhite crystalline solid ($t_R$ 4.61 min (conditions 3), MH+=327.2, $^1$H-NMR in DMSO-d6: 8.85 (dd, 1H); 8.28 (dd, 1H); 8.20 (d, 1H); 7.85 (s, 1H); 7.78-7.68 (2H, m); 7.44 (dd, 1H); 7.29 (d, 1H); 4.95 (q, 1H); 1.79 (d, 3H)).

EXAMPLE 256

3-((R)-1-Imidazo[1,2-a]pyridin-6-yl-ethyl)-6-(1-methyl-1H-pyrazol-4-yl)-imidazo[1,2-b]pyridazine

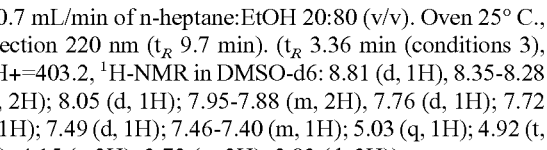

The title compound was obtained from the chiral separation of compound of Example 255 with a Preparative HPLC on a Chiralpak AD-H 5 µm (250×4.0 mm) column with a flow of 0.7 mL/min of n-heptane:EtOH 20:80 (v/v). Oven 25° C., detection 220 nm ($t_R$ 9.7 min). ($t_R$ 3.36 min (conditions 3), MH+=403.2, $^1$H-NMR in DMSO-d6: 8.81 (d, 1H), 8.35-8.28 (m, 2H); 8.05 (d, 1H); 7.95-7.88 (m, 2H), 7.76 (d, 1H); 7.72 (s, 1H); 7.49 (d, 1H); 7.46-7.40 (m, 1H); 5.03 (q, 1H); 4.92 (t, 1H); 4.15 (t, 2H); 3.72 (q, 2H); 2.83 (d, 3H)).

EXAMPLE 257

3-((R)-1-Imidazo[1,2-a]pyridin-6-yl-ethyl)-6-(1-methyl-1H-pyrazol-4-yl)-imidazo[1,2-b]pyridazine The title compound was obtained from the chiral separation of compound of Example 255 with a Preparative HPLC on a Chiralpak AD-H 5 µm (250×4.0 mm) column with a flow of 0.7 mL/min of n-heptane:EtOH 20:80 (v/v). Oven 25° C., detection 220 nm ($t_R$ 22.0 min). ($t_R$ 3.36 min (conditions 3), MH+=403.2, $^1$H-NMR in DMSO-d6: 8.81 (d, 1H), 8.35-8.28 (m, 2H); 8.05 (d, 1H); 7.95-7.88 (m, 2H), 7.76 (d, 1H); 7.72 (s, 1H); 7.49 (d, 1H); 7.46-7.40 (m, 1H); 5.03 (q, 1H); 4.92 (t, 1H); 4.15 (t, 2H); 3.72 (q, 2H); 2.83 (d, 3H)).

EXAMPLE 258

(rac)-7-Fluoro-6-{1-[6-(1-piperidin-4-yl-1H-pyrazol-4-yl)-imidazo[1,2-b]pyridazin-3-yl]-ethyl}-quinoline

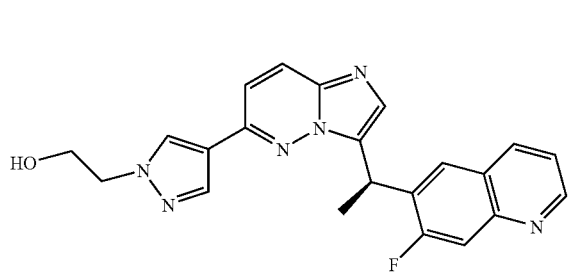 [SMILES: C[C@H](c1cc2cccnc2cc1F)c1cnc2ccc(-c3cnn(CCO)c3)nn12]

The title compound was prepared in analogy to Stage 239.1 using (rac)-6-[1-(6-chloro-imidazo[1,2-b]pyridazin-3-yl)-ethyl]-7-fluoro-quinoline (Stage 255.2) instead of 6-[(S)-1-

(6-chloro-imidazo[1,2-b]pyridazin-3-yl)-ethyl]-quinoline ($t_R$ 3.11 min (conditions 3), MH+=442.2).

EXAMPLE 259

(rac)-7-Fluoro-6-(1-{6-[1-(1-methyl-piperidin-4-yl)-1H-pyrazol-4-yl]-imidazo[1,2-b]pyridazin-3-yl}-ethyl)-quinoline

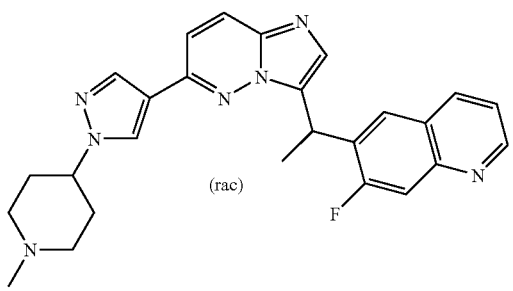 [SMILES: CC(c1cc2cccnc2cc1F)c1cnc2ccc(-c3cnn(C4CCN(C)CC4)c3)nn12]

The title compound was obtained in analogy to Example 181, using (rac)-7-Fluoro-6-{1-[6-(1-piperidin-4-yl-1H-pyrazol-4-yl)-imidazo[1,2-b]pyridazin-3-yl]-ethyl}-quinoline (Example 258) instead of 7-Fluoro-6-[6-(1-piperidin-4-yl-1H-pyrazol-4-yl)-imidazo[1,2-b]pyridazin-3-ylmethyl]-quinoline ($t_R$ 3.16 min (conditions 3), MH+=456.2).

EXAMPLE 260

(rac)-{1-[3-(7-fluoro-quinolin-6-ylmethyl)-imidazo[1,2-b]pyridazin-6-yl]-pyrrolidin-3-yl}-methylamine

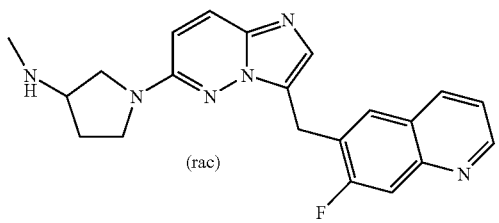 [SMILES: CNC1CCN(c2ccc3ncc(Cc4cc5cccnc5cc4F)n3n2)C1]

(rac)-{1-[3-(7-Fluoro-quinolin-6-ylmethyl)-imidazo[1,2-b]pyridazin-6-yl]-pyrrolidin-3-yl}-methyl-carbamic acid tert-butyl ester (Stage 260.1, 179 mg, 0.376 mmol) was dissolved in DCM (7.5 mL) and TFA (3 mL). The RM was stirred at rt for 1 h. A basic work up (1 M Na$_2$CO$_3$) followed by a crystallization in Et$_2$O afforded the title compound as white crystals ($t_R$ 2.28 min (conditions 13), MH+=377, $^1$H-NMR in DMSO-d6: 8.83 (m, 1H); 8.30 (d, 1H); 7.93 (d, 1H); 7.75 (m, 2H); 7.48 (dd, 1H); 7.35 (s, 1H); 6.74 (d, 1H); 4.37 (s, 2H); 3.52-3.35 (m, 3H); 3.23-3.17 (m, 2H); 2.27 (s, 3H); 2.07 (m, 1H); 1.86 (bs, 1H); 1.80 (m, 1H)).

Stage 260.1

(rac)-{1-[3-(7-fluoro-quinolin-6-ylmethyl)-imidazo[1,2-b]pyridazin-6-yl]-pyrrolidin-3-yl}-methyl-carbamic acid tert-butyl ester 6-(6-Chloro-imidazo[1,2-b]pyridazin-3-ylmethyl)-7-fluoro-quinoline (Stage 173.1, 150 mg, 0.474 mmol), KF (139 mg, 2.372 mmol) and (rac)-methyl-pyrrolidin-3-yl-carbamic acid tert-butyl ester (285 mg, 1.423 mmol) were suspended in NMP (1.5 mL). The RM was stirred at 170° C. for 1 h. The mixture was diluted with TBME and washed with water (3×). The aqueous phases were further extracted with TBME (1×). The combined organic layer was dried over Na$_2$SO$_4$, filtered and concentrated in vacuo. The residue was crystallized in Et$_2$O to afford the title compound as a beige solid ($t_R$ 3.91 min (conditions 13), MH+=477).

EXAMPLE 261

(S)-1-[3-(7-Fluoro-quinolin-6-ylmethyl)-imidazo[1,2-b]pyridazin-6-yl]-pyrrolidin-3-ol

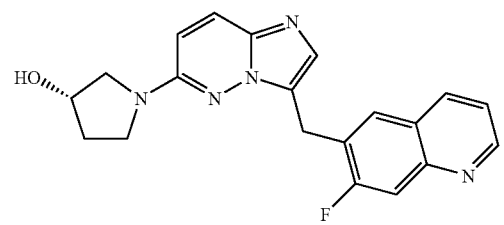 [SMILES: O[C@H]1CCN(c2ccc3ncc(Cc4cc5cccnc5cc4F)n3n2)C1]

6-(6-Chloro-imidazo[1,2-b]pyridazin-3-ylmethyl)-7-fluoro-quinoline (Stage 173.1, 100 mg, 0.316 mmol), KF (92 mg, 1.581 mmol) and (S)-3-hydroxypyrrolidine (83 mg, 0.949 mmol) were suspended in NMP (1.5 mL). The RM was stirred at 170° C. for 1 h. The mixture was diluted with DCM/MeOH (95:5) and washed with water (2×). The aqueous phases were further extracted with DCM/MeOH (95:5) (2×). The combined organic layer was dried over Na$_2$SO$_4$, filtered and concentrated. The residue was crystallized in DCM to afford the title compound as a beige solid ($t_R$ 2.63 min (conditions 13), MH+=364).

EXAMPLE 262

(R)-1-[3-(7-Fluoro-quinolin-6-ylmethyl)-imidazo[1,2-b]pyridazin-6-yl]-pyrrolidin-3-ol

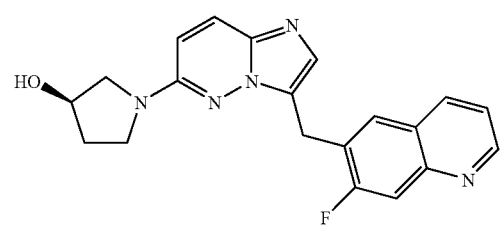 [SMILES: O[C@@H]1CCN(c2ccc3ncc(Cc4cc5cccnc5cc4F)n3n2)C1]

The title compound was obtained in analogy to Example 261 by replacing (S)-3-hydroxypyrrolidine with (R)-3-hydroxypyrrolidine ($t_R$ 2.62 min (conditions 13), MH+=364).

EXAMPLE 263

5,7-Difluoro-6-[6-(1H-pyrazol-4-yl)-imidazo[1,2-b]pyridazin-3-ylmethyl]-quinoline

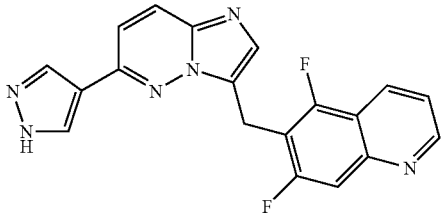 [SMILES: Fc1cc2ncccc2c(F)c1Cc1cnc2ccc(-c3cn[nH]c3)nn12]

6-(6-Chloro-imidazo[1,2-b]pyridazin-3-ylmethyl)-5,7-difluoro-quinoline (Stage 171.2, 100 mg, 0.299 mmol) was dissolved in DME (3 mL) under argon atm. 4-(4,4,5,5-Tetramethyl-[1,3,2]dioxaborolan-2-yl)-pyrazole-1-carboxylic acid tert-butyl ester (136 mg, 0.449 mmol) was added, followed by 2 M $K_2CO_3$ (0.40 mL) and $PdCl_2(PPh_3)_2$ (10.5 mg, 0.015 mmol). The RM was stirred at 90° C. for 11 h. It was then taken into a mixture of EtOAc and brine and extracted. The combined organic phase was dried on $Na_2SO_4$. After evaporation of the solvent the crude was purified by flash chromatography in silica gel with the eluent DCM/MeOH=10:1. The collected fractions containing product were concentrated, dried under vacuo. The title compound was obtained as a white solid ($t_R$ 2.97 min (conditions 13), MH+=363).

EXAMPLE 264

(rac)-1-[6-(1-Methyl-1H-pyrazol-4-yl)-imidazo[1,2-b]pyridazin-3-yl]-1-quinolin-6-yl-ethanol

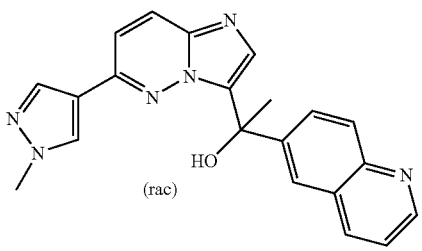 [SMILES: Cn1cc(-c2ccc3ncc(C(C)(O)c4ccc5ncccc5c4)n3n2)cn1]

The title compound was prepared in analogy to Example 174 using (rac)-1-(6-chloro-imidazo[1,2-b]pyridazin-3-yl)-1-quinolin-6-yl-ethanol (Stage 154.1) instead of (rac)-1-(6-chloro-imidazo[1,2-b]pyridazin-3-yl)-1-(7-fluoro-quinolin-6-yl)-ethanol ($t_R$ 2.92 min (conditions 3), MH+=371.3).

EXAMPLE 265

(rac)-1-(7-Fluoro-quinolin-6-yl)-1-{6-[1-(2-hydroxyethyl)-1H-pyrazol-4-yl]-imidazo[1,2-b]pyridazin-3-yl}-ethanol

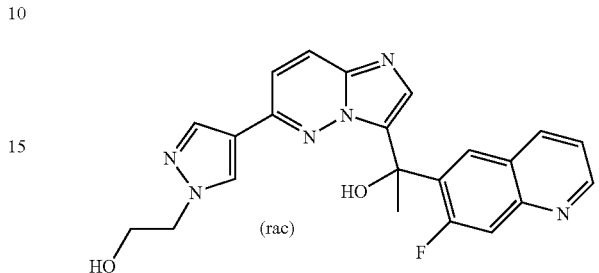

(rac)-1-(6-Chloro-imidazo[1,2-b]pyridazin-3-yl)-1-(7-fluoro-quinolin-6-yl)-ethanol (Stage 174.1, 200 mg, 0.584 mmol) was dissolved in DME (4 mL) under argon atm. 1-[2-(Tetrahydro-pyran-2-yloxy)-ethyl]-4-(4,4,5,5-tetramethyl-[1,3,2]dioxaborolan-2-yl)-1H-pyrazole (Stage 171.4, 282 mg, 0.875 mmol) was added, followed by 2 M $K_2CO_3$ (0.79 mL) and $PdCl_2(PPh_3)_2$ (20.5 mg, 0.029 mmol). The RM was stirred at 90° C. for 1.5 h. It was then taken into a mixture of EtOAc and 1 M $Na_2CO_3$ and extracted. The organic phase was dried on $Na_2SO_4$, filtered and evaporation of the solvent. The residue was dissolved in DCM (16 mL), 4 M HCl (dioxane, 0.438 mL, 1.751 mmol) were added at 10° C. The mixture was stirred at rt for 1 h. The solvent was evaporated and the residue was diluted with EtOAc/MeOH (95:5) and washed with 1 M $Na_2CO_3$ (1×). The aqueous phases were further extracted with EtOAc (1×). The combined organic layer was dried over $Na_2SO_4$, filtered and concentrated. The residue was crystallized in DCM/$Et_2O$ to afford the title compound as a slightly yellow solid ($t_R$ 2.37 min (conditions 13), MH+=419). $^1$H-NMR in DMSO-d6: 8.86 (m, 1H), 8.64 (m, 2H), 8.02 (d, 1H), 7.93 (s, 1H), 7.82 (s, 1H), 7.58-7.50 (m, 2H), 7.45-7.40 (m, 2H), 6.25 (s, 1H), 4.86 (t, 1H), 4.00 (m, 2H), 3.60 (m, 2H), 2.15 (s, 3H).

EXAMPLE 266

(R)-1-(7-Fluoro-quinolin-6-yl)-1-{6-[1-(2-hydroxyethyl)-1H-pyrazol-4-yl]-imidazo[1,2-b]pyridazin-3-yl}-ethanol

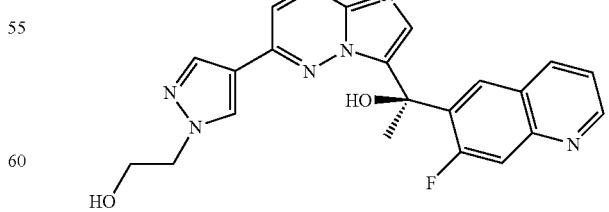

The title compound was obtained from the chiral separation of compound of Example 265 with a preparative Chiralpak IA (20 um) 10.5×50 cm column with a flow of 15 mL/min of n-heptane/TBME/ethanol 50:20:30. Oven 20° C., detection 254 nm. ($t_R$ 17 min). ($t_R$ 2.37 min (conditions 13), MH+=419, $^1$H-NMR in DMSO-d6: DMSO-d6: 8.86 (m, 1H), 8.64 (m, 2H), 8.02 (d, 1H), 7.93 (s, 1H), 7.82 (s, 1H), 7.58-7.50 (m, 2H), 7.45-7.40 (m, 2H), 6.25 (s, 1H), 4.86 (t, 1H), 4.00 (m, 2H), 3.60 (m, 2H), 2.15 (s, 3H)

EXAMPLE 267

(rac)-1-(5,7-Difluoro-quinolin-6-yl)-1-{6-[1-(2-hydroxy-ethyl)-1H-pyrazol-4-yl]-imidazo[1,2-b]pyridazin-3-yl}-ethanol

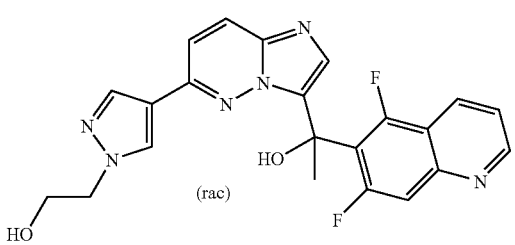 [SMILES: CC(O)(c1c(F)cc2ncccc2c1F)c1cnc2ccc(-c3cnn(CCO)c3)nn12]

The title compound was obtained in analogy to Example 265 by replacing (rac)-1-(6-chloro-imidazo[1,2-b]pyridazin-3-yl)-1-(7-fluoro-quinolin-6-yl)-ethanol (Stage 174.1) with (rac)-1-(6-chloro-imidazo[1,2-b]pyridazin-3-yl)-1-(5,7-difluoro-quinolin-6-yl)-ethanol (Stage 182.2) ($t_R$ 2.72 min (conditions 13), MH+=437). $^1$H-NMR in DMSO-d6: 8.93 (m, 1H), 8.53 (d, 1H), 8.11 (s, 1H), 8.03 (d, 1H), 7.82 (s, 1H), 7.65 (s, 1H), 7.60-7.40 (m, 3H), 6.43 (s, 1H), 4.90 (t, 1H), 4.10 (m, 2H), 3.65 (m, 2H), 2.23 (s, 3H).

EXAMPLE 268

(R)-1-(5,7-Difluoro-quinolin-6-yl)-1-{6-[1-(2-hydroxy-ethyl)-1H-pyrazol-4-yl]-imidazo[1,2-b]pyridazin-3-yl}-ethanol

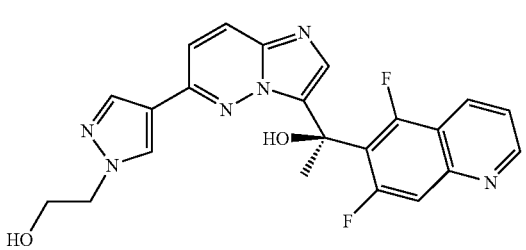 [SMILES: C[C@@](O)(c1c(F)cc2ncccc2c1F)c1cnc2ccc(-c3cnn(CCO)c3)nn12]

The title compound was obtained from the chiral separation of compound of Example 267 with a preparative Chiralpak AD (20 um) 5×50 cm column with a flow of 60-150 mL/min of n-heptane/EtOH/MeOH 50:25:25. Oven 20° C., detection 220 nm ($t_R$ 21 min). ($t_R$ 2.72 min (conditions 13). MH+=437). $^1$H-NMR in DMSO-d6: 8.93 (m, 1H), 8.53 (d, 1H), 8.11 (s, 1H), 8.03 (d, 1H), 7.82 (s, 1H), 7.65 (s, 1H), 7.60-7.40 (m, 3H), 6.43 (s, 1H), 4.90 (t, 1H), 4.10 (m, 2H), 3.65 (m, 2H), 2.23 (s, 3H)).

EXAMPLE 269

(rac)-1-(5,7-Difluoro-quinolin-6-yl)-1-[6-(1-methyl-1H-pyrazol-4-yl)-imidazo[1,2-b]pyridazin-3-yl]-ethanol

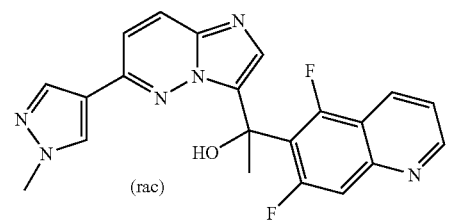 [SMILES: Cn1cc(-c2ccc3ncc(C(C)(O)c4c(F)cc5ncccc5c4F)n3n2)cn1]

The title compound was obtained in analogy to Example 174 by replacing 1-(6-chloro-imidazo[1,2-b]pyridazin-3-yl)-1-(7-fluoro-quinolin-6-yl)-ethanol (Stage 174.1) with 1-(6-chloro-imidazo[1,2-b]pyridazin-3-yl)-1-(5,7-difluoro-quinolin-6-yl)-ethanol (Stage 182.2) ($t_R$ 2.91 min (conditions 13), MH+=407). $^1$H-NMR in DMSO-d6: 8.93 (m, 1H), 8.53 (d, 1H), 8.05 (s, 1H), 8.03 (d, 1H), 7.82 (s, 1H), 7.62 (s, 1H), 7 57 (m, 1H), 7.53 (d, 1H), 7.38 (d, 1H), 6.43 (s, 1H), 3.77 (s, 3H), 2.23 (s, 3H).

EXAMPLE 270

(R)-1-(5,7-Difluoro-quinolin-6-yl)-1-[6-(1-methyl-1H-pyrazol-4-yl)-imidazo[1,2-b]pyridazin-3-yl]-ethanol

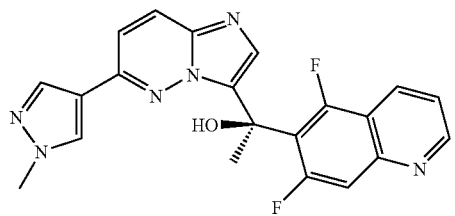 [SMILES: Cn1cc(-c2ccc3ncc([C@](C)(O)c4c(F)cc5ncccc5c4F)n3n2)cn1]

The title compound was obtained from the chiral separation of compound of Example 269 with a preparative HPLC on a Chiralpak AD (20 um) 5×50 cm column with a flow of 50 mL/min of heptane/EtOH/MeOH 40:30:30. Oven 20° C., detection 210 nm ($t_R$ 75 min). ($t_R$ 2.91 min (conditions 13). MH+=407). $^1$H-NMR in DMSO-d6: 8.93 (m, 1H), 8.53 (d, 1H), 8.05 (s, 1H), 8.03 (d, 1H), 7.82 (s, 1H), 7.62 (s, 1H), 7.57 (m, 1H), 7.53 (d, 1H), 7.38 (d, 1H), 6.43 (s, 1H), 3.77 (s, 3H), 2.23 (s, 3H)

EXAMPLE 271

(rac)-6-[1-(6-Chloro-imidazo[1,2-b]pyridazin-3-yl)-ethyl]-quinoline

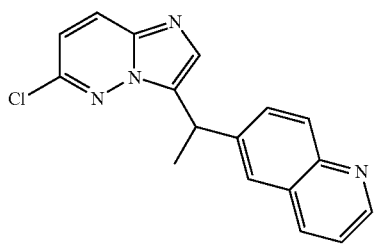 [SMILES: CC(c1ccc2ncccc2c1)c1cnc2ccc(Cl)nn12]

The title compound was prepared in analogy to Stage 255.2 using (rac)-1-(6-chloro-imidazo[1,2-b]pyridazin-3-yl)-1-quinolin-6-yl-ethanol (Stage 154.1) instead of (rac)-1-(6-chloro-imidazo[1,2-b]pyridazin-3-yl)-1-(7-fluoro-quinolin-6-yl)-ethanol ($t_R$ 3.88 min (conditions 3), MH+=309.1).

EXAMPLE 272

6-[(R)-1-(6-Chloro-imidazo[1,2-b]pyridazin-3-yl)-ethyl]-quinoline

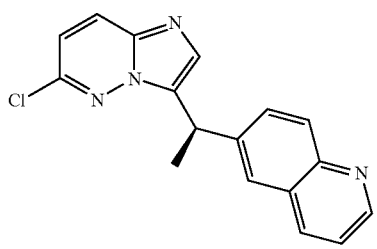 [SMILES: C[C@H](c1ccc2ncccc2c1)c1cnc2ccc(Cl)nn12]

The title compound was obtained from the chiral separation of compound of Example 271 with a Preparative HPLC on a Chiralpak AD (5×50 cm) column with a flow of 50 mL/min EtOH 100%. Oven 20° C., detection 210 nm ($t_R$ 116 min). ($t_R$ 2.86 min (conditions 2), MH+=344.3).

EXAMPLE 273

6-[(S)-1-(6-Chloro-imidazo[1,2-b]pyridazin-3-yl)-ethyl]-quinoline

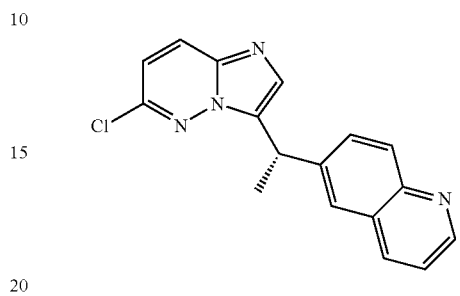

The title compound was obtained from the chiral separation of compound of Example 271 with a Preparative HPLC on a Chiralpak AD (5×50 cm) column with a flow of 50 mL/min EtOH 100%. Oven 20° C., detection 210 nm ($t_R$ 74 min). ($t_R$ 2.86 min (conditions 2), MH+=344.3).

EXAMPLE 274

(rac)-6-[1-(6-Chloro-imidazo[1,2-b]pyridazin-3-yl)-2,2,2-trifluoro-ethyl]-quinoline

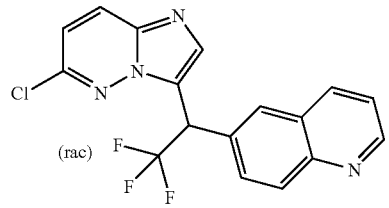 [SMILES: FC(F)(F)C(c1ccc2ncccc2c1)c1cnc2ccc(Cl)nn12]

Iodine (105 mg, 0.412 mmol) and $H_3PO_2$ (0.225 mL of a 50% aqueous solution, 2.059 mmol) were added to a solution of (rac)-1-(6-chloro-imidazo[1,2-b]pyridazin-3-yl)-2,2,2-trifluoro-1-(quinolin-6-yl)ethanol (Stage 274.1, 52 mg, 0.137 mmol) in acetic acid (1.4 mL). The RM was heated at 150° C. for 45 min under microwave irradiations. The solvent was removed. The residue was taken up with EtOAc and extracted with 1N HCl twice. The combined aqueous layers was basified to pH 14 with NaOH pellets. It was then extracted with EtOAc/MeOH (9:1) twice. Combined organic layers was dried over $Na_2SO_4$, filtered and concentrated. After purification by preparative HPLC with acetonitrile and water (+0.1% TFA), the fraction containing the product was lyophilized to give a TFA salt of the title compound ($t_R$ 1.0 min (conditions 1), MH+=363).

Stage 274.1

(6-chloro-imidazo[1,2-b]pyridazin-3-yl)-quinolin-6-yl-methanone (Stage 1.2, 50 mg, 0.162 mmol) was dissolved in DMF (5 mL) and (trifluoromethyl)trimethylsilane (1.294 mL, 8.10 mmol) and KF (4.70 mg, 0.081 mmol) were introduced. After 30 min at rt, 1 N HCl was added to the RM. It was stirred at rt for 20 h. the reaction was not completed. It was then heated at 150° C. under microwave irradiations for 5 min. It was extracted with EtOAc twice. Combined organic layers was washed with brine and dried over Na₂SO₄. It was filtered and the solvent was removed to afford as brown solid 1-(6-chloro-imidazo[1,2-b]pyridazin-3-yl)-2,2,2-trifluoro-1-(quinolin-6-yl)ethanol (t$_R$ 0.8 min (conditions 2), MH+=379).

EXAMPLE 275

2-(5-{(S)-1-[6-(1-Methyl-1H-pyrazol-4-yl)-imidazo[1,2-b]pyridazin-3-yl]-ethyl}-indazol-1-yl)ethanol

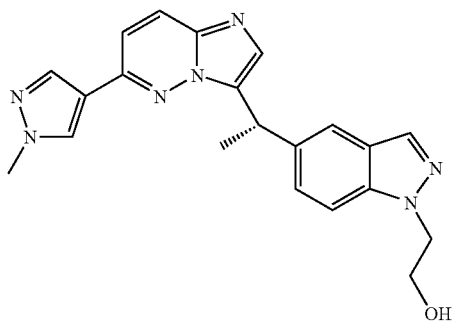 [SMILES: C[C@@H](c1ccc2c(cnn2CCO)c1)c1cnc2ccc(-c3cnn(C)c3)nn12]

The title compound was prepared in analogy to Example 285 using 6-(1-methyl-1H-pyrazol-4-yl)-3-((S)-1-{1-[2-(tetrahydro-pyran-2-yloxy)-ethyl]-1H-indazol-5-yl}-ethyl)-imidazo[1,2-b]pyridazine (Stage 275.1) instead of 3-(4,6-difluoro-1-methyl-1H-indazol-5-ylmethyl)-6-{1-[2-(tetrahydro-pyran-2-yloxy)-ethyl]-1H-pyrazol-4-yl}-imidazo[1,2-b]pyridazine (t$_R$ 3.45 min (conditions 2), MH+=388.3).
Stage 275.1

(1-Methyl-1H-pyrazol-4-yl)-3-((S)-1-{1-[2-(tetrahydro-pyran-2-yloxy)-ethyl]-1H-indazol-5-yl}-ethyl)-imidazo[1,2-b]pyridazine 6-(1-Methyl-1H-pyrazol-4-yl)-3-((S)-1-{1-[2-(tetrahydro-pyran-2-yloxy)-ethyl]-1H-indazol-5-yl}-ethyl)-imidazo[1,2-b]pyridazine (Example 195, 34 mg, 0.1 mmol) was added to a suspension of NaH (55%, 4.8 mg 0.11 mmol) in dry THF (0.5 mL) at 0° C. The RM was allowed to stir at rt for 15 min and 2-(2-bromo-ethoxy)-tetrahydro-pyran (0.024 mL, 0.150 mmol) was added at 0° C. It was stirred additionally 7 h at rt, then overnight at 60° C., and finally 7 h at 120° C. in a pressure safe capped vial. After cooling at rt the RM was taken-up in DCM, washed with brine, the organic phase was dried over MgSO₄ and concentrated under reduced pressure. The residue was purified by flash chromatography (CombiFlash® Companion System®, with RediSep® silica gel column, EtOAc/MeOH=100:0->80:20) to afford 6-(1-methyl-1H-pyrazol-4-yl)-3-((S)-1-{2-[2-(tetrahydro-pyran-2-yloxy)-ethyl]-2H-indazol-5-yl}-ethyl)imidazo[1,2-b]pyridazine and the title compound (t$_R$ 4.05 min (conditions 2), MH+=472.3).

EXAMPLE 276

3-(1-Methyl-1H-indazol-5-ylmethyl)-6-(1-methyl-1H-pyrazol-4-yl)-imidazo[1,2-b]pyridazine

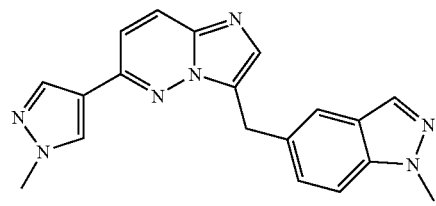 [SMILES: Cn1cc(-c2ccc3ncc(Cc4ccc5c(cnn5C)c4)n3n2)cn1]

The title compound was prepared in analogy to Example 10 using (rac)-(1-methyl-1H-indazol-5-yl)-[6-(1-methyl-1H-pyrazol-4-yl)-imidazo[1,2-b]pyridazin-3-yl]-methanol (Stage 276.1) instead of (rac)-imidazo[1,2-a]pyridin-6-yl-[6-(1-methyl-1H-pyrazol-4-yl)-imidazo[1,2-b]pyridazin-3-yl]-methanol (t$_R$ 3.71 min (conditions 3), MH+=344.3).
Stage 276.1
(rac)-(1-Methyl-1H-indazol-5-yl)-[6-(1-methyl-1H-pyrazol-4-yl)-imidazo[1,2-b]pyridazin-3-yl]-methanol was prepared in analogy to Example 9 using (rac)-(6-chloro-imidazo[1,2-b]pyridazin-3-yl)-(1-methyl-1H-indazol-5-yl)-methanol (Stage 276.2) instead of (rac)-(6-chloro-imidazo[1,2-b]pyridazin-3-yl)-imidazo[1,2-a]pyridin-6-yl-methanol (Stage 9.1) (t$_R$ 3.33 min (conditions 3), MH+=360.3).
Stage 276.2
(rac)-(6-Chloro-imidazo[1,2-b]pyridazin-3-yl)-(1-methyl-1H-indazol-5-yl)-methanol was prepared in analogy to Stage 9.1 using 1-methyl-1H-indazole-5-carbaldehyde (Stage 276.3) instead of imidazo[1,2-a]pyridine-6-carbaldehyde (t$_R$ 3.98 min (conditions 3), MH+=314.2).
Stage 276.3
1-Methyl-1H-indazole-5-carbaldehyde was prepared like described in published patent application WO2006040052 (t$_R$ 4.17 min (conditions 3), MH+=161).

EXAMPLE 277

3-(6-Fluoro-1-methyl-1H-indazol-5-ylmethyl)-6-(1-methyl-1H-pyrazol-4-yl)-imidazo[1,2-b]pyridazine

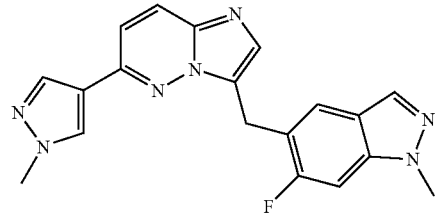 [SMILES: Cn1cc(-c2ccc3ncc(Cc4cc5cnn(C)c5cc4F)n3n2)cn1]

3-(6-Fluoro-1H-indazol-5-ylmethyl)-6-(1-methyl-1H-pyrazol-4-yl)-imidazo[1,2-b]pyridazine (Example 167, 18.6 mg, 0.054 mmol) was dissolved in DMF (0.310 mL) and cooled down to 0° C. NaH (1.9 mg, 0.080 mmol) was added and the RM was stirred for 30 min. Then iodomethane (4.02

μL) was introduced and it was allowed to warm up to rt. After 2.5 h of stirring, water was added and it was extracted with EtOAc. Organic layer was washed with brine and dried over Na$_2$SO$_4$, filtered and concentrated. The residue was purified by preparative HPLC with acetonitrile and water (+0.1% TFA). The fractions were joined and were lyophilized. The residue was dissolved in MeOH and it was passed through an SPE cartridge of HCO$_3^-$ to remove the TFA salt. The filtrate was evaporated to give the free salt of the title compound as a white solid (t$_R$ 1.0 min (conditions 2), MH+=362).

EXAMPLE 278

(rac)-3-[1-(6-Fluoro-1-methyl-1H-indazol-5-yl)-ethyl]-6-(1-methyl-1H-pyrazol-4-yl)-imidazo[1,2-b]pyridazine

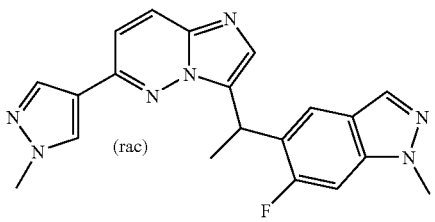 [SMILES: CC(c1cc2cnn(C)c2cc1F)c1cnc2ccc(-c3cnn(C)c3)nn12]

(rac)-6-Chloro-3-[1-(6-fluoro-1-methyl-1H-indazol-5-yl)-ethyl]-imidazo[1,2-b]pyridazine (Stage 278.1), 240 mg, 0.728 mmol) was introduced in a microwave reactor together with 1-methyl-4-(4,4,5,5-tetramethyl-[1,3,2]dioxaborolan-2-yl)-1H-pyrazole (227 mg, 1.092 mmol) and DME (5 mL). The mixture was purged with argon for 5 min. Tetrakis-(triphenylphosphine)-palladium (42.1 mg) and 2 M Na$_2$CO$_3$ (1.31 mL) were added and the mixture was flushed with argon before being sealed. The RM was submitted to microwave irradiation at 150° C. 30 min. Then it was diluted with EtOAc and washed with water, brine, dried over Na$_2$SO$_4$, filtered and evaporated. The residue was purified by preparative HPLC with acetonitrile and water (+0.1% TFA) to afford the title compound as a white solid (t$_R$ 1.03 min (conditions 2), MH+=376) 1H-NMR in DMSO-d6: 8.29 (s, 1H); 8.05 (d, 1H); 7.93 (s, 1H); 7.67 (s, 1H); 7.58 (d, 1H); 7.53 (d, 1H); 7.46 (d, 1H); 7.23 (d, 1H); 4.92 (q, 1H); 3.94 (s, 3H); 3.88 (s, 3H); 1.76 (d, 3H)).

Stage 278.1

(rac)-6-Chloro-3-[1-(6-fluoro-1-methyl-1H-indazol-5-yl)-ethyl]-imidazo[1,2-b]pyridazine (rac)-1-(6-Chloro-imidazo[1,2-b]pyridazin-3-yl)-1-(6-fluoro-1-methyl-1H-indazol-5-yl)-ethanol (Stage 278.2, 2 g, 5.78 mmol) was dissolved in acetic acid (80 mL) and introduced in 4 microwave reactors. Iodide (1.84 g×4, 29 mmol), followed by H$_3$PO$_2$ 50% (2.36 mL×4, 87 mmol) were then added into each reactor. Then they were submitted to microwave irradiations 5 min at 150° C. After combination, it was basified by a 2.5 M NaOH solution and extracted twice with EtOAc. The organics were joined and washed with brine, dried over Na$_2$SO$_4$ and the solvent was removed. The residue was purified by flash chromatography (CombiFlash® Companion System®, with 120 g RediSep® silica gel column, DCM/MeOH=100:0->94:6 in 30 min). The collected fractions containing product were evaporated and the residue was dried under vacuum to afford the title compound (t$_R$ 1.15 min (conditions 2), MH+=330).

Stage 278.2

(rac)-1-(6-Chloro-imidazo[1,2-b]pyridazin-3-yl)-1-(6-fluoro-1-methyl-1H-indazol-5-yl)-ethanol (6-Chloro-imidazo[1,2-b]pyridazin-3-yl)-(6-fluoro-1-methyl-1H-indazol-5-yl)-methanone (Stage 278.3, 3.7 g, 11.22 mmol) was dissolved in THF (250 mL) with heating under Argon. The solution was let to cool down and methylmagnesium bromide (3 M, 7.48 mL) was added. The mixture was stirred at rt for 1 h. It was then diluted with EtOAc and washed with a saturated NaHCO$_3$ sol. The aqueous phase was extracted twice with EtOAc. The combined organics were washed with brine, dried over Na$_2$SO$_4$, filtered and evaporated. The residue was purified by flash chromatography (CombiFlash® Companion System®, with 120 g RediSep® silica gel column, DCM/MeOH=100:0->94:6 in 20 min). The collected fractions containing product were evaporated and the residue was dried under vacuum to afford the title compound (t$_R$ 1.14 min (conditions 2), MH+=346)

Stage 278.3

(6-Chloro-imidazo[1,2-b]pyridazin-3-yl)-(6-fluoro-1-methyl-1H-indazol-5-yl)-methanone (rac)-(6-Chloro-imidazo[1,2-b]pyridazin-3-yl)-(6-fluoro-1-methyl-1H-indazol-5-yl)-methanol (Stage 278.4, 4.2 g, 12.66 mmol) was suspended in DCM (250 mL). Dess-Martin periodinane (10.64 g, 38.0 mmol) was added and the mixture was stirred at rt for 1.5 h. The mixture was evaporated to dryness and the residue was taken in 1 M NaOH and sonicated. After 15 min of stirring, it was filtered. The precipitate was dried under vacuum overnight to afford the title compound (t$_R$ 1.13 min (conditions 2), MH+=330)

Stage 278.4

(rac)-(6-Chloro-imidazo[1,2-b]pyridazin-3-yl)-(6-fluoro-1-methyl-1H-indazol-5-yl)-methanol was obtained in analogy to Stage 171.3 by replacing 5,7-difluoro-quinoline-6-carbaldehyde with 6-fluoro-1-methyl-1H-indazole-5-carbaldehyde (Intermediate H) (t$_R$ 0.94 min (conditions 2), MH+=332).

EXAMPLE 279

(rac)-2-(4-{3-[1-(6-Fluoro-1-methyl-1H-indazol-5-yl)-ethyl]-imidazo[1,2-b]pyridazin-6-yl}-pyrazol-1-yl)-ethanol

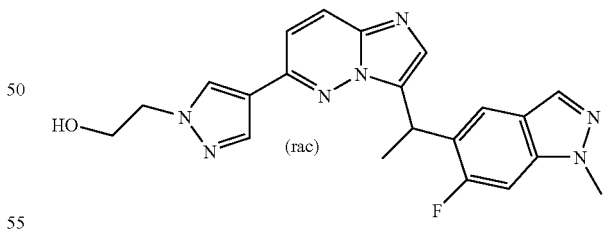

(rac)-3-[1-(6-Fluoro-1-methyl-1H-indazol-5-yl)-ethyl]-6-{1-[2-(tetrahydro-pyran-2-yloxy)-ethyl]-1H-pyrazol-4-yl}-imidazo[1,2-b]pyridazine (Stage 279.1, 250 mg, 0.511 mmol) was dissolved in DCM (5 mL). HCl in dioxane (4 N, 0.5 mL) was added and the RM was stirred 1 h at rt. It was then diluted with EtOAc and washed with a saturated NaHCO$_3$ sol. The aqueous phase was extracted twice with EtOAc. The combined organics were washed with brine, dried over Na$_2$SO$_4$, filtered and evaporated. The residue was purified by preparative HPLC with acetonitrile and water (+0.1% TFA) to afford the title compound as a white solid (t$_R$ 0.98 min (conditions 2), MH+=406, 1H-NMR in DMSO-d6: 8.39 (s, 1H); 8.07 (d, 2H); 8.01 (d, 1H); 7.69 (s, 1H); 7.61 (s, 1H); 7.51 (d, 1H); 7.47 (d, 1H); 7.23 (d, 1H); 4.95 (t, 1H); 4.76 (q, 1H); 4.18 (t, 2H); 3.78 (s, 3H); 3.75 (q, 2H); 1.79 (d, 3H)).

Stage 279.1

(rac)-3-[1-(6-Fluoro-1-methyl-1H-indazol-5-yl)-ethyl]-6-{1-[2-(tetrahydro-pyran-2-yloxy)-ethyl]-1H-pyrazol-4-yl}-imidazo[1,2-b]pyridazine (rac)-6-Chloro-3-[1-(3-methyl-3H-benzoimidazol-5-yl)-ethyl]-imidazo[1,2-b]pyridazine (Stage 278.1, 250 mg, 0.758 mmol) was introduced in a microwave reactor together with 1-[2-(tetrahydro-pyran-2-yloxy)-ethyl]-4-(4,4,5,5-tetramethyl-[1,3,2]dioxaborolan-2-yl)-1H-pyrazole (Stage 171.4, 366 mg, 1.137 mmol) and DME (5 mL). The mixture was purged with argon for 5 min. Tetrakis-(triphenylphosphine)-palladium (35 mg) and 2 M Na$_2$CO$_3$ (1.36 mL) were added and the mixture was flushed with argon before being sealed. The RM was submitted to microwave irradiation at 150° C. 30 min. Then it was diluted with EtOAc and washed with water, brine, dried over Na$_2$SO$_4$, filtered and evaporated. The residue was purified by flash chromatography (CombiFlash® Companion System®, with 40 g RediSep® silica gel column, DCM/MeOH=100:0->92:8 in 25 min). The collected fractions containing product were evaporated and the residue was dried under vacuum to afford the title compound (t$_R$ 1.17 min (conditions 2), MH+=490)

EXAMPLE 280

2-(4-{3-[(S)-1-(6-Fluoro-1-methyl-1H-indazol-5-yl)-ethyl]-imidazo[1,2-b]pyridazin-6-yl}-pyrazol-1-yl)-ethanol

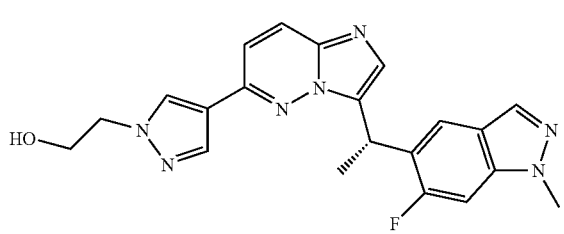 [SMILES: C[C@@H](c1cc2cnn(C)c2cc1F)c1cnc2ccc(-c3cnn(CCO)c3)nn12]

The title compound was obtained by the chiral separation of compound of Example 279 with a Preparative HPLC on a Chiralcel OD (50×500 mm) column with a flow of 60 mL/min of n-Heptane/EtOH/MeOH 8:1:1 (v/v). Oven 25° C., detection 220 nm. (t$_R$ 0.98 min (conditions 2), MH+=406).

EXAMPLE 281

2-{4-[3-(6-Fluoro-1-methyl-1H-indazol-5-ylmethyl)-imidazo[1,2-b]pyridazin-6-yl]-pyrazol-1-yl}-ethanol

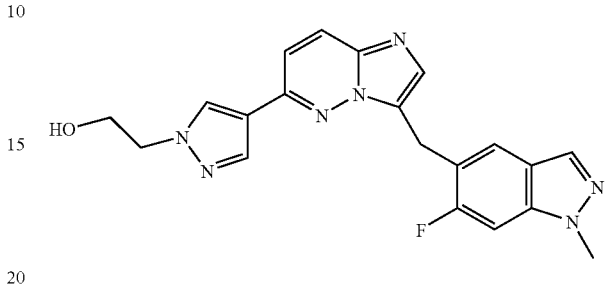

3-(6-Fluoro-1-methyl-1H-indazol-5-yl methyl)-6-{1-[2-(tetrahydro-pyran-2-yloxy)-ethyl]-1H-pyrazol-4-yl}-imidazo[1,2-b]pyridazine (Stage 281.1, 269 mg, 566 µmol) was dissolved in DCM (5 mL). HCl in dioxane (4 N, 283 µl) was added and the RM was stirred 1 h at rt. The solvent was totally evaporated and the residue was taken up with EtOAc and washed with saturated NaHCO$_3$ and brine. The organic layer was dried over Na$_2$SO$_4$ and solvent evaporated under vacuo. The residue was purified by preparative HPLC with acetonitrile and water (+0.1% TFA). The acetonitrile was removed and the aqueous solution was basified with 5% NaHCO$_3$. It was extracted 3 times with EtOAc and then the organics were joined and washed with brine. It was dried over Na$_2$SO$_4$ and the solvent was removed. The residue was triturated with pentane and the precipitate was filtered off to give the title compound a white solid (t$_R$ 0.93 min (conditions 2), MH+=392, 1H-NMR in DMSO-d6: 8.42 (s, 1H); 8.1 (s, 1H); 8.02 (d, 1H); 7.97 (s, 1H); 7.75 (d, 1H); 7.52 (t, 3H); 4.95 (m, 1H); 4.40 (s, 2H); 4.21 (t, 2H); 3.96 (s, 3H); 3.77 (m, 2H)).

Stage 281.1

3-(6-Fluoro-1-methyl-1H-indazol-5-ylmethyl)-6-{1-[2-(tetrahydro-pyran-2-yloxy)-ethyl]-1H-pyrazol-4-yl}-imidazo[1,2-b]pyridazine 6-Chloro-3-(6-fluoro-1-methyl-1H-indazol-5-ylmethyl)-imidazo[1,2-b]pyridazine (Stage 281.2, 268 mg, 849 µmol) was introduced in a microwave reactor together with 1-[2-(tetrahydropyran-2-yloxy)-ethyl]-4-(4,4,5,5-tetramethyl-[1,3,2]dioxaborolan-2-yl)-1H-pyrazole (Stage 171.4, 410 mg, 1.273 mmol) and DME (5 mL). The mixture was purged with Argon for 5 min. Tetrakis-(triphenylphosphine)-palladium (39.2 mg) and 2 M Na$_2$CO$_3$ (1.528 mL) were added and the mixture was flushed with argon before being sealed. The RM was submitted to microwave irradiation at 150° C. 30 min. The RM was diluted with EtOAc and washed with water, brine, dried over Na$_2$SO$_4$, filtered and evaporated. The residue was purified by flash chromatography (CombiFlash® Companion System®, with 40 g RediSep® silica gel column, DCM/MeOH=100:0->94:6 in 45 min). The collected fractions containing product were evaporated and the residue was dried under vacuum to afford the title compound as an oil (t$_R$ 1.13 min (conditions 2), MH+=476)

Stage 281.2

6-Chloro-3-(6-fluoro-1-methyl-1H-indazol-5-ylmethyl)-imidazo[1,2-b]pyridazine (rac)-(6-Chloro-imidazo[1,2-b]pyridazin-3-yl)-(6-fluoro-1-methyl-1H-indazol-5-yl)-methanol (Stage 278.4, 1 g, 3.01 mmol) was dissolved in acetic acid (80 mL) and introduced in 4 microwave reactors. Iodide (956 mg×4, 15.07 mmol), followed by H$_3$PO$_2$ 50% (1.2 m×4, 45.2 mmol) were then added into each reactor. Then they were submitted to microwave irradiations 5 min at 150° C. After combination, it was basified by a 2.5 M NaOH solution and extracted twice with EtOAc. The organics were joined and washed with brine, dried over Na$_2$SO$_4$ and the solvent was removed. The residue was triturated with Et$_2$O to afford the title compound (t$_R$ 1.26 min (conditions 2), MH+=316)

EXAMPLE 282

3-(6-Fluoro-1-methyl-1H-indazol-5-ylmethyl)-6-(1-piperidin-4-yl-1H-pyrazol-4-yl)-imidazo[1,2-b]pyridazine

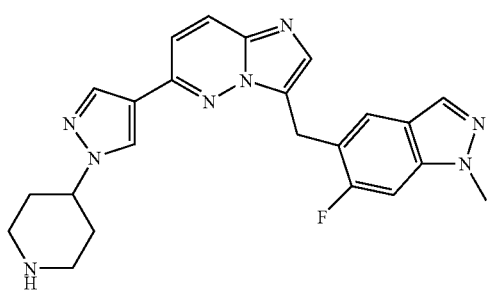 [SMILES: Cn1ncc2cc(Cc3cnc4ccc(-c5cnn(C6CCNCC6)c5)nn34)c(F)cc21]

The title compound was obtained in analogy to Stage 180.1 by replacing 6-(6-chloro-imidazo[1,2-b]pyridazin-3-ylmethyl)-7-fluoro-quinoline (Stage 180.2) with 6-chloro-3-(6-fluoro-1-methyl-1H-indazol-5-ylmethyl)-imidazo[1,2-b]pyridazine (Stage 281.2) and with an additional final Boc-deprotection in DCM with TFA (t$_R$ 0.85 min (conditions 2), MH+=431)

EXAMPLE 283

3-(6-Fluoro-1-methyl-1H-indazol-5-ylmethyl)-6-[1-(1-methyl-piperidin-4-yl)-1H-pyrazol-4-yl]-imidazo[1,2-b]pyridazine

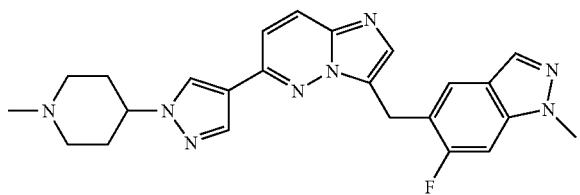

To abs. MeOH (2 mL) stirred at rt were added 3-(6-fluoro-1-methyl-1H-indazol-5-ylmethyl)-6-(1-piperidin-4-yl-1H-pyrazol-4-yl)-imidazo[1,2-b]pyridazine (Example 282, 79 mg, 0.184 mmol), formaldehyde (0.068 mL, 0.918 mmol) and NaBH$_3$CN (58 mg, 0.918 mmol). The RM was then brought to pH 5-6 with addition of acetic acid and stirred at rt for 2 h. It was then taken into EtOAc and washed with saturated NaHCO$_3$ sol. The organic layer was then washed with brine, dried on Na$_2$SO$_4$, filtered and evaporated. The residue was then purified by preparative HPLC with acetonitrile and water (+0.1% TFA) to afford the title compound (t$_R$ 0.85 min (conditions 2), MH+=445).

EXAMPLE 284

3-(4,6-Difluoro-1-methyl-1H-indazol-5-ylmethyl)-6-(1-methyl-1H-pyrazol-4-yl)-imidazo[1,2-b]pyridazine

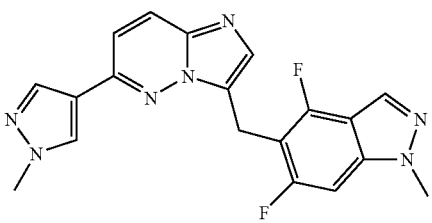 [SMILES: Cn1cc(-c2ccc3ncc(Cc4c(F)cc5c(cnn5C)c4F)n3n2)cn1]

In a microwave vial were introduced under argon 1-methyl-4-(4,4,5,5-tetramethyl-[1,3,2]dioxaborolan-2-yl)-1H-pyrazole (23 mg, 0.112 mmol) and 6-chloro-3-(4,6-difluoro-1-methyl-1H-indazol-5-ylmethyl)-imidazo[1,2-b]pyridazine (Stage 284.1, 25 mg, 0.075 mmol) with 0.3 mL DME. The solution was degassed with argon, before adding PdCl$_2$(PPh$_3$)$_2$ (1.5 mg) and 2 M K$_2$CO$_3$ (0.101 mL). The RM was then stirred at 80°-90° C. for 30 min. Additional 1-methyl-4-(4,4,5,5-tetramethyl-[1,3,2]dioxaborolan-2-yl)-1H-pyrazole (10 mg, 0.048 mmol) and PdCl$_2$(PPh$_3$)$_2$ (1.5 mg) were added. The RM was then diluted with DCM and washed with sat. aqueous NaHCO$_3$ and brine. The organic layer was dried over Na$_2$SO$_4$, filtered, evaporated to dryness and the residue was purified (CombiFlash® Companion System®, with RediSep® silica gel column, EtOAc/MeOH=100:0->80:20) to afford the title compound as a beige crystalline powder (t$_R$ 3.91 min (conditions 3), MH+=380.2, $^1$H-NMR in DMSO-d6: 8.36 (s, 1H); 8.18 (s, 1H); 8.05 (s, 1H); 8.02 (d, 1H); 7.50 (m, 2H); 7.45 (s, 1H); 4.40 (s, 2H); 3.97 (s, 3H); 3.90 (s, 3H)).

Stage 284.1

6-Chloro-3-(4,6-difluoro-1-methyl-1H-indazol-5-ylmethyl)-imidazo[1,2-b]pyridazine was obtained in analogy to Example 9 starting with (rac)-(6-chloro-imidazo[1,2-b]pyridazin-3-yl)-(4,6-difluoro-1-methyl-1H-indazol-5-yl)-methanol (Stage 284.2) instead of (rac)-imidazo[1,2-a]pyridin-6-yl-[6-(1-methyl-1H-pyrazol-4-yl)-imidazo[1,2-b]pyridazin-3-yl]-methanol. A beige powder was obtained (t$_R$ 5.21 min (conditions 3), MH+=334.3).

Stage 284.2

(rac)-(6-Chloro-imidazo[1,2-b]pyridazin-3-yl)-(4,6-difluoro-1-methyl-1H-indazol-5-yl)-methanol was obtained in analogy to Stage 195.4 by reacting 4,6-difluoro-1-methyl-1H-indazole-5-carbaldehyde (Intermediate I) instead of 2-(2- trimethylsilanyl-ethoxymethyl)-2H-indazole-5-carbaldehyde. A beige powder was obtained ($t_R$ 4.18 min (conditions 3), MH+=350.2).

EXAMPLE 285

2-{4-[3-(4,6-Difluoro-1-methyl-1H-indazol-5-ylmethyl)-imidazo[1,2-b]pyridazin-6-yl]-pyrazol-1-yl}-ethanol

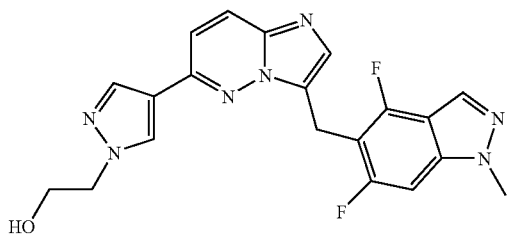 [SMILES: Cn1ncc2c(F)c(Cc3cnc4ccc(-c5cnn(CCO)c5)nn34)c(F)cc21]

To a solution of 3-(4,6-difluoro-1-methyl-1H-indazol-5-ylmethyl)-6-{1-[2-(tetrahydro-pyran-2-yloxy)-ethyl]-1H-pyrazol-4-yl}-imidazo[1,2-b]pyridazine (Stage 285.1, 30 mg, 0.061 mmol) in dioxane (2 mL) stirred at 0° C. was added a solution of HCl in dioxane (4 M, 0.152 mL). The RM was stirred 1 h at rt, poured in a solution 10% NaHCO$_3$, and the aqueous phase was extracted with DCM. The combined organic phases were dried over MgSO$_4$ and concentrated under reduced pressure. The residue was purified by flash chromatography (CombiFlash® Companion System®, with RediSep® silica gel column, hexane/EtOAc=100:0->80:20) to afford the title compound as a white powder ($t_R$ 3.68 min (conditions 3), MH+=410.2, $^1$H-NMR in DMSO-d6: 8.38 (s, 1H); 8.19 (s, 1H); 8.06 (s, 1H); 8.04 (d, 1H); 7.53-7.46 (m, 3H); 4.97 (t, 1H); 4.40 (s, 2H); 4.18 (t, 2H); 3.97 (s, 3H); 3.76 (q, 2H)).

Stage 285.1

3-(4,6-Difluoro-1-methyl-1H-indazol-5-ylmethyl)-6-{1-[2-(tetrahydro-pyran-2-yloxy)-ethyl]-1H-pyrazol-4-yl}-imidazo[1,2-b]pyridazine was prepared in analogy to Example 284 using 1-[2-(Tetrahydro-pyran-2-yloxy)-ethyl]-4-(4,4,5,5-tetramethyl-[1,3,2]dioxaborolan-2-yl)-1H-pyrazole (Stage 171.4) instead of 1-Methyl-4-(4,4,5,5-tetramethyl-[1,3,2]dioxaborolan-2-yl)-1H-pyrazole ($t_R$ 4.35 min (conditions 3), MH+=494.2).

EXAMPLE 286

(rac)-[6-(1-Methyl-1H-pyrazol-4-yl)-imidazo[1,2-b]pyridazin-3-yl]-[1,5]naphthyridin-2-ylmethanol

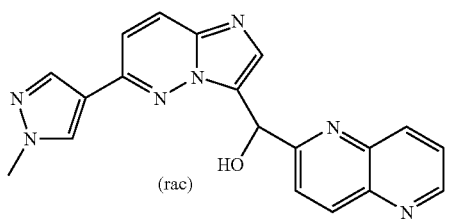 [SMILES: Cn1cc(-c2ccc3ncc(C(O)c4ccc5ncccc5n4)n3n2)cn1]

The title compound was prepared in analogy to Example 9 using (rac)-(6-chloro-imidazo[1,2-b]pyridazin-3-yl)-[1,5] naphthyridin-2-yl-methanol (Stage 286.1) instead of (rac)-(6-chloro-imidazo[1,2-b]pyridazin-3-yl)-imidazo[1,2-a]pyridin-6-yl-methanol (Stage 9.1) ($t_R$ 3.14 min (conditions 3), MH+=358.1).

Stage 286.1

(rac)-(6-Chloro-imidazo[1,2-b]pyridazin-3-yl)-[1,5] naphthyridin-2-yl-methanol was prepared in analogy to Stage 9.1 using [1,5]naphthyridine-2-carbaldehyde (Stage 286.2) instead of imidazo[1,2-a]pyridine-6-carbaldehyde ($t_R$ 3.57 min (conditions 3), MH+=312.1).

Stage 286.2

[1,5]Naphthyridine-2-carbaldehyde was prepared like described in published patent application WO2006040052. ($t_R$ 0.9 min (conditions 1), MH+=159, $^1$H-NMR in DMSO-d6: 10.13 (s, 1H); 9.15 (d, 1H); 8.65 (d, 2H); 8.22 (d, 1H); 7.92 (dd, 1H)).

EXAMPLE 287

3-(3-Methyl-1H-indazol-5-ylmethyl)-6-(1-methyl-1H-pyrazol-4-yl)-imidazo[1,2-b]pyridazine

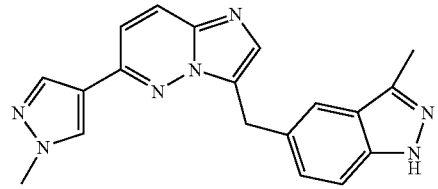 [SMILES: Cc1n[nH]c2ccc(Cc3cnc4ccc(-c5cnn(C)c5)nn34)cc12]

The title compound was prepared in analogy to Example 167 (all Stages) using 3-methyl-1-(2-trimethylsilanylmethoxy-ethyl)-1H-indazole-5-carbaldehyde (Stage 287.1) instead of a mixture of 6-fluoro-1-(2-trimethylsilanylethoxymethyl)-1H-indazole-5-carbaldehyde and 6-fluoro-2-(2-trimethylsilanyl-ethoxymethyl)-2H-indazole-5-carbaldehyde (Stage 164.5) ($t_R$ 3.61 min (conditions 3), MH+=344.3).

Stage 287.1

3-Methyl-1-(2-trimethylsilanylmethoxy-ethyl)-1H-indazole-5-carbaldehyde was prepared in analogy to Stage 150.4 using 3-methyl-1H-indazole-5-carbaldehyde (Stage 287.2) instead of 2H-indazole-5-carbaldehyde ($t_R$ 7.74 min (conditions 3), MH+=291.3).

Stage 287.2

3-Methyl-1H-indazole-5-carbaldehyde 5-Bromo-3-methyl-1H-indazole was prepared in analogy to Stage 150.5 using 5-bromo-3-methyl-1H-indazole with 3.2 eq. t-BuLi at −78° C. instead of 5-bromo-1H-indazole with 2.5 eq. n-BuLi at −40° C. ($t_R$ 3.94 min (conditions 3), MH−=159.1).

EXAMPLE 288

3-(2-Fluoro-imidazo[1,2-a]pyridin-6-ylmethyl)-6-(1-methyl-1H-pyrazol-4-yl)-imidazo[1,2-b]pyridazine

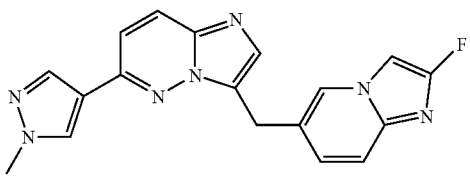 [SMILES: Cn1cc(-c2ccc3ncc(Cc4ccc5nc(F)cn5c4)n3n2)cn1]

To a solution 3-imidazo[1,2-a]pyridin-6-ylmethyl-6-(1-methyl-1H-pyrazol-4-yl)-imidazo[1,2-b]pyridazine (Example 10, 20 mg, 0.061) in dry THF (2 mL) was added NaH (55%, 5.83 mg, 0.134 mmol) and Selecfluor® (47 mg, 0.134 mmol). After 30 min additional NaH (55%, 5.83 mg, 0.134 mmol) and Selecfluor® (47 mg, 0.134 mmol) were added and the RM was stirred overnight at rt. The solvent was removed under reduced pressure and the residue was purified by flash chromatography (CombiFlash® Companion System®, with RediSep® silica gel column, DCM/DCM/MeOH 19:1=100:0->0:100) to afford the title compound ($t_R$ 2.84 min (conditions 3), MH+=348.1).

EXAMPLE 289

6-(1-Ethyl-1H-pyrazol-4-yl)-3-imidazo[1,2-a]pyridin-6-ylmethyl-imidazo[1,2-b]pyridazine

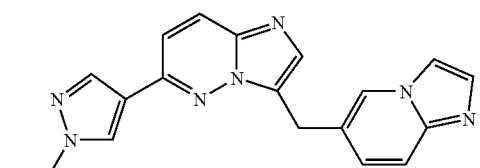

The title compound was prepared in analogy to Example 9 using chloro-3-imidazo[1,2-a]pyridin-6-ylmethyl-imidazo[1,2-b]pyridazine (Example 74) instead of (rac)-(6-chloro-imidazo[1,2-b]pyridazin-3-yl)-imidazo[1,2-a]pyridin-6-yl-methanol (Stage 9.1) and 1-ethyl-4-(4,4,5,5-tetramethyl-[1,3,2]dioxaborolan-2-yl)-1H-pyrazole instead of 1-methyl-4-(4,4,5,5-tetramethyl-[1,3,2]dioxaborolan-2-yl)-1H-pyrazole ($t_R$ 2.88 min (conditions 3), MH+=344.1).

EXAMPLE 290

3-Imidazo[1,2-a]pyridin-6-ylmethyl-6-(1H-pyrazol-4-yl)-imidazo[1,2-b]pyridazine

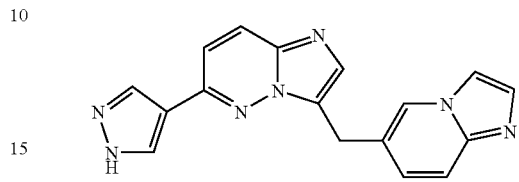

The title compound was prepared in analogy to Example 251 using chloro-3-imidazo[1,2-a]pyridin-6-ylmethyl-imidazo[1,2-b]pyridazine (Example 74) instead of 6-[(S)-1-(6-chloro-imidazo[1,2-b]pyridazin-3-yl)-ethyl]-quinoline ($t_R$ 2.51 min (conditions 3), MH+=316.1).

EXAMPLE 291

3-Imidazo[1,2-a]pyridin-6-ylmethyl-6-(1-piperidin-4-yl-1H-pyrazol-4-yl)-imidazo[1,2-b]pyridazine

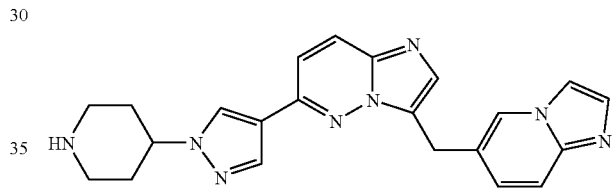

The title compound was prepared in analogy to Stage 239.1 using chloro-3-imidazo[1,2-a]pyridin-6-ylmethyl-imidazo[1,2-b]pyridazine (Example 74) instead of 6-[(S)-1-(6-chloro-imidazo[1,2-b]pyridazin-3-yl)-ethyl]-quinoline ($t_R$ 2.42 min (conditions 3), MH+=399.1).

EXAMPLE 292

(rac)-6-Chloro-3-(1-imidazo[1,2-a]pyridin-6-yl-ethyl)-imidazo[1,2-b]pyridazine

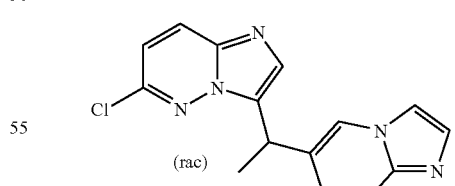

Iodine (4.8 g, 18.91 mmol) and $H_3PO_2$ (5.1 mL of a 50% aqueous solution, 46.8 mmol) were added to a solution of (rac)-1-(6-chloro-imidazo[1,2-b]pyridazin-3-yl)-1-(imidazo[1,2-a]pyridin-6-yl)ethanol (Stage 292.1, 1.85 g, 5.90 mmol) in acetic acid (50 mL). The RM was portion wise in 3 different microwave reactors and was heated at 150° C. for 5 min under microwave irradiations. It was basified with 2.5 N NaOH solution and then it was extracted twice with EtOAc/MeOH (9:1) twice. Combined organic layers was washed with brine and dried over Na$_2$SO$_4$, filtered and concentrated to give the title compound as a brown solid (t$_R$ 0.5 min (conditions 2), MH+=298)

Stage 292.1

(rac)-1-(6-Chloroimidazo[1,2-b]pyridazin-3-yl)-1-(imidazo[1,2-a]pyridin-6-yl)ethanol (6-Chloro-imidazo[1,2-b]pyridazin-3-yl)-imidazo[1,2-a]pyridin-6-yl-methanone (Stage 292.2, 4.0 g, 13.44 mmol) was suspended in dioxane (400 mL) and it was heated at 90° C. When all the material was in solution, it was cooled down to 50° C. and the 3 M methylmagnesium bromide solution (28.8 mL, 40.3 mmol) was added. It was refluxed for 2 h. Then it was cooled down to rt and the precipitate formed was filtered off. It was taken up with EtOAc/MeOH (9:1) and washed with saturated NaHCO$_3$ solution and brine. The organic layer was dried over Na$_2$SO$_4$, filtered and concentrated to give the title compound as a brown solid (t$_R$ 0.3 min (conditions 2), MH+=314)

Stage 292.2

(6-Chloroimidazo[1,2-b]pyridazin-3-yl)(imidazo[1,2-a]pyridin-6-yl)methanone (rac)-1-(6-chloro-imidazo[1,2-b]pyridazin-3-yl)-1-(imidazo[1,2-a]pyridin-6-yl)ethanol (Stage 9.1, 5 g, 16.68 mmol) was suspended in acetone (334 mL) with 2-iodoxybenzoic acid (45%, 14.01 g, 22.5 mmol). It was refluxed for 2 h. The RM was then cooled down to rt and the solvent was removed. The residue was triturated with 2.5 N NaOH solution and the precipitated was filtered off and dried to give the title compound as a beige solid (t$_R$ 0.6 min (conditions 2), MH+=298).

EXAMPLE 293

(rac)-3-(1-Imidazo[1,2-a]pyridin-6-yl-ethyl)-6-(1-methyl-1H-pyrazol-4-yl)-imidazo[1,2-b]pyridazine

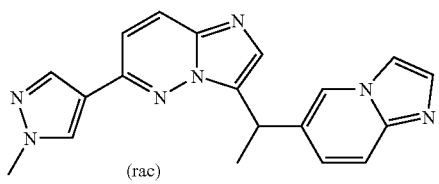 [SMILES: CC(c1ccc2nccn2c1)c1cnc2ccc(-c3cnn(C)c3)nn12]

The title compound was prepared in analogy to Example 9 using (rac)-6-chloro-3-(1-imidazo[1,2-a]pyridin-6-yl-ethyl)-imidazo[1,2-b]pyridazine (Example 292) instead of (rac)-(6-chloro-imidazo[1,2-b]pyridazin-3-yl)-imidazo[1,2-a]pyridin-6-yl-methanol (Stage 9.1) (t$_R$ 2.8 min (conditions 3), MH+=344.2).

EXAMPLE 294

3-((R)-1-Imidazo[1,2-a]pyridin-6-yl-ethyl)-6-(1-methyl-1H-pyrazol-4-yl)-imidazo[1,2-b]pyridazine

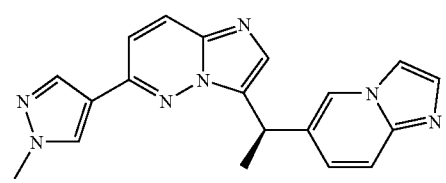 [SMILES: C[C@H](c1ccc2nccn2c1)c1cnc2ccc(-c3cnn(C)c3)nn12]

The title compound was obtained from the chiral separation of compound of Example 293 with a Preparative HPLC on a Chiralpak ADOOSC-JF004 (5×500 mm) column with a flow of 60 mL/min of EtOH:MeOH 60:40 (v/v). Oven 20° C., detection 210 nm (t$_R$ 36.5 min). (t$_R$ 2.86 min (conditions 2), MH+=344.3).

EXAMPLE 295

3-((S)-1-Imidazo[1,2-a]pyridin-6-yl-ethyl)-6-(1-methyl-1H-pyrazol-4-yl)-imidazo[1,2-b]pyridazine

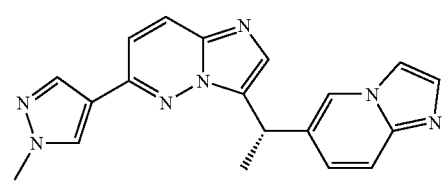 [SMILES: C[C@@H](c1ccc2nccn2c1)c1cnc2ccc(-c3cnn(C)c3)nn12]

The title compound was obtained from the chiral separation of compound of Example 293 with a Preparative HPLC on a Chiralpak ADOOSC-JF004 (5×500 mm) column with a flow of 60 mL/min of EtOH:MeOH 60:40 (v/v). Oven 20° C., detection 210 nm (t$_R$ 43.5 min). (t$_R$ 2.86 min (conditions 2), MH+=344.3).

EXAMPLE 296

3-(3-Bromo-imidazo[1,2-a]pyridin-6-ylmethyl)-6-(1-methyl-1H-pyrazol-4-yl)-imidazo[1,2-b]pyridazine

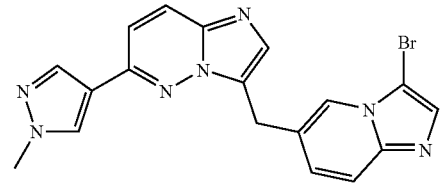 [SMILES: Cn1cc(-c2ccc3ncc(Cc4ccc5ncc(Br)n5c4)n3n2)cn1]

3-Imidazo[1,2-a]pyridin-6-ylmethyl-6-(1-methyl-1H-pyrazol-4-yl)-imidazo[1,2-b]pyridazine (Example 10, 10 mg, 0.030 mmol) was dissolved in DCM (0.3 mL) with NBS (5.9 mg, 0.033 mmol). The RM was stirred at rt for 2 h. The solvent was removed. The residue was purified by preparative HPLC with acetonitrile and water (+0.1% TFA). The fractions were joined and the acetonitrile was removed. The aqueous solution was basified with 5% NaHCO$_3$ solution and it was extracted with EtOAc/MeOH (9:1) twice. Combined organic layers was washed with brine and dried over Na$_2$SO$_4$, filtered and concentrated. The solid obtained was triturated with Et$_2$O. The precipitate was filtered off to afford the title compound as a white solid (t$_R$ 0.7 min (conditions 2), MH+=408).

EXAMPLE 297

6-[6-(1-Methyl-1H-pyrazol-4-yl)-imidazo[1,2-b]pyridazin-3-ylmethyl]-imidazo[1,2-a]pyridine-3-carbaldehyde

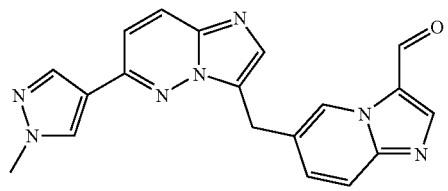 [SMILES: Cn1cc(-c2ccc3ncc(Cc4ccc5ncc(C=O)n5c4)n3n2)cn1]

DMF (2 mL) was cooled down to 0° C. and then POCl$_3$ (0.130 mL, 1.397 mmol) was added slowly. The solution was stirred for 10 min then it was warmed up to rt and the 3-(imidazo[1,2-a]pyridin-6-ylmethyl)-6-(1-methyl-1H-pyrazol-4-yl)imidazo[1,2-b]pyridazine (Example 10, 200 mg, 0.607 mmol) was introduced. The RM was warmed up to 120° C. and stirred for 2 h. It was cooled down to rt and water was added. It was extracted twice with EtOAc. Combined organic layers was washed with brine and dried over Na$_2$SO$_4$, filtered and concentrated. The residue was purified by flash chromatography (CombiFlash® Companion System®, with RediSep® silica gel column, 0 to 20% MeOH in DCM) to afford after evaporation of the solvent the title compound as a yellow solid (t$_R$ 0.7 min (conditions 2), MH+=358).

EXAMPLE 298

3-(3-Chloro-imidazo[1,2-a]pyridin-6-ylmethyl)-6-(1-methyl-1H-pyrazol-4-yl)-imidazo[1,2-b]pyridazine

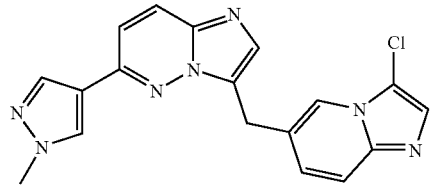 [SMILES: Cn1cc(-c2ccc3ncc(Cc4ccc5ncc(Cl)n5c4)n3n2)cn1]

3-Imidazo[1,2-a]pyridin-6-ylmethyl-6-(1-methyl-1H-pyrazol-4-yl)-imidazo[1,2-b]pyridazine (Example 10, 33.6 mg, 0102 mmol) was dissolved in DCM (1 mL) with N-chlorosuccinimide (15 mg, 0.112 mmol). The RM was stirred at rt for 22 h. The solvent was removed. The residue was purified by preparative HPLC with acetonitrile and water (+0.1% TFA). The fractions were joined and the acetonitrile was removed. The aqueous solution was basified with 5% NaHCO$_3$ solution and it was extracted with EtOAc twice. Combined organic layers was washed with brine and dried over Na$_2$SO$_4$, filtered and concentrated to afford the white title compound (t$_R$ 0.7 min (conditions 2), MH+=364).

EXAMPLE 299

6-(1-Methyl-1H-pyrazol-4-yl)-3-(3-vinyl-imidazo[1,2-a]pyridin-6-ylmethyl)-imidazo[1,2-b]pyridazine

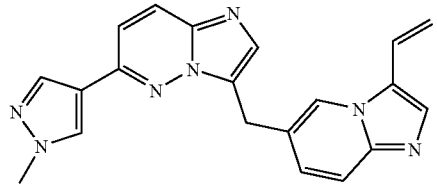 [SMILES: C=Cc1cnc2ccc(Cc3cnc4ccc(-c5cnn(C)c5)nn34)cn12]

3-(3-Bromo-imidazo[1,2-a]pyridin-6-ylmethyl)-6-(1-methyl-1H-pyrazol-4-yl)-imidazo[1,2-b]pyridazine (Example 296, 50 mg, 0.122 mmol) was dissolved in dioxane (0.5 mL) in a microwave reactor. Then tributyl(vinyl)tin (36.9 µL, 0.122 mmol) and tetrakis(triphenylphosphine)palladium (1.4 mg, 0.001 mmol) were introduced. The RM was heated at 150° C. for 30 min under microwave irradiations. The solvent was removed and The residue was purified by preparative HPLC with acetonitrile and water (+0.1% TFA). The fractions were joined and were lyophilized. The residue was dissolved in MeOH and it was passed through an SPE cartridge of HCO$_3^-$ to remove the TFA salt. The filtrate was evaporated to give the free salt of the title compound as a yellow solid (t$_R$ 0.7 min (conditions 2), MH+=356).

EXAMPLE 300

{6-[6-(1-Methyl-1H-pyrazol-4-yl)-imidazo[1,2-b]pyridazin-3-ylmethyl]-imidazo[1,2-a]pyridin-3-yl}-methanol

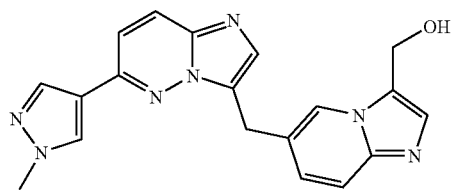 [SMILES: Cn1cc(-c2ccc3ncc(Cc4ccc5ncc(CO)n5c4)n3n2)cn1]

6-[6-(1-Methyl-1H-pyrazol-4-yl)-imidazo[1,2-b]pyridazin-3-ylmethyl]-imidazo[1,2-a]pyridine-3-carbaldehyde (Example 297, 50 mg, 0.140 mmol) was dissolved in MeOH (3 mL) and water (1 mL) then NaBH$_4$ (2.6 mg, 0.070 mmol) was added. The RM was stirred at rt for 30 min. It was quenched with water and EtOAc. The precipitate formed was filtered off. The filtrate was concentrated then was triturated with MeOH. The salt was filtered off. The filtrate was concentrated and then triturated again with Et$_2$O, The precipitate was filtered off and it was purified by flash chromatography (CombiFlash® Companion System®, with RediSep® silica gel column, 0 to 20% MeOH in DCM) to afford after evaporation of the solvent the title compound as a yellow solid ($t_R$ 0.6 min (conditions 2), MH+=360).

EXAMPLE 301

1-{6-[6-(1-Methyl-1H-pyrazol-4-yl)-imidazo[1,2-b]pyridazin-3-ylmethyl]-imidazo[1,2-a]pyridin-3-yl}-ethanone

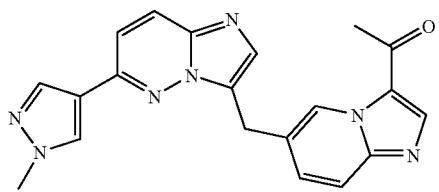 [SMILES: CC(=O)c1cnc2ccc(Cc3cnc4ccc(-c5cnn(C)c5)nn34)cn12]

3-(3-Bromo-imidazo[1,2-a]pyridin-6-ylmethyl)-6-(1-methyl-1H-pyrazol-4-yl)-imidazo[1,2-b]pyridazine (Example 296, 100 mg, 0.245 mmol) was dissolved in dioxane (0.98 mL) in a microwave reactor. Then tributyl(1-ethoxyvinyl)tin (85 μL, 0.245 mmol) and tetrakis(triphenylphosphine)palladium (2.8 mg, 0.002 mmol) were introduced. The RM was heated at 150° C. for 1 h under microwave irradiations. The solvent was removed and the residue was purified by flash chromatography (CombiFlash® Companion System®, with RediSep® silica gel column, 0 to 20% MeOH in DCM). Combined fractions were concentrated and the residue was triturated with Et$_2$O. The precipitate was filtered off and dried to afford the title compound as a white solid ($t_R$ 0.7 min (conditions 2), MH+=372).

EXAMPLE 302

6-[6-(1-Methyl-1H-pyrazol-4-yl)-imidazo[1,2-b]pyridazin-3-ylmethyl]-imidazo[1,2-a]pyridine-3-carbonitrile

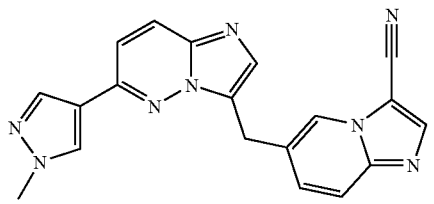 [SMILES: Cn1cc(-c2ccc3ncc(Cc4ccc5ncc(C#N)n5c4)n3n2)cn1]

3-(3-Bromo-imidazo[1,2-a]pyridin-6-ylmethyl)-6-(1-methyl-1H-pyrazol-4-yl)-imidazo[1,2-b]pyridazine (Example 296, 55 mg, 0.135 mmol) was introduced in a microwave reactor with NMP (150 μL) and CuCN (15.7 mg, 0.175 mmol). The RM was heated at 200° C. for 10+15 min. The black solid obtained was taken up with DMF. Water was added to the mixture and it was extracted with EtOAc/MeOH (9:1) twice. Combined organic layers was washed with 10% ammonia solution. The organic layer was dried over Na$_2$SO$_4$ filtered and concentrated. The residue was purified by flash chromatography (CombiFlash® Companion System®, with RediSep® silica gel column, 0 to 20% MeOH in DCM). Combined fractions were concentrated. The white solid obtained was a repurified by preparative HPLC with acetonitrile and water (+0.1% TFA). The fractions were joined and were lyophilized. The residue was dissolved in MeOH and it was passed through an SPE cartridge of HCO$_3^-$ to remove the TFA salt. The filtrate was evaporated to give the free salt of the title compound as a white solid ($t_R$ 0.8 min (conditions 2), MH+=355).

EXAMPLE 303

1-{6-[6-(1-Methyl-1H-pyrazol-4-yl)-imidazo[1,2-b]pyridazin-3-ylmethyl]-imidazo[1,2-a]pyridin-3-yl}-ethanol

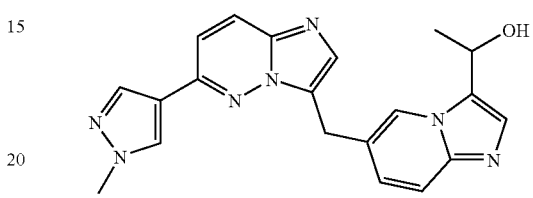

1-{6-[6-(1-Methyl-1H-pyrazol-4-yl)-imidazo[1,2-b]pyridazin-3-ylmethyl]-imidazo[1,2-a]pyridin-3-yl}-ethanone (Example 301, 50 mg, 0.135 mmol) was dissolved in MeOH (3 mL) and water (1 mL) then NaBH$_4$ (3.1 mg, 0.081 mmol) was added. The RM was stirred at rt for 2 h. More equivalents of NaBH$_4$ (3 times 5.1 mg, 0.135 mmol) were added to RM over 18 h. Then dioxane was added and it was stirred at 60° C. for 2 h. It was quenched with EtOAc and solvents were removed. The residue was purified by preparative HPLC with acetonitrile and water (+0.1% TFA). The fractions were joined and lyophilized. The residue was dissolved in MeOH and it was passed through an SPE cartridge of HCO$_3^-$ to remove the TFA salt. The filtrate was evaporated to give the free salt compound of the title compound as a white solid ($t_R$ 0.6 min (conditions 2), MH+=374).

EXAMPLE 304

1-{6-[6-(1-Methyl-1H-pyrazol-4-yl)-imidazo[1,2-b]pyridazin-3-ylmethyl]-imidazo[1,2-a]pyridin-3-yl}-ethane-1,2-diol

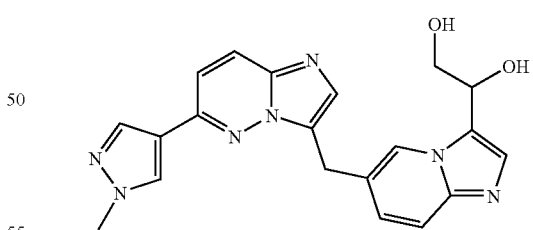

6-(1-Methyl-1H-pyrazol-4-yl)-3-(3-vinyl-imidazo[1,2-a]pyridin-6-ylmethyl)-imidazo[1,2-b]pyridazine (Example 299, 49 mg, 0.138 mmol) was dissolved in dioxane (0.69 mL) and water (0.69 mL) then KMnO$_4$ (21.8 mg, 0.138 mmol) and 2.5 M NaOH solution (0.165 mL, 0.414 mmol) were added. The RM was stirred at rt for 3 h. It was then filtered through Celite and the solvent was removed. The residue was purified by preparative HPLC with acetonitrile and water (+0.1% TFA). The fractions were joined and were lyophilized. The residue was dissolved in MeOH and it was passed through an SPE cartridge of HCO$_3^-$ to remove the TFA salt. The filtrate was evaporated and the residue was triturated with pentane. The precipitate was filtered off and dried to afford the title compound as a white solid ($t_R$ 0.3 min (conditions 2), MH+=390).

EXAMPLE 305

3-{6-[6-(1-Methyl-1H-pyrazol-4-yl)-imidazo[1,2-b]pyridazin-3-ylmethyl]-imidazo[1,2-a]pyridin-3-yl}-benzonitrile

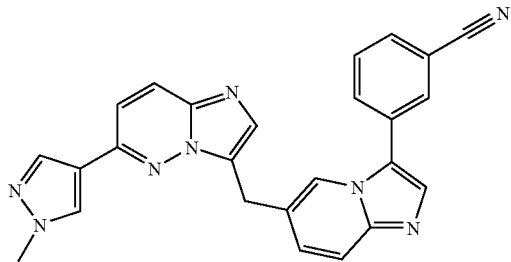 [SMILES: Cn1cc(-c2ccc3ncc(Cc4ccc5ncc(-c6cccc(C#N)c6)n5c4)n3n2)cn1]

3-(3-Bromo-imidazo[1,2-a]pyridin-6-ylmethyl)-6-(1-methyl-1H-pyrazol-4-yl)-imidazo[1,2-b]pyridazine (Example 296, 80 mg, 0.196 mmol) was dissolved in DME (0.653 mL) with 3-cyanophenylboronic acid (28.2 mg, 0.196 mmol), 2 M Na$_2$CO$_3$ solution (0.353 mL, 0.705 mmol) and tetrakis(triphenylphosphine)palladium (11.3 mg, 0.010 mmol). The RM was heated at 150° C. 5 min under microwave irradiations. It was taken up with EtOAc and washed with 10% Na$_2$CO$_3$ solution and brine. The precipitate from the aqueous layer was filtered off and dried to afford the title compound as a grey solid ($t_R$ 0.8 min (conditions 2), MH+=431).

EXAMPLE 306

6-(1-Methyl-1H-pyrazol-4-yl)-3-(3-pyridin-3-yl-imidazo[1,2-a]pyridin-6-ylmethyl)-imidazo[1,2-b]pyridazine

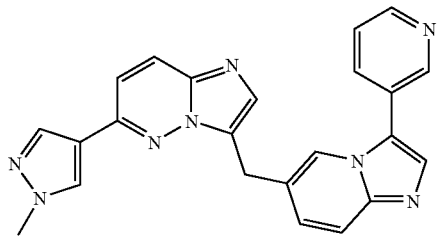 [SMILES: Cn1cc(-c2ccc3ncc(Cc4ccc5ncc(-c6cccnc6)n5c4)n3n2)cn1]

3-(3-Bromo-imidazo[1,2-a]pyridin-6-ylmethyl)-6-(1-methyl-1H-pyrazol-4-yl)-imidazo[1,2-b]pyridazine (Example 296, 80 mg, 0.196 mmol) was dissolved in DME (0.653 mL) with pyridin-3-ylboronic acid (24.1 mg, 0.196 mmol), 2 M Na$_2$CO$_3$ solution (0.353 mL, 0.705 mmol) and tetrakis(triphenylphosphine)palladium (11.3 mg, 0.010 mmol). The RM was heated at 150° C. 5 min under microwave irradiations. It was taken up with EtOAc and washed with 10% Na$_2$CO$_3$ solution and brine. Then it was dried over Na$_2$SO$_4$, filtered and concentrated. The residue was dissolved in MeOH and passed through an SPE cartridge of PL-Thiol MP to remove the palladium. Then the filtrate was purified by preparative HPLC with acetonitrile and water (+0.1% TFA). The fractions were joined and were lyophilized. The residue was dissolved in MeOH and it was passed through an SPE cartridge of HCO$_3^-$ to remove the TFA salt. The filtrate was evaporated to give the free salt of the title compound as a white solid ($t_R$ 0.6 min (conditions 2), MH+=407).

EXAMPLE 307

6-(1-Methyl-1H-pyrazol-4-yl)-3-[3-(1-methyl-1H-pyrazol-4-yl)-imidazo[1,2-a]pyridin-6-ylmethyl]-imidazo[1,2-b]pyridazine

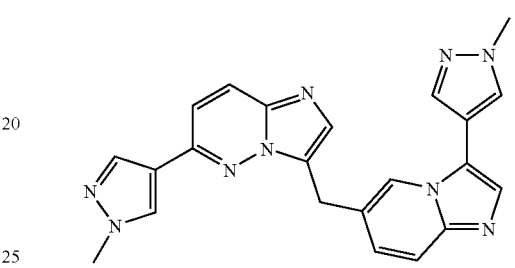

3-(3-Bromo-imidazo[1,2-a]pyridin-6-ylmethyl)-6-(1-methyl-1H-pyrazol-4-yl)-imidazo[1,2-b]pyridazine (Example 296, 77 mg, 0.189 mmol) was dissolved in DME (0.629 mL) with 1-methyl-4-(4,4,5,5-tetramethyl-1,3,2-dioxaborolan-2-yl)-1H-pyrazole (39.2 mg, 0.189 mmol), 2 M Na$_2$CO$_3$ solution (0.339 mL, 0.679 mmol) and tetrakis(triphenylphosphine)palladium (10.9 mg, 0.009 mmol). The RM was heated at 150° C. 5 min under microwave irradiations. It was taken up with EtOAc and washed with 10% Na$_2$CO$_3$ solution and brine. Then it was dried over Na$_2$SO$_4$, filtered and concentrated. The residue was dissolved in MeOH and passed through an SPE cartridge of PL-Thiol MP to remove the palladium. Then the filtrate was purified by preparative HPLC with acetonitrile and water (+0.1% TFA). The fractions were joined and acetonitrile was removed. The aqueous solution was basified with 5% NaHCO$_3$ solution and was extracted with EtOAc twice. Combined organic layers was washed with brine and dried over Na$_2$SO$_4$. It was filtered to afford after evaporation of the solvent the title compound as a white solid ($t_R$ 0.7 min (conditions 2), MH+=410).

EXAMPLE 308

(rac)-3-(1-Imidazo[1,2-a]pyridin-6-yl-ethyl)-6-m-tolyl-imidazo[1,2-b]pyridazine

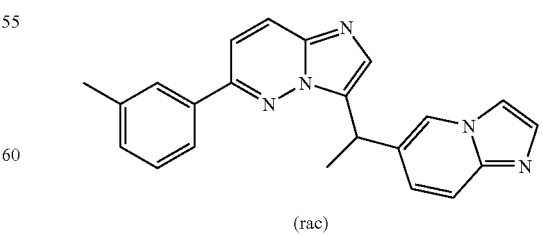

(rac)

(rac)-6-Chloro-3-(1-imidazo[1,2-a]pyridin-6-yl-ethyl)-imidazo[1,2-b]pyridazine (Example 292, 200 mg, 0.672 mmol) was dissolved in DME (3.36 mL) with 3-tolylboronic acid (91 mg, 0.672 mmol), 2 M Na$_2$CO$_3$ solution (1.21 mL, 2.418 mmol) and tetrakis(triphenylphosphine)palladium (38.8 mg, 0.034 mmol). The RM was heated at 150° C. 5 min under microwave irradiations. It was taken up with EtOAc and washed with 10% Na$_2$CO$_3$ solution and brine. Then it was dried over Na$_2$SO$_4$, filtered and concentrated. The residue was purified by flash chromatography (CombiFlash® Companion System®, with RediSep® silica gel column, 0 to 20% MeOH in DCM). Combined fractions were concentrated. The white solid obtained was a repurified by preparative HPLC with acetonitrile and water (+0.1% TFA). The fractions were joined and were lyophilized. The residue was dissolved in MeOH and it was passed through an SPE cartridge of HCO$_3^-$ to remove the TFA salt. The filtrate was evaporated to give the free salt of the title compound as a white solid ($t_R$ 0.9 min (conditions 2), MH+=354).

EXAMPLE 309

(rac)-3-[1-(3-Bromo-imidazo[1,2-a]pyridin-6-yl)-ethyl]-6-(1-methyl-1H-pyrazol-4-yl)imidazo[1,2-b]pyridazine

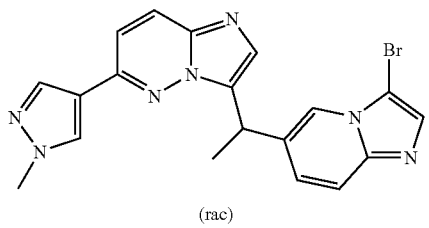 [SMILES: CC(c1ccc2ncc(Br)n2c1)c1cnc2ccc(-c3cnn(C)c3)nn12]

(rac)

(rac)-3-(1-Imidazo[1,2-a]pyridin-6-yl-ethyl)-6-(1-methyl-1H-pyrazol-4-yl)-imidazo[1,2-b]pyridazine (Example 293, 607 mg, 1.768 mmol) was dissolved in DCM (18 mL) and NBS (346 mg, 1.944 mmol) was added. It was stirred at rt for 30 min then the solvent was removed. The residue was purified by flash chromatography (CombiFlash® Companion System®, with RediSep® silica gel column, 0 to 20% MeOH in DCM). Combined fractions were concentrated to give the title compound as a yellow solid ($t_R$ 0.7 min (conditions 2), MH+=422, $^1$H-NMR in DMSO-d6: 8.47 (s, 1H); 8.37 (s, 1H); 8.04 (m, 2H); 7.78 (s, 1H); 7.67 (s, 1H); 7.54 (d, 1H); 7.47 (d, 1H); 7.32 (d, 1H); 4.81 (q, 1H); 3.89 (s, 3H); 1.80 (d, 3H)).

EXAMPLE 310

(rac)-2-(4-{3-[1-(3-Bromo-imidazo[1,2-a]pyridin-6-yl)-ethyl]-imidazo[1,2-b]pyridazin-6-yl}-pyrazol-1-yl)-ethanol

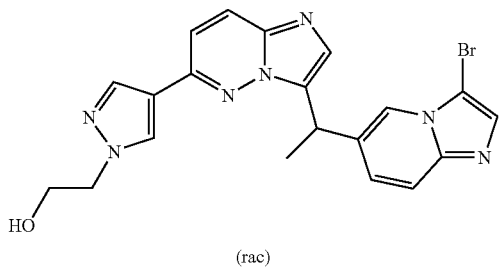 [SMILES: CC(c1ccc2ncc(Br)n2c1)c1cnc2ccc(-c3cnn(CCO)c3)nn12]

(rac)

(rac)-3-(1-Imidazo[1,2-a]pyridin-6-yl-ethyl)-6-{1-[2-(tetrahydro-pyran-2-yloxy)-ethyl]-1H-pyrazol-4-yl}-imidazo[1,2-b]pyridazine (obtained by analogy of Stage 185.1 by replacing (rac)-6-chloro-3-[1-(3-methyl-3H-benzoimidazol-5-yl)-ethyl]-imidazo[1,2-b]pyridazine with (rac)-6-chloro-3-(1-imidazo[1,2-a]pyridin-6-yl-ethyl)-imidazo[1,2-b]pyridazine (Example 292), 150 mg, 0.328 mmol) was dissolved in DCM (3.3 mL) and NBS (64.2 mg, 0.984 mmol) was added. It was stirred at rt for 3 h then the solvent was removed. The residue was purified by flash chromatography (CombiFlash® Companion System®, with RediSep® silica gel column, 0 to 20% MeOH in DCM). Combined fractions were concentrated and dissolved in DCM (1 mL) with 4 N HCl in dioxane (0.246 mL, 0.984 mmol). The RM was stirred at rt for 2 min. The solvent was removed and the residue was purified by preparative HPLC with acetonitrile and water (+0.1% TFA). The fractions were joined and acetonitrile was removed. The aqueous solution was basified with 5% NaHCO$_3$ solution and was extracted with EtOAc twice. Combined organic layers was washed with brine and dried over Na$_2$SO$_4$. It was filtered to afford after evaporation of the solvent the title compound as a white solid ($t_R$ 0.7 min (conditions 2), MH+=452, $^1$H-NMR in DMSO-d6: 8.46 (s, 1H); 8.40 (s, 1H); 8.04 (m, 2H); 7.78 (s, 1H); 7.67 (s, 1H); 7.52 (m, 2H); 7.33 (d, 1H); 4.95 (t, 1H); 4.76 (q, 1H); 4.18 (t, 2H); 3.75 (q, 2H); 1.80 (d, 3H)).

EXAMPLE 311

2-(4-{3-[(S)-1-(3-Bromo-imidazo[1,2-a]pyridin-6-yl)-ethyl]-imidazo[1,2-b]pyridazin-6-yl}-pyrazol-1-yl)-ethanol

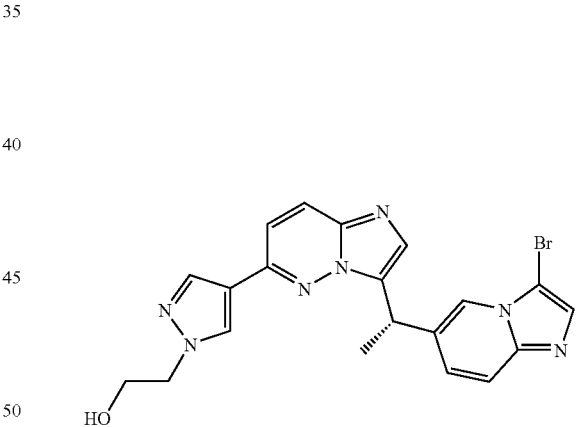

The title compound was obtained from the chiral separation of compound of Example 310 using a preparative HPLC on a Chiralpak AD 20 um 500×50 mm column with a flow of 60-120 mL/min of n-heptane:EtOH 50:50 Oven 20° C., detection 220 nm. ($t_R$ 0.7 min (conditions 2), MH+=452, $^1$H-NMR in DMSO-d6: 8.46 (s, 1H); 8.40 (s, 1H); 8.04 (m, 2H); 7.78 (s, 1H); 7.67 (s, 1H); 7.52 (m, 2H); 7.33 (d, 1H); 4.95 (t, 1H); 4.76 (q, 1H); 4.18 (t, 2H); 3.75 (q, 2H); 1.80 (d, 3H)).

EXAMPLE 312

(rac)-3-[1-(3-Bromo-imidazo[1,2-a]pyridin-6-yl)-ethyl]-6-m-tolyl-imidazo[1,2-b]pyridazine

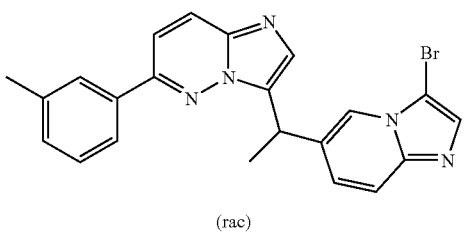 [SMILES: Cc1cccc(-c2ccc3ncc(C(C)c4ccc5ncc(Br)n5c4)n3n2)c1]

(rac)

(rac)-3-(1-Imidazo[1,2-a]pyridin-6-yl-ethyl)-6-m-tolyl-imidazo[1,2-b]pyridazine (Example 308, 100 mg, 0.283 mmol) was dissolved in DCM (2.8 mL) and NBS (50.4 mg, 0.283 mmol) was added. It was stirred at rt for 1 h then the solvent was removed. The residue was purified by flash chromatography (CombiFlash® Companion System®, with RediSep® silica gel column, 0 to 20% MeOH in DCM). Combined fractions were concentrated. The residue was repurified by preparative HPLC with acetonitrile and water (+0.1% TFA). The fractions were joined and acetonitrile was removed. The aqueous solution was basified with 5% $NaHCO_3$ solution and was extracted with EtOAc twice. Combined organic layers was washed with brine and dried over $Na_2SO_4$. It was filtered to afford the title compound after evaporation of the solvent as a white solid. ($t_R$ 1.0 min (conditions 2), MH+=432).

C-Met Enzyme Assay

A number of compounds of the present invention were assayed in an antibody based kinase phosphorylation assay as follows.

EPK cMET Profiling Assay:

The EPK kinase assay for cMET receptor tyrosine kinase was developed, using the purified recombinant GST-fusion protein, containing the cytoplasmic domain of the enzyme. GST-cMET (969-1390) was purified by affinity chromatography.

The kinase assay is based on the LanthaScreen™ technology. LanthaScreen™ is the detection of Time-Resolved Fluorescence Resonance Energy Transfer (TR-FRET) using lanthanide chelates to measure interactions between various binding partners. In a TR-FRET kinase assay, a long-lifetime lanthanide donor species is conjugated to an antibody that specifically binds to a phosphorylated product of a kinase reaction that is labeled with a suitable acceptor fluorophore. This antibody-mediated interaction brings the lanthanide donor and the acceptor into proximity such that resonance energy transfer can take place, resulting in a detectible increase in the FRET signal.

The kinase reactions were performed in 384 well microtiter plates in a total reaction volume of 9.05 μL. The assay plates were prepared with 0.05 μL per well of test compound in the appropriate test concentration, as described under "preparation of compound dilutions". The reactions were started by combining 4.5 μL of ATP solution with 4.5 μL of enzyme-substrate mix (consisting of kinase and substrate). The final concentrations in the kinase reactions were 35 mM Tris/HCl, 1 mM DTT, 0.025% Tween20, 10 μM sodium orthovanadate, 0.25% BSA, 0.6% DMSO, 10 mM $MgCl_2$, 3 mM $MnCl_2$, 2 μM ATP, 50 nM Fluorescein-PolyEAY, and 0.3 nM enzyme. The reactions were incubated for 60 minutes at room temperature and stopped by adding 4.5 μL of stop buffer (50 mM EDTA, 0.04% NP40, 20 mM Tris/HCl).

Subsequently 4.5 μL of detection mix (50 mM Tris/HCl, 2 mM DTT, 0.05% Tween20, 20 μM sodium orthovanadate, 1% BSA, 1.72 μg/ml Tb-PY20 antibody) were added to the stopped reactions. After 30 minutes incubation at room temperature, the plates were measured in a BMG Pherastar fluorescence reader. The effect of compound on the enzymatic activity was in all assays obtained from the linear progress curves and determined from one reading (end point measurement). Results are summarized in Table 1 below.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at −20° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 100 μL of individual compound dilutions including standard compound and controls of the 4 "pre-dilution plates" were transferred into a 384 "master plate" including the following concentrations 1,820, 564, 182, 54.6, 18.2, 5.46, 1.82 and 0.546 μM, respectively in 90% of DMSO.

Assay plates: Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 μL. This led to a final compound concentration of 10, 3.0, 1.0, 0.3, 0.1, 0.03, 0.01 and 0.003 μM and a final DMSO concentration of 0.5% in the assay.

TABLE 1

| Example | c-Met IC50 [uM] |
|---|---|
| 1 | 0.14 |
| 2 | 0.014 |
| 3 | 3.95 |
| 4 | 0.28 |
| 5 | 0.053 |
| 6 | 0.014 |
| 7 | 0.05 |
| 8 | 0.27 |
| 9 | 0.17 |
| 10 | 0.0215 |
| 11 | 0.91 |
| 12 | 0.0325 |
| 13 | 0.0735 |
| 15 | 0.0095 |
| 16 | 0.0945 |
| 17 | 0.21 |
| 18 | 0.0655 |
| 19 | 0.215 |

TABLE 1-continued

| Example | c-Met IC50 [uM] |
|---|---|
| 20 | 0.06 |
| 21 | 0.0275 |
| 22 | 0.0074 |
| 23 | 0.125 |
| 24 | 0.0235 |
| 25 | 0.048 |
| 26 | 0.02 |
| 27 | 0.11 |
| 28 | 0.24 |
| 29 | 0.04 |
| 30 | 0.091 |
| 31 | 0.23 |
| 33 | 0.37 |
| 34 | 0.23 |
| 35 | 0.079 |
| 36 | 0.065 |
| 37 | 0.03 |
| 38 | 0.039 |
| 39 | 0.072 |
| 40 | 0.13 |
| 41 | 0.056 |
| 42 | 0.45 |
| 43 | 0.35 |
| 45 | 0.1 |
| 46 | 0.057 |
| 47 | 0.1 |
| 48 | 0.19 |
| 49 | 0.023 |
| 50 | 0.95 |
| 51 | 0.095 |
| 52 | 0.24 |
| 53 | 0.11 |
| 54 | 0.12 |
| 55 | 0.031 |
| 56 | 0.25 |
| 57 | 0.063 |
| 58 | 0.25 |
| 59 | 0.56 |
| 60 | 0.34 |
| 62 | 0.039 |
| 63 | 0.19 |
| 64 | 0.079 |
| 65 | 0.16 |
| 66 | 0.06 |
| 67 | 0.16 |
| 68 | 0.48 |
| 69 | 0.82 |
| 70 | 0.062 |
| 71 | 0.024 |
| 73 | 0.048 |
| 74 | 0.2 |
| 75 | 0.3 |
| 76 | 0.3 |
| 77 | 0.225 |
| 78 | 0.009 |
| 79 | 0.044 |
| 80 | 0.038 |
| 81 | 0.076 |
| 82 | 0.22 |
| 83 | 0.115 |
| 84 | 0.049 |
| 85 | 0.095 |
| 86 | 0.16 |
| 87 | 0.37 |
| 88 | 0.012 |
| 89 | 0.026 |
| 90 | 0.074 |
| 91 | 0.029 |
| 92 | 0.032 |
| 93 | 0.39 |
| 96 | 0.19 |
| 97 | 0.61 |
| 98 | 0.11 |
| 99 | 0.12 |
| 101 | 0.13 |
| 102 | 0.038 |
| 103 | 0.55 |
| 106 | 0.074 |
| 107 | 0.02 |
| 108 | 0.0098 |
| 109 | 0.062 |
| 110 | 0.042 |
| 111 | 0.34 |
| 112 | 0.22 |
| 113 | 0.084 |
| 114 | 0.056 |
| 115 | 0.095 |
| 116 | 0.98 |
| 117 | 0.63 |
| 118 | 0.22 |
| 119 | 0.042 |
| 120 | 0.069 |
| 121 | 0.02 |
| 122 | 0.073 |
| 123 | 0.087 |
| 124 | 0.18 |
| 125 | 0.13 |
| 126 | 0.016 |
| 127 | 0.09 |
| 128 | 0.029 |
| 129 | 0.069 |
| 131 | 0.18 |
| 132 | 0.05 |
| 133 | 0.47 |
| 134 | 0.57 |
| 135 | 0.047 |
| 136 | 0.35 |
| 137 | 0.1 |
| 138 | 0.96 |
| 139 | 0.13 |
| 140 | 0.31 |
| 141 | 0.44 |
| 142 | 0.21 |
| 143 | 0.044 |
| 144 | 0.0032 |
| 146 | 0.068 |
| 147 | 0.082 |
| 148 | 0.016 |
| 149 | 0.031 |
| 150 | 0.056 |
| 151 | 0.064 |
| 152 | 0.89 |
| 155 | 0.86 |
| 156 | 0.19 |
| 157 | 0.007 |
| 158 | 0.54 |
| 159 | 0.014 |
| 160 | 0.012 |
| 162 | 0.034 |
| 163 | 0.11 |
| 164 | 0.054 |
| 165 | 0.012 |
| 167 | 0.006 |
| 169 | 0.4 |
| 170 | 0.006 |
| 171 | <0.003 |
| 172 | 0.010 |
| 173 | 0.004 |
| 174 | 0.12 |
| 175 | 0.038 |
| 177 | 0.02 |
| 179 | 0.015 |
| 180 | 0.145 |
| 181 | 0.065 |
| 182 | 0.003 |
| 183 | 0.2 |
| 184 | <0.003 |
| 185 | 0.056 |
| 187 | 0.019 |
| 188 | 0.0056 |
| 189 | 0.095 |
| 190 | 0.056 |

TABLE 1-continued

| Example | c-Met IC50 [uM] |
|---|---|
| 191 | <0.003 |
| 192 | <0.003 |
| 193 | 0.25 |
| 194 | 0.018 |
| 195 | 0.014 |
| 196 | 0.036 |
| 197 | 0.061 |
| 199 | 0.0355 |
| 200 | 0.023 |
| 202 | 0.068 |
| 205 | 0.047 |
| 206 | 0.031 |
| 207 | 0.31 |
| 208 | 0.052 |
| 210 | 0.052 |
| 211 | 0.086 |
| 212 | 0.054 |
| 215 | 0.13 |
| 216 | 0.1 |
| 217 | 0.084 |
| 219 | 0.12 |
| 220 | 0.33 |
| 221 | 0.24 |
| 222 | 0.25 |
| 223 | 0.033 |
| 224 | 0.028 |
| 225 | 0.025 |
| 226 | 0.025 |
| 227 | 0.078 |
| 228 | 0.099 |
| 229 | 0.52 |
| 230 | 0.027 |
| 231 | 0.026 |
| 232 | 0.066 |
| 233 | 0.12 |
| 234 | 0.11 |
| 235 | 0.22 |
| 236 | 0.37 |
| 237 | 0.17 |
| 238 | 0.23 |
| 239 | 0.031 |
| 240 | 0.0084 |
| 241 | 0.0375 |
| 242 | 0.086 |
| 243 | 0.037 |
| 244 | 0.087 |
| 245 | 0.044 |
| 246 | <0.003 |
| 247 | 0.066 |
| 248 | 0.37 |
| 249 | 0.38 |
| 250 | 0.015 |
| 251 | 0.021 |
| 252 | 0.28 |
| 253 | 0.013 |
| 254 | 0.033 |
| 255 | 0.036 |
| 257 | <0.003 |
| 258 | 0.043 |
| 259 | 0.023 |
| 260 | 0.0052 |
| 261 | 0.12 |
| 262 | 0.042 |
| 263 | 0.01 |
| 267 | 0.26 |
| 273 | 0.021 |
| 275 | 0.15 |
| 276 | 0.082 |
| 277 | 0.061 |
| 278 | 0.021 |
| 279 | 0.015 |
| 281 | 0.077 |
| 282 | 0.087 |
| 284 | 0.15 |
| 285 | 0.011 |
| 288 | 0.85 |
| 289 | 0.14 |
| 290 | 0.12 |
| 291 | 0.59 |
| 292 | 0.08 |
| 293 | 0.023 |
| 294 | 0.82 |
| 295 | 0.019 |
| 296 | 0.057 |
| 297 | 0.13 |
| 298 | 0.13 |
| 299 | 0.27 |
| 300 | 0.3 |
| 301 | 0.071 |
| 302 | 0.094 |
| 303 | 0.19 |
| 304 | 0.33 |
| 305 | 0.26 |
| 306 | 0.1 |
| 307 | 0.32 |
| 308 | 0.082 |
| 309 | 0.016 |
| 310 | 0.01 |

The invention claimed is:
1. A compound selected from:
(rac)-[6-(1-Methyl-1H-pyrazol-4-yl)-imidazo[1,2-b]pyridazin-3-yl]-quinolin-6-yl-methanol;
6-[6-(1-Methyl-1H-pyrazol-4-yl)-imidazo[1,2-b]pyridazin-3-ylmethyl]-quinoline;
(rac)-(4-Methoxy-phenyl)-[6-(1-methyl-1H-pyrazol-4-yl)-imidazo[1,2-b]pyridazin-3-yl]-methanol;
3-(4-methoxy-benzyl)-6-(1-methyl-1H-pyrazol-4-yl)-imidazo[1,2-b]pyridazine;
4-[6-(1-Methyl-1H-pyrazol-4-yl)-imidazo[1,2-b]pyridazin-3-ylmethyl]-phenol;
6-{Difluoro-[6-(1-methyl-1H-pyrazol-4-yl)-imidazo[1,2-b]pyridazin-3-yl]-methyl}-quinoline;
6-[6-(1-Piperidin-4-yl-1H-pyrazol-4-yl)-imidazo[1,2-b]pyridazin-3-ylmethyl]-quinoline;
3-Benzofuran-5-ylmethyl-6-(1-methyl-1H-pyrazol-4-yl)-imidazo[1,2-b]pyridazine;
(rac)-Imidazo[1,2-a]pyridin-6-yl-[6-(1-methyl-1H-pyrazol-4-yl)-imidazo[1,2-b]pyridazin-3-yl]-methanol;
3-Imidazo[1,2-a]pyridin-6-ylmethyl-6-(1-methyl-1H-pyrazol-4-yl)-imidazo[1,2-b]pyridazine;
(rac)-[6-(1-Methyl-1H-pyrazol-4-yl)-imidazo[1,2-b]pyridazin-3-yl]-quinoxalin-6-yl-methanol;
3-Benzothiazol-6-ylmethyl-6-(1-methyl-1H-pyrazol-4-yl)-imidazo[1,2-b]pyridazine;
3-(2-Methyl-benzothiazol-6-ylmethyl)-6-(1-methyl-1H-pyrazol-4-yl)-imidazo[1,2-b]pyridazine;
2-Chloro-4-(3-quinolin-6-ylmethyl-imidazo[1,2-b]pyridazin-6-yl)-benzamide;
6-(6-Naphthalen-2-yl-imidazo[1,2-b]pyridazin-3-ylmethyl)-quinoline;
6-[6-(3-Trifluoromethyl-phenyl)-imidazo[1,2-b]pyridazin-3-ylmethyl]-quinoline;
6-[6-(4-Bromo-phenyl)-imidazo[1,2-b]pyridazin-3-ylmethyl]-quinoline;
3-(3-Quinolin-6-ylmethyl-imidazo[1,2-b]pyridazin-6-yl)-phenylamine;
1-[4-(3-Quinolin-6-ylmethyl-imidazo[1,2-b]pyridazin-6-yl)-phenyl]-ethanone;
6-[6-(3-Nitro-phenyl)-imidazo[1,2-b]pyridazin-3-ylmethyl]-quinoline;

6-[6-(4-Methylsulfanyl-phenyl)-imidazo[1,2-b]pyridazin-3-ylmethyl]-quinoline;
3-(3-Quinolin-6-ylmethyl-imidazo[1,2-b]pyridazin-6-yl)-benzaldehyde;
6-[6-(4-Fluoro-phenyl)-imidazo[1,2-b]pyridazin-3-ylmethyl]-quinoline;
3-(3-Quinolin-6-ylmethyl-imidazo[1,2-b]pyridazin-6-yl)-benzonitrile;
6-[6-(4-Chloro-phenyl)-imidazo[1,2-b]pyridazin-3-ylmethyl]-quinoline;
N-[3-(3-Quinolin-6-ylmethyl-imidazo[1,2-b]pyridazin-6-yl)-phenyl]-acetamide;
6-(6-Pyridin-3-yl-imidazo[1,2-b]pyridazin-3-ylmethyl)-quinoline;
6-(6-Benzofuran-2-yl-imidazo[1,2-b]pyridazin-3-ylmethyl)-quinoline;
6-(6-Naphthalen-1-yl-imidazo[1,2-b]pyridazin-3-ylmethyl)-quinoline;
6-[6-(4-Trifluoromethyl-phenyl)-imidazo[1,2-b]pyridazin-3-ylmethyl]-quinoline;
6-[6-(4-Methoxy-phenyl)-imidazo[1,2-b]pyridazin-3-ylmethyl]-quinoline;
Dimethyl-[3-(3-quinolin-6-ylmethyl-imidazo[1,2-b]pyridazin-6-yl)-phenyl]-amine;
6-[6-(1-Methyl-1H-indol-5-yl)-imidazo[1,2-b]pyridazin-3-ylmethyl]-quinoline;
6-(6-Benzo[b]thiophen-2-yl-imidazo[1,2-b]pyridazin-3-ylmethyl)-quinoline;
6-(6-Quinolin-3-yl-imidazo[1,2-b]pyridazin-3-ylmethyl)-quinoline;
6-[6-(6-Methoxy-naphthalen-2-yl)-imidazo[1,2-b]pyridazin-3-ylmethyl]-quinoline;
6-[6-(5-Chloro-thiophen-2-yl)-imidazo[1,2-b]pyridazin-3-ylmethyl]-quinoline;
6-(6-Isoquinolin-4-yl-imidazo[1,2-b]pyridazin-3-ylmethyl)-quinoline;
6-[6-(4-Trifluoromethoxy-phenyl)-imidazo[1,2-b]pyridazin-3-ylmethyl]-quinoline;
6-[6-(4-Butyl-phenyl)-imidazo[1,2-b]pyridazin-3-ylmethyl]-quinoline;
6-[6-(1H-Indol-5-yl)-imidazo[1,2-b]pyridazin-3-ylmethyl]-quinoline;
6-[6-(1-Propyl-1H-pyrazol-4-yl)-imidazo[1,2-b]pyridazin-3-ylmethyl]-quinoline;
6-[6-(6-Chloro-pyridin-3-yl)-imidazo[1,2-b]pyridazin-3-ylmethyl]-quinoline;
6-[6-(2-Chloro-pyridin-4-yl)-imidazo[1,2-b]pyridazin-3-ylmethyl]-quinoline;
6-(6-Benzo[1,3]dioxol-5-yl-imidazo[1,2-b]pyridazin-3-ylmethyl)-quinoline;
6-(6-Benzo[1,2,5]oxadiazol-5-yl-imidazo[1,2-b]pyridazin-3-ylmethyl)-quinoline;
6-[6-(3-Chloro-phenyl)-imidazo[1,2-b]pyridazin-3-ylmethyl]-quinoline;
6-(6-Pyrimidin-5-yl-imidazo[1,2-b]pyridazin-3-ylmethyl)-quinoline;
1-[3-(3-Quinolin-6-ylmethyl-imidazo[1,2-b]pyridazin-6-yl)-phenyl]-ethanone;
6-[6-(2-Methoxy-pyrimidin-5-yl)-imidazo[1,2-b]pyridazin-3-ylmethyl]-quinoline;
3-(3-Quinolin-6-ylmethyl-imidazo[1,2-b]pyridazin-6-yl)-benzamide;
N-Methyl-3-(3-quinolin-6-ylmethyl-imidazo[1,2-b]pyridazin-6-yl)-benzamide;
N,N-Dimethyl-3-(3-quinolin-6-ylmethyl-imidazo[1,2-b]pyridazin-6-yl)-benzamide;
3-(3-Quinolin-6-ylmethyl-imidazo[1,2-b]pyridazin-6-yl)-benzoic acid ethyl ester;
6-[6-(1H-Indol-4-yl)-imidazo[1,2-b]pyridazin-3-ylmethyl]-quinoline;
6-[6-(6-Methoxy-pyridin-3-yl)-imidazo[1,2-b]pyridazin-3-ylmethyl]-quinoline;
6-[6-(2,3-Dihydro-benzofuran-5-yl)-imidazo[1,2-b]pyridazin-3-ylmethyl]-quinoline;
3-[4-(3-Quinolin-6-ylmethyl-imidazo[1,2-b]pyridazin-6-yl)-phenyl]-propan-1-ol;
6-(6-Thiophen-3-yl-imidazo[1,2-b]pyridazin-3-ylmethyl)-quinoline;
N-(2-Dimethylamino-ethyl)-3-(3-quinolin-6-ylmethyl-imidazo[1,2-b]pyridazin-6-yl)-benzamide;
2-Fluoro-5-(3-quinolin-6-ylmethyl-imidazo[1,2-b]pyridazin-6-yl)-benzonitrile;
6-[6-(3-Chloro-4-fluoro-phenyl)-imidazo[1,2-b]pyridazin-3-ylmethyl]-quinoline;
6-[6-(2H-Pyrazol-3-yl)-imidazo[1,2-b]pyridazin-3-ylmethyl]-quinoline;
2-Fluoro-N-methyl-4-(3-quinolin-6-ylmethyl-imidazo[1,2-b]pyridazin-6-yl)-benzamide;
2-Chloro-N-methyl-4-(3-quinolin-6-ylmethyl-imidazo[1,2-b]pyridazin-6-yl)-benzamide;
3-(3-Quinolin-6-ylmethyl-imidazo[1,2-b]pyridazin-6-yl)-benzoic acid;
5-(3-Quinolin-6-ylmethyl-imidazo[1,2-b]pyridazin-6-yl)-pyridin-2-ol;
2-(3-Imidazo[1,2-a]pyridin-6-ylmethyl-imidazo[1,2-b]pyridazin-6-ylamino)-ethanol;
[(R)-1-(3-Imidazo[1,2-a]pyridin-6-ylmethyl-imidazo[1,2-b]pyridazin-6-yl)-pyrrolidin-3-yl]-dimethyl-amine;
(rac)-(6-Isobutylamino-imidazo[1,2-b]pyridazin-3-yl)-quinolin-6-yl-methanol;
sec-Butyl-(3-quinolin-6-ylmethyl-imidazo[1,2-b]pyridazin-6-yl)-amine;
Isobutyl-(3-quinolin-6-ylmethyl-imidazo[1,2-b]pyridazin-6-yl)-amine;
(3-Quinolin-6-ylmethyl-imidazo[1,2-b]pyridazin-6-yl)-(tetrahydro-furan-2-ylmethyl)-amine;
Cyclopentyl-(3-quinolin-6-ylmethyl-imidazo[1,2-b]pyridazin-6-yl)-amine;
Benzyl-(3-quinolin-6-ylmethyl-imidazo[1,2-b]pyridazin-6-yl)-amine;
(1-Methyl-piperidin-4-yl)-(3-quinolin-6-ylmethyl-imidazo[1,2-b]pyridazin-6-yl)-amine;
6-(6-Morpholin-4-yl-imidazo[1,2-b]pyridazin-3-ylmethyl)-quinoline;
Dimethyl-[1-(3-quinolin-6-ylmethyl-imidazo[1,2-b]pyridazin-6-yl)-piperidin-4-yl]-amine;
Methyl-[1-(3-quinolin-6-ylmethyl-imidazo[1,2-b]pyridazin-6-yl)-pyrrolidin-3-yl]-carbamic acid tert-butyl ester;
Dimethyl-[(R)-1-(3-quinolin-6-ylmethyl-imidazo[1,2-b]pyridazin-6-yl)-pyrrolidin-3-yl]-amine;
(2-Methoxy-ethyl)-(3-quinolin-6-ylmethyl-imidazo[1,2-b]pyridazin-6-yl)-amine;
(1-Ethyl-propyl)-(3-quinolin-6-ylmethyl-imidazo[1,2-b]pyridazin-6-yl)-amine;
Isopropyl-(3-quinolin-6-ylmethyl-imidazo[1,2-b]pyridazin-6-yl)-amine;
2-(3-Quinolin-6-ylmethyl-imidazo[1,2-b]pyridazin-6-ylamino)-ethanol;
4-Methyl-thiazol-2-yl)-(3-quinolin-6-ylmethyl-imidazo[1,2-b]pyridazin-6-yl)-amine;
(2-Pyrrolidin-1-yl-ethyl)-(3-quinolin-6-ylmethyl-imidazo[1,2-b]pyridazin-6-yl)-amine;

(1-Ethyl-pyrrolidin-2-ylmethyl)-(3-quinolin-6-ylmethyl-imidazo[1,2-b]pyridazin-6-yl)-amine;
Cyclooctyl-(3-quinolin-6-ylmethyl-imidazo[1,2-b]pyridazin-6-yl)-amine;
(1,1-Dimethyl-propyl)-(3-quinolin-6-ylmethyl-imidazo[1,2-b]pyridazin-6-yl)-amine;
1,1-Dioxo-tetrahydro-l1ambda*6*-thiophen-3-yl)-(3-quinolin-6-ylmethyl -imidazo[1,2-b]pyridazin-6-yl)-amine;
(2-Phenyl-propyl)-(3-quinolin-6-ylmethyl-imidazo[1,2-b]pyridazin-6-yl)-amine;
N,N-Dimethyl-N'-(3-quinolin-6-ylmethyl-imidazo[1,2-b]pyridazin-6-yl)-propane-1,3-diamine;
(1-Phenyl-ethyl)-(3-quinolin-6-ylmethyl-imidazo[1,2-b]pyridazin-6-yl)-amine;
Phenethyl-(3-quinolin-6-ylmethyl-imidazo[1,2-b]pyridazin-6-yl)-amine;
Dimethyl-(3-quinolin-6-ylmethyl-imidazo[1,2-b]pyridazin-6-yl)-amine;
(S)-1-(3-Quinolin-6-ylmethyl-imidazo[1,2-b]pyridazin-6-yl)-pyrrolidin-3-ol;
(R)-1-(3-Quinolin-6-ylmethyl-imidazo[1,2-b]pyridazin-6-yl)-pyrrolidin-3-ol;
6-[6-(1,4-Dioxa-8-aza-spiro[4.5]dec-8-yl)-imidazo[1,2-b]pyridazin-3-ylmethyl]-quinoline;
(3-Quinolin-6-ylmethyl-imidazo[1,2-b]pyridazin-6-yl)-(2,2,2-trifluoro-ethyl)-amine;
6-(6-Imidazol-1-yl-imidazo[1,2-b]pyridazin-3-ylmethyl)-quinoline;
6-[6-(2-Methyl-imidazol-1-yl)-imidazo[1,2-b]pyridazin-3-ylmethyl]-quinoline;
(1-Benzyl-pyrrolidin-3-yl)-(3-quinolin-6-ylmethyl-imidazo[1,2-b]pyridazin-6-yl) -amine;
6-[6-(4-Methyl-imidazol-1-yl)-imidazo[1,2-b]pyridazin-3-ylmethyl]-quinoline;
(3-Chloro-phenyl)-(3-quinolin-6-ylmethyl-imidazo[1,2-b]pyridazin-6-yl)-amine;
Phenyl-(3-quinolin-6-ylmethyl-imidazo[1,2-b]pyridazin-6-yl)-amine;
6-[6-((R)-3-fluoro-pyrrolidin-1-yl)-imidazo[1,2-b]pyridazin-3-ylmethyl]-quinoline;
6-[6-((S)-3-Fluoro-pyrrolidin-1-yl)-imidazo[1,2-b]pyridazin-3-ylmethyl]-quinoline;
(4-Piperidin-1-ylmethyl-phenyl)-(3-quinolin-6-ylmethyl-imidazo[1,2-b]pyridazin-6-yl)-amine;
(3-Quinolin-6-ylmethyl-imidazo[1,2-b]pyridazin-6-yl)-(3-trifluoromethyl-phenyl) -amine;
(2-Chloro-phenyl)-(3-quinolin-6-ylmethyl-imidazo[1,2-b]pyridazin-6-yl)-amine;
Pyridin-3-yl-(3-quinolin-6-ylmethyl-imidazo[1,2-b]pyridazin-6-yl)-amine;
Pyrimidin-2-yl-(3-quinolin-6-ylmethyl-imidazo[1,2-b]pyridazin-6-yl)-amine;
Pyrimidin-4-yl-(3-quinolin-6-ylmethyl-imidazo[1,2-b]pyridazin-6-yl)-amine;
(2-Ethyl-2H-pyrazol-3-yl)-(3-quinolin-6-ylmethyl-imidazo[1,2-b]pyridazin-6-yl) -amine;
7-[6-(4-Methyl-pyrazol-1-yl)-imidazo[1,2-b]pyridazin-3-ylmethyl]-quinoline;
6-(6-Pyrazol-1-yl-imidazo[1,2-b]pyridazin-3-ylmethyl)-quinoline;
(3-Chloro-4-methyl-phenyl)-(3-quinolin-7-ylmethyl-imidazo[1,2-b]pyridazin-6-yl)-amine;
(2,3-Dichloro-phenyl)-(3-quinolin-6-ylmethyl-imidazo[1,2-b]pyridazin-6-yl)-amine;
(3-Chloro-4-fluoro-phenyl)-(3-quinolin-6-ylmethyl-imidazo[1,2-b]pyridazin-6-yl) -amine;
(3-Chloro-phenyl)-methyl-(3-quinolin-6-ylmethyl-imidazo[1,2-b]pyridazin-6-yl) -amine;
(3-Methanesulfonyl-phenyl)-(3-quinolin-6-ylmethyl-imidazo[1,2-b]pyridazin-6-yl) -amine;
(3-Methoxy-phenyl)-(3-quinolin-6-ylmethyl-imidazo[1,2-b]pyridazin-6-yl)-amine;
Benzo[1,2,5]oxadiazol-4-yl-(3-quinolin-7-ylmethyl-imidazo[1,2-b]pyridazin-6-yl) -amine;
2-(4-{4-[3-(7-Fluoro-quinolin-6-ylmethyl)-imidazo[1,2-b]pyridazin-6-yl]-pyrazol-1-yl}-piperidin-1-yl)-ethanol;
6-{6-[1-(1-Ethyl-piperidin-4-yl)-1H-pyrazol-4-yl]-imidazo[1,2-b]pyridazin-3-ylmethyl}-7-fluoro-quinoline;
7-Fluoro-6-(6-{1-[1-(2,2,2-trifluoro-ethyl)-piperidin-4-yl]-1H-pyrazol-4-yl}-imidazo[1,2-b]pyridazin-3-ylmethyl)-quinoline;
3-(1H-Indazol-5-ylmethyl)-6-(1-methyl-1H-pyrazol-4-yl)-imidazo[1,2-b]pyridazine;
(R)-[6-(1-Methyl-1H-pyrazol-4-yl)-imidazo[1,2-b]pyridazin-3-yl]-quinolin-6-yl -methanol;
(S)-[6-(1-Methyl-1H-pyrazol-4-yl)-imidazo[1,2-b]pyridazin-3-yl]-quinolin-6-yl -methanol;
(rac)-6-{1-[6-(1-Methyl-1H-pyrazol-4-yl)-imidazo[1,2-b]pyridazin-3-yl]-ethyl}-1,2,3,4-tetrahydro-quinoline;
(rac)-6-{1-[6-(1-Methyl-1H-pyrazol-4-yl)-imidazo[1,2-b]pyridazin-3-yl]-ethyl}-quinoline;
6-{(R)-1-[6-(1-Methyl-1H-pyrazol-4-yl)-imidazo[1,2-b]pyridazin-3-yl]-ethyl}-quinoline;
6-{(S)-1-[6-(1-Methyl-1H-pyrazol-4-yl)-imidazo[1,2-b]pyridazin-3-yl]-ethyl}-quinoline;
5-Fluoro-6-[6-(1-methyl-1H-pyrazol-4-yl)-imidazo[1,2-b]pyridazin-3-ylmethyl]-quinoline;
(rac)-(2-Amino-imidazo[1,2-a]pyridin-6-yl)-[6-(1-methyl-1H-pyrazol-4-yl) -imidazo[1,2-b]pyridazin-3-yl]-methanol;
3-(1H-Benzoimidazol-5-ylmethyl)-6-(1-methyl-1H-pyrazol-4-yl)-imidazo[1,2-b]pyridazine;
6-{1-[6-(1-Methyl-1H-pyrazol-4-yl)-imidazo[1,2-b]pyridazin-3-yl]-cyclopropyl}-quinoline;
(rac)-3-[1-(6-Fluoro-1H-indazol-5-yl)-ethyl]-6-(1-methyl-1H-pyrazol-4-yl) -imidazo[1,2-b]pyridazine;
3-[(S)-1-(6-Fluoro-1H-indazol-5-yl)-ethyl]-6-(1-methyl-1H-pyrazol-4-yl) -imidazo[1,2-b]pyridazine;
3-[(R)-1-(6-Fluoro-1H-indazol-5-yl)-ethyl]-6-(1-methyl-1H-pyrazol-4-yl) -imidazo[1,2-b]pyridazine;
3-(6-Fluoro-1H-indazol-5-ylmethyl)-6-(1-methyl-1H-pyrazol-4-yl)-imidazo[1,2-b]pyridazine;
(rac)-2,2,2-Trifluoro-1-[6-(1-methyl-1H-pyrazol-4-yl)-imidazo[1,2-b]pyridazin-3-yl]-1-quinolin-6-yl-ethanol;
6-[6-(1-Methyl-1H-pyrazol-4-yl)-imidazo[1,2-b]pyridazin-3-ylmethyl]-7-trifluoromethyl-quinoline;
5,7-Difluoro-6-[6-(1-methyl-1H-pyrazol-4-yl)-imidazo[1,2-b]pyridazin-3-ylmethyl]-quinoline;
2-{4-[3-(5,7-Difluoro-quinolin-6-ylmethyl)-imidazo[1,2-b]pyridazin-6-yl]-pyrazol-1-yl}-ethanol;
7-Fluoro-6-[6-(1-methyl-1H-pyrazol-4-yl)-imidazo[1,2-b]pyridazin-3-ylmethyl]-quinoline;
(rac)-1-(7-Fluoro-quinolin-6-yl)-1-[6-(1-methyl-1H-pyrazol-4-yl)-imidazo[1,2-b]pyridazin-3-yl]-ethanol;
(R)-1-(7-Fluoro-quinolin-6-yl)-1-[6-(1-methyl-1H-pyrazol-4-yl)-imidazo[1,2-b]pyridazin-3-yl]-ethanol;
[4-(3-Quinolin-6-ylmethyl-imidazo[1,2-b]pyridazin-6-yl)-pyrazol-1-yl]-acetonitrile;
(rac)-2-{4-[3-(1-Quinolin-6-yl-ethyl)-imidazo[1,2-b]pyridazin-6-yl]-pyrazol-1-yl}-ethanol;

2-{4-[3-((R)-1-Quinolin-6-yl-ethyl)-imidazo[1,2-b]pyridazin-6-yl]-pyrazol-1-yl}-ethanol;
2-{4-[3-((S)-1-Quinolin-6-yl-ethyl)-imidazo[1,2-b]pyridazin-6-yl]-pyrazol-1-yl}-ethanol;
7-Fluoro-6-[6-(1-piperidin-4-yl-1H-pyrazol-4-yl)-imidazo[1,2-b]pyridazin-3-ylmethyl]-quinoline;
(rac)-2-(4-{3-[1-(5,7-Difluoro-quinolin-6-yl)-ethyl]-imidazo[1,2-b]pyridazin-6-yl}-pyrazol-1-yl)-ethanol;
2-(4-{3-[(R)-1-(5,7-Difluoro-quinolin-6-yl)-ethyl]-imidazo[1,2-b]pyridazin-6-yl}-pyrazol-1-yl)-ethanol;
2-(4-{3-[(S)-1-(5,7-Difluoro-quinolin-6-yl)-ethyl]-imidazo[1,2-b]pyridazin-6-yl}-pyrazol-1-yl)-ethanol;
(rac)-2-(4-{3-[1-(3-Methyl-3H-benzoimidazol-5-yl)-ethyl]-imidazo[1,2-b]pyridazin-6-yl}-pyrazol-1-yl)-ethanol;
2-(4-{3-[(R)-1-(3-Methyl-3H-benzoimidazol-5-yl)-ethyl]-imidazo[1,2-b]pyridazin-6-yl}-pyrazol-1-yl)-ethanol;
2-(4-{3-[(S)-1-(3-Methyl-3H-benzoimidazol-5-yl)-ethyl]-imidazo[1,2-b]pyridazin-6-yl}-pyrazol-1-yl)-ethanol;
(rac)-2-(4-{3-(5-Chloro-quinolin-6-yl)-ethyl]-imidazo[1,2-b]pyridazin-6-yl}-pyrazol-1-yl)-ethanol;
(rac)-2-(4-{3-[1-Imidazo[1,2-a]pyridin-6-yl-ethyl]-imidazo[1,2-b]pyridazin-6-yl}-pyrazol-1-yl]-ethanol;
(rac)-2-(4-{3-[1-(2H-Indazol-5-yl)-ethyl]-imidazo[1,2-b]pyridazin-6-yl}-pyrazol-1-yl)-ethanol;
(rac)-5,7-Difluoro-6-{1-[6-(1-methyl-1H-pyrazol-4-yl)-imidazo[1,2-b]pyridazin-3-yl]-ethyl}-quinoline;
5,7-Difluoro-6-{(S)-1-[6-(1-methyl-1H-pyrazol-4-yl)-imidazo[1,2-b]pyridazin-3-yl]-ethyl}-quinoline;
5,7-Difluoro-6-{(R)-1-[6-(1-methyl-1H-pyrazol-4-yl)-imidazo[1,2-b]pyridazin-3-yl]-ethyl}-quinoline;
3-[(S)-1-(6-Fluoro-1-methyl-1H-indazol-5-yl)-ethyl]-6-(1-methyl-1H-pyrazol-4-yl) -imidazo[1,2-b]pyridazine;
3-[(S)-1-(2H-Indazol-5-yl)-ethyl]-6-(1-methyl-1H-pyrazol-4-yl)-imidazo[1,2-b]pyridazine;
3-[(S)-1-(1-Methyl-1H-indazol-5-yl)-ethyl]-6-(1-methyl-1H-pyrazol-4-yl) -imidazo[1,2-b]pyridazine;
6-{Difluoro-[6-(1-piperidin-4-yl-1H-pyrazol-4-yl)-imidazo[1,2-b]pyridazin-3-yl]-methyl}-quinoline;
6-(1-Methyl-1H-pyrazol-4-yl)-3-(1H-pyrrolo[2,3-b]pyridin-3-ylmethyl)-imidazo[1,2-b]pyridazine;
3-(3-Methyl-3H-benzoimidazol-5-ylmethyl)-6-(1-methyl-1H-pyrazol-4-yl) -imidazo[1,2-b]pyridazine;
3-Fluoro-4-[6-(1-methyl-1H-pyrazol-4-yl)-imidazo[1,2-b]pyridazin-3-ylmethyl]-phenol;
3-(4-Bromo-2-fluoro-benzyl)-6-(1-methyl-1H-pyrazol-4-yl)-imidazo[1,2-b]pyridazine;
3-(2,4-Difluoro-benzyl)-6-(1-methyl-1H-pyrazol-4-yl)-imidazo[1,2-b]pyridazine;
3-(7-Fluoro-imidazo[1,2-a]pyridin-6-ylmethyl)-6-(1-methyl-1H-pyrazol-4-yl) -imidazo[1,2-b]pyridazine;
(rac)-3-[1-(3-Methyl-3H-benzoimidazol-5-yl)-ethyl]-6-(1-methyl-1H-pyrazol-4-yl) -imidazo[1,2-b]pyridazine;
2-[4-(3-Quinolin-6-ylmethyl-imidazo[1,2-b]pyridazin-6-yl)-pyrazol-1-yl]-ethanol;
6-[6-(1-Ethyl-1H-pyrazol-4-yl)-imidazo[1,2-b]pyridazin-3-ylmethyl]-quinoline;
6-[6-(1H-Pyrazol-4-yl)-imidazo[1,2-b]pyridazin-3-ylmethyl]-quinoline;
2-[4-(3-Imidazo[1,2-a]pyridin-6-ylmethyl-imidazo[1,2-b]pyridazin-6-yl)-pyrazol-1-yl]-ethanol;
2-[4-(3-Imidazo[1,2-a]pyridin-6-ylmethyl-imidazo[1,2-b]pyridazin-6-yl)-pyrazol-1-yl]-ethanol;
2-{4-[3-(3-Methyl-3H-benzoimidazol-5-ylmethyl)-imidazo[1,2-b]pyridazin-6-yl]-pyrazol-1-yl}-ethanol;
3-Fluoro-4-{6-[1-(2-hydroxy-ethyl)-1H-pyrazol-4-yl]-imidazo[1,2-b]pyridazin-3-ylmethyl}-phenol;
4-{6-[1-(2-Hydroxy-ethyl)-1H-pyrazol-4-yl]-imidazo[1,2-b]pyridazin-3-ylmethyl}-phenol;
(rac)-4-(1-{6-[1-(2-Hydroxy-ethyl)-1H-pyrazol-4-yl]-imidazo[1,2-b]pyridazin-3-yl}-ethyl)-phenol;
(rac)-4-{1-[6-(1-Methyl-1H-pyrazol-4-yl)-imidazo[1,2-b]pyridazin-3-yl]-ethyl}-phenol;
(rac)-5-Chloro-6-{1-[6-(1-piperidin-4-yl-1H-pyrazol-4-yl)-imidazo[1,2-b]pyridazin-3-yl]-ethyl}-quinoline;
(rac)-5-Chloro-6-{1-[6-(1-methyl-1H-pyrazol-4-yl)-imidazo[1,2-b]pyridazin-3-yl]-ethyl}-quinoline;
2-{4-[3-(5-Chloro-quinolin-6-ylmethyl)-imidazo[1,2-b]pyridazin-6-yl]-pyrazol-1-yl}-ethanol;
5-Chloro-6-[6-(1-piperidin-4-yl-1H-pyrazol-4-yl)-imidazo[1,2-b]pyridazin-3-ylmethyl]-quinoline;
(rac)-(3-Methyl-3H-benzoimidazol-5-yl)-[6-(1-methyl-1H-pyrazol-4-yl) -imidazo[1,2-b]pyridazin-3-yl]-methanol;
7-Fluoro-6-{6-[1-(2-pyrrolidin-1-yl-ethyl)-1H-pyrazol-4-yl]-imidazo[1,2-b]pyridazin-3-ylmethyl}-quinoline;
7-Fluoro-6-{6-[1-(2-morpholin-4-yl-ethyl)-1H-pyrazol-4-yl]-imidazo[1,2-b]pyridazin-3-ylmethyl}-quinoline;
7-Fluoro-6-{6-[1-(2-methoxy-ethyl)-1H-pyrazol-4-yl]-imidazo[1,2-b]pyridazin-3-ylmethyl}-quinoline;
6-{6-[1-(2-Pyrrolidin-1-yl-ethyl)-1H-pyrazol-4-yl]-imidazo[1,2-b]pyridazin-3-ylmethyl}-quinoline;
Methyl-{2-[4-(3-quinolin-6-ylmethyl-imidazo[1,2-b]pyridazin-6-yl)-pyrazol-1-yl]-ethyl}-amine;
6-{(S)-1-[6-(1H-Pyrazol-4-yl)-imidazo[1,2-b]pyridazin-3-yl]-ethyl}-quinoline;
7-Chloro-6-[6-(1-methyl-1H-pyrazol-4-yl)-imidazo[1,2-b]pyridazin-3-ylmethyl]-quinoline;
7-Chloro-6-[6-(1-ethyl-1H-pyrazol-4-yl)-imidazo[1,2-b]pyridazin-3-ylmethyl]-quinoline;
2-{4-[3-(7-Chloro-quinolin-6-ylmethyl)-imidazo[1,2-b]pyridazin-6-yl]-pyrazol-1-yl}-ethanol;
5,7-Difluoro-6-[6-(1-piperidin-4-yl-1H-pyrazol-4-yl)-imidazo[1,2-b]pyridazin-3-ylmethyl]-quinoline;
(rac)-(5-Fluoro-quinolin-6-yl)-[6-(1-methyl-1H-pyrazol-4-yl)-imidazo[1,2-b]pyridazin-3-yl]-methanol;
(rac)-7-Fluoro-quinolin-6-yl)-[6-(1-methyl-1H-pyrazol-4-yl)-imidazo[1,2-b]pyridazin-3-yl]-methanol;
(rac)-[6-(1-Ethyl-1H-pyrazol-4-yl)-imidazo[1,2-b]pyridazin-3-yl]-(7-fluoro-quinolin -6-yl)-methanol;
6-[6-(1-Ethyl-1H-pyrazol-4-yl)-imidazo[1,2-b]pyridazin-3-ylmethyl]-7-fluoro -quinoline;
7-Fluoro-6-[6-(1H-pyrazol-4-yl)-imidazo[1,2-b]pyridazin-3-ylmethyl]-quinoline;
(rac)-(7-Fluoro-quinolin-6-yl)-[6-(1H-pyrazol-4-yl)-imidazo[1,2-b]pyridazin-3-yl]-methanol;
(rac)-7-Fluoro-6-{1-[6-(1-methyl-1H-pyrazol-4-yl)-imidazo[1,2-b]pyridazin-3-yl]-ethyl}-quinoline;
2-{4-[3-(7-Fluoro-quinolin-6-ylmethyl)-imidazo[1,2-b]pyridazin-6-yl]-pyrazol-1-yl}-ethanol;
(rac)-2-(4-{3-[1-(7-Fluoro-quinolin-6-yl)-ethyl]-imidazo[1,2-b]pyridazin-6-yl}-pyrazol-1-yl)-ethanol;
3-((R)-1-Imidazo[1,2-a]pyridin-6-yl-ethyl)-6-(1-methyl-1H-pyrazol-4-yl) -imidazo[1,2-b]pyridazine;
(rac)-7-Fluoro-6-{1-[6-(1-piperidin-4-yl-1H-pyrazol-4-yl)-imidazo[1,2-b]pyridazin-3-yl]-ethyl}-quinoline;
(S)-1-[3-(7-Fluoro-quinolin-6-ylmethyl)-imidazo[1,2-b]pyridazin-6-yl]-pyrrolidin-3-ol;
(R)-1-[3-(7-Fluoro-quinolin-6-ylmethyl)-imidazo[1,2-b]pyridazin-6-yl]-pyrrolidin-3-ol;

5,7-Difluoro-6-[6-(1H-pyrazol-4-yl)-imidazo[1,2-b]pyridazin-3-ylmethyl]-quinoline;
(rac)-1-[6-(1-Methyl-1H-pyrazol-4-yl)-imidazo[1,2-b]pyridazin-3-yl]-1-quinolin-6-yl-ethanol;
(rac)-1-(7-Fluoro-quinolin-6-yl)-1-{6-[1-(2-hydroxyethyl)-1H-pyrazol-4-yl]-imidazo [1,2-b]pyridazin-3-yl}-ethanol;
(R)-1-(7-Fluoro-quinolin-6-yl)-1-{6-[1-(2-hydroxyethyl)-1H-pyrazol-4-yl]-imidazo [1,2-b]pyridazin-3-yl}-ethanol;
(rac)-1-(5,7-Difluoro-quinolin-6-yl)-1-{6-[1-(2-hydroxyethyl)-1H-pyrazol-4-yl]-imidazo [1,2-b]pyridazin-3-yl}-ethanol;
(R)-1-(5,7-Difluoro-quinolin-6-yl)-1-{6-[1-(2-hydroxyethyl)-1H-pyrazol-4-yl]-imidazo [1,2-b]pyridazin-3-yl}-ethanol;
(rac)-1-(5,7-Difluoro-quinolin-6-yl)-1-[6-(1-methyl-1H-pyrazol-4-yl)-imidazo[1,2-b]pyridazin-3-yl]-ethanol;
(R)-1-(5,7-Difluoro-quinolin-6-yl)-1-[6-(1-methyl-1H-pyrazol-4-yl)-imidazo[1,2-b]pyridazin-3-yl]-ethanol;
2-(5-{(S)-1-[6-(1-Methyl-1H-pyrazol-4-yl)-imidazo[1,2-b]pyridazin-3-yl]-ethyl}-indazol-1-yl)-ethanol;
3-(1-Methyl-1H-indazol-5-ylmethyl)-6-(1-methyl-1H-pyrazol-4-yl)-imidazo[1,2-b]pyridazine;
3-(6-Fluoro-1-methyl-1H-indazol-5-ylmethyl)-6-(1-methyl-1H-pyrazol-4-yl) -imidazo [1,2-b]pyridazine;
(rac)-3-[1-(6-Fluoro-1-methyl-1H-indazol-5-yl)-ethyl]-6-(1-methyl-1H-pyrazol-4-yl) -imidazo [1,2-b]pyridazine;
(rac)-2-(4-{3-[1-(6-Fluoro-1-methyl-1H-indazol-5-yl)-ethyl]-imidazo[1,2-b]pyridazin-6-yl}-pyrazol-1-yl)-ethanol;
2-(4-{3-[(S)-1-(6-Fluoro-1-methyl-1H-indazol-5-yl)-ethyl]-imidazo[1,2-b]pyridazin -6-yl}-pyrazol-1-yl)-ethanol;
2-{4-[3-(6-Fluoro-1-methyl-1H-indazol-5-ylmethyl)-imidazo[1,2-b]pyridazin-6-yl]-pyrazol-1-yl}-ethanol;
3-(6-Fluoro-1-methyl-1H-indazol-5-ylmethyl)-6-(1-piperidin-4-yl-1H-pyrazol-4-yl) -imidazo[1,2-b]pyridazine;
3-(4,6-Difluoro-1-methyl-1H-indazol-5-ylmethyl)-6-(1-methyl-1H-pyrazol-4-yl) -imidazo[1,2-b]pyridazine;
2-{4-[3-(4,6-Difluoro-1-methyl-1H-indazol-5-ylmethyl)-imidazo[1,2-b]pyridazin-6-yl]-pyrazol-1-yl1-ethanol;
(rac)-[6-(1-Methyl-1H-pyrazol-4-yl)-imidazo[1,2-b]pyridazin-3-yl]-[1,5]naphthyridin-2-yl-methanol;
3-(3-Methyl-1H-indazol-5-ylmethyl)-6-(1-methyl-1H-pyrazol-4-yl)-imidazo[1,2-b]pyridazine;
3-(2-Fluoro-imidazo[1,2-a]pyridin-6-ylmethyl)-6-(1-methyl-1H-pyrazol-4-yl) -imidazo [1,2-b]pyridazine;
6-(1-Ethyl-1H-pyrazol-4-yl)-3-imidazo[1,2-a]pyridin-6-ylmethyl-imidazo[1,2-b]pyridazine;
3-Imidazo[1,2-a]pyridin-6-ylmethyl-6-(1H-pyrazol-4-yl)-imidazo[1,2-b]pyridazine;
3-Imidazo[1,2-a]pyridin-6-ylmethyl-6-(1-piperidin-4-yl-1H-pyrazol-4-yl) -imidazo[1,2-b]pyridazine;
(rac)-3-(1-Imidazo[1,2-a]pyridin-6-yl-ethyl)-6-(1-methyl-1H-pyrazol-4-yl) -imidazo [1,2-b]pyridazine;
3-((R)-1-Imidazo[1,2-a]pyridin-6-yl-ethyl)-6-(1-methyl-1H-pyrazol-4-yl) -imidazo [1,2-b]pyridazine;
3-((S)-1-Imidazo[1,2-a]pyridin-6-yl-ethyl)-6-(1-methyl-1H-pyrazol-4-yl) -imidazo [1,2-b]pyridazine;
3-(3-Bromo-imidazo[1,2-a]pyridin-6-ylmethyl)-6-(1-methyl-1H-pyrazol-4-yl) -imidazo [1,2-b]pyridazine;
3-(3-Chloro-imidazo[1,2-a]pyridin-6-ylmethyl)-6-(1-methyl-1H-pyrazol-4-yl) -imidazo [1,2-b]pyridazine;
6-(1-Methyl-1H-pyrazol-4-yl)-3-(3-vinyl-imidazo[1,2-a]pyridin-6-ylmethyl) -imidazo [1,2-b]pyridazine;
{6-[6-(1-Methyl-1H-pyrazol-4-yl)-imidazo[1,2-b]pyridazin-3-ylmethyl]-imidazo[1,2-a]pyridin-3-yl}-methanol;
6-[6-(1-Methyl-1H-pyrazol-4-yl)-imidazo[1,2-b]pyridazin-3-ylmethyl]-imidazo[1,2-a]pyridine-3-carbonitrile;
1-{6-[6-(1-Methyl-1H-pyrazol-4-yl)-imidazo[1,2-b]pyridazin-3-ylmethyl]-imidazo [1,2-a]pyridin-3-yl}-ethanol;
(rac)-3-(1-Imidazo[1,2-a]pyridin-6-yl-ethyl)-6-m-tolyl-imidazo[1,2-b]pyridazine;
(rac)-3-[1-(3-Bromo-imidazo[1,2-a]pyridin-6-yl)-ethyl]-6-(1-methyl-1H-pyrazol-4-yl)-imidazo[1,2-b]pyridazine;
(rac)-2-(4-{3-[1-(3-Bromo-imidazo[1,2-a]pyridin-6-yl)-ethyl]-imidazo[1,2-b]pyridazin-6-yl}-pyrazol-1-yl)-ethanol;
2-(4-{3-[(S)-1-(3-Bromo-imidazo[1,2-a]pyridin-6-yl)-ethyl]-imidazo[1,2-b]pyridazin -6-yl}-pyrazol-1-yl)-ethanol; and
(rac)-3-[1-(3-Bromo-imidazo[1,2-a]pyridin-6-yl)-ethyl]-6-m-tolyl-imidazo[1,2-b]pyridazine; or a pharmaceutically acceptable salt thereof.

2. A pharmaceutical composition comprising a therapeutically effective amount of a compound of claim 1 in free form or in pharmaceutically acceptable salt form as an active ingredient; one or more pharmaceutically acceptable carrier material(s) or diluents.

3. A combined pharmaceutical composition, adapted for simultaneous or sequential administration, comprising a therapeutically effective amount of a compound of claim 1 in free form or in pharmaceutically acceptable salt form; therapeutically effective amount(s) of one or more combination partners; one or more pharmaceutically acceptable carrier material(s) or diluents.

* * * * *